US012698282B2

(12) United States Patent
Inghardt et al.

(10) Patent No.: US 12,698,282 B2
(45) Date of Patent: Aug. 4, 2026

(54) INHIBITORS OF MYELOPEROXIDASE

(71) Applicant: ASTRAZENECA AB, Södertälje (SE)

(72) Inventors: Tord Inghardt, Södertälje (SE); Eva-Lotte Lindstedt, Södertälje (SE); Ulrik Jurva, Södertälje (SE); Nidhal Selmi, Södertälje (SE)

(73) Assignee: AstraZeneca AB, Södertälje (SE)

( * ) Notice: Subject to any disclaimer, the term of this patent is extended or adjusted under 35 U.S.C. 154(b) by 419 days.

(21) Appl. No.: 18/451,210

(22) Filed: Aug. 17, 2023

(65) Prior Publication Data

US 2024/0166642 A1 May 23, 2024

Related U.S. Application Data

(60) Provisional application No. 63/398,939, filed on Aug. 18, 2022.

(51) Int. Cl.
*C07D 419/14* (2006.01)

(52) U.S. Cl.
CPC .................................. *C07D 419/14* (2013.01)

(58) Field of Classification Search
CPC .. C07D 419/14; C07D 473/22; C07D 487/04; A61P 35/00; A61P 1/16; A61P 9/00; A61P 11/00; A61P 13/12; A61P 25/00; A61P 29/00; A61K 31/519
USPC .................................................... 544/280, 66
See application file for complete search history.

(56) References Cited

U.S. PATENT DOCUMENTS

| | | | |
|---|---|---|---|
| 3,919,210 | A | 11/1975 | Hardtmann |
| 3,969,506 | A | 7/1976 | Hardtmann |
| 6,413,975 | B1 | 7/2002 | Chasin et al. |
| 9,249,087 | B2 | 2/2016 | Kozikowski et al. |
| 9,616,063 | B2 | 4/2017 | Inghardt et al. |
| 10,016,430 | B2 | 7/2018 | Inghardt et al. |
| 2005/0130983 | A1 | 6/2005 | Kim et al. |
| 2016/0152623 | A1 | 6/2016 | Inghardt et al. |

(Continued)

FOREIGN PATENT DOCUMENTS

| | | | |
|---|---|---|---|
| CH | 532068 | A | 12/1972 |
| CN | 1926119 | A | 3/2007 |
| CN | 101072778 | A | 11/2007 |

(Continued)

OTHER PUBLICATIONS

Aldib I., et al., "Evaluation of New Scaffolds of Myeloperoxidase Inhibitors by Rational Design Combined with High-Throughput Virtual Screening", Journal of Medicinal Chemistry, vol. 55, 2012, pp. 7208-7218.

(Continued)

*Primary Examiner* — Taylor V Oh
(74) *Attorney, Agent, or Firm* — Choate, Hall & Stewart LLP; Michael A. Shinall; William C. Howland, III

(57) ABSTRACT

The specification generally relates to compounds of Formula (I), (Ia), and (Ib):

(I)

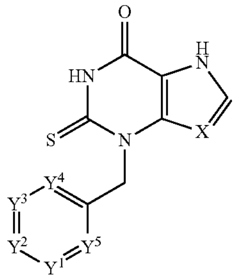

(Ia)

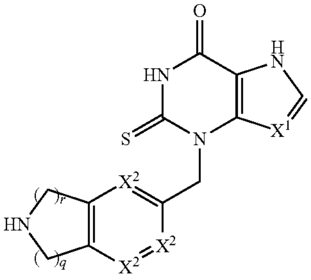

(Ib)

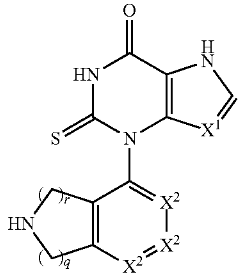

and pharmaceutically acceptable salts thereof, where X, $Y^1$, $Y^2$, $Y^3$, $Y^4$, and $Y^5$ and $X^1$, $X^2$, r, and q, have any of the meanings defined herein, together with compositions containing them and their use in therapy. The compounds are inhibitors of the enzyme MPO, and are thereby particularly useful in the treatment or prophylaxis of diseases or conditions in which modulation of the activity of the enzyme myeloperoxidase (MPO) is desirable, including diseases with inflammatory, cardiovascular, respiratory, renal, hepatic and/or neurological components, as well as neutrophilic driven diseases.

17 Claims, No Drawings

(56) References Cited

U.S. PATENT DOCUMENTS

2021/0298611 A1 9/2021 Stocker et al.

FOREIGN PATENT DOCUMENTS

| | | | |
|---|---|---|---|
| CN | 101124228 | A | 2/2008 |
| CN | 106083741 | A | 11/2016 |
| CN | 112409331 | A | 2/2021 |
| CN | 115403584 | * | 11/2022 |
| CN | 115403584 | A | 11/2022 |
| CN | 116514816 | A | 8/2023 |
| DE | 2025248 | A1 | 12/1970 |
| DE | 2234174 | A1 | 1/1973 |
| DE | 2257376 | A1 | 5/1973 |
| IN | 2000MA00775 | A | 9/2007 |
| WO | 9500516 | A1 | 1/1995 |
| WO | 0059449 | A2 | 10/2000 |
| WO | 03089430 | A1 | 10/2003 |
| WO | 2005037835 | A1 | 4/2005 |
| WO | 2006062465 | A1 | 6/2006 |
| WO | 2007120097 | A1 | 10/2007 |
| WO | 2007120098 | A1 | 10/2007 |
| WO | 2007142576 | A1 | 12/2007 |
| WO | 2007142577 | A1 | 12/2007 |
| WO | 2008152420 | A1 | 12/2008 |
| WO | 2009025618 | A1 | 2/2009 |
| WO | 2010068171 | A1 | 6/2010 |
| WO | 2012106343 | A2 | 8/2012 |
| WO | 2012129792 | A1 | 10/2012 |
| WO | 2013000108 | A1 | 1/2013 |
| WO | 2013000267 | A1 | 1/2013 |
| WO | 2013068875 | A1 | 5/2013 |
| WO | 2016087338 | A1 | 6/2016 |
| WO | 2016088838 | A1 | 6/2016 |
| WO | 2017209265 | A1 | 12/2017 |
| WO | 2017209267 | A1 | 12/2017 |
| WO | 2019016074 | A1 | 1/2019 |
| WO | 2020021300 | A1 | 1/2020 |
| WO | WO-2024/038131 | A1 | 2/2024 |

OTHER PUBLICATIONS

An X.N., et al., "CD206+CD68+ Mono-Macrophages and Serum Soluble CD206 Level are Increased in Antineutrophil Cytoplasmic Antibodies Associated Glomerulonephritis", BMC Immunology, vol. 23, No. 55, 2022, pp. 1-13.

Anderson A.C., "The Process of Structure-Based Drug Design," Chemistry and Biology, 2003, vol. 10, pp. 787-797.

Antonelou M., et al., "Therapeutic Myeloperoxidase Inhibition Attenuates neutrophil activation, ANCA-Mediated Endothelial Damage and Crescentic Glomerulonephritis", Jun. 13, 2019, 42 Pages.

Asselbergs F.W., et al., "Myeloperoxidase Polymorphism Related to Cardiovascular Events in Coronary Artery Disease", The American Journal of Medicine, vol. 116, Mar. 15, 2004, pp. 429-430.

Baldus S., et al., "Endothelial Transcytosis of Myeloperoxidase Confers Specificity to Vascular ECM Proteins as Targets of Tyrosine Nitration", The Journal of Clinical Investigation, vol. 108, No. 12, Dec. 2001, pp. 1759-1770.

Bjornsdottir H., et al., "Neutrophil NET Formation is Regulated from the Inside by Myeloperoxidase-Processed Reactive Oxygen Species", Free Radical Biology and Medicine, vol. 89, 2015, pp. 1024-1035.

Campbell M.J., et al., "Myeloperoxidase Inhibitor AZD5904 Enhances Human Sperm Function in Vitro", Human Reproduction, vol. 36, No. 3, 2021, pp. 560-570.

"Cardiovascular Diseases (CVDs)", World Health Organization, Jun. 11, 2021, pp. 1-6.

"Cardiovascular Diseases (CVDs)," World Health Organization, May 17, 2017, 6 Pages, https://www.who.int/news-room/fact-sheets/detail/cardiovascular-diseases-(cvds).

Chai W., et al., "Inhibiting Myeloperoxidase Prevents Onset and Reverses Established High-Fat Diet-Induced Microvascular Insulin Resistance", American Journal of Physiology, Endocrinology and Metabolism, vol. 317, 2019, pp. E1063-E1069.

Cheng D., et al., "Inhibition of MPO (Myeloperoxidase) Attenuates Endothelial Dysfunction in Mouse Models of Vascular Inflammation and Atherosclerosis", 2019, pp. 1448-1457.

Churg A., et al., "Late Intervention with a Myeloperoxidase Inhibitor Stops Progression of Experimental Chronic Obstructive Pulmonary Disease", American Journal of Respiratory and Critical Care Medicine, vol. 185, No. 1, Jan. 1, 2012, pp. 34-43.

Davies M.J., et al., "The Role of Myeloperoxidase in Biomolecule Modification, Chronic Inflammation, and Disease", Antioxidants and Redox Signaling, vol. 32, No. 13, 2020, pp. 957-981.

Dickerhof N., et al., "Myeloperoxidase Inhibition Decreases Morbidity and Oxidative Stress in Mice with Cystic Fibrosis-like Lung Inflammation", Free Radical Biology and Medicine, vol. 152, 2020, pp. 91-99.

Do Carmo R.F., et al., "Myeloperoxidase Gene Polymorphism Predicts Fibrosis Severity in Women with Hepatitis C", Human Immunology, vol. 75, 2014, pp. 766-770.

Eiserich J.P., et al., "Myeloperoxidase, A Leukocyte-Derived Vascular No. Oxidase", Science, vol. 296, 5 Pages, Jun. 28, 2002, pp. 2391-2394.

Ekerot P., et al., "Systems Pharmacology Modeling of Drug-Induced Modulation of Thyroid Hormones in Dogs and Translation to Human", Pharmaceutical Research, vol. 30, 2013, pp. 1513-1524.

Forbes L.V., et al., "Potent Reversible Inhibition of Myeloperoxidase by Aromatic Hydroxamates", The Journal of Biological Chemistry, Dec. 20, 2013, vol. 288, No. 51, pp. 36636-36647.

Freshney R.I., "Culture of Animal Cells: A Manual of Basic Technique and Specialized Application," Sixth Edition, Alan R. Liss, Inc., 2010, 5 Pages.

Fulop F., et al., "Saturated Heterocycles, 248 [1]. Synthesis of 2,4-Dioxo and 4-0xo-2-thioxo Derivatives of Octahydrocyclopenta[d]pyrimidines", Journal of Heterocyclic Chemistry, Jul.-Aug. 1997, pp. 1211-1217.

Hampton M.B., et al., "Inside the Neutrophil Phagosome: Oxidants, Myeloperoxidase, and Bacterial Killing", Blood, The Journal of The American Society of Hematology, vol. 92, No. 9, Nov. 1, 1998, pp. 3007-3017.

Hosseini M., et al., "Targeting Myeloperoxidase Disrupts Mitochondrial Redox Balance and Overcomes Cytarabine Resistance in Human Acute Myeloid Leukemia", Metabolism and Chemical Biology, 2019, pp. 5191-5203.

Imrich J., et al., "C NMR Study of 1-Substituted 2-Thioxo-4(1H,3H) Quinazolinones Employing the 1 D and 2D Methods", Chemical Papers, vol. 47, No. 2, 1993, pp. 102-105.

Inghardt T., et al., "Discovery of AZD4831, a Mechanism-Based Irreversible Inhibitor of Myeloperoxidase, As a Potential Treatment for Heart Failure with Preserved Ejection Fraction", Journal of Medicinal Chemistry, vol. 65, 2022, pp. 11485-11496.

International Preliminary Report on Patentability for International Application No. PCT/EP2015/077998, mailed Jun. 15, 2017, 8 Pages.

International Search Report and Written Opinion for International Application No. PCT/EP2015/077998, mailed Feb. 1, 2016, 9 Pages.

International Search Report and Written Opinion for International Application No. PCT/EP2023/072655, mailed Oct. 5, 2023, 12 Pages.

Klinke A., et al., "Myeloperoxidase Aggravates Pulmonary Arterial Hypertension by Activation of vascular Rho- kinase", JCI Insight, Jun. 2018, 18 pages.

Kolaczkowska E., et al., "Neutrophil Recruitment and Function in Health and Inflammation", Nature Reviews Immunology, vol. 13, Mar. 2013, pp. 159-175.

Koop A.C., et al., "Therapeutic Targeting of Myeloperoxidase Attenuates NASH in Mice", Hepatology Communications, vol. 4, No. 10, 2020, pp. 1441-1458.

Koscik D., et al. "New Synthesis of 2-amino-4-0xopyridol,2-e)-1,3-Thiazines and 1-alkyl(aryl)pyrido[3,2-e]-2-thiouracils", vol. 48, 1983, pp. 3315-3328.

(56) References Cited

OTHER PUBLICATIONS

Lau D., et al., "Myeloperoxidase Mediates Neutrophil Activation by Association with CD11b/CD18 Integrins", PNAS, vol. 102, No. 2, Jan. 11, 2005, pp. 431-436.
Makela R., et al., "Myeloperoxidase Gene Variation and Coronary Flow Reserve in Young Healthy Men", Journal of Biomedical Science, 2004, vol. 11, pp. 59-64.
Malmquist J., et al., "Imaging Agents for Myeloperoxidase," Journal of Labelled Compounds and Radiopharmaceuticals, 2012, vol. 55, pp. 393-399.
Marugan J.J., et al., "Evaluation of 2-thioxo-2,3,5,6,7,8-hexahydropyrimido[4,5-d]pyrimidin-4(1H)-one analogues as GAA Activators", European Journal of Medicinal Chemistry, vol. 45, No. 2010, pp. 1880-1897.
Miyaki M., et al., "N→N Alkyl and Glycosyl Migration of Purines and Pyrimidines, N→N Alkyl and Glycosyl Migration of Purine Derivatives", Chemical and Pharmaceutical Bulletin, vol. 18, No. 7, 1970, pp. 1446-1456.
Mollenhauer M., et al., "Myeloperoxidase Mediates Postischemic Arrhythmogenic Ventricular Remodeling", Circulation Research, Jun. 23, 2017, 30 Pages, vol. 121, No. 1, pp. 56-70.
Nahon P., et al., "A Variant in Myeloperoxidase Promoter Hastens the Emergence of Hepatocellular Carcinoma in Patients with HCV-Related Cirrhosis", Journal of Hepatology, vol. 56, 2012, pp. 426-432.
Nahon P., et al., "Myeloperoxidase and Superoxide Dismutase 2 Polymorphisms Comodulate the Risk of Hepatocellular Carcinoma and Death in Alcoholic Cirrhosis", Hepatology, vol. 50, No. 5, 2009, pp. 1484-1493.
Nauseef W.M., et al., "Biosynthesis of Human Myeloperoxidase", Archives of Biochemistry and Biophysics, Mar. 15, 2018, 22 Pages, vol. 642, pp. 1-9.
Nilsson L.B., et al., "Investigation of Absolute and Relative Response for Three Different Liquid Chromatography/Tandem Mass Spectrometry Systems, the Impact of Ionization and Detection Saturation", Rapid Communications in Mass Spectrometry, 2012, vol. 26, pp. 1399-1406.
Piedrafita F.J., et al., "An Alu Element in the Myeloperoxidase Promoter Contains a Composite SP1-Thyroid Hormone-Retinoic Acid Response Element", The Journal of Biological Chemistry, vol. 271, No. 24, Jun. 14, 1996, pp. 14412-14420.
Piek A., et al., "Pharmacological Myeloperoxidase (MPO) Inhibition in an Obese/Hypertensive Mouse Model Attenuates Obesity and Liver Damage, but not Cardiac Remodeling", Scientific Reports, vol. 9, No. 18765, 2019, 12 Pages.
Pritchard K.M., et al., "Reaction of Ph3P(SCN)2 with Further Orthohydroxy Carboxylic Acid Systems, Including Substituted β-Keto Acids: Synthesis of Novel 2-Thio-1,3-oxazines and Their Subsequent Transformation with Amines", Synthetic Communications, vol. 38, 2008, pp. 4076-4096.
Ra H.J., et al., "Control of Matrix Metalloproteinase Catalytic Activity", Matrix Biology, Oct. 2007, 17 Pages, vol. 26, No. 8, pp. 587-596.
Ramachandra C.J.A., et al., "Inhibiting Cardiac Myeloperoxidase Alleviates the Relaxation Defect in Hypertrophic Cardiomyocytes", Cardiovascular Research, vol. 118, 2022, pp. 517-530.
Rashid I., et al., "Myeloperoxidase is a Potential Molecular Imaging and Therapeutic Target for the Identification and Stabilization of high-risk Atherosclerotic Plaque", European Heart Journal, vol. 39, 2018, pp. 3301-3310.
Rudolph V., et al., "A Myeloperoxidase Promoter Polymorphism is Independently Associated with Mortality in Patients with Impaired Left Ventricular Function", Free Radical Biology and Medicine, vol. 47, 2009, pp. 1584-1590.
Singh H., et al., "Thiopegan Derivatives Part XXXI: Unambiguous Synthesis of 2-Substituted-9, 10-thiopegan Derivatives", Journal of the Indian Chemical Society, vol. 41, No. 12, 1964, pp. 855-856.
Sinha S.K.P., et al., "Quinazolones: Part XIII—A New Approach to the Synthesis of Some Oxazolo- and Thiazolo-quinazolones", Indian Journal of Chemistry, vol. 28B, Mar. 1989, pp. 274-276.
Sirota J.C., et al., "Elevated Serum Uric Acid Levels Are Associated With Non-Alcoholic Fatty Liver Disease Independently of Metabolic Syndrome Features in the United States: Liver Ultrasound Data from the National Health and Nutrition Examination Survey", Metabolism, 2013, 15 Pages, vol. 62, No. 3, pp. 392-399, Doi: 10.1016/j.metabol.2012.08.013.
Stamp L.K., et al., "Myeloperoxidase and Oxidation of Uric Acid in Gout: Implications for the Clinical Consequences of Hyperuricaemia", Rheumatology, vol. 53, 2014, pp. 1958-1965.
Tang N., et al., "Myeloperoxidase G-463A Polymorphism and Susceptibility to Coronary Artery Disease: A Meta-Analysis", Gene, vol. 523, 2013, pp. 152-157.
Tannergren C., et al., "Physiologically Based Biopharmaceutics Modeling of Regional and Colon Absorption in Humans", European Journal of Pharmaceutics and Biopharmaceutics, vol. 186, 2023, pp. 144-159.
Therkelsen F.D., et al., "Multiple Pathways in the Synthesis of New Annelated Analogues of 6-benzyl-1-(ethoxymethyl)-5-isopropyluracil (emivirine)", Organic and Biomolecular Chemistry, vol. 1, 2003, pp. 2908-2918.
Thiel K.A., "Structure-Aided Drug Design'S Next Generation," Nature Biotechnology, May 2004, vol. 22, No. 5, pp. 513-519.
Tiden A-K., et al., "2-Thioxanthines are Mechanism-Based Inactivators of Myeloperoxidase That Block Oxidative Stress During Inflammation," The Journal of Biological Chemistry, Oct. 28, 2011, vol. 286, No. 43, pp. 37578-37589.
Van Schooten F.J., et al., "Myeloperoxidase (MPO)-463G→A Reduces MPO Activity and DNA Adduct Levels in Bronchoalveolar Lavages of Smokers", Cancer Epidemiology Biomarkers, vol. 13, No. 5, 16 Pages, 2004, pp. 828-833.
Wang K., et al., "Design and Synthesis of Imidazole and Triazole Derivatives as Lp-PLA2 Inhibitors and the Unexpected Discovery of Highly Potent Quaternary Ammonium Salts", Bioorganic and Medicinal Chemistry Letters, vol. 23, 2013, pp. 1187-1192.
Wang K., et al., "Triazole Derivatives: A Series of Darapladib Analogues as Orally Active Lp-PLA2 Inhibitors", Bioorganic and Medicinal Chemistry Letters, vol. 23, No. 10, May 15, 2013, pp. 2897-2901.
WOO P.W.K., et al., "Inhibitors of Human Purine Nucleoside Phosphorylase Synthesis and Biological Activities of 8-Amino-3-benzylhypoxanthine and Related Analogues", Journal of Medicinal Chemistry, vol. 35, No. 8, 1992, pp. 1451-1457.

* cited by examiner

INHIBITORS OF MYELOPEROXIDASE

RELATED APPLICATIONS

The application claims the benefit of priority to U.S. application No. 63/398,939, filed on Aug. 18, 2022, which is incorporated herein by reference in its entirety.

BACKGROUND

Myeloperoxidase (MPO) is a heme-containing enzyme primarily expressed in neutrophilic granulocytes (neutrophils). MPO is one member of a diverse protein family of mammalian peroxidases that also includes eosinophil peroxidase (EPX), lactoperoxidase (LPO), thyroid peroxidase (TPO) and others. MPO is activated by hydrogen peroxide, the source of which can be superoxide dismutase (SOD)-catalyzed NADPH-derived superoxide anion and xanthine oxidase-derived superoxide anion and hydrogen peroxide formed upon purine oxidation. MPO catalyzes two electron oxidation of halides (primarily chloride) and pseudohalides (like thiocyanate), forming the microbicidal hypohalous acids hypochlorous acid (bleach) and hypothiocyanous acid. These can, in turn, act on a broad number of protein, lipid and nucleic acid targets, causing dysfunction and further inflammation[1]. In addition, MPO catalyzes one electron oxidation of numerous electron-rich substrates through the so-called peroxidation cycle, yielding free radicals that are harmful in themselves (e.g. urate radicals[2]) or that may interfere with physiological functions driven by nitric oxide (NO), either by direct oxidation of NO, or by generation of free radicals oxidizing NO[1].

By numbers, neutrophils are the dominating leukocyte population (50-70% of blood leukocytes in humans), representing a highly dynamic cellular population that is part of the first line defense towards stressors, be it microbial or sterile triggers. Within neutrophils, preformed MPO is stored at millimolar concentration in granules, which fuse with phagosomes containing the engulfed microbial prey, causing activation of MPO and killing of the microbe[3]. In addition, MPO can also be released to the outside of the cells where the oxidative activity may cause damage to adjacent tissue and dysfunction or modulation of biochemical and cellular processes, such as tissue remodeling and fibrosis. The release can either occur as a result of degranulation or NETosis, in which webs of decondensed DNA dressed with intracellular proteins such as MPO, so called neutrophil extracellular traps (NETs), are released[4]. In addition, MPO is also released constitutively[5]. The enzyme is highly cationic and is therefore trapped at negatively charged structures extracellularly, such as proteoglycans in the vascular wall and on extracellular matrix in the interstitium[6].

Given the dominance of neutrophils in inflammatory biology and the abundance of MPO in neutrophils (estimated to 5% of the dry weight of the cells), it is not surprising that a plethora of disease conditions is postulated to be associated with a pathological role of myeloperoxidase. These conditions encompass not only “traditional” inflammatory diseases, such as inflammatory bowel disease and the autoimmune diseases rheumatoid arthritis and systemic lupus erythematosus, but also other common diseases in which inflammation is emerging as an important pathophysiological component e.g. cardiovascular disease, neurodegenerative disease, kidney disease, respiratory disease, metabolic disease, obesity, and cancer[1].

A pathophysiological role of MPO is further supported by human genetic studies and rodent interventional studies. In humans, a common polymorphism in the MPO-promotor that regulates transcription[7] and tissue MPO activity[8], have been shown to be associated with coronary microvascular dysfunction[9], mortality in heart failure[10], risk for coronary artery disease[11] as well as outcomes thereof[12], risk of developing hepatitis C-associated liver fibrosis and cirrhosis[13,14] and risk of hepatocellular carcinoma and death in alcohol-associated liver-cirrhosis[15]. In rodent in vivo and in human in vitro experiments, efficacy using selective MPO-inhibitors have been reported for several diseases and/or conditions: preservation of cardiac function in post-myocardial infarction models[16], stabilization of atherosclerotic plaques[17], amelioration of pulmonary artery hypertension 18, glomerulonephritis[19] and cystic fibrosis[20], reduction of liver steatosis and fibrosis[21,22], attenuation of vascular dysfunction in conditions of inflammatory vascular dysfunction[23], normalization of microvascular function[24], improvement of relaxation in human cardiomyocytes[25], and inhibition of NETosis in human neutrophils[26].

How MPO contributes to the different disease conditions may vary depending on condition, although some mechanisms may be of importance in several of these conditions. In addition to damage and dysfunction caused by MPO-derived reactive oxygen species such as hypochlorous acid[1], MPO also appears to play a regulatory role in inflammation that serves to amplify the inflammatory response by activation of neutrophils[27] and via activation of proteinases that cleave latent forms into active effector proteins, e.g. cytokines[28]. The mechanistic association between MPO and fibrosis is possibly also multifactorial, e.g. i) secondary to increased inflammation ii) by activation of myofibroblasts[29] and iii) by increasing collagen secretion per se[30]. Finally, active MPO oxidizes NO directly (as well as indirectly) via the peroxidation cycle and thereby impairs mechanisms driven by nitric oxide, such as smooth muscle cell relaxation[31]. This latter mechanism is likely to be of particular importance for the association between MPO and microvascular dysfunction and the resulting impaired blood supply to the tissues, as MPO is trapped on proteoglycans and transcytosed by endothelial cells and spatially deposited in the subendothelial compartment between the NO-producing endothelium and the NO-receiving smooth muscles[32].

Taken together, there is medical need as well as a good rationale for an orally active inhibitor of MPO for the treatment of chronic inflammatory conditions. In order to increase the therapeutic index of such a medication, it is necessary to obtain an MPO inhibitor being selective for MPO over TPO. The thyroid gland is an important regulator of thermogenic and metabolic functions, and TPO plays a central role by iodination of tyrosine residues, forming the thyroid hormones T4 and T3. TPO activation is under the control of thyroid stimulating hormone, and T4 and T3 are part of a negative feedback mechanism, thus resulting in compensatory increased thyroid stimulating hormone as a result of decreased levels of T3 and T4 upon TPO inhibition[33].

WO2003/089430, WO2005/037835, WO2007/120097, WO2007/120098 and WO2007/142576 disclose thioxantine derivatives and the use thereof as MPO inhibitors in therapy.

WO2006/062465 and WO2007/142577 disclose 2-thioxo-1,2,3,4-tetrahydro-pyrrolo[3,2-d]pyrimidin-4-one derivatives claimed to be inhibitors of MPO. It is stated that the compounds may show selectivity against related enzymes such as TPO.

WO2009/025618 discloses thioxantine and 2-thioxo-1,2,3,4-tetrahydro-pyrrolo[3,2-d]pyrimidin-4-one derivatives and the use of MPO inhibitors for the treatment of multiple system atrophy (MSA) and Huntington's disease (HD) and for neuroprotection.

J. Labelled Compounds and Radiopharmaceuticals, 2012, 55, 393-399, discloses some tritiated, 13C and 14C labeled thioxantine derivatives as well as a 14C labeled pyrrolo[3,2-d]pyrimidin-4-one compound. The compounds are stated to be inactivators of MPO.

J. Biol. Chem., 2011, 286, 37578-37589, discloses certain thioxantine derivatives. The compounds are stated to inhibit MPO in plasma and decrease protein chlorination in a mouse model. The compounds are also claimed to be poor inhibitors of TPO.

WO2013/068875 discloses thiopyrimidone derivatives claimed to be MPO inhibitors.

WO2016/087338 discloses thioxopyrrolopyrimidone derivatives stated to be MPO inhibitors.

Therefore, there is a need for novel MPO inhibitors useful in therapy. There is also a need for novel MPO inhibitors having improved selectivity for the MPO enzyme over the TPO enzyme, as well as MPO inhibitors having suitable pharmacological properties.

DETAILED DESCRIPTION

This detailed description and its specific examples, while indicating embodiments, are intended for purposes of illustration only. Therefore, there is no limitation to the illustrative embodiments described in this specification. In addition, it is to be appreciated that various features that are, for clarity reasons, described in the context of separate embodiments, also may be combined to form a single embodiment. Conversely, various features that are, for brevity reasons, described in the context of a single embodiment, also may be combined to form sub-combinations thereof.

Listed below are definitions of various terms used in the specification and claims.

The term "halo" means fluoro, chloro, bromo, and iodo. In an embodiment, halo is fluoro or chloro.

The term "N-heterocycle" refers to a partially or completely saturated hydrocarbon ring system, i.e., non-aromatic, wherein at least one of the ring carbon atoms is replaced with a nitrogen.

For the avoidance of doubt it is to be understood that where in this specification a group is qualified by "defined above" the said group encompasses the first occurring and broadest definition as well as each and all of the other definitions for that group. It is to be understood that any of definitions, claims, aspects or embodiments of the variable groups of the formulae disclosed herein, may be combined with any other definitions, claims, aspects or embodiments herein (unless the context does not permit) to provide further embodiments of the specification.

Certain embodiments disclosed herein provide compounds, compositions, and methods for inhibiting myeloperoxidase, as well as methods for treating myeloperoxidase related diseases or conditions.

Compounds

One embodiment disclosed herein provides a compound of formula (I)

(I)

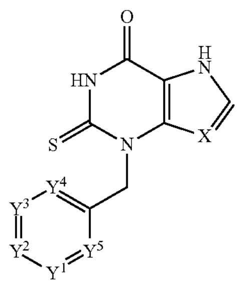

wherein

X=CH or N $Y^1$=$CZ^1$ or N, $Y^2$=$CZ^2$ or N, $Y^3$=$CZ^3$ or N, $Y^4$=$CZ^4$ or N, and $Y^5$=$CZ^5$ or N $Z^1$, $Z^2$, $Z^3$, $Z^4$, and $Z^5$, are, if present, independently, H, halo, $CF_3$, Q or T, provided that no more than one of $Y^1$, $Y^2$, $Y^3$, $Y^4$, or $Y^5$ is N, at least two of $Y^1$, $Y^2$, $Y^3$, $Y^4$ or $Y^5$ are CH, no more than one of $Z^1$, $Z^2$, $Z^3$, $Z^4$, and $Z^5$ is halo or $CF_3$, and one, and only one, of $Z^1$, $Z^2$, $Z^3$, $Z^4$, and $Z^5$ is Q or T, Q is

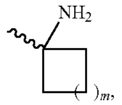

wherein m is 0, 1, 2, or 3,

T is

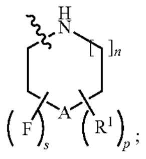

p is 0 or 1, s is 0, 1 or 2, n is 0, 1 or 2,

A is $CH_2$, $CF_2$, CHF, $CHR^2$, $CFR^2$, $NR^3$, or O, wherein;

$R^1$ and $R^2$, if present, are independently $CH_2F$, $CHF_2$, or $CF_3$ $R^3$, if present, is independently H or $CH_3$, or any stereoisomer thereof or pharmaceutically acceptable salt thereof.

In one embodiment a compound of any of formula (I) is provided.

In one embodiment a pharmaceutically acceptable salt of a compound of any of formula (I) is provided.

Another embodiment disclosed herein provides a compound having the structure:

(II)

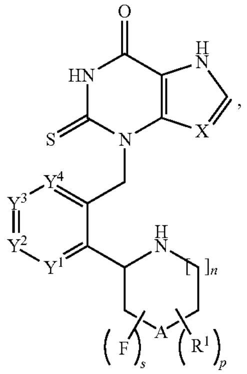

or any stereoisomer thereof or pharmaceutically acceptable salt thereof, wherein X, $Y^1$, $Y^2$, $Y^3$, $Y^4$, A, $R^1$, n, p, and s, are defined as above for formula (I).

Yet another embodiment disclosed herein provides a compound:

(III)

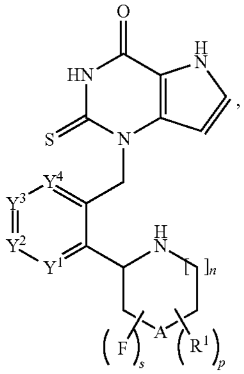

or any stereoisomer thereof or pharmaceutically acceptable salt thereof, wherein X, $Y^1$, $Y^2$, $Y^3$, $Y^4$, A, $R^1$, n, p, and s, are defined as above for formula (I).

Some embodiments disclosed herein provide a compound having the structure:

(IV)

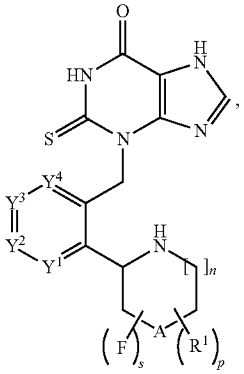

or any stereoisomer thereof or pharmaceutically acceptable salt thereof, wherein X, $Y^1$, $Y^2$, $Y^3$, $Y^4$, A, $R^1$, n, p, and s, are defined as above for formula (I).

Some embodiments disclosed herein provide a compound of formula (I), formula (II), or formula (III), or any stereoisomer thereof or pharmaceutically acceptable salt thereof, wherein $Y^1$ is N and $Y^2$, $Y^3$, are $Y^4$ are CH.

Some embodiments disclosed herein provide a compound of formula (I), formula (II), formula (III), or formula (IV), or any stereoisomer thereof or pharmaceutically acceptable salt thereof, wherein $Y^1$ is N and $Y^2$, $Y^3$, are $Y^4$ are CH.

Some embodiments disclosed herein provide a compound of formula (I), formula (II), or formula (III), or any stereoisomer thereof or pharmaceutically acceptable salt thereof, wherein $Y^2$ is N and $Y^1$, $Y^3$, are $Y^4$ are CH.

Some embodiments disclosed herein provide a compound of formula (I), formula (II), formula (III), or formula (IV), or any stereoisomer thereof or pharmaceutically acceptable salt thereof, wherein $Y^2$ is N and $Y^1$, $Y^3$, are $Y^4$ are CH.

Some embodiments disclosed herein provide a compound of formula (I), formula (II), or formula (III), or any stereoisomer thereof or pharmaceutically acceptable salt thereof, wherein $Y^3$ is N and $Y^1$, $Y^2$, are $Y^4$ are CH.

Some embodiments disclosed herein provide a compound of formula (I), formula (II), formula (III), or formula (IV) or any stereoisomer thereof or pharmaceutically acceptable salt thereof, wherein $Y^3$ is N and $Y^1$, $Y^2$, are $Y^4$ are CH.

Some embodiments disclosed herein provide a compound of formula (I), formula (II), or formula (III), or any stereoisomer thereof or pharmaceutically acceptable salt thereof, wherein $Y^4$ is N and $Y^1$, $Y^2$, are $Y^3$ are CH.

Some embodiments disclosed herein provide a compound of formula (I), formula (II), formula (III), or formula (IV), or any stereoisomer thereof or pharmaceutically acceptable salt thereof, wherein $Y^4$ is N and $Y^1$, $Y^2$, are $Y^3$ are CH.

Some embodiments disclosed herein provide a compound of formula (I), formula (II), or formula (III), or any stereoisomer thereof or pharmaceutically acceptable salt thereof, wherein n is 0.

Some embodiments disclosed herein provide a compound of formula (I), formula (II), formula (III), or formula (IV), or any stereoisomer thereof or pharmaceutically acceptable salt thereof, wherein n is 0.

Some embodiments disclosed herein provide a compound of formula (I), formula (II), or formula (III), or any stereoisomer thereof or pharmaceutically acceptable salt thereof, wherein n is 1.

Some embodiments disclosed herein provide a compound of formula (I), formula (II), formula (III), or formula (IV), or any stereoisomer thereof or pharmaceutically acceptable salt thereof, wherein n is 1.

Some embodiments disclosed herein provide a compound of formula (I), formula (II), or formula (III), or any stereoisomer thereof or pharmaceutically acceptable salt thereof, wherein n is 2.

Some embodiments disclosed herein provide a compound of formula (I), formula (II), formula (III), or formula (IV), or any stereoisomer thereof or pharmaceutically acceptable salt thereof, wherein n is 2.

Some embodiments disclosed herein provide a compound of formula (I), formula (II), or formula (III), or any stereoisomer thereof or pharmaceutically acceptable salt thereof, wherein A is $NR^3$.

Some embodiments disclosed herein provide a compound of formula (I), formula (II), formula (III), or formula (IV), or any stereoisomer thereof or pharmaceutically acceptable salt thereof, wherein A is $NR^3$.

Some embodiments disclosed herein provide a compound of formula (I), formula (II), or formula (III), or any stereoisomer thereof or pharmaceutically acceptable salt thereof, wherein A is $NR^3$ and $R^3$ is $CH_3$.

Some embodiments disclosed herein provide a compound of formula (I), formula (II), formula (III), or formula (IV), or any stereoisomer thereof or pharmaceutically acceptable salt thereof, wherein A is $NR^3$ and $R^3$ is $CH_3$.

Some embodiments disclosed herein provide a compound of formula (I), formula (II), or formula (III), or any stereoisomer thereof or pharmaceutically acceptable salt thereof, wherein A is $NR^3$ and $R^3$ is H.

Some embodiments disclosed herein provide a compound of formula (I), formula (II), formula (III), or formula (IV), or any stereoisomer thereof or pharmaceutically acceptable salt thereof, wherein A is $NR^3$ and $R^3$ is H.

Some embodiments disclosed herein provide a compound of formula (I), formula (II), or formula (III), or any stereoisomer thereof or pharmaceutically acceptable salt thereof, wherein A is $CH_2$, $CF_2$, CHF, $CHR^2$, or $CFR^2$.

Some embodiments disclosed herein provide a compound of formula (I), formula (II), formula (III), or formula (IV), or any stereoisomer thereof or pharmaceutically acceptable salt thereof, wherein A is $CH_2$, $CF_2$, CHF, $CHR^2$, or $CFR^2$.

Some embodiments disclosed herein provide a compound of formula (I), formula (II), or formula (III), or any stereoisomer thereof or pharmaceutically acceptable salt thereof, wherein A is $CH_2$.

Some embodiments disclosed herein provide a compound of formula (I), formula (II), formula (III), or formula (IV), or any stereoisomer thereof or pharmaceutically acceptable salt thereof, wherein A is $CH_2$.

Some embodiments disclosed herein provide a compound of formula (I), formula (II), or formula (III), or any stereoisomer thereof or pharmaceutically acceptable salt thereof, wherein A is CHF.

Some embodiments disclosed herein provide a compound of formula (I), formula (II), formula (III), or formula (IV), or any stereoisomer thereof or pharmaceutically acceptable salt thereof, wherein A is CHF.

Some embodiments disclosed herein provide a compound of formula (I), formula (II), or formula (III), or any stereoisomer thereof or pharmaceutically acceptable salt thereof, wherein A is $CF_2$.

Some embodiments disclosed herein provide a compound of formula (I), formula (II), formula (III), or formula (IV), or any stereoisomer thereof or pharmaceutically acceptable salt thereof, wherein A is $CF_2$.

Some embodiments disclosed herein provide a compound of formula (I), formula (II), or formula (III), or any stereoisomer thereof or pharmaceutically acceptable salt thereof, wherein A is $CHR^2$.

Some embodiments disclosed herein provide a compound of formula (I), formula (II), formula (III), or formula (IV), or any stereoisomer thereof or pharmaceutically acceptable salt thereof, wherein A is $CHR^2$.

Some embodiments disclosed herein provide a compound of formula (I), formula (II), or formula (III), or any stereoisomer thereof or pharmaceutically acceptable salt thereof, wherein A is $CHR^2$ and $R^2$ is $CH_2F$.

Some embodiments disclosed herein provide a compound of formula (I), formula (II), formula (III), or formula (IV), or any stereoisomer thereof or pharmaceutically acceptable salt thereof, wherein A is $CHR^2$ and $R^2$ is $CH_2F$.

Some embodiments disclosed herein provide a compound of formula (I), formula (II), or formula (III), or any stereoisomer thereof or pharmaceutically acceptable salt thereof, wherein A is $CHR^2$ and $R^2$ is $CHF_2$.

Some embodiments disclosed herein provide a compound of formula (I), formula (II), formula (III), or formula (IV), or any stereoisomer thereof or pharmaceutically acceptable salt thereof, wherein A is $CHR^2$ and $R^2$ is $CHF_2$.

Some embodiments disclosed herein provide a compound of formula (I), formula (II), or formula (III), or any stereoisomer thereof or pharmaceutically acceptable salt thereof, wherein A is $CHR^2$ and $R^2$ is $CF_3$.

Some embodiments disclosed herein provide a compound of formula (I), formula (II), formula (III), or formula (IV), or any stereoisomer thereof or pharmaceutically acceptable salt thereof, wherein A is $CHR^2$ and $R^2$ is $CF_3$.

Some embodiments disclosed herein provide a compound of formula (I), formula (II), or formula (III), or any stereoisomer thereof or pharmaceutically acceptable salt thereof, wherein s is 0.

Some embodiments disclosed herein provide a compound of formula (I), formula (II), formula (III), or formula (IV), or any stereoisomer thereof or pharmaceutically acceptable salt thereof, wherein s is 0.

Some embodiments disclosed herein provide a compound of formula (I), formula (II), or formula (III), or any stereoisomer thereof or pharmaceutically acceptable salt thereof, wherein s is 1.

Some embodiments disclosed herein provide a compound of formula (I), formula (II), formula (III), or formula (IV), or any stereoisomer thereof or pharmaceutically acceptable salt thereof, wherein s is 1.

Some embodiments disclosed herein provide a compound of formula (I), formula (II), or formula (III), or any stereoisomer thereof or pharmaceutically acceptable salt thereof, wherein s is 2.

Some embodiments disclosed herein provide a compound of formula (I), formula (II), formula (III), or formula (IV), or any stereoisomer thereof or pharmaceutically acceptable salt thereof, wherein s is 2.

Some embodiments disclosed herein provide a compound of formula (I), formula (II), or formula (III), or any stereoisomer thereof or pharmaceutically acceptable salt thereof, wherein p is 0.

Some embodiments disclosed herein provide a compound of formula (I), formula (II), formula (III), or formula (IV), or any stereoisomer thereof or pharmaceutically acceptable salt thereof, wherein p is 0.

Some embodiments disclosed herein provide a compound of formula (I), formula (II), or formula (III), or any stereoisomer thereof or pharmaceutically acceptable salt thereof, wherein p is 1.

Some embodiments disclosed herein provide a compound of formula (I), formula (II), formula (III), or formula (IV), or any stereoisomer thereof or pharmaceutically acceptable salt thereof, wherein p is 1.

Some embodiments disclosed herein provide a compound of formula (I), or any stereoisomer thereof or pharmaceutically acceptable salt thereof, wherein $Y^5$ is $CZ^5$, and $Z^5$ is T or Q.

Some embodiments disclosed herein provide a compound of formula (I), or any stereoisomer thereof or pharmaceutically acceptable salt thereof, wherein $Y^5$ is $CZ^5$, and $Z^5$ is T.

Some embodiments disclosed herein provide a compound of formula (I), or any stereoisomer thereof or pharmaceutically acceptable salt thereof, wherein $Y^5$ is $CZ^5$, and $Z^5$ is T and T is

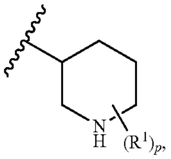, 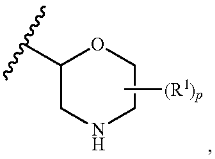, or

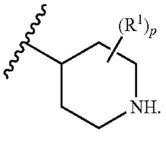

In further embodiments, p is 0.

Some embodiments disclosed herein provide a compound of formula (I), or any stereoisomer thereof or pharmaceutically acceptable salt thereof, wherein $Y^5$ is $CZ^5$, $Z^5$ is T or Q, and $Y^1$, $Y^2$, $Y^3$ and $Y^4$ are CH. In further embodiments $Z^5$ is T. In still further embodiments, T is

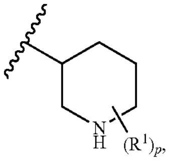, 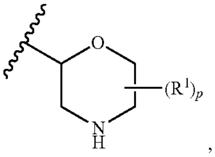, or

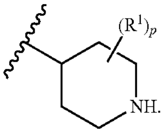

In yet further embodiments, p is 0.

Some embodiments disclosed herein provide a compound of formula (I), or any stereoisomer thereof or pharmaceutically acceptable salt thereof, wherein $Y^5$ is $CZ^5$, $Z^5$ is T or Q, and one of $Y^1$, $Y^2$, $Y^3$ and $Y^4$ is N.

Some embodiments disclosed herein provide a compound of formula (I), or any stereoisomer thereof or pharmaceutically acceptable salt thereof, wherein $Y^5$ is $CZ^5$, $Z^5$ is T or Q, and two of $Y^1$, $Y^2$, $Y^3$ and $Y^4$ are CH, one of $Y^1$, $Y^2$, $Y^3$ and $Y^4$ is N, and one of $Y^1$, $Y^2$, $Y^3$ and $Y^4$ is CCl.

Some embodiments disclosed herein provide a compound of formula (I), or any stereoisomer thereof or pharmaceutically acceptable salt thereof, wherein $Z^1$ and $Z^5$, together with the atoms they are bound to, form a five- or six-membered N-heterocycle. In further embodiments, $Y^2$, $Y^3$, and $Y^4$ are CH.

Some embodiments disclosed herein provide a compound of formula (I), or any stereoisomer thereof or pharmaceutically acceptable salt thereof wherein $Z^2$ and $Z^3$, together with the atoms they are bound to, form a five- or six-membered N-heterocycle. In further embodiments, $Y^1$, $Y^4$, and $Y^5$ are CH.

Some embodiments disclosed herein provide a compound of formula (I), or any stereoisomer thereof or pharmaceutically acceptable salt thereof wherein $Y^2$ is Q. In further embodiments, m=1.

Some embodiments disclosed herein provide a compound of formula (I), or any stereoisomer thereof or pharmaceutically acceptable salt thereof wherein $Y^3$ is Q. In further embodiments, m=1.

Some embodiments disclosed herein provide a compound of formula (I), or any stereoisomer thereof or pharmaceutically acceptable salt thereof wherein $Y^4$ is Q. In further embodiments, m=1.

Some embodiments disclosed herein provide a compound of formula (I), or any stereoisomer thereof or pharmaceutically acceptable salt thereof wherein X is CH.

Some embodiments disclosed herein provide a compound of formula (I), or any stereoisomer thereof or pharmaceutically acceptable salt thereof wherein X is N.

Some embodiments disclosed herein provide, or any stereoisomer thereof or pharmaceutically acceptable salt thereof, of a compound selected from:

1-(2-(Piperidin-2-yl)benzyl)-2-thioxo-1,2,3,5-tetrahydro-4H-pyrrolo[3,2-d]pyrimidin-4-one,
(R)-1-(2-(piperidin-2-yl)benzyl)-2-thioxo-1,2,3,5-tetrahydro-4H-pyrrolo[3,2-d]pyrimidin-4-one,
(S)-1-(2-(piperidin-2-yl)benzyl)-2-thioxo-1,2,3,5-tetrahydro-4H-pyrrolo[3,2-d]pyrimidin-4-one,
1-(4-Chloro-2-(piperidin-2-yl)benzyl)-2-thioxo-1,2,3,5-tetrahydro-4H-pyrrolo[3,2-d]pyrimidin-4-one,
(R)-1-(4-Chloro-2-(piperidin-2-yl)benzyl)-2-thioxo-1,2,3,5-tetrahydro-4H-pyrrolo[3,2-d]pyrimidin-4-one,
(S)-1-(4-Chloro-2-(piperidin-2-yl)benzyl)-2-thioxo-1,2,3,5-tetrahydro-4H-pyrrolo[3,2-d]pyrimidin-4-one,
1-(4-Chloro-2-(pyrrolidin-2-yl)benzyl)-2-thioxo-1,2,3,5-tetrahydro-4H-pyrrolo[3,2-d]pyrimidin-4-one,
(R)-1-(4-Chloro-2-(pyrrolidin-2-yl)benzyl)-2-thioxo-1,2,3,5-tetrahydro-4H-pyrrolo[3,2-d]pyrimidin-4-one,
(S)-1-(4-Chloro-2-(pyrrolidin-2-yl)benzyl)-2-thioxo-1,2,3,5-tetrahydro-4H-pyrrolo[3,2-d]pyrimidin-4-one,
1-(4-Chloro-2-(morpholin-3-yl)benzyl)-2-thioxo-1,2,3,5-tetrahydro-4H-pyrrolo[3,2-d]pyrimidin-4-one,
(R)-1-(4-Chloro-2-(morpholin-3-yl)benzyl)-2-thioxo-1,2,3,5-tetrahydro-4H-pyrrolo[3,2-d]pyrimidin-4-one,
(S)-1-(4-chloro-2-(morpholin-3-yl)benzyl)-2-thioxo-1,2,3,5-tetrahydro-4H-pyrrolo[3,2-d]pyrimidin-4-one,
3-(4-Chloro-2-(morpholin-3-yl)benzyl)-2-thioxo-1,2,3,7-tetrahydro-6H-purin-6-one,
1-(2-(Azepan-2-yl)benzyl)-2-thioxo-1,2,3,5-tetrahydro-4H-pyrrolo[3,2-d]pyrimidin-4-one,
(R)-1-(2-(Azepan-2-yl)benzyl)-2-thioxo-1,2,3,5-tetrahydro-4H-pyrrolo[3,2-d]pyrimidin-4-one,
(S)-1-(2-(Azepan-2-yl)benzyl)-2-thioxo-1,2,3,5-tetrahydro-4H-pyrrolo[3,2-d]pyrimidin-4-one,
(R)-3-(2-(Azepan-2-yl)-4-chlorobenzyl)-2-thioxo-1,2,3,7-tetrahydro-6H-purin-6-one,
(S)-3-(2-(Azepan-2-yl)-4-chlorobenzyl)-2-thioxo-1,2,3,7-tetrahydro-6H-purin-6-one,
(R)-1-(2-(Morpholin-3-yl)benzyl)-2-thioxo-1,2,3,5-tetrahydro-4H-pyrrolo[3,2-d]pyrimidin-4-one,
(S)-1-(2-(Morpholin-3-yl)benzyl)-2-thioxo-1,2,3,5-tetrahydro-4H-pyrrolo[3,2-d]pyrimidin-4-one
1-(2-(4-Methylpiperazin-2-yl)benzyl)-2-thioxo-1,2,3,5-tetrahydro-4H-pyrrolo[3,2-d]pyrimidin-4-one,
rac-2-Thioxo-1-(2-((2R,4S)-4-(trifluoromethyl)piperidin-2-yl)benzyl)-1,2,3,5-tetrahydro-4H-pyrrolo[3,2-d]pyrimidin-4-one,
2-Thioxo-1-(2-((2R,4S)-4-(trifluoromethyl)piperidin-2-yl)benzyl)-1,2,3,5-tetrahydro-4H-pyrrolo[3,2-d]pyrimidin-4-one,
2-Thioxo-1-(2-((2S,4R)-4-(trifluoromethyl)piperidin-2-yl)benzyl)-1,2,3,5-tetrahydro-4H-pyrrolo[3,2-d]pyrimidin-4-one,
2-Thioxo-1-(2-(5-(trifluoromethyl)piperidin-2-yl)benzyl)-1,2,3,5-tetrahydro-4H-pyrrolo[3,2-d]pyrimidin-4-one,
1-(2-(4,4-Difluoropiperidin-2-yl)benzyl)-2-thioxo-1,2,3,5-tetrahydro-4H-pyrrolo[3,2-d]pyrimidin-4-one,
(R)-1-(2-(4,4-Difluoropiperidin-2-yl)benzyl)-2-thioxo-1,2,3,5-tetrahydro-4H-pyrrolo[3,2-d]pyrimidin-4-one, (S)-1-(2-(4,4-Difluoropiperidin-2-yl)benzyl)-2-thioxo-1,2,3,5-tetrahydro-4H-pyrrolo[3,2-d]pyrimidin-4-one,
rac-2-Thioxo-3-(2-((2R,4S)-4-(trifluoromethyl)piperidin-2-yl)benzyl)-1,2,3,7-tetrahydro-6H-purin-6-one,
2-Thioxo-3-(2-((2R,4S)-4-(trifluoromethyl)piperidin-2-yl)benzyl)-1,2,3,7-tetrahydro-6H-purin-6-one,
2-Thioxo-3-(2-((2S,4R)-4-(trifluoromethyl)piperidin-2-yl)benzyl)-1,2,3,7-tetrahydro-6H-purin-6-one,
3-(2-(4,4-Difluoropiperidin-2-yl)benzyl)-2-thioxo-1,2,3,7-tetrahydro-6H-purin-6-one,
3-(2-(5-Fluoropiperidin-2-yl)benzyl)-2-thioxo-1,2,3,7-tetrahydro-6H-purin-6-one,
2-Thioxo-1-((2-(−4-(trifluoromethyl)piperidin-2-yl)pyridin-3-yl)methyl)-1,2,3,5-tetrahydro-4H-pyrrolo[3,2-d]pyrimidin-4-one,
rac-2-Thioxo-1-((2-((2R,4S)-4-(trifluoromethyl)piperidin-2-yl)pyridin-3-yl)methyl)-1,2,3,5-tetrahydro-4H-pyrrolo[3,2-d]pyrimidin-4-one,
2-Thioxo-1-((2-((cis)-4-(trifluoromethyl)piperidin-2-yl)pyridin-3-yl)methyl)-1,2,3,5-tetrahydro-4H-pyrrolo[3,2-d]pyrimidin-4-one,
2-Thioxo-1-((2-((2R,4S)-4-(trifluoromethyl)piperidin-2-yl)pyridin-3-yl)methyl)-1,2,3,5-tetrahydro-4H-pyrrolo[3,2-d]pyrimidin-4-one,
2-Thioxo-1-((2-((2S,4R)-4-(trifluoromethyl)piperidin-2-yl)pyridin-3-yl)methyl)-1,2,3,5-tetrahydro-4H-pyrrolo[3,2-d]pyrimidin-4-one,
rac-2-Thioxo-1-(2-((2R,4R)-4-(trifluoromethyl)piperidin-2-yl)benzyl)-1,2,3,5-tetrahydro-4H-pyrrolo[3,2-d]pyrimidin-4-one,
2-Thioxo-1-(2-((trans)-4-(trifluoromethyl)piperidin-2-yl)benzyl)-1,2,3,5-tetrahydro-4H-pyrrolo[3,2-d]pyrimidin-4-one,
2-Thioxo-1-(2-((2R,4R)-4-(trifluoromethyl)piperidin-2-yl)benzyl)-1,2,3,5-tetrahydro-4H-pyrrolo[3,2-d]pyrimidin-4-one,
2-Thioxo-1-(2-((2S,4S)-4-(trifluoromethyl)piperidin-2-yl)benzyl)-1,2,3,5-tetrahydro-4H-pyrrolo[3,2-d]pyrimidin-4-one,
rac-2-thioxo-3-(2-((2R,4R)-4-(trifluoromethyl)piperidin-2-yl)benzyl)-1,2,3,7-tetrahydro-6H-purin-6-one,
2-thioxo-3-(2-((trans)-4-(trifluoromethyl)piperidin-2-yl)benzyl)-1,2,3,7-tetrahydro-6H-purin-6-one,
2-Thioxo-3-(2-((2R,4R)-4-(trifluoromethyl)piperidin-2-yl)benzyl)-1,2,3,7-tetrahydro-6H-purin-6-one,
2-Thioxo-3-(2-((2S,4S)-4-(trifluoromethyl)piperidin-2-yl)benzyl)-1,2,3,7-tetrahydro-6H-purin-6-one,
rac-1-(2-((2R,4S)-4-(Difluoromethyl)piperidin-2-yl)benzyl)-2-thioxo-1,2,3,5-tetrahydro-4H-pyrrolo[3,2-d]pyrimidin-4-one,
1-(2-((2R,4S)-4-(Difluoromethyl)piperidin-2-yl)benzyl)-2-thioxo-1,2,3,5-tetrahydro-4H-pyrrolo[3,2-d]pyrimidin-4-one,
1-(2-((2S,4R)-4-(difluoromethyl)piperidin-2-yl)benzyl)-2-thioxo-1,2,3,5-tetrahydro-4H-pyrrolo[3,2-d]pyrimidin-4-one,
1-((2-(Piperidin-2-yl)pyridin-3-yl)methyl)-2-thioxo-1,2,3,5-tetrahydro-4H-pyrrolo[3,2-d]pyrimidin-4-one,
rac-2-Thioxo-1-((3-((2R,4S)-4-(trifluoromethyl)piperidin-2-yl)pyridin-2-yl)methyl)-1,2,3,5-tetrahydro-4H-pyrrolo[3,2-d]pyrimidin-4-one,
2-Thioxo-1-((3-((cis)-4-(trifluoromethyl)piperidin-2-yl)pyridin-2-yl)methyl)-1,2,3,5-tetrahydro-4H-pyrrolo[3,2-d]pyrimidin-4-one,
2-Thioxo-1-((3-((2R,4S)-4-(trifluoromethyl)piperidin-2-yl)pyridin-2-yl)methyl)-1,2,3,5-tetrahydro-4H-pyrrolo[3,2-d]pyrimidin-4-one,
2-Thioxo-1-((3-((2S,4R)-4-(trifluoromethyl)piperidin-2-yl)pyridin-2-yl)methyl)-1,2,3,5-tetrahydro-4H-pyrrolo[3,2-d]pyrimidin-4-one,
rac-2-Thioxo-1-((3-((2R,4S)-4-(trifluoromethyl)piperidin-2-yl)pyridin-4-yl)methyl)-1,2,3,5-tetrahydro-4H-pyrrolo[3,2-d]pyrimidin-4-one,
2-Thioxo-1-((3-((cis)-4-(trifluoromethyl)piperidin-2-yl)pyridin-4-yl)methyl)-1,2,3,5-tetrahydro-4H-pyrrolo[3,2-d]pyrimidin-4-one,
2-Thioxo-1-((3-((2R,4S)-4-(trifluoromethyl)piperidin-2-yl)pyridin-4-yl)methyl)-1,2,3,5-tetrahydro-4H-pyrrolo[3,2-d]pyrimidin-4-one,
2-Thioxo-1-((3-((2S,4R)-4-(trifluoromethyl)piperidin-2-yl)pyridin-4-yl)methyl)-1,2,3,5-tetrahydro-4H-pyrrolo[3,2-d]pyrimidin-4-one,
1-(4-(1-Aminocyclobutyl)benzyl)-2-thioxo-1,2,3,5-tetrahydro-4H-pyrrolo[3,2-d]pyrimidin-4-one,
1-(3-(1-Aminocyclobutyl)benzyl)-2-thioxo-1,2,3,5-tetrahydro-4H-pyrrolo[3,2-d]pyrimidin-4-one,
1-(2-(Piperidin-3-yl)benzyl)-2-thioxo-1,2,3,5-tetrahydro-4H-pyrrolo[3,2-d]pyrimidin-4-one,
1-(2-(morpholin-2-yl)benzyl)-2-thioxo-1,2,3,5-tetrahydro-4H-pyrrolo[3,2-d]pyrimidin-4-one,
(R)-1-(2-(Morpholin-2-yl)benzyl)-2-thioxo-1,2,3,5-tetrahydro-4H-pyrrolo[3,2-d]pyrimidin-4-one,
(S)-1-(2-(morpholin-2-yl)benzyl)-2-thioxo-1,2,3,5-tetrahydro-4H-pyrrolo[3,2-d]pyrimidin-4-one,
1-(2-(Piperidin-4-yl)benzyl)-2-thioxo-1,2,3,5-tetrahydro-4H-pyrrolo[3,2-d]pyrimidin-4-one,
rac-2-Thioxo-1-((2-((2R,4R)-4-(trifluoromethyl)piperidin-2-yl)pyridin-3-yl)methyl)-1,2,3,5-tetrahydro-4H-pyrrolo[3,2-d]pyrimidin-4-one,
2-Thioxo-1-((2-((trans)-4-(trifluoromethyl)piperidin-2-yl)pyridin-3-yl)methyl)-1,2,3,5-tetrahydro-4H-pyrrolo[3,2-d]pyrimidin-4-one,
2-Thioxo-1-((2-((2R,4R)-4-(trifluoromethyl)piperidin-2-yl)pyridin-3-yl)methyl)-1,2,3,5-tetrahydro-4H-pyrrolo[3,2-d]pyrimidin-4-one,
2-Thioxo-1-((2-((2S,4S)-4-(trifluoromethyl)piperidin-2-yl)pyridin-3-yl)methyl)-1,2,3,5-tetrahydro-4H-pyrrolo[3,2-d]pyrimidin-4-one, and
pharmaceutically acceptable salts thereof.

Another embodiment disclosed herein provides a compound of formula (Ia)

(Ia)

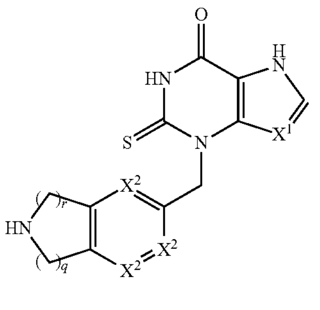

wherein,
$X^1$=CH or N,
each $X^2$ is, independently, CH, CF, or CCl, and
r and q are 0, 1, or 2, provided r+q=2 or 3,
or any stereoisomer thereof or pharmaceutically acceptable salt thereof.

Another embodiment disclosed herein provides a compound of formula (Ib)

(Ib)

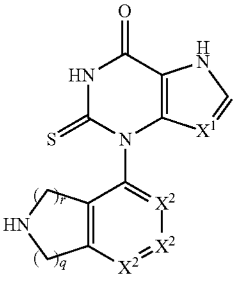

wherein, $X^1$=CH or N, each $X^2$ is, independently, CH, CF, or CCl, and r and q are 0, 1, or 2, provided that r+q=2 or 3 or any stereoisomer thereof or pharmaceutically acceptable salt thereof.

Some embodiments disclosed herein provide a compound of formula (Ia) or (Ib), or any stereoisomer thereof or pharmaceutically acceptable salt thereof wherein each $X^2$ are CH.

Some embodiments disclosed herein provide a compound of formula (Ia) or (Ib), or any stereoisomer thereof or pharmaceutically acceptable salt thereof wherein r is 1 and q is 1.

Some embodiments disclosed herein provide a compound of formula (Ia) or (Ib), or any stereoisomer thereof or pharmaceutically acceptable salt thereof wherein r is 1 and q is 2 or r is 2 and q is 1.

Some embodiments disclosed herein provide a compound of formula (Ia) or (Ib), or any stereoisomer thereof or pharmaceutically acceptable salt thereof wherein r is 0 and q is 2 or r is 2 and q is 0.

Some embodiments disclosed herein provide a compound of formula (Ia) or (Ib), or any stereoisomer thereof or pharmaceutically acceptable salt thereof wherein $X^1$ is CH.

Some embodiments disclosed herein provide a compound of formula (Ia) or (Ib), or any stereoisomer thereof or pharmaceutically acceptable salt thereof wherein $X^1$ is N.

Some embodiments disclosed herein provide, or any stereoisomer thereof or pharmaceutically acceptable salt thereof, of a compound selected from:

1-((1,2,3,4-Tetrahydroisoquinolin-8-yl)methyl)-2-thioxo-1,2,3,5-tetrahydro-4H-pyrrolo[3,2-d]pyrimidin-4-one, 1-(Isoindolin-5-ylmethyl)-2-thioxo-1,2,3,5-tetrahydro-4H-pyrrolo[3,2-d]pyrimidin-4-one, 1-(Isoindolin-4-ylmethyl)-2-thioxo-1,2,3,5-tetrahydro-4H-pyrrolo[3,2-d]pyrimidin-4-one, and pharmaceutically acceptable salts thereof.

Some embodiments disclosed herein provide a compound having the structure:

(IIa)

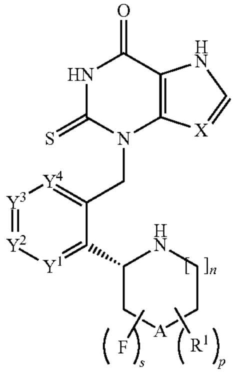

or (IIb)

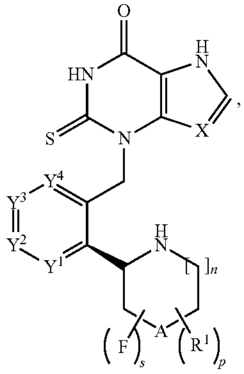

, wherein X, $Y^1$, $Y^2$, $Y^3$, $Y^4$, A, $R^1$, n, p, and s, are defined as above for formula (II).

One embodiment disclosed herein provides a compound having the structure:

(IIIa)

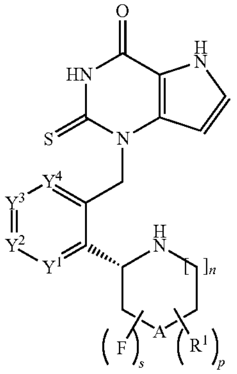

or

-continued (IIIb)

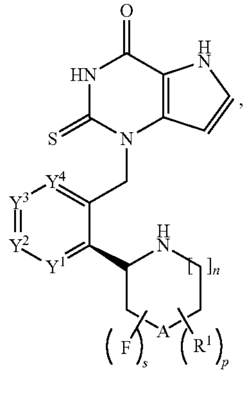

wherein $Y^1$, $Y^2$, $Y^3$, $Y^4$, A, $R^1$, n, p, and s, are defined as above for formula (III).

One embodiment disclosed herein provides a compound having the structure:

(IVa)

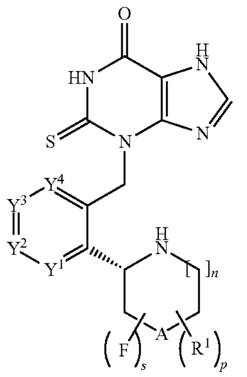

or (IVb)

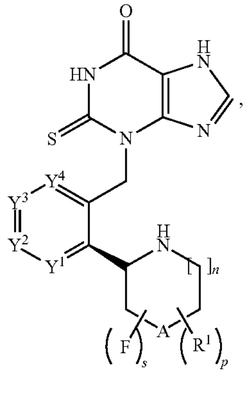

wherein $Y^1$, $Y^2$, $Y^3$, $Y^4$, A, $R^1$, n, p, and s, are defined as above for formula (IV).

It shall be noted that any one of these specific compounds may be disclaimed from any of the herein mentioned embodiments.

In some embodiments there are provided processes for the preparation of compounds of the compounds of formulae (I), (Ia), (Ib), (II), (IIa), (IIb), (III), (IIIa), (IIIb), (IV), (IVa), or (IVb), the compounds disclosed herein, and pharmaceutically acceptable salts thereof and the intermediates used in the preparation thereof.

Some embodiments disclosed herein provide a product obtainable by any of the processes or examples disclosed herein.

Further, because of the fact that the absolute configuration of the enantiomers of the compounds disclosed herein was determined by a spectroscopy study, rather than by for instance an X-ray study, it is to be understood that the R and S designation will be reversed should the results from said spectroscopic study for one reason or another be proven wrong.

Medical and Pharmaceutical Use

The compounds of formulae (I), (Ia), (Ib), (II), (IIa), (IIb), (III), (IIIa), (IIIb), (IV), (IVa), or (IVb), the compounds disclosed herein, and pharmaceutically acceptable salts thereof, are useful because they possess pharmacological activity as inhibitors of the enzyme MPO.

The compounds of formulae (I), (Ia), (Ib), (II), (IIa), (IIb), (III), (IIIa), (IIIb), (IV), (IVa), or (IVb), the compounds disclosed herein, and pharmaceutically acceptable salts thereof are indicated for use in the treatment or prophylaxis of diseases or conditions in which modulation of the activity of the enzyme myeloperoxidase (MPO) is desirable. In particular, linkage of MPO activity to disease has been implicated in numerous diseases, including diseases with inflammatory, cardiovascular, respiratory, renal, hepatic and/or neurological components, as well as neutrophilic driven diseases.

The disclosed compounds are indicated for use in the treatment or prophylaxis of inflammatory diseases or conditions, or diseases or conditions with an inflammatory component, in mammals, including humans, which are responsive to inhibition of MPO. Such diseases or conditions include, but are not limited to, autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, and type 2 diabetes.

The disclosed compounds are indicated for use in the treatment or prophylaxis of cardiovascular diseases or conditions in mammals, including humans, which are responsive to inhibition of MPO. Such cardiovascular diseases or conditions include, but are not limited to, coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, and chemotherapy-induced cardiotoxicity.

The disclosed compounds are also indicated for use in the treatment or prophylaxis of neurological diseases and conditions in mammals, including humans, in which microvascular dysfunction is prominent.

The disclosed compounds are also indicated for use in the treatment or prophylaxis of neurological diseases and conditions in mammals, including humans, which are responsive to inhibition of MPO. Such diseases and conditions include, but are not limited to diseases with a neuroinflammatory response. These diseases and conditions include, but are not limited to, Alzheimer's disease, Parkinson's disease, stroke, multiple sclerosis (MS), multiple system atrophy (MSA), amyotrophic lateral sclerosis (ALS), and epilepsy.

The disclosed compounds are also indicated for use in the treatment or prophylaxis of neutrophilic driven diseases and conditions in mammals, including humans. Such diseases and conditions include, but are not limited to chronic rhinosinusitis, chronic rhinosinusitis with nasal polyps (CRSwNP), neutrophilic asthma, idiopathic pulmonary fibrosis (IPF), neutrophilic lung disease, and acute respiratory distress syndrome (ARDS).

The disclosed compounds are indicated for use in the treatment or prophylaxis of inflammatory diseases or conditions, or diseases or conditions with an inflammatory component, in mammals, including humans, which are responsive to inhibition of MPO. Such diseases or conditions include, but are not limited to, autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, type 2 diabetes, bronchiectasis, COVID-19 (or SARS CoV2) induced renal failure, diabetic kidney disease (DKD), endometriosis, end-stage kidney disease (ESKD), Immunoglobulin A vasculitis (Henoch-Schonlein Purpura), Immunoglobulin A nephropathy (IgAN), lupus nephritis, diabetic CKD, hypertensive CKD, and/or obesity with CKD.

The disclosed compounds are indicated for use in the treatment or prophylaxis of cardiovascular diseases or conditions in mammals, including humans, which are responsive to inhibition of MPO. Such cardiovascular diseases or conditions include, but are not limited to, coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, chemotherapy-induced cardiotoxicity, prolonging the time to/prevention of reoccurrence of Atrial fibrillation/flutter after cardioversion, arrhythmogenic right ventricular cardiomyopathy, atherosclerotic cardiovascular disease (ASCVD), halting the progression and/or causing regression of atheroma, COVID-19 (or SARS CoV2) induced heart failure, COVID-19 (or SARS CoV2) induced cardiomyopathy, cardiovascular disease, heart failure with preserved ejection fraction (HFpEF) renal crossover, first or recurrent myocardial infarction, peripheral arterial disease, restrictive cardiomyopathy, unclassified cardiomyopathy, inhibition of plaque rupture, amelioration of the inflammation associated with plaque rupture, secondary myocardial infarction, ST segment elevation myocardial infarction, and/or non-ST segment elevation myocardial infarction.

The disclosed compounds are also indicated for use in the treatment or prophylaxis of neurological diseases and conditions in mammals, including humans, which are responsive to inhibition of MPO. Such diseases and conditions include, but are not limited to diseases with a neuroinflammatory response. These diseases and conditions include, but are not limited to, Alzheimer's disease, Parkinson's disease, stroke, multiple sclerosis (MS), multiple system atrophy (MSA), amyotrophic lateral sclerosis (ALS), epilepsy, acute ischaemic stroke, and/or subarachnoid haemorrhage.

The disclosed compounds are indicated for use in the treatment of cancer.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening or identified through specific biomarker pattern to be particularly susceptible to developing the disease or condition.

For the above-mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formulae (I), (Ia), (Ib), (II), (IIa), (IIb), (III), (IIIa), (IIIb), (IV), (IVa), or (IVb), or a compound disclosed herein, and pharmaceutically acceptable derivatives thereof, may be used on their own, or in the form of appropriate pharmaceutical compositions in which the compound or derivative is in admixture with a pharmaceutically acceptable adjuvant, diluent or carrier. Thus, another aspect concerns a pharmaceutical composition comprising a novel compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier. Thus, another aspect concerns a pharmaceutical composition which comprises a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, and at least one pharmaceutically acceptable excipient. Administration may be by, but is not limited to, enteral (including oral, sublingual or rectal), intranasal, inhalation, intravenous, topical or other parenteral routes. Conventional procedures for the selection and preparation of suitable pharmaceutical formulations are described in, for example, *Pharmaceuticals—The Science of Dosage Form Designs*, M. E. Aulton, Churchill Livingstone, $2^{nd}$ Ed. 2002.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in therapy, especially in the prevention or treatment of one or more conditions or diseases where inhibition of MPO would be beneficial.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in in the prevention or treatment of one or more conditions or diseases with an inflammatory component wherein inhibition of MPO would be beneficial in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in therapy, especially in the prevention or treatment of one or more cardiovascular diseases wherein inhibition of MPO would be beneficial in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of one or more neurological diseases wherein inhibition of MPO would be beneficial in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in therapy, especially in the prevention or treatment of one or more neutrophilic driven diseases wherein inhibition of MPO would be beneficial in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of inflammatory diseases or conditions, or diseases or conditions with an inflammatory component, such as, but not limited to, autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, or type 2 diabetes in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of cardiovascular diseases or conditions, such as, but not limited to, coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), vascular dysfunction, atherosclerosis, ischemic heart disease, atrial fibrillation, pericarditis, diastolic dysfunction, plaque rupture, abdominal aortic aneurysm, and chemotherapy-induced cardiotoxicity, in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of cardiovascular diseases or conditions, such as, but not limited to, coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, and chemotherapy-induced cardiotoxicity, in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of neurological diseases and conditions including, but not limited to diseases with a neuroinflammatory response, such as but not limited to, Alzheimer's disease, Parkinson's disease, stroke, multiple sclerosis (MS), multiple system atrophy (MSA), amyotrophic lateral sclerosis (ALS), and epilepsy in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of one or more neutrophilic driven diseases, such as, but not limited to, chronic rhinosinusitis, chronic rhinosinusitis with nasal polyps (CRSwNP), neutrophilic asthma, idiopathic pulmonary fibrosis (IPF), neutrophilic lung disease, and acute respiratory distress syndrome (ARDS), in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of inflammatory diseases or conditions, or diseases or conditions with an inflammatory component, such as, but not limited to, autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, type 2 diabetes, bronchiectasis, COVID-19 (or SARS CoV2) induced renal failure, diabetic kidney disease (DKD), endometriosis, end-stage kidney disease (ESKD), Immunoglobulin A vasculitis (Henoch-Schonlein Purpura), Immunoglobulin A nephropathy (IgAN), lupus nephritis, diabetic CKD, hypertensive CKD, and/or obesity with CKD, in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of cardiovascular diseases or conditions, such as, but not limited to, coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, chemotherapy-induced cardiotoxicity, prolonging the time to/prevention of reoccurrence of Atrial fibrillation/flutter after cardioversion, arrhythmogenic right ventricular cardiomyopathy, atherosclerotic cardiovascular disease (ASCVD), halting the progression and/or causing regression of atheroma, COVID-19 (or SARS CoV2) induced heart failure, COVID-19 (or SARS CoV2) induced cardiomyopathy, cardiovascular disease, heart failure with preserved ejection fraction (HFpEF) renal crossover, first or recurrent myocardial infarction, peripheral arterial disease, restrictive cardiomyopathy, unclassified cardiomyopathy, inhibition of plaque rupture, amelioration of the inflammation associated with plaque rupture, secondary myocardial infarction, ST segment elevation myocardial infarction, and/or non-ST segment elevation myocardial infarction, in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of neurological diseases and conditions including, but not limited to diseases with a neuroinflammatory response, such as but not limited to, Alzheimer's disease, Parkinson's disease, stroke, multiple sclerosis (MS), multiple system atrophy (MSA), amyotrophic lateral sclerosis (ALS), epilepsy, acute ischaemic stroke, and/or subarachnoid haemorrhage, in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the treatment of cancer in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of coronary artery disease in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of acute coronary syndrome in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of heart failure in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of heart failure with reduced ejection fraction in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of heart failure with preserved ejection fraction in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of chronic kidney disease (CKD) in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of cardiorenal syndrome (CRS) in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of non-alcoholic steatohepatitis (NASH) in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of arrhythmia in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of chronic obstructive pulmonary disease (COPD) in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of sickle cell disease in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of acute kidney injury (AKI), in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of non-cystic fibrosis bronchiectasis (NCFB), in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of anti-neutrophilic cytoplasmic autoantibody (ANCA)-associated vasculitis, in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of Alzheimer's disease in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of Parkinson's disease in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of nephritis in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of inflammatory bowel disease (IBD) in a mammal, particularly a human.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the prevention or treatment of irritable bowel syndrome (IBS), in a mammal, particularly a human.

In some embodiments there is provided a method of treating, preventing, or reducing the risk of, one or more diseases or conditions in which inhibition of the enzyme MPO is beneficial which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more diseases or conditions with an inflammatory component which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more cardiovascular diseases or conditions which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more neurological diseases or conditions which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more neutrophilic driven diseases or conditions which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more diseases or conditions with an inflammatory component, such as, but not limited to, autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, or type 2 diabetes, which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more cardiovascular diseases or conditions, such as, but not limited to, coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), vascular dysfunction, atherosclerosis, ischemic heart disease, atrial fibrillation, pericarditis, diastolic dysfunction, plaque rupture, abdominal aortic aneurysm, and chemotherapy-induced cardiotoxicity, which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more cardiovascular diseases or conditions, such as, but not limited to, coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, and chemotherapy-induced cardiotoxicity, which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more neurological diseases or conditions, such as but not limited to diseases with a neuroinflammatory response, such as but not limited to, Alzheimer's disease, Parkinson's disease, stroke, multiple sclerosis (MS), multiple system atrophy (MSA), amyotrophic lateral sclerosis (ALS), and epilepsy which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more neutrophilic driven diseases or conditions, such as, but not limited to, chronic rhinosinusitis, chronic rhinosinusitis with nasal polyps (CRSwNP), neutrophilic asthma, idiopathic pulmonary fibrosis (IPF), neutrophilic lung disease, and acute respiratory distress syndrome (ARDS), which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more diseases or conditions with an inflammatory component, such as, but not limited to, autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, type 2 diabetes, bronchiectasis, COVID-19 (or SARS CoV2) induced renal failure, diabetic kidney disease (DKD), endometriosis, end-stage kidney disease (ESKD), Immunoglobulin A vasculitis (Henoch-Schonlein Purpura), Immunoglobulin A nephropathy (IgAN), lupus nephritis, diabetic CKD, hypertensive CKD, and/or obesity with CKD, which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more cardiovascular diseases or conditions, such as, but not limited to, coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, chemotherapy-induced cardiotoxicity, prolonging the time to/prevention of reoccurrence of Atrial fibrillation/flutter after cardioversion, arrhythmogenic right ventricular cardiomyopathy, atherosclerotic cardiovascular disease (ASCVD), halting the progression and/or causing regression of atheroma, COVID-19 (or SARS CoV2) induced heart failure, COVID-19 (or SARS CoV2) induced cardiomyopathy, cardiovascular disease, heart failure with preserved ejection fraction (HFpEF) renal crossover, first or recurrent myocardial infarction, peripheral arterial disease, restrictive cardiomyopathy, unclassified cardiomyopathy, inhibition of plaque rupture, amelioration of the inflammation associated with plaque rupture, secondary myocardial infarction, ST segment elevation myocardial infarction, and/or non-ST segment elevation myocardial infarction, which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of one or more neurological diseases or conditions, such as but not limited to diseases with a neuroinflammatory response, such as but not limited to, Alzheimer's disease, Parkinson's disease, stroke, multiple sclerosis (MS), multiple system atrophy (MSA), amyotrophic lateral sclerosis (ALS), epilepsy, acute ischaemic stroke, and/or subarachnoid haemorrhage, which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating cancer which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of coronary artery disease which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of acute coronary syndrome which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of heart failure which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of heart failure with reduced ejection fraction which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of heart failure with preserved ejection fraction which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of chronic kidney disease (CKD) which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of cardiorenal syndrome (CRS) which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of non-alcoholic steatohepatitis (NASH) which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of arrhythmia which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of chronic obstructive pulmonary disease (COPD) which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of sickle cell disease which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of anti-neutrophilic cytoplasmic autoantibody (ANCA)-associated vasculitis which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of acute kidney injury (AKI) which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of non-cystic fibrosis bronchiectasis (NCFB), which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of Alzheimer's disease which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of Parkinson's disease which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of nephritis which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of inflammatory bowel disease (IBD) which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a method of treating, preventing, or reducing the risk of irritable bowel syndrome (IBS) which comprises administering to a person suffering from or at risk of, said disease or condition, a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the manufacture of a medicament for use in the treatment or prophylaxis of diseases or conditions in which modulation of the activity of the enzyme myeloperoxidase (MPO) is desirable.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the manufacture of a medicament for use in the treatment or prophylaxis of diseases or conditions with inflammatory, cardiovascular, and/or neurological components, and/or neutrophilic driven diseases.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the manufacture of a medicament for use in the treatment or prophylaxis of autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, and/or type 2 diabetes.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the manufacture of a medicament for use in the treatment or prophylaxis of coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, and/or chemotherapy-induced cardiotoxicity.

In some embodiments there is provided a compound of formulae (I), (Ia), (Ib), (II), (IIa), (Iib), (III), (IIIa), (IIIb), (IV), (Iva), or (Ivb), or a compound disclosed herein, or a pharmaceutically acceptable salt thereof, for use in the manufacture of a medicament for use in the treatment or prophylaxis of Alzheimer's disease, Parkinson's disease, stroke, multiple sclerosis (MS), multiple system atrophy (MSA), amyotrophic lateral sclerosis (ALS), and/or epilepsy.

In some embodiments there is provided a compound of formulae (I), (Ia), (Ib), (II), (Iia), (Iib), (III), (IIIa), (IIIb), (IV), (Iva), or (Ivb), or a compound disclosed herein, or a pharmaceutically acceptable salt thereof, for use in the manufacture of a medicament for use in the treatment or prophylaxis of chronic rhinosinusitis, chronic rhinosinusitis with nasal polyps (CRSwNP), neutrophilic asthma, idiopathic pulmonary fibrosis (IPF), neutrophilic lung disease, and acute respiratory distress syndrome (ARDS).

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the manufacture of a medicament for use in the treatment or prophylaxis of autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, type 2 diabetes, bronchiectasis, COVID-19 (or SARS CoV2) induced renal failure, diabetic kidney disease (DKD), endometriosis, end-stage kidney disease (ESKD), Immunoglobulin A vasculitis (Henoch-Schonlein Purpura), Immunoglobulin A nephropathy (IgAN), lupus nephritis, diabetic CKD, hypertensive CKD, and/or obesity with CKD.

In some embodiments there is provided a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, for use in the manufacture of a medicament for use in the treatment or prophylaxis of coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, chemotherapy-induced cardiotoxicity, prolonging the time to/prevention of reoccurrence of Atrial fibrillation/flutter after cardioversion, arrhythmogenic right ventricular cardiomyopathy, atherosclerotic cardiovascular disease (ASCVD), halting the progression and/or causing regression of atheroma, COVID-19 (or SARS CoV2) induced heart failure, COVID-19 (or SARS CoV2) induced cardiomyopathy, cardiovascular disease, heart failure with preserved ejection fraction (HFpEF) renal crossover, first or recurrent myocardial infarction, peripheral arterial disease, restrictive cardiomyopathy, unclassified cardiomyopathy, inhibition of plaque rupture, amelioration of the inflammation associated with plaque rupture, secondary myocardial infarction, ST segment elevation myocardial infarction, and/or non-ST segment elevation myocardial infarction.

In some embodiments there is provided a compound of formulae (I), (Ia), (Ib), (II), (IIa), (Iib), (III), (IIIa), (IIIb), (IV), (Iva), or (Ivb), or a compound disclosed herein, or a pharmaceutically acceptable salt thereof, for use in the manufacture of a medicament for use in the treatment or prophylaxis of Alzheimer's disease, Parkinson's disease, stroke, multiple sclerosis (MS), multiple system atrophy (MSA), amyotrophic lateral sclerosis (ALS), epilepsy, acute ischaemic stroke, and/or subarachnoid haemorrhage.

In some embodiments there is provided a compound of formulae (I), (Ia), (Ib), (II), (Iia), (Iib), (III), (IIIa), (IIIb), (IV), (Iva), or (Ivb), or a compound disclosed herein, or a pharmaceutically acceptable salt thereof, for use in the manufacture of a medicament for use in the treatment of cancer.

In some embodiments there is provided a pharmaceutical formulation comprising a therapeutically effective amount of a compound of formulae (I), (Ia), (Ib), (II), (Iia), (Jib), (III), (IIIa), (IIIb), (IV), (Iva), or (Ivb), or a compound disclosed herein, or a pharmaceutically acceptable salt thereof, and a pharmaceutically acceptable diluent, excipient and/or inert carrier.

In some embodiments there is provided a pharmaceutical formulation comprising a compound of formulae (I), (Ia), (Ib), (II), (Iia), (Jib), (III), (IIIa), (IIIb), (IV), (Iva), or (Ivb), or a compound disclosed herein, or a pharmaceutically acceptable salt thereof, in admixture with a pharmaceutically acceptable adjuvant, diluent or carrier, for use in therapy, especially in the prevention or treatment of one or more conditions or diseases where inhibition of MPO would be beneficial.

In a some embodiments there is provided a pharmaceutical formulation comprising a compound of formulae (I), (Ia), (Ib), (II), (Iia), (Jib), (III), (IIIa), (IIIb), (IV), (Iva), or (Ivb), or a compound disclosed herein, or a pharmaceutically acceptable salt thereof, in admixture with a pharmaceutically acceptable adjuvant, diluent or carrier, for use in therapy, especially in the prevention or treatment of one or more conditions or diseases where inhibition of MPO would be beneficial.

In some embodiments there is provided a pharmaceutical formulation comprising a compound of formulae (I), (Ia), (Ib), (II), (Iia), (Jib), (III), (IIIa), (IIIb), (IV), (Iva), or (Ivb), or a compound disclosed herein, or a pharmaceutically acceptable salt thereof, in admixture with a pharmaceutically acceptable adjuvant, diluent or carrier, for use in in the prevention or treatment of one or more conditions or diseases with an inflammatory component wherein inhibition of MPO would be beneficial in a mammal, particularly a human.

In some embodiments there is provided a pharmaceutical formulation comprising a compound of formulae (I), (Ia), (Ib), (II), (Iia), (Jib), (III), (IIIa), (IIIb), (IV), (Iva), or (Ivb), or a compound disclosed herein, or a pharmaceutically acceptable salt thereof, in admixture with a pharmaceutically acceptable adjuvant, diluent or carrier, for use in therapy, especially in the prevention or treatment of one or more cardiovascular diseases wherein inhibition of MPO would be beneficial in a mammal, particularly a human.

In some embodiments there is provided a pharmaceutical formulation comprising a compound of formulae (I), (Ia), (Ib), (II), (Iia), (Jib), (III), (IIIa), (IIIb), (IV), (Iva), or (Ivb), or a compound disclosed herein, or a pharmaceutically acceptable salt thereof, in admixture with a pharmaceutically acceptable adjuvant, diluent or carrier, for use in the prevention or treatment of one or more neurological diseases wherein inhibition of MPO would be beneficial in a mammal, particularly a human.

In some embodiments there is provided a pharmaceutical formulation comprising a compound of formulae (I), (Ia), (Ib), (II), (Iia), (Jib), (III), (IIIa), (IIIb), (IV), (Iva), or (Ivb), or a compound disclosed herein, or a pharmaceutically acceptable salt thereof, in admixture with a pharmaceutically acceptable adjuvant, diluent or carrier, for use in therapy, especially in the prevention or treatment of one or more neutrophilic driven diseases wherein inhibition of MPO would be beneficial in a mammal, particularly a human.

In some embodiments there is provided a pharmaceutical formulation comprising a compound of formulae (I), (Ia), (Ib), (II), (Iia), (Jib), (III), (IIIa), (IIIb), (IV), (Iva), or (Ivb), or a compound disclosed herein, or a pharmaceutically acceptable salt thereof, in admixture with a pharmaceutically acceptable adjuvant, diluent or carrier, for use in the prevention or treatment of inflammatory diseases or conditions, or diseases or conditions with an inflammatory component, such as, but not limited to, autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, or type 2 diabetes in a mammal, particularly a human.

In some embodiments there is provided a pharmaceutical formulation comprising a compound of formulae (I), (Ia), (Ib), (II), (Iia), (Jib), (III), (IIIa), (IIIb), (IV), (Iva), or (Ivb), or a compound disclosed herein, or a pharmaceutically acceptable salt thereof, in admixture with a pharmaceutically acceptable adjuvant, diluent or carrier, for use in the prevention or treatment of cardiovascular diseases or conditions, such as, but not limited to, coronary artery disease, acute coronary syndrome, heart failure, heart failure with reduced ejection fraction (HfrEF), heart failure with preserved ejection fraction (HfpEF), arrhythmia, cardiomyopathy, dilated cardiomyopathy, hypertrophic cardiomyopathy, myocardial infarction, hypertension, pulmonary arterial hypertension (PAH), vascular dysfunction, atherosclerosis, ischemic heart disease, atrial fibrillation, pericarditis, diastolic dysfunction, plaque rupture, abdominal aortic aneurysm, and chemotherapy-induced cardiotoxicity in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of cardiovascular diseases or conditions, such as, but not limited to, coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, and chemotherapy-induced cardiotoxicity in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of neurological diseases and conditions including, but not limited to diseases with a neuroinflammatory response, such as but not limited to, Alzheimer's disease, Parkinson's disease, stroke, multiple sclerosis (MS), multiple system atrophy (MSA), amyotrophic lateral sclerosis (ALS), and epilepsy in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of one or more neutrophilic driven diseases, such as, but not limited to, chronic rhinosinusitis, chronic rhinosinusitis with nasal polyps (CRSwNP), neutrophilic asthma, idiopathic pulmonary fibrosis (IPF), neutrophilic lung disease, and acute respiratory distress syndrome (ARDS), in a mammal, particularly a human.

In some embodiments there is provided a pharmaceutical formulation comprising a compound of formulae (I), (Ia), (Ib), (II), (Iia), (Jib), (III), (IIIa), (IIIb), (IV), (Iva), or (Ivb), or a compound disclosed herein, or a pharmaceutically acceptable salt thereof, in admixture with a pharmaceutically acceptable adjuvant, diluent or carrier, for use in the prevention or treatment of inflammatory diseases or conditions, or diseases or conditions with an inflammatory component, such as, but not limited to, autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, type 2 diabetes, bronchiectasis, COVID-19 (or SARS CoV2) induced renal failure, diabetic kidney disease (DKD), endometriosis, end-stage kidney disease (ESKD), Immunoglobulin A vasculitis (Henoch-Schonlein Purpura), Immunoglobulin A nephropathy (IgAN), lupus nephritis, diabetic CKD, hypertensive CKD, and/or obesity with CKD, in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of cardiovascular diseases or conditions, such as, but not limited to, coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy, myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, chemotherapy-induced cardiotoxicity, prolonging the time to/prevention of reoccurrence of Atrial fibrillation/flutter after cardioversion, arrhythmogenic right ventricular cardiomyopathy, atherosclerotic cardiovascular disease (ASCVD), halting the progression and/or causing regression of atheroma, COVID-19 (or SARS CoV2) induced heart failure, COVID-19 (or SARS CoV2) induced cardiomyopathy, cardiovascular disease, heart failure with preserved ejection fraction (HFpEF) renal crossover, first or recurrent myocardial infarction, peripheral arterial disease, restrictive cardiomyopathy, unclassified cardiomyopathy, inhibition of plaque rupture, amelioration of the inflammation associated with plaque rupture, secondary myocardial infarction, ST segment elevation myocardial infarction, and/or non-ST segment elevation myocardial infarction, in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of neurological diseases and conditions including, but not limited to diseases with a neuroinflammatory response, such as but not limited to, Alzheimer's disease, Parkinson's disease, stroke, multiple sclerosis (MS), multiple system atrophy (MSA), amyotrophic lateral sclerosis (ALS), epilepsy, acute ischaemic stroke, and/or subarachnoid haemorrhage in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the treatment of cancer, in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of coronary artery disease in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of acute coronary syndrome in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of heart failure in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of heart failure with reduced ejection fraction in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of heart failure with preserved ejection fraction in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of chronic kidney disease (CKD) in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of cardiorenal syndrome (CRS) in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of non-alcoholic steatohepatitis (NASH) in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of arrhythmia in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of chronic obstructive pulmonary disease (COPD) in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of sickle cell disease in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of anti-neutrophilic cytoplasmic autoantibody (ANCA)-associated vasculitis, in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of Alzheimer's disease in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of Parkinson's disease in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of nephritis in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of inflammatory bowel disease (IBD) in a mammal, particularly a human.

In some embodiments there is provided a pharmaceutical formulation comprising a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, in admixture with a pharmaceutically acceptable adjuvant, diluent or carrier, for use in the prevention or treatment of irritable bowel syndrome (IBS), in a mammal, particularly a human.

In some embodiments, plasma urate levels may be used as a stratifying tool and a pharmacodynamic biomarker for MPO inhibitor treatment with a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof.

In still a further embodiment, there is provided a method of identifying patients suitable for MPO inhibitor treatment with a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, encompassing the measurement of plasma urate levels.

In some embodiments, predictive biomarkers, i.e. features or variables reflecting an involvement of MPO in disease pathology, may be used as a stratifying tool and a pharmacodynamic biomarker for MPO inhibitor treatment with a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof. Such biomarkers include, but are not limited to, biomarkers of neutrophil activation (MPO, NGAL, sTNFR1, sTNFR2, calprotectin, UPAR, blood neutrophil counts or percentages, blood neutrophil/lymphocyte ratio), other inflammatory prognostic biomarkers (GDF15, FGF23, sTRAIL-R2), biomarkers of systemic inflammation (IL6, C-reactive protein or other acute phase proteins), biomarkers of increased purine catabolism (urate) and purine oxidation (allantoin), biomarkers of iron deficiency (transferrin saturation, ferritin, hemoglobin), biomarkers of extracellular matrix remodeling (MMP7, TIMP4, osteopontin), biomarkers of renal dysfunction (eGFR, UACR, cystatin C), biomarkers of nitric oxide production SDMA, ADMA, Arg, cGMP). Several of these biomarkers may be quantified from blood, plasma, sera, urine, feaces or saliva.

In still a further embodiment, there is provided a method of identifying patients suitable for MPO inhibitor treatment with a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, encompassing the measurement of such predicitive biomarkers as disclosed herein.

In some embodiments, a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, when tested in an MPO binding assay, for example Test A described below, have an $IC_{50}$ less than 10 μM.

In some embodiments, a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, when tested in an MPO binding assay, for example Test A described below, have an $IC_{50}$ less than 5 μM.

In some embodiments, a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, when tested in an MPO binding assay, for example Test A described below, have an $IC_{50}$ less than 1 μM.

In some embodiments, a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, when tested in an MPO binding assay, for example Test A described below, have an $IC_{50}$ less than 0.5 μM.

In some embodiments, a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, when tested in an MPO binding assay, for example Test A described below, have an $IC_{50}$ less than 0.2 μM.

The compounds of formulae (I), (Ia), (Ib), (II), (IIa), (IIb), (III), (IIIa), (IIIb), (IV), (IVa), or (IVb), or a compound disclosed herein, or a pharmaceutically acceptable salt thereof also display a promising pharmacological profiles by separating desired and undesired effects in vivo.

These and other embodiments are described in greater detail herein below, where further aspects will be apparent to one skilled in the art from reading this specification.

Pharmacological Properties

The compounds of formulae (I), (Ia), (Ib), (II), (IIa), (IIb), (III), (IIIa), (IIIb), (IV), (IVa), or (IVb), or a compound disclosed herein, or a pharmaceutically acceptable salt thereof. are believed to be useful in the prevention or treatment of various conditions wherein the modulation of the activity of the enzyme myeloperoxidase (MPO) is desirable, including, but not limited to, diseases with inflammatory, cardiovascular, and/or neurological components, as well as neutrophilic driven diseases.

For the avoidance of doubt, as used herein, the term "treatment" includes therapeutic and/or prophylactic treatment.

When a compound or salt described herein is administered as therapy for treating a disorder, a "therapeutically effective amount" is an amount sufficient to reduce or completely alleviate symptoms or other detrimental effects of the disorder, cure the disorder, reverse, completely stop, or slow the progress of the disorder or reduce the risk of the disorder getting worse.

The compounds described herein are thus indicated both in the therapeutic and/or prophylactic treatment of these conditions.

The compounds described herein have the advantage that they may be more efficacious, be less toxic, be more selective, be more potent, produce fewer side effects, be more easily absorbed, and/or have a better pharmacokinetic profile (e.g. higher oral bioavailability and/or lower clearance), than compounds known in the prior art.

Combination Therapy

The compounds of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, may also be administered in conjunction with other compounds used for the treatment of the above conditions.

In some embodiments, there is a combination therapy wherein a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, and a second active ingredient are administered concurrently, sequentially or in admixture, for the treatment of one or more of the conditions listed above. Such a combination may be used in combination with one or more further active ingredients.

Compounds described herein may be of use in treating cardiovascular, metabolic and renal disease in combination with agents that are cardiac therapies,
anti-hypertensives,
diuretics,
peripheral vasodilators,
lipid modifying agents,
anti-diabetic,
anti-inflammatory, or
anti-coagulant.

Examples of the above include, but are not restricted to, digitalis glycosides, anti-arrhythmics, calcium channel antagonists, ACE inhibitors, angiotensin receptor blockers (e.g. Valsartan), endothelin receptor blockers, β-blockers, thiazide diuretics, loop diuretics, cholesterol synthesis inhibitors such as statins (e.g. Rosuvastatin), cholesterol absorption inhibitors, cholesterylester transfer protein (CETP) inhibitors, anti-diabetic drugs such as insulin and analogues, GLP-1 analogues, sulphonamides, dipeptidyl peptidase 4 inhibitors, thiazolidinediones, SGLT-2 inhibitors, and anti-inflammatory drugs such as NSAID's and CCR2 antagonists, anti-coagulants such as heparins, thrombin inhibitors and inhibitors of factor Xa, platelet aggregation inhibitors, P2X7 antagonists and neprilysin inhibitors (e.g. Sacubitril).

When used in a combination therapy, it is contemplated that the compounds of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, and the other active ingredients may be administered in a single composition, completely separate compositions, or a combination thereof. It also is contemplated that the active ingredients may be administered concurrently, simultaneously, sequentially, or separately. The particular composition(s) and dosing frequency(ies) of the combination therapy will depend on a variety of factors, including, for example, the route of administration, the condition being treated, the species of the patient, any potential interactions between the active ingredients when combined into a single composition, any interactions between the active ingredients when they are administered to the animal patient, and various other factors known to physicians (in the context of human patients), veterinarians (in the context of non-human patients), and others skilled in the art.

Pharmaceutical Compositions

There is provided a method of treatment of a condition where inhibition of MPO is required, which method comprises administration of a therapeutically effective amount of a compound of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, to a person suffering from, or susceptible to, such a condition.

The compounds of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, will normally be administered via the oral, topical, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt thereof, in a pharmaceutically acceptable dosage form. Depending upon the disorder and patient to be treated and the route of administration, the compositions may be administered at varying doses. Conventional procedures for the selection and preparation of suitable pharmaceutical formulations are described in, for example, *Pharmaceuticals—The Science of Dosage Form Designs*, M. E. Aulton, Churchill Livingstone, $2^{nd}$ Ed. 2002.

The optimum dosage and frequency of administration will depend on the particular condition being treated and its severity; the species of the patient; the age, sex, size and weight, diet, and general physical condition of the particular patient; brain/body weight ratio; other medication the patient may be taking; the route of administration; the formulation; and various other factors known to physicians and others skilled in the art.

In some embodiments there is provided a pharmaceutical formulation comprising a compound of formulae (I), (Ia), (Ib), (II), (IIa), (IIb), (III), (IIIa), (IIIb), (IV), (IVa), or (IVb), a compound disclosed herein, a pharmaceutically acceptable salt thereof, or a pharmaceutically acceptable derivative thereof, in admixture with a pharmaceutically acceptable adjuvant, diluent and/or carrier.

The compounds of formulae (I), (Ia), (Ib), (II), (IIa), (IIb), (III), (IIIa), (IIIb), (IV), (IVa), or (IVb), or a compound disclosed herein, or a pharmaceutically acceptable salt thereof, may be present in the pharmaceutical formulation in a concentration from 0.1 to 99.5%, such as from 0.5 to 95%, by weight of the total formulation.

Some embodiments encompass pharmaceutically acceptable salts of the compounds of formulae (I), (Ia), (Ib), (II), (IIa), (IIb), (III), (IIIa), (IIIb), (IV), (IVa), or (IVb).

Some embodiments encompass pharmaceutically acceptable salts of the compounds disclosed herein.

Such a salt may be advantageous due to one or more of its chemical or physical properties, such as stability in differing temperatures and humidities, or a desirable solubility in $H_2O$, oil, or other solvent. In some instances, a salt may be used to aid in the isolation or purification of the compound. In some embodiments (particularly where the salt is intended for administration to an animal, e.g. a human, or is a reagent for use in making a compound or salt intended for administration to an animal), the salt is pharmaceutically acceptable.

The term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

Where the compound is sufficiently basic, pharmaceutically acceptable salts include, but are not limited to, inorganic or organic acid addition salts.

For reviews on suitable salts, see Berge et al., *J. Pharm. Sci.*, 1977, 66, 1-19 or *Handbook of Pharmaceutical Salts: Properties, selection and use*, P. H. Stahl, P. G. Vermuth, IUPAC, Wiley-VCH, 2002.

Where an acid co-former is a solid at r.t. and there is no or only partial proton transfer between the compound of formulae (I), (Ia), (Ib), (II), (IIa), (IIb), (III), (IIIa), (IIIb), (IV), (IVa), or (IVb), or a compound disclosed herein and such an acid co-former, a co-crystal of the co-former and said compound may result rather than a salt. All such co-crystal forms of the compound of formulae (I), (Ia), (Ib), (II), (IIa), (IIb), (III), (IIIa), (IIIb), (IV), (IVa), or (IVb), or a compound disclosed herein are encompassed herein.

It is also to be understood that certain compounds of formulae (I), (Ia), (Ib) (II), (IIa), (IIb), (III), (IIIa), (IIIb), (IV), (IVa), or (IVb), or certain compounds disclosed herein may exist in solvated form, e.g. hydrates, including solvates of a pharmaceutically acceptable salt of a compound of formulae (I), (Ia), (Ib), (II), (IIa), (IIb), (III), (IIIa), (IIIb), (IV), (IVa), or (IVb), or a compound disclosed herein.

In some embodiments, certain compounds of formulae (I), (Ia), (Ib), (II), (IIa), (IIb), (III), (IIIa), (IIIb), (IV), (IVa), or (IVb), or certain compounds disclosed herein may exist as racemates and racemic mixtures, single enantiomers, individual diastereomers and diastereomeric mixtures.

Certain compounds of formulae (I), (Ia), (Ib), (II), (IIa), (IIb), (III), (IIIa), (IIIb), (IV), (IVa), or (IVb), or certain compounds disclosed herein, may also contain linkages (e.g. carbon-carbon bonds, carbon-nitrogen bonds such as amide bonds) wherein bond rotation is restricted about that particular linkage, e.g. restriction resulting from the presence of a ring bond or double bond. Stereoisomers may be separated using conventional techniques, e.g. chromatography or fractional crystallization, or the stereoisomers may be made by stereoselective synthesis.

In some embodiments, the compounds of formulae (I), (Ia), (Ib), (II), (IIa), (IIb), (III), (IIIa), (IIIb), (IV), (IVa), or (IVb), compounds disclosed herein, and pharmaceutically acceptable salts thereof, encompass any isotopically-labelled (or "radio-labelled") derivatives of such a compound. Such a derivative is a derivative of said compound wherein one or more atoms are replaced by an atom having an atomic mass or mass number different from the atomic mass or mass number typically found in nature. Examples of isotopes that may be incorporated include $^{2}H$ (also written as "D" for deuterium).

In some embodiments, the compounds of formulae (I), (Ia), (Ib), (II), (IIa), (IIb), (III), (IIIa), (IIIb), (IV), (IVa), or (IVb) and compounds disclosed herein, may be administered in the form of a prodrug, or a pharmaceutically acceptable salt thereof, which is broken down in the human or animal body to give said compound of formulae (I), (Ia), (Ib), (II), (IIa), (IIb), (III), (IIIa), (IIIb), (IV), (IVa), or (IVb) or compound disclosed herein.

Various forms of prodrugs are known in the art. For examples of prodrug derivatives, see: *Nature Reviews Drug Discovery* 2008, 7, 255 and references cited therein.

Intermediate compounds may also exist in enantiomeric forms and may be used as purified enantiomers, diastereomers, racemates or mixtures.

EXAMPLES

The following abbreviations were used:

Abs Absolute

AcOH Acetic acid

Aq Aqueous

Boc tert-Butoxycarbonyl
$Boc_2O$ Di-tert-butyl dicarbonate
BnOH Phenylmethanol
Bu Butyl
n-BuLi 1-Butyllithium
n-BuOH 1-Buthanol
t-BuOH tert-Buthanol
Brine Saturated aqueous sodium chloride solution
Calcd Calculated
CataXCium A Di(adamantan-1-yl)(butyl)phosphane (CAS Reg. No. 321921-71-5)
Cbz Benzyloxycarbonyl
CPME Cyclopentylmethyl ether
DAST N,N-diethyl-1,1,1-trifluoro-$l^4$-sulfanamine
DCE Dichloroethane
DCM Dichloromethane
DEA Diethylamine
DIPEA N-ethyl-N-isopropyl-propan-2-amine
DMAP N,N-dimethylpyridin-4-amine
DMF N,N-dimethylformamide
DMP 3-oxo-$1l^5$-benzo[d][1,2]iodaoxole-1,1,1(3H)-triyl triacetate
DMSO Dimethyl sulfoxide
DPPA Diphenyl phosphorazidate
Dppf 1,1'-bis(diphenylphosphino)ferrocene
EDC 3-(((ethylimino)methylene)amino)-N,N-dimethyl-propan-1-amine
ESI Electrospray ionization
Et Ethyl
$Et_2O$ Diethyl ether
EtOAc Ethyl acetate
EtOH Ethanol
FA Formic acid
Fmoc (9H-fluoren-9-yl)methyl carbonyl
g Gram
G3 Generation 3
h Hour(s)
HPLC High performance liquid chromatography
HOAc Acetic acid
IPA 2-propyl alcohol
iPr Isopropyl
HRMS High resolution mass spectrometry
L Litre
LiHMDS Lithium bis(trimethylsilyl)amide
LC Liquid chromatography
M Molar
Me Methyl
MeCN Acetonitrile
mL Millilitre
mL Microlitre
MeOH Methanol
Min Minutes
Mmol Millimole
MS Mass spectrometry
MTBE Methyl tert-butyl ether
NIS 1-iodopyrrolidine-2,5-dione
NMR Nuclear magnetic resonance
OAc Acetat
OEt Ethoxy
Pd—C Palladium on charcoal
Ph Phenyl
Rt Room temperature
Sat Saturated
SFC Supercritical fluid chromatography
TEA Triethylamine
TFA Trifluoroacetic acid
THF Tetrahydrofuran
TMEDA $N^1,N^1,N^2,N^2$-tetramethylethane-1,2-diamine
TLC Thin layer chromatography
Ts Tosyl or 4-methylbenzenesulfonyl
TsOH 4-Methylbenzenesulfonic acid General Conditions (i) operations were carried out at room temperature (rt), i.e. in the range 17 to 28° C. and where needed under an atmosphere of an inert gas such as $N_2$;

(ii) where reactions refer to being degassed or purged, this can be performed for example by purging the reaction solvent with a constant flow of nitrogen for a suitable period of time (for example 5 to 10 min) or by repeatedly evacuating the vessel and backfill with appropriate inert atmosphere (for example nitrogen (g) or argon (g));

(iii) where reactions refer to the use of a microwave reactor, one of the following microwave reactors were used: Biotage Initiator, Personal Chemistry Emrys Optimizer, Personal Chemistry Smith Creator or CEM Explorer;

(iv) in general, the course of reactions was followed by thin layer chromatography (TLC) and/or analytical high performance liquid chromatography (HPLC or UPLC) which was usually coupled to a mass spectrometer (LCMS).

(v) when necessary, organic solutions were dried over anhydrous $MgSO_4$ or $Na_2SO_4$, or by using ISOLUTE® Phase Separator, and work-up procedures were carried out using traditional phase separating techniques. When a drying agent such as e.g. $MgSO_4$ or $Na_2SO_4$ is used for drying an organic layer, it is understood that said organic layer is filtered before concentration of said layer.

(vi), evaporations were carried out either by rotary evaporation in vacuo or in a Genevac HT-4/EZ-2 or Biotage V10;

(vii) unless otherwise stated, flash column chromatography was performed on straight phase silica, using either Merck Silica Gel (Art. 9385) or prep-packed cartridges such as Biotage® SNAP cartridges (40-63 μm silica, 4-330 g), Biotage® Sfär Silica HC D cartridges (20 μm, 10-100 g), Interchim puriFlash™ cartridges (25 μm, 4-120 g), Interchim puriFlash™ cartridges (50 μm, 25-330 g), Grace™ GraceResolv™ Silica Flash Cartridges (4-120 g) or Agela Flash Colum Silica-CS cartridges (80-330 g), or on reversed phase silica using Agela Technologies C-18, spherical cartridges (20-35 μm, 100 A, 80-330 g), manually or automated using a Grace Reveleris® X2 Flash system or similar system;

(viii) preparative reverse phase HPLC and preparative reverse phase SFC were performed using standard HPLC and SFC instruments, respectively, equipped with either a MS and/or UV triggered fraction collecting instrument, using either isocratic or a gradient of the mobile phase as described in the experimental section.

Relevant fractions were collected, combined and freeze-dried or evaporated to give the purified compound or relevant fractions were collected, combined and concentrated at reduced pressure, extracted with DCM or EtOAc, and the organic phase was dried either over $Na_2SO_4$ or by using a phase-separator, and then concentrated at reduced pressure to give the purified compound.

(ix) chiral preparative chromatography was carried out using HPLC or SFC on a standard HPLC or SFC instruments, respectively, and using either isocratic or gradient run with mobile phase as described in the experimental section;

(x) yields, where present, are not necessarily the maximum attainable, and when necessary, reactions were repeated if a larger amount of the reaction product was required;

(xi) where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;

(xii) in general, the structures of the end-products of the compounds described herein were confirmed by nuclear magnetic resonance (NMR) and/or mass spectral techniques; proton NMR chemical shift values were measured on the delta scale using Bruker Avance III 300, 400, 500 and 600 spectrometers, operating at $^1$H frequencies of 300, 400, 500 and 600 MHz, respectively. The experiments were typically recorded at 25° C. Chemical shifts are given in ppm with the solvent as internal standard. Protons on heteroatoms such as NH and OH protons are only reported when detected in NMR and can therefore be missing. In certain instances, protons can be masked or partially masked by solvent peaks and will therefore either be missing and not reported or reported as multiplets overlapping with solvent. The following abbreviations have been used (and derivatives thereof, e.g. dd, doublet of doublets, etc.): s, singlet; d, doublet; t, triplet; q, quartet; m, multiplet; br, broad; qn, quintet; p, pentet. In some cases, the structures of the end-products of the compounds disclosed herein might appear as rotamers in the NMR-spectrum, in which instances only peaks of the major rotamer are reported. Electrospray mass spectral data were obtained using a Waters Acquity UPLC coupled to a Waters single quadrupole mass spectrometer or similar equipment, acquiring both positive and negative ion data, and generally, only ions relating to the parent structure are reported; high resolution electrospray mass spectral data were obtained using a Waters XEVO qToF mass spectrometer or similar equipment, coupled to a Waters Acquity UPLC, acquiring either positive and negative ion data, and generally, only ions relating to the parent structure are reported (xiii) intermediates were not necessarily fully purified but their structures and purity were assessed by TLC, analytical HPLC/UPLC, and/or NMR analysis and/or mass spectrometry;

(xiv) unless stated otherwise compounds containing an asymmetric carbon and/or sulfur atom were not resolved;

(xv) in general Examples and Intermediate compounds are named using ChemDraw Professional version 20.1.1.125 from PerkinElmer. ChemDraw Professional version 20.1.1.125 generates the names of chemical structures using the Cahn-Ingold-Prelog (CIP) rules for stereochemistry and follows IUPAC rules as closely as possible when generating chemical names. Stereoisomers are differentiated from each other by stereodescriptors cited in names and assigned in accordance with the CIP rules.

ChemDraw is optionally using labels in the graphical representation of stereocenters such as '&' and 'or' to describe the configuration of the stereochemical centers present in the structure.

In general chemical structures of Examples and Intermediates containing the label '&' at a stereocenter, means the configuration of such Example or Intermediate at that stereocenter is a mixture of both (R) and (S); and a label 'or' means the configuration of such Example or Intermediate at that stereocenter is either (S) or (R). Absolute, unspecified, '&', and 'or' stereocenters can all be present in a single structure.

In general, the '&' and 'or' label at each stereocenter present in a structure may also include a number. The numbers indicate that stereocenters may or may not vary independently to each other, so that if two or more stereocenters do not vary independently of each other. i.e., are fixed relative to each other, they have the same number, but if they do vary independently of each other they have different numbers. For example, if a compound has two stereocenters in a ring which are independent of each other, the one stereocenter will be labelled "or1" (or "&1") and the other labelled "or2" (or "&2") whereas if a compound has two stereocenters in a ring and they are fixed relative to each other and do not vary independently of each other, both stereocenters would be labelled "or1" (or "&1") and if a compound had two stereocenters that are fixed relative to each other and a third stereocenter that varies independently to the former stereocenters, the first two stereocenters would both be labelled "or1" (or "&1") and the third labeled "or2" (or "&2")

It is further noted that as an artifact of this automatic labelling from ChemDraw, in some examples, two isomers are represented side by side, with the stereocenter(s) in isomer 1 labelled with a "or1" and the stereocenter(s) in isomer 2 labelled with a "or2". It is to be understood that these two compounds are believed to be isomers of each other, as demonstrated by different properties, e.g., different elution times on a chiral HPLC.

In general, for chemical structures of Examples and Intermediates where all stereocenters present are racemic, no flag is designated to the stereocenter(s) and the structure is drawn with a straight bond at each stereocenter.

In general for structures of Examples and Intermediates where all of the stereocenters are designated as '&', the structure is named with a "rac-" prefix. For structures of Examples and Intermediates where all of the stereocenters are designated as 'or', the structure is named with a "rel-" prefix.

In general the label "Isomer 1" corresponds to the first eluted isomer, and "Isomer 2" corresponds to the second eluted isomer, on a given chiral HPLC column and eluent, and are used to distinguish two isomers containing one or more stereocenters with absolute unknown configuration.

In general, for Examples or Intermediates containing more than one stereocenter the relative stereochemistry is described using configurational descriptors 'S' and 'R' for the stereogenic centers and using the "rac-" or "rel-" prefix cited at the front of the name.

It is to be understood that an Example or Intermediate named with the "rel-" prefix is a single isomer, and while the stereocenter(s) in the isomer have been designated as "R" or "S", the actual stereochemistry of that particular isomer could be the opposite of the label. For example, while Example 12a (Isomer 1) is named "rel-(R)-1-(2-(4,4-Difluoropiperidin-2-yl)benzyl)-2-thioxo-1,2,3,5-tetrahydro-4H-pyrrolo[3,2-d]pyrimidin-4-one", Example 12a may be "(S)-

1-(2-(4,4-Difluoropiperidin-2-yl)benzyl)-2-thioxo-1,2,3,5-tetrahydro-4H-pyrrolo[3,2-d]pyrimidin-4-one". For example, while Example 18b (Isomer 1) is named "rel-2-thioxo-3-(2-((2R,4R)-4-(trifluoromethyl)piperidin-2-yl)benzyl)-1,2,3,7-tetrahydro-6H-purin-6-one", Example 18b may be "rel-2-thioxo-3-(2-((2S,4S)-4-(trifluoromethyl)piperidin-2-yl)benzyl)-1,2,3,7-tetrahydro-6H-purin-6-one".

It is to be understood that an Example or Intermediate named with the "rac-" prefix is a mixture of isomers, and while the relative stereochemistry of the stereocenters in the isomer have been designated with "R" or "S" descriptors, the actual stereochemistry of that particular isomer mixture contains also the opposite of said descriptors. For example, while Example 17b is named "rac-2-thioxo-1-(2-((2R,4R)-4-(trifluoromethyl)piperidin-2-yl)benzyl)-1,2,3,5-tetrahydro-4H-pyrrolo[3,2-d]pyrimidin-4-one", Example 17b also contains "2-thioxo-1-(2-((2S,4S)-4-(trifluoromethyl)piperidin-2-yl)benzyl)-1,2,3,5-tetrahydro-4H-pyrrolo[3,2-d]pyrimidin-4-one".

Preparation of the Compounds

General Schema

In another aspect there is provided a process for preparing compounds of the formula (I) and formula (II) or a pharmaceutically acceptable salt thereof, which process comprises:

a) The compounds of formula (I) in which $Y^1$, $Y^2$, $Y^3$, $Y^4$, $Y^5$ and X are defined as above can be formed by reacting a compound of formula (V), in which $Y^1$, $Y^2$, $Y^3$, $Y^4$, $Y^5$ and X are defined as in formula (I) and $LG_1$ is a suitable leaving group such as $(C_1$-$C_4)$alkoxy (such as OEt) or $NH_2$, (V)

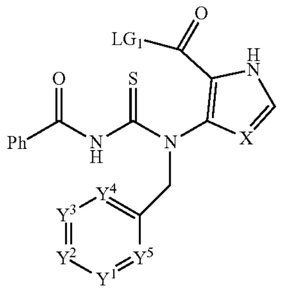

with a base such as $Cs_2CO_3$, NaOH, $NH_3$ or $NH_4OH$. Typically the reaction is carried out in a suitable organic solvent for example MeOH or EtOH for a prolonged time (e.g. 3-24 h) at temperatures ranging typically from 20° C. to 80° C.

Where necessary, the resultant compound of formula (I) may be converted into a pharmaceutically acceptable salt of formula (I), and where desired the resultant compound of formula (I) may be separated into its individual optical isomers.

The compounds of formula (V) may be prepared by reacting a compound of formula (VI) in which $Y^1$, $Y^2$, $Y^3$, $Y^4$, $Y^5$ and X are defined as in formula (I) and $LG_1$ is defined as above.

(VI)

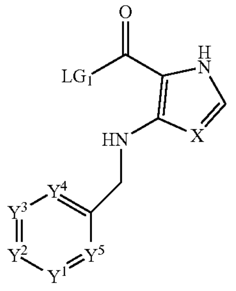

with benzoyl isothiocyanate (1 to 3 eq). The reaction is typically carried out in an inert organic solvent such as for example DCM or MeCN at rt for 1 to 24 h. Optionally the reactions can be carried out in the presence of an organic base such as DIPEA.

The compounds of formula (VI) above can be prepared by reacting a compound of formula (VII) in which $Y^1$, $Y^2$, $Y^3$, $Y^4$ and $Y^5$ are defined as in formula (I) with a compound of formula (VIII) wherein X and $LG_1$ are defined as above.

(VII)

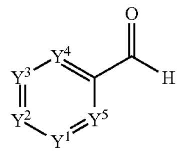

(VIII)

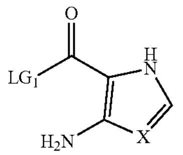

The conditions are such that a reductive alkylation of the compounds of the formula (VIII) forms an N—C bond between the nitrogen atom of the compounds of formula (VIII) and the carbon atom of the aldehyde group of the compounds of formula (VII). The reaction conditions are conventional reductive alkylation conditions. Usually, the amine compound, as a hydrochloride salt, is treated with DIPEA or TEA and HOAc in an organic solvent e.g. EtOH, MeOH, DCM or DCE, and in the presence of the aldehyde compound of formula (VII). After the mixture has been stirred for some time, e.g. at rt, a reducing agent, such as $NaBH_3CN$, $NaBH_4$ or $NaBH(OAc)_3$, is added and the resultant mixture is stirred at temperatures ranging typically from 20° C. to 80° C. until the reaction is complete, e.g. for 1 to 20 h, to give the compound of formula (VI). (See for example, *J. Org. Chem* 1996, 61, 3849).

Certain compounds of formula (VII) in which $Y^1$, $Y^2$, $Y^3$, $Y^4$ and $Y^5$ are defined as in formula (I) may be prepared from the compounds of formula (IX), (X), (XI) and (XII) according to the Methods illustrated in Scheme TA1 and the following descriptions and by methods analogous to those described in the examples.

Scheme TA1

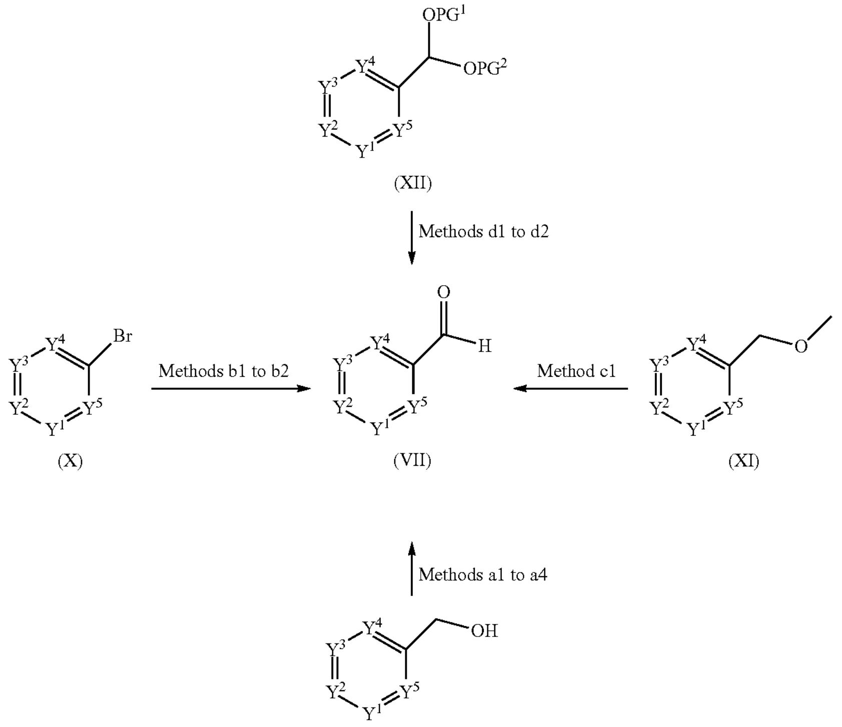

(XII)

(X) (VII) (XI)

(IX)

Method a1: A compound in accordance to formula (VII) can be obtained by reacting a compound of formula (IX) with pyridine×$SO_3$ (e.g. 2 eq) in the presence of TEA (e.g. 3.5 eq) in DMSO at rt until the reaction is complete (1 to 17 h). (Parikh-Doering conditions, *J. Am. Chem. Soc.* 1967, 89, 5505).

Method a2: A compound in accordance to formula (VII) can be obtained by reacting a compound of formula (IX) with pyridinium chlorochromate (PCC) (e.g. 1.5 eq) in an inert organic solvent such as for instance DCM at rt for a prolonged time (e.g. 1-2 h). (*Synthesis,* 1982, 245).

Method a3: A compound in accordance to formula (VII) can be obtained by reacting a compound of formula (IX) with DMP (e.g. 1.1 to 2 eq) in an inert organic solvent such as for instance DCM at temperatures ranging typically from 0° C. to 30° C. for a prolonged time (e.g. 1 h). (*J. Am. Chem. Soc.* 1991, 113, 7277).

Method a4: A compound in accordance to formula (VII) can be obtained by reacting a compound of formula (IX) with an excess of active $MnO_2$ (e.g. 5-7 eq) in an inert organic solvent such as for instance DCM at rt for a prolonged time (e.g. 48 h) (*Synthesis,* 1976, 65).

Method b1: A compound in accordance to formula (VII) can be obtained by treating a compound of formula (X) with synthesis gas ($H_2$/CO, 1/1) in the presence of a catalyst, which may as such e.g. be a mixture of diacetoxypalladium, di((3S,5S,7S)-adamantan-1-yl)(butyl)-phosphine and tetramethylethylenediamine, in an organic solvent, such as for instance toluene. Typically, the reaction is performed at about 5 bar and at about 100° C. for about (6 to 21 h). (Angew. Chem. Int. ed. 2006, 45, 154).

Method b2: A compound in accordance to formula (VII) can be obtained by treating a compound of formula (X) with a strong base, such as e.g. butyllithium in an inert solvent, such as e.g. THF, and then treating the resultant mixture with DMF. The reaction can be carried out at a low temperature such as e.g. at −78° C. to −60° C.

Method c1: A compound in accordance to formula (VII) can be obtained by treating a compound of formula (XI) with nitric acid (4-8 eq) in an inert organic solvent as for instance DCM. The reaction is usually carried out at rt for a prolonged time (24-72 h)

Method d1: A compound in accordance to formula (VII) can be obtained by treating a compound of formula (XII), wherein $PG^1$ and $PG^2$ are protecting groups, which may be the same as each other, e.g. methyl or ethyl, and, which may or may not be connected to each other to form a ring, (e.g. $—CH_2—CH_2—$ or $—CH_2—CH_2—CH_2—$), with an acid such as TsOH (e.g. 0.1-0.2 eq) in a mixture of water/acetone at temperatures ranging typically from 25° C. to 60° C. for a prolonged time (typically overnight).

Method d2: A compound in accordance to formula (VII) can be obtained by treating a compound of formula (XII), wherein $PG^1$ and $PG^2$ are defined as above with an excess aqueous HCl in MeCN at temperatures ranging typically from 25° C. to 90° C. for a prolonged time (typically overnight).

The compounds of formula (VIII) in which X and $LG_1$ are as defined above, are commercially available, known in the art or may be prepared in conventional manner known by a person skilled in the art.

The compounds of formula (IX), (X), (XI) and (XII) are commercially available, known in the art or may be prepared by methods analogous to those described in the examples and in the descriptions following below or in a conventional manner known by a person skilled in the art.

The compounds of formula (II) in which $Y^1$, $Y^2$, $Y^3$, $Y^4$, X, A, $R^1$, n, p and s are defined as above in Formula (II) can be formed by reacting a compound of formula (XIII), in which $Y^1$, $Y^2$, $Y^3$, $Y^4$, X, A, $R^1$, n, p and s are defined as above and $LG_1$ is as defined above.

(XIII)

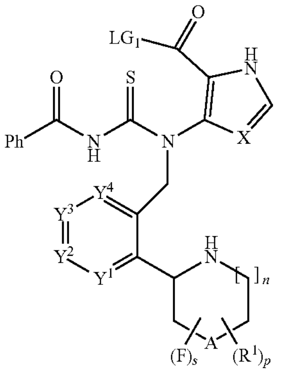

with a base such as $Cs_2CO_3$, NaOH, $NH_3$ or $NH_4OH$. Typically the reaction is carried out in a suitable organic solvent for example MeOH or EtOH for a prolonged time (3-24 h) at temperatures ranging typically from 20° C. to 80° C. Where necessary, the resultant compound of formula (II) may be converted into a pharmaceutically acceptable salt of formula (II), and where desired the resultant compound of formula (II) may be separated into its individual optical isomers.

The compounds of formula (XIII) may be prepared by reacting a compound of formula (XIV) in which $Y^1$, $Y^2$, $Y^3$, $Y^4$, X, A, $R^1$, n, p and s are defined as in formula above in Formula (II) and $LG_1$ is as defined above.

(XIV)

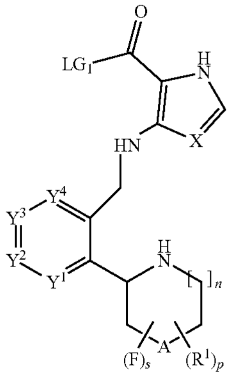

with benzoyl isothiocyanate (1 to 3 eq). The reaction is typically carried out in an inert organic solvent such as for example DCM or MeCN at rt for 1 to 24 h. Optionally the reactions can be carried out in the presence of an organic base such as DIPEA.

The compounds of formula (XIV) above can be prepared by reacting a compound of formula (XV) in which $Y^1$, $Y^2$, $Y^3$, $Y^4$, A, $R^1$, n, p and s are defined as in formula (I) with a compound of formula (VIII) wherein X and $LG_1$ are defined as above.

(XV)

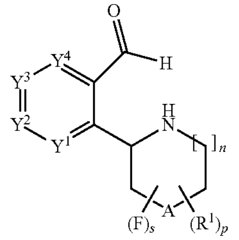

(VIII)

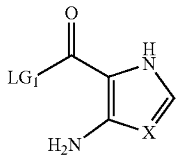

The conditions are such that a reductive alkylation of the compounds of the formula (VIII) forms an N—C bond between the nitrogen atom of the compounds of formula (VIII) and the carbon atom of the aldehyde group of the compounds of formula (XV). The reaction conditions are conventional reductive alkylation conditions. Usually, the amine compound, as a hydrochloride salt, is treated with DIPEA or TEA and HOAc in an organic solvent e.g. EtOH, MeOH, DCM or DCE, and in the presence of the aldehyde compound of formula (XV). After the mixture has been stirred for some time, e.g. at rt, a reducing agent, such as $NaBH_3CN$, $NaBH_4$ or $NaBH(OAc)_3$, is added and the resultant mixture is stirred at temperatures ranging typically from 20° C. to 80° C. until the reaction is complete, e.g. for 1 to 20 h, to give the compound of formula (XIV). (See for example, *J. Org. Chem* 1996, 61, 3849).

The compounds of formula (VIII) in which X and $LG_1$ are as defined above, are commercially available, known in the art, or may be prepared in conventional manner known by a person skilled in the art.

Certain compounds of formula (XV) in which $Y^1$, $Y^2$, $Y^3$, $Y^4$, A, $R^1$, n, p and s are defined as in formula (I) may be prepared from the compounds of formula (XVI), (XVII), (XVIII) and (XIX) according to the Methods illustrated in Scheme TA2 and the following descriptions and by methods analogous to those described in the examples.

Scheme TA2

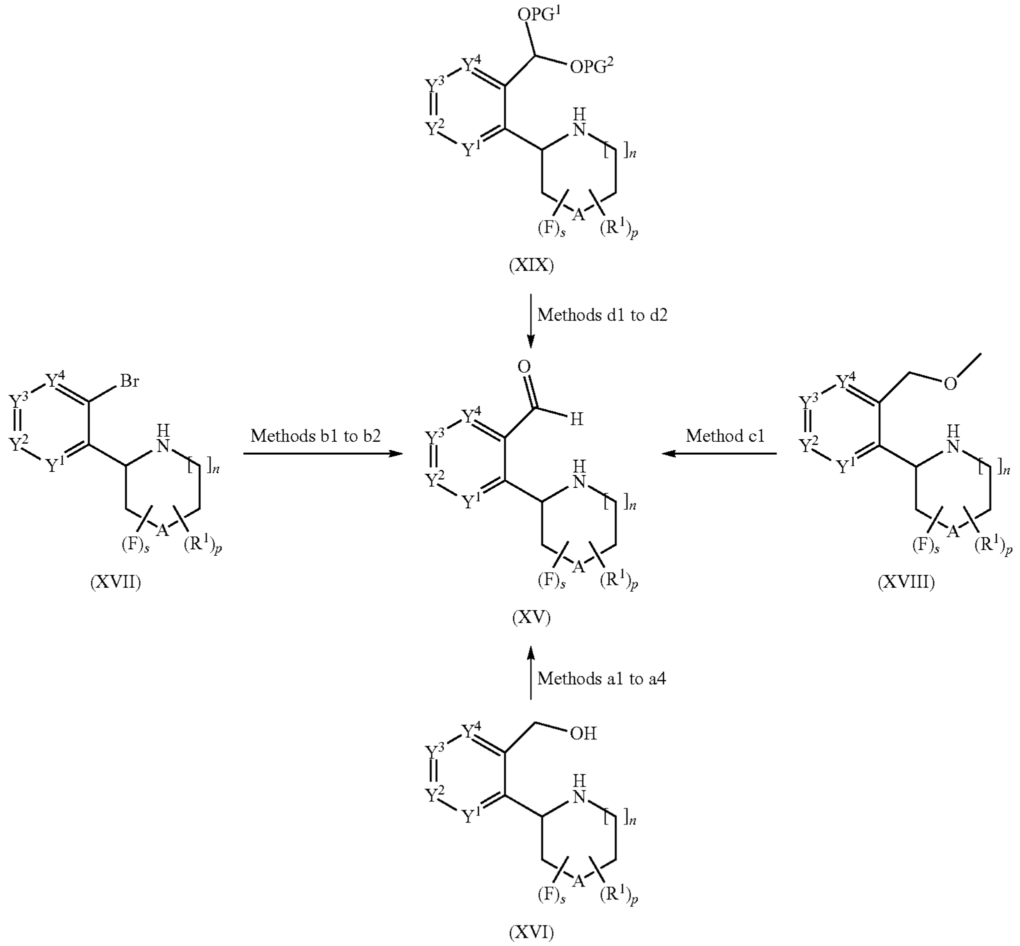

Method a1: A compound in accordance to formula (XV) can be obtained by reacting a compound of formula (XVI) with pyridine×$SO_3$ (e.g. 2 eq) in the presence of TEA (e.g. 3.5 eq) in DMSO at rt until the reaction is complete (1 to 17 h). (Parikh-Doering conditions, *J. Am. Chem. Soc.* 1967, 89, 5505).

Method a2: A compound in accordance to formula (XV) can be obtained by reacting a compound of formula (XVI) with pyridinium chlorochromate (PCC) (e.g. 1.5 eq) in an inert organic solvent such as for instance DCM at rt for a prolonged time (e.g. 1-2 h). (*Synthesis,* 1982, 245).

Method a3: A compound in accordance to formula (XV) can be obtained by reacting a compound of formula (XVI) with DMP (e.g. 1.1 to 2 eq) in an inert organic solvent such as for instance DCM at temperatures ranging typically from 0° C. to 30° C. for a prolonged time (e.g. 1 h). (*J. Am. Chem. Soc.* 1991, 113, 7277).

Method a4: A compound in accordance to formula (XV) can be obtained by reacting a compound of formula (XVI) with an excess of active $MnO_2$ (e.g. 5-7 eq) in an inert organic solvent such as for instance DCM at rt for a prolonged time (e.g. 48 h) (*Synthesis,* 1976, 65).

Method b1: A compound in accordance to formula (XV) can be obtained by treating a compound of formula (XVII) with synthesis gas ($H_2$/CO, 1/1) in the presence of a catalyst, which may e.g. be a mixture of diacetoxypalladium, di((3S, 5S,7S)-adamantan-1-yl)(butyl)-phosphine and tetramethylethylenediamine, in an organic solvent, such as for instance toluene. Typically, the reaction is performed at about 5 bar and at about 100° C. for about 6 to 21 h. (Angew. Chem. Int. ed. 2006, 45, 154).

Method b2: A compound in accordance to formula (XV) can be obtained by treating a compound of formula (XVII) with a strong base, such as e.g. butyllithium in an inert solvent, such as e.g. THF, and then treating the resultant mixture with DMF. The reaction can be carried out at a low temperature such as e.g. at −78° C. to −60° C.

Method c1: A compound in accordance to formula (XV) can be obtained by treating a compound of formula (XVIII) with nitric acid (4-8 eq) in an inert organic solvent as for instance DCM. The reaction is usually carried out at rt for a prolonged time (24-72 h)

Method d1: A compound in accordance to formula (XV) can be obtained by treating a compound of formula (XIX), wherein $PG^1$ and $PG^2$ are defined as above, with an acid such as TsOH (e.g. 0.1-0.2 eq) in a mixture of water/acetone at temperatures ranging typically from 25° C. to 60° C. for a prolonged time (typically overnight).

Method d2: A compound in accordance to formula (XV) can be obtained by treating a compound of formula (XIX), wherein $PG^1$ and $PG^2$ are defined as above with an excess aqueous HCl in MeCN at temperatures ranging typically from 25° C. to 90° C. for a prolonged time (typically overnight).

The compounds of formula (VIII) in which X and $LG_1$ are as defined above, are commercially available, known in the art or may be prepared in conventional manner known by a person skilled in the art.

The compounds of Formula (XVI), (XVII), (XVIII) and (XIX) are commercially available, known in the art or may be prepared by methods analogous to those described in the examples and in the descriptions following below or in a conventional manner known by a person skilled in the art.

Certain compounds of formula (XVI), (XVII), (XVIII) and (XIX) in which $Y^1$, $Y^2$, $Y^3$, $Y^4$, A, $R^1$, n, p and s are defined as in formula (I) and $FG^1$ is $CH_2OH$, Br, $CH_2$—OMe or $CH(OPG^1)(OPG^2)$, wherein $PG^1$ and $PG^2$ are defined as above, may be prepared according to the Methods illustrated in Scheme TA3

Scheme TA3

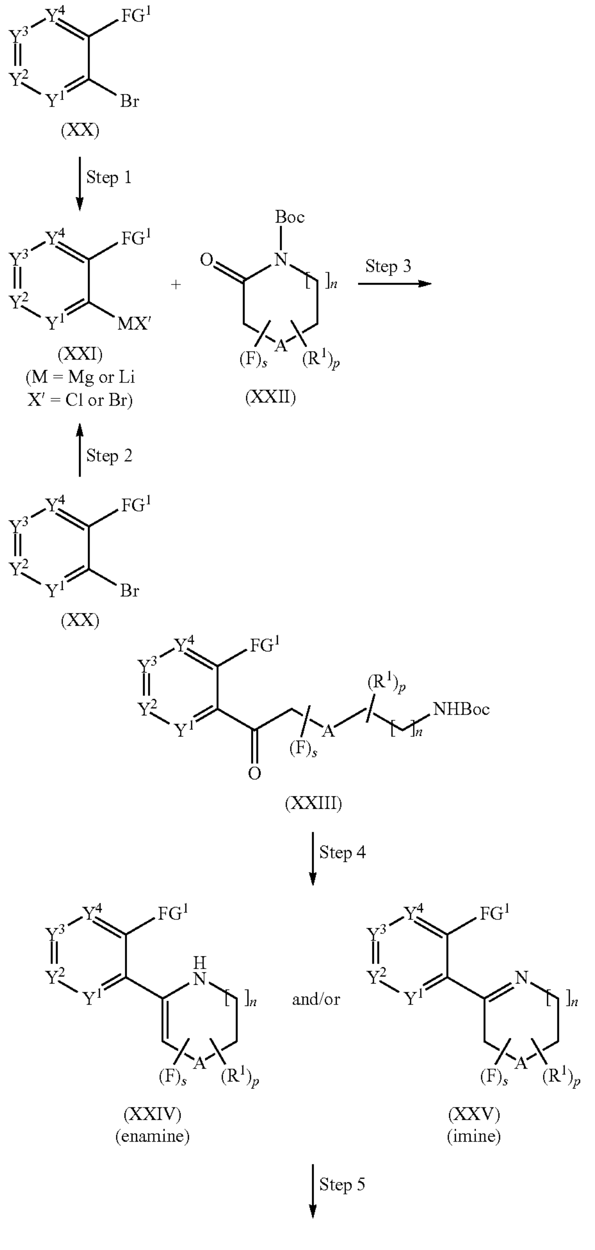

(XX)
(XXI)
(M = Mg or Li
X' = Cl or Br)
+
(XXII)
(XX)
(XXIII)
(XXIV)
(enamine)
and/or
(XXV)
(imine)

-continued

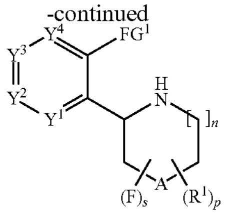

(XVI), (XVII),
(XVIII) and (XIX)

Step 1: A compound in accordance with formula (XXI), in which $Y^1$, $Y^2$, $Y^3$, $Y^4$ and $FG^1$ are as previously defined and M is Li, can be obtained by treating a compound with formula (XX) in which $Y^1$, $Y^2$, $Y^3$, $Y^4$ and $FG^1$ are as previously defined, with a strong base, such as e.g. butyllithium in an inert organic solvent, such as e.g. THF. The reaction is can be carried out at a low temperatures such as e.g. at −78° C. under an inert atmosphere, e.g. nitrogen.

Step 2: A compound in accordance with formula (XXI), in which $Y^1$, $Y^2$, $Y^3$, $Y^4$ and $FG^1$ are as previously defined and M is Mg, can be obtained by treating a compound with formula (XX) in which $Y^1$, $Y^2$, $Y^3$, $Y^4$ and $FG^1$ are as previously defined with iPrMgClxLiCl (Turbo Grignard) in an inert organic solvent, such as e.g. THF. The reaction can be carried out at temperatures ranging from −40° C. to rt depending on the substrates used, under an inert atmosphere, e.g. nitrogen. (*Chem. Eur. J.* 2019, 25, 2695).

Step 3: A compound in accordance with formula (XXIII) in which $Y^1$, $Y^2$, $Y^3$, $Y^4$, A, $R^1$, n, p and s are defined as in formula (I) and $FG^1$ is defined as above, can be obtained by reacting a compound of formula (XXI) wherein $Y^1$, $Y^2$, $Y^3$, $Y^4$ and $FG^1$ are as previously defined and M is Mg or Li with a compound of formula (XXII) in an inert organic solvent, such as e.g. THF. The reaction can be carried out at temperatures ranging from −78° C. to rt depending on the substrates used under an inert atmosphere, e.g. nitrogen.

Step 4: A compound in accordance with formula (XXIV) (enamine) and/or formula (XXV) (imine) in which $Y^1$, $Y^2$, $Y^3$, $Y^4$, A, $R^1$, n, p, and s are defined as in formula (I) and $FG^1$ is defined as above, can be obtained by treating a compound of formula (XXIII) with a strong acid such as TFA or HCl. The reaction is carried out in an inert organic solvent such as e.g. DCM or MeOH at temperatures ranging from 20° C. to 100° C. The compounds of formula (XXIV) and formula (XXV) can either be isolated before reduction, or for compounds of formula (XXV) can be reduced in situ, according to the procedures described in step 5.

Step 5: Certain compounds in accordance with formula (XVI), (XVII), (XVIII) and (XIX) in which $Y^1$, $Y^2$, $Y^3$, $Y^4$, A, $R^1$, n, p and s are defined as in formula (I) and $FG^1$ is defined as above can be obtained by either methods described in i) to iii) below:

i) treating a compound of formula (XXV) as defined above with a reducing agent such as e.g. $NaBH_4$, $NaBH(OAc)_3$ or $NaBH_3CN$. The reaction is carried out in an intert organic solvent such as e.g. MeOH, DCM or THF at rt or, ii) treating a compound of formula (XXIV) as defined above with a metal catalyst such as e.g. Pd/C, $Pd(OH)_2/C$ or $PtO_2$ under an atmosphere of hydrogen at about rt for a prolonged time. The reaction is carried out in an inert organic solvent such as e.g. HOAc, MeOH, EtOAc or a mixture of HOAc/MeOH. Optionally the reaction may be carried out in the presence of an organic base such as e.g. DIPEA or, iii) reacting a compound of formula (XXIV) as defined above with $LiBHEt_3$ in an inert organic solvent such as e.g. THF at about 0° C. to about rt.

Certain compounds of formula (XVI), (XVII), (XVIII) and (XIX) in which $Y^1$, $Y^2$, $Y^3$, $Y^4$, and n are as defined in formula (I) and $FG^1$ is defined as above, s is 0, p is 0 and A is $CH_2$ may be prepared according to the Methods illustrated in Scheme TA4.

Scheme TA4

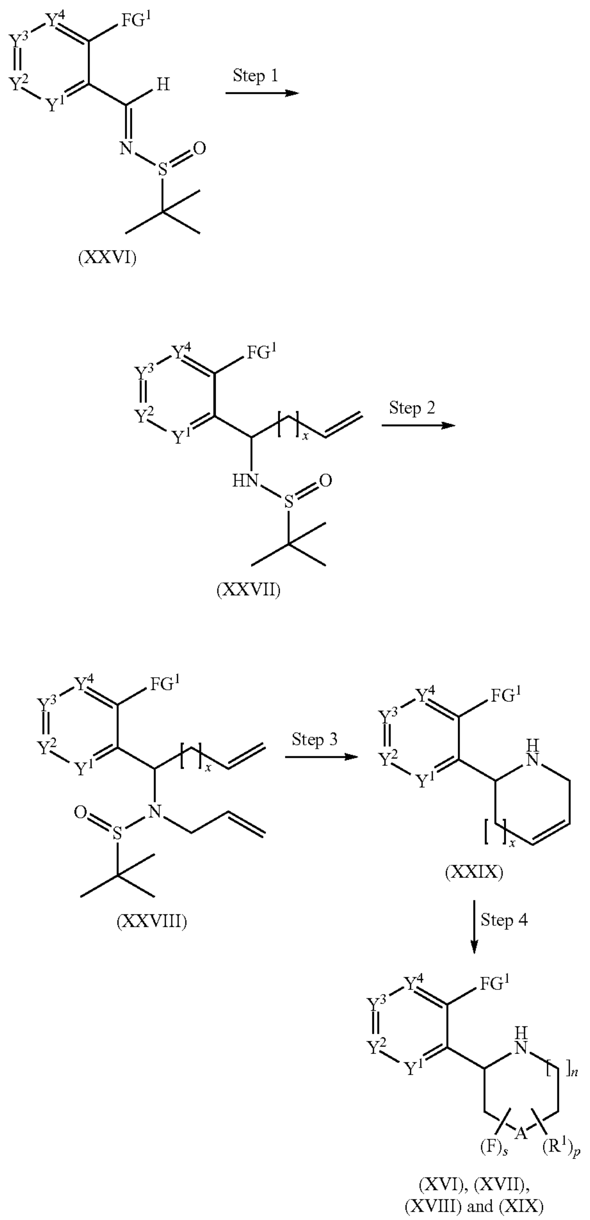

(XXVI)

(XXVII)

(XXVIII)

(XXIX)

(XVI), (XVII), (XVIII) and (XIX)

Step 1: A compound in accordance with formula (XXVII), in which $Y^1$, $Y^2$, $Y^3$, $Y^4$ and $FG^1$ are as previously defined and x is 0, 1 or 2 can be obtained by reacting a compound with formula (XXVI) with a Grignard reagent, $CH_2{=}CH{-}(CH_2)_x{-}MgBr$ wherein x is 0, 1 or 2, optionally in the presence of $CeCl_3$, in an inert solvent, such as e.g. THFor DCM, at about −78° C., and optionally separating the obtained intermediate into its diastereomers by conventional methods, such as e.g. by silica gel chromatography. (*Chem. Rev.* 2010, 110, 3600)

Step 2: A compound in accordance with formula (XXVIII), in which $Y^1$, $Y^2$, $Y^3$, $Y^4$ and $FG^1$ are as previously defined and x is 0, 1 or 2 can be obtained by reacting a compound with formula (XXVII) defined as above with allylbromide in the presence of a strong base such as e.g. LiHMDS or NaH in an inert organic solvent such as e.g. THF at about rt to 60° C.

Step 3: A compound in accordance with formula (XXIX), in which $Y^1$, $Y^2$, $Y^3$, $Y^4$ and $FG^1$ are as previously defined and x is 0, 1 or 2 can be obtained by reacting a compound with formula (XXVIII) defined as above with a metathesis catalyst such as for example e.g. the Grubbs II catalyst. The reaction is carried out in an inert organic solvent such as e.g. DCM at about rt to 40° C. for a prolonged reaction time. Optionally, the N-sulfinyl group is removed by treatment with a strong acid such as for example HCl in an organic solvent e.g. MeOH. (*Chem. Soc. Rev.* 2018, 47, 4510).

Step 4: Certain compounds of formula (XVI), (XVII), (XVIII) and (XIX) in which $Y^1$, $Y^2$, $Y^3$, $Y^4$ and n are defined as in formula (I) and $FG^1$ is defined as above, s is 0, p is 0 and A is $CH_2$ can be obtained by reduction of a compound of formula (XXIX) as defined formula (I) with a metal catalyst such as e.g. Pd/C under an atmosphere of hydrogen at rt for a prolonged time. The reaction is carried out in an inert organic solvent such as e.g. MeOH, THF or EtOAc.

Certain compounds of formula (XVI), (XVIII) and (XIX) in which $Y^1$, $Y^2$, $Y^3$ and $Y^4$ are C—H, C-halo or C—$CF_3$, n is 1, p is 0 or 1, s is 0, A is $CH_2$ or CH—$R^2$, $R^1$ and $R^2$ are as defined in formula (I), and $FG^2$ is $CH_2OH$, $CH_2OMe$ or $CH(OPG^1)(OPG^2)$, wherein $PG^1$ and $PG^2$ are defined as above, may be prepared according to the Method illustrated in Scheme TA5.

Scheme TA5

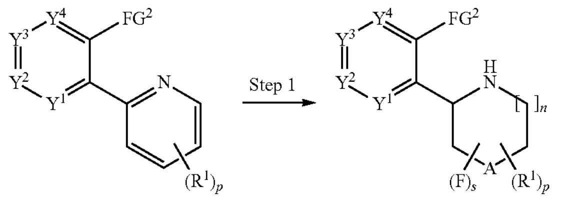

(XXX)

(XVI), (XVIII) and (XIX)

Step 1:

Compounds of formula (XVI), (XVIII) or (XIX), defined as in Scheme TA5, may be obtained by treating a compound of formula (XXX) in which $Y^1$, $Y^2$, $Y^3$ and $Y^4$ are C—H, C-halo or C—$CF_3$, p is 0 or 1, $R^1$ is as defined in formula (I) and $FG^2$ is $CH_2OH$, $CH_2OMe$ or $CH(OPG^1)(OPG^2)$, wherein $PG^1$ and $PG^2$ are defined as above, with a metal catalyst such as e.g. $PtO_2$ under an atmosphere of hydrogen (1 to 5 bar) at about rt for a prolonged time. The reaction can be carried out under acidic conditions e.g. in HOAc or in a mixture of HCl/MeOH or HCl/EtOH.

Certain compounds of formula (XVI), (XVIII) and (XIX) in which $Y^1$, $Y^2$, $Y^3$ and $Y^4$ defined as in formula (I), n is 0, 1 or 2, p is 0 or 1, s is 0, A is $CH_2$ or CH—$R^2$ and $R^1$ and $R^2$ are as defined as in formula (I), and $FG^2$ is defined as above may be prepared according to the Methods illustrated in Scheme TA6.

Scheme TA6

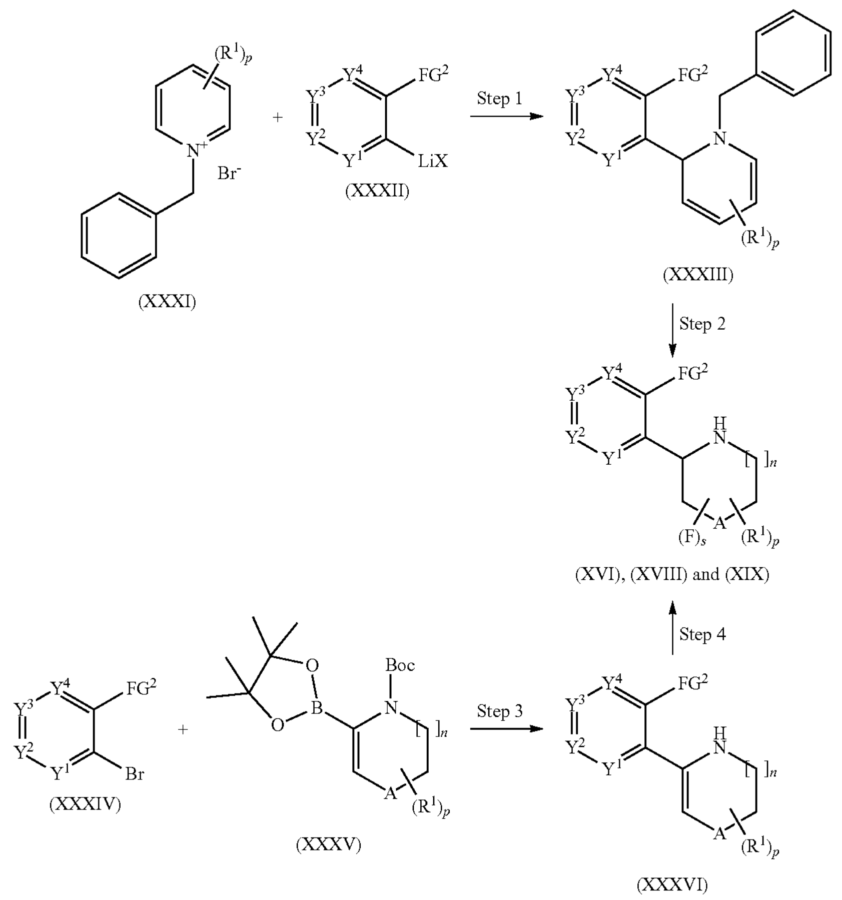

(XXXI)
(XXXII)
(XXXIII)
(XVI), (XVIII) and (XIX)
(XXXIV)
(XXXV)
(XXXVI)

Step 1: A compound in accordance with formula (XXXIII), in which $Y^1$, $Y^2$, $Y^3$ and $Y^4$ are defined as in formula (I), p is 0 or 1, $R^1$ is as defined in formula (I), and $FG^2$ is defined as above may be obtained by reacting a compound with formula (XXXI), in which p is 0 or 1 and $R^1$ is as defined in formula (I), with a compound of formula (XXXII), wherein $Y^1$, $Y^2$, $Y^3$ and $Y^4$ and are defined as in formula (I) and $FG^2$ is defined as above. The reaction is carried out in an inert organic solvent such as e.g. THF at lower temperatures e.g. about −78° C. under an atmosphere of nitrogen until completion of the reaction. Compounds of formula (XXXII) may be prepared from the corresponding bromide according to the procedure described in Scheme TA3 (step 1). Compounds of formula (XXXI) may be prepared by reaction of the corresponding pyridine compound with benzyl bromide using conditions known to a person skilled in the art.

Step 2: Certain compounds of formula (XVI), (XVIII) and (XIX) in which $Y^1$, $Y^2$, $Y^3$ and $Y^4$ defined as in formula (I), n is 0, 1 or 2, p is 0 or 1, s is 0, A is $CH_2$ or CH—$R^2$ and $R^1$ and $R^2$ are as defined as in formula (I), and $FG^2$ is defined as above, can be obtained by reduction of a compound of formula (XXXIII) as defined above with a metal catalyst such as e.g. Pd/C or $Pd(OH)_2/C$ under an atmosphere of hydrogen at rt for a prolonged time. The reaction is carried out in an inert organic solvent such as e.g. MeOH.

Step 3: A compound in accordance with formula (XXXVI), in which $Y^1$, $Y^2$, $Y^3$ and $Y^4$ are defined as in formula (I), p is 0 or 1, n is 0, 1 or 2, $R^1$ is as defined in formula (I), and $FG^2$ is defined as above can be obtained by reacting a compound with formula (XXXV), in which p is 0 or 1, n is 0, 1, or 2 and $R^1$ is as defined in formula (I), with a compound of formula (XXXIV), wherein $Y^1$, $Y^2$, $Y^3$ and $Y^4$ and are defined as in formula (I) and $FG^2$ is defined as above. The reaction is carried out in the presence of a pallidum catalyst such as e.g. CataCXium A-Pd-G3 and a base such as e.g. $K_2CO_3$, or $Cs_2CO_3$ in a mixture of on organic solvent such as dioxane and water at slightly elevated temperatures, e.g. 60° C. to 100° C., for a prolonged reaction time. Compounds of formula (XXXV) may in turn be prepared according to the procedures described in for example *J. Org. Chem* 2005, 70, 7324.

Step 4: Certain compounds of formula (XVI), (XVIII) and (XIX) in which $Y^1$, $Y^2$, $Y^3$ and $Y^4$ defined as in formula (I), n is 0, 1 or 2, p is 0 or 1, s is 0, A is $CH_2$ or CH—$R^2$ and $R^1$ and $R^2$ are as defined as in formula (I), and $FG^2$ is defined as above by reduction of a compound of formula (XXXVI) as defined above with a metal catalyst such as e.g. Pd/C or $Pd(OH)_2/C$ under an atmosphere of hydrogen at rt for a prolonged time. The reaction may be carried out in an inert organic solvent such as e.g. MeOH optionally in the presence of an acid such as HOAc.

Certain compounds of formula (XVI), (XVII), (XVIII) and (XIX) in which $Y^1$, $Y^2$, $Y^3$ and $Y^4$ defined as in formula (I), n is 1, p is 0, s is 0 and A is 0, $FG^1$ is as defined above, may be prepared according to the Method illustrated in Scheme TA7.

Scheme TA7

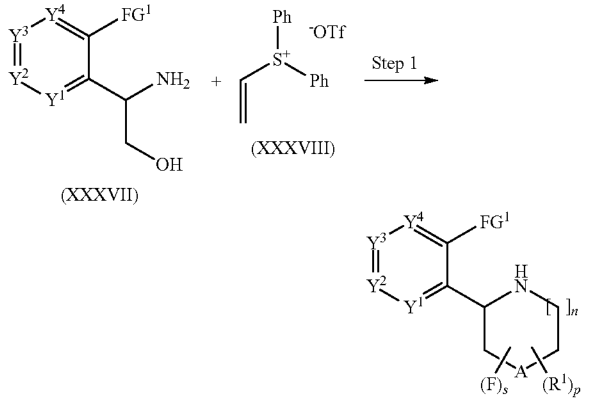

(XXXVII)

(XXXVIII)

(XVI), (XVII), (XVIII) and (XIX)

Step 1: Reacting a compound of formula (XXXVII) wherein $Y^1$, $Y^2$, $Y^3$ and $Y^4$ is as defined in formula (I) and $FG^1$ is as defined above with a compound of formula (XXXVIII). The reaction is carried out in an inert organic solvent such as e.g. DCM in the presence of an organic amine base such as e.g. TEA (2-3 eq) at temperatures ranging from 0° C. to 40° C. (*Angew. Chem. Int. Ed. Engl.* 2008, 47, 3784).

Certain compounds of formula (IX), (X), (XI) and (XII) in which $Y^3$ and $Y^4$ are defined as in formula (I), and one of $Y^1$, $Y^2$ or $Y^5$ is C-Q, wherein Q and m are as defined in formula (I) and $FG^1$ is as defined above, may be prepared according to the Methods illustrated in Scheme TA8.

Scheme TA8

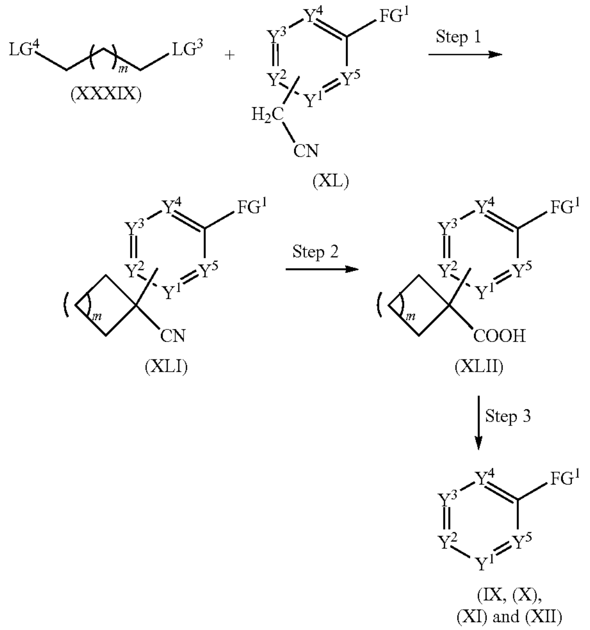

(XXXIX)

(XL)

(XLI)

(XLII)

(IX, (X), (XI) and (XII)

Step 1: A compound in accordance with formula (XLI) in which $Y^3$ and $Y^4$ are defined as in formula (I), and one of $Y^1$, $Y^2$ or $Y^5$ is C-Q, wherein Q and m are as defined in formula (I) can be obtained by reacting a compound of formula (XXXIX), in which m is defined as above, $LG^3$ and $LG^4$ are suitable leaving groups, which may be the same or different, such as for example Cl, Br, I, OMs or OTs, with a compound of formula (XL) defined as above. The reaction is carried out in an inert organic solvent such as e.g. DMF in the presence of a strong base such as e.g. NaH at temperatures ranging from 0° C. to 40° C.

Step 2: A compound in accordance with formula (XLII) in which $Y^3$ and $Y^4$ are defined as in formula (I), and one of $Y^1$, $Y^2$ or $Y^5$ is C-Q, wherein Q and m are as defined in formula (I) can be obtained by hydrolysis of a compound of formula (XLI) defined as above. The reaction is carried out in an alcohol organic solvent such as e.g. n-butyl alcohol or alike in the presence of a strong base such as e.g. NaOH or KOH at temperatures ranging from 40° C. to 120° C. Optionally, the reaction can be carried out in the presence of water.

Step 3: Certain compounds of formula (IX), (X), (XI) and (XII) in which $Y^3$ and $Y^4$ are defined as in formula (I), and one of $Y^1$, $Y^2$ or $Y^5$ is C-Q, wherein Q and m are as defined in formula (I) and $FG^1$ is as defined above, may be prepared by a Curtius rearrangement of a compound of formula (XLII). The reaction may be carried out by treatment with DPPA in an inert organic solvent such as for example THF, toluene, MeCN, acetone or alike in the presence of an alcohol e.g. tert-BuOH or BnOH and an organic base such as e.g. TEA or DIPEA at temperatures ranging from about 20° C. to 120° C. This may be followed by a deprotection of the amine (e.g. Boc or Cbz) using standard conditions. (*ChemMedChem.* 2018, 13, 2351).

Certain compounds of formula (IX), (XI) and (XII) in which $Y^1$, $Y^2$, $Y^3$ and $Y^4$ are C—H, C-halo or C—$CF_3$, $Y^5$ is C-T, wherein T is as defined in formula (I) and n is 1, p is 0 or 1, s is 0, A is $CH_2$ or CH—$R^2$, $R^1$ and $R^2$ are as defined in formula (I), and $FG^2$ is as defined above may be prepared according to the Method illustrated in Scheme TA9.

Scheme TA9

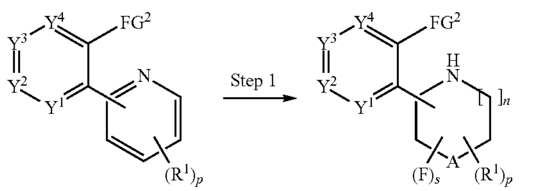

(XLIII)

(IX), (XI) and (XII)

Step 1: Treating a compound of formula (XLIII) in which $Y^1$, $Y^2$, $Y^3$ and $Y^4$ are C—H, C-halo or C—$CF_3$, p is 0 or 1, $R^1$ is as defined in formula (I) and $FG^2$ is as defined above with a metal catalyst such as e.g. $PtO_2$ under an atmosphere of hydrogen (1 to 5 bar) at about rt for a prolonged reaction time. The reaction can be carried out under acidic conditions e.g. in HOAc or in a mixture of HCl/MeOH or HCl/EtOH.

It will also be appreciated that in some of the reactions mentioned herein it may be necessary/desirable to protect any sensitive groups in the compounds. The instances where protection is necessary or desirable, suitable methods for protection are known to those skilled in the art. Conventional protecting groups may be used in accordance with standard practice (for illustration see "Protective groups in Organic Chemistry", edited by J W F McOmie, Plenum Press (1973), and "Protective Groups in Organic Synthesis", $4^{th}$ edition, T. W. Greene & P. G. M Wutz, Wiley-Interscince (2007)). Thus, if reactants include groups such as amino, aldehyde, carboxy or hydroxy it may be desirable to protect the group in some of the reactions mentioned herein.

Suitable protecting groups for hydroxy include optionally substituted and/or unsaturated alkyl groups (e.g. methyl, allyl, benzyl or tert-butyl). Suitable protecting groups for carboxylic acids include ($C_1$-$C_6$)alkyl or benzyl esters. Suitable protecting groups for amino include allyl, tert-butyloxycarbonyl, benzyloxycarbonyl, p-toluensulfonyl, 9-fluorenylmethoxycrbonyl, 4-methylbenzenesulfinyl, tert-butylsulfinyl or p-methoxybensyl. Suitable protecting groups for aldehyde include acetals such as e.g. dimethoxy, 1,3-dioxolanes or 1,3-dioxanes.

The protecting groups may be removed at any convenient stage in the synthesis using conventional techniques well known in the chemical art. It will be appreciated by those skilled in the art how a compound comprising such a group can be deprotected (see "Protective groups in Organic Chemistry", edited by J W F McOmie, Plenum Press (1973), and "Protective Groups in Organic Synthesis", 4$^{rd}$ edition, T. W. Greene & P. G. M Wutz, Wiley-Interscince (2007)).

Persons skilled in the art will appreciate that certain compounds of formula (V) to (XLIII) described above may also be referred to as being "protected derivatives".

Persons skilled in the art will appreciate that in order to obtain compounds disclosed herein in an alternative, and on some occasions, more convenient, manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

Persons skilled in the art will appreciate that chiral isomers of compounds herein can be resolved at any stage in the synthetic process using chiral resolving agents described in the literature and known to person skilled in the art, or using chiral chromatography methods described in the literature and known to person skilled in the art, or as described further in the Examples. Stereo centers may also be introduced by asymmetric synthesis. All stereoisomers are included within the scope of the disclosure.

Persons skilled in the art will appreciate that a —C═O, —CHO or C—OH group can be transferred into a —$CF_2$, —$CF_2H$ or C—F respectively using a fluorinating agent such as for example DAST, XtalFluor-E, XtalFluor-M or Deoxo-Fluor. (*J. Org. Chem.* 2010, 75, 3401).

Persons skilled in the art will appreciate that starting materials for any of the above processes can in some cases be commercially available.

Persons skilled in the art will appreciate that processes could for some starting materials above be found in the general common knowledge.

It will also be understood that some of the compounds described in the processes above may exhibit the phenomenon of tautomerism and the processes described above includes any tautomeric form.

In another aspect there is provided the Intermediates disclosed herein. In another aspect there is provided the Intermediates or salts or any stereoisomer thereof or pharmaceutically acceptable salts thereof. In another aspect there is provided the Intermediates or salts thereof such as pharmaceutically acceptable salts thereof.

INTERMEDIATES

Intermediate 1 tert-Butyl 2-(2-((4-oxo-2-thioxo-2,3,4,5-tetrahydro-1H-pyrrolo[3,2-d]pyrimidin-1-yl)methyl)phenyl)piperidine-1-carboxylate

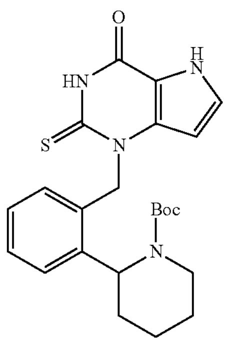

Step A. (2-(Pyridin-2-yl)phenyl)methanol

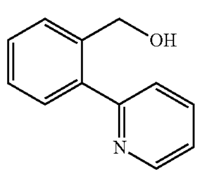 [SMILES: OCc1ccccc1-c1ccccn1]

Benzo[c][1,2]oxaborol-1(3H)-ol (50.4 g, 375.96 mmol) and 2M $Na_2CO_3$(aq) (216 mL, 410.14 mmol) were added to a mixture of $Pd(Ph_3P)_4$ (3.95 g, 3.42 mmol) and 2-bromopyridine (32.6 mL, 341.78 mmol) in toluene (500 mL) and the mixture was stirred at 90° C. until completion of the reaction (checked by LC-MS). The reaction was cooled to rt and the organics were isolated and washed with water (600 mL). The product was extracted into HCl(aq) (1M, 300 mL). The pH of the aqueous phase was adjusted to 10 with NaOH(aq) (3.8 M) and the product was back extracted into EtOAc. The organics were dried ($Na_2SO_4$) and evaporated to dryness to give the crude product (53.9 g, 85%) as a yellow oil. MS (ESI): m/z $[M+H]^+$186.

Step B. (2-(Piperidin-2-yl)phenyl)methanol

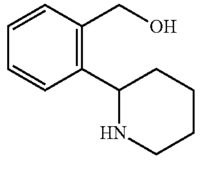 [SMILES: OCc1ccccc1C1CCCCN1]

A solution of (2-(pyridin-2-yl)phenyl)methanol (168 g, 907 mmol) in AcOH (1200 mL) was degassed with $N_2$(g) for 30 min and then platinum (IV) oxide (4.48 g, 18.14 mmol) was added and the slurry was transferred to a 3 L hydrogenation reactor and hydrogenated at 5 bar until completion of the reduction. The reaction mixture was filtered and most of the AcOH was evaporated and when the residue weighted approximately 380 g, water (1 L) was added and the water phase was washed twice with DCM (1 L and 300 mL). The combined DCM phase was washed with water (200 mL) and the combined acidic water phases were made alkaline with 50% NaOH(aq) to pH 12-13 to give a precipitate. The solids was filtered off, washed with water (3×500 mL) and dried in vacuum at 45° C. for 90 h to give the title compound (148 g, 87%) as a solid. $^1$H NMR (400 MHz, DMSO) δ 1.3-1.61 (4H, m), 1.69 (1H, d), 1.83 (1H, d), 2.26 (1H, s), 2.59-2.74 (1H, m), 3.01 (1H, d), 3.71-3.82 (1H, m), 4.56 (2H, dd), 5.67 (1H, s), 7.16-7.26 (2H, m), 7.33 (1H, dd), 7.43-7.5 (1H, m)

Step C. tert-Butyl 2-(2-(hydroxymethyl)phenyl) piperidine-1-carboxylate

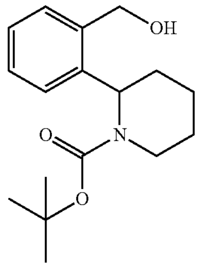 [SMILES: CC(C)(C)OC(=O)N1CCCCC1c1ccccc1CO]

$Boc_2O$ (12.44 g, 57.0 mmol) dissolved in DCM (40 mL) was added to a solution of (2-(piperidin-2-yl)phenyl)methanol (10.9 g, 57.0 mmol) and DIPEA (19.91 mL, 114 mmol) in DCM (100 mL). The reaction mixture was stirred at rt overnight. The reaction was washed with water (2×100 mL), dried (passed through a phase separator) and evaporated in vacuo to give 26 g of the crude product which was purified by flash chromatography using a gradient of 0-25% EtOAc in heptane as mobile phase to afford the title compound (15.2 g, 92%) as a transparent oil. MS (ESI): m/z $[M+H]^+$ 292.

Step D. tert-Butyl 2-(2-formylphenyl)piperidine-1-carboxylate

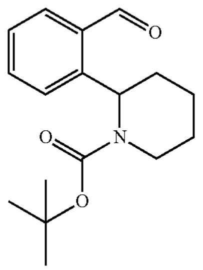 [SMILES: CC(C)(C)OC(=O)N1CCCCC1c1ccccc1C=O]

Sulfur trioxide pyridine complex (7.37 g, 46.33 mmol) dissolved in DMSO (21 mL) was added dropwise to a cold (around 14° C., internal temperature never over 25° C.) mixture of tert-butyl 2-(2-(hydroxymethyl)phenyl)piperidine-1-carboxylate (6.75 g, 23.2 mmol), TEA (11.2 mL, 81.1 mmol) and DMSO (14 mL). The resulting mixture was stirred at rt for 2 h. MTBE (250 mL) and sat $NaHCO_3$(aq) (150 mL) was added and the organic phase was separated and washed with water (2×100 mL). The organic phase was dried ($Na_2SO_4$), filtered and evaporated to give the crude title compound (6.60 g, 98%) as an amber oil. MS (ESI): m/z $[M+H]^+$290.

Step E. tert-Butyl 2-(2-(((2-(ethoxycarbonyl)-1H-pyrrol-3-yl)amino)methyl)phenyl)piperidine-1-carboxylate

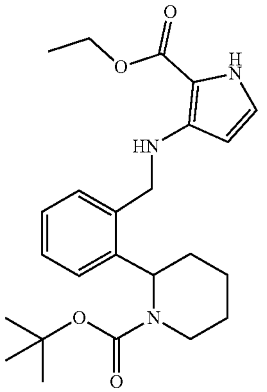 [SMILES: CCOC(=O)c1[nH]ccc1NCc1ccccc1C1CCCCN1C(=O)OC(C)(C)C]

$NaBH_3CN$ (1.564 g, 24.88 mmol) was added in five portions (exothermic) to a mixture of ethyl 3-amino-1H-pyrrole-2-carboxylate hydrochloride (4.35 g, 22.81 mmol), DIPEA (3.97 mL, 22.81 mmol), tert-butyl 2-(2-formylphenyl)piperidine-1-carboxylate (6.0 g, 20.7 mmol), AcOH (2.39 mL, 41.5 mmol) and EtOH (99.5%) (60 mL) to give a brownish mixture. The reaction was stirred at rt overnight, quenched with water and evaporated. The crude product was taken up in a mixture of DCM and sat $NaHCO_3$(aq). The DCM-phase was dried through a phase separator and evaporated to give the crude product (12.07 g) as an amber oil. MS (ESI): m/z $[M+H]^+$428.

Step F. tert-Butyl 2-(2-((3-benzoyl-1-(2-(ethoxycarbonyl)-1H-pyrrol-3-yl)thioureido)methyl)phenyl) piperidine-1-carboxylate

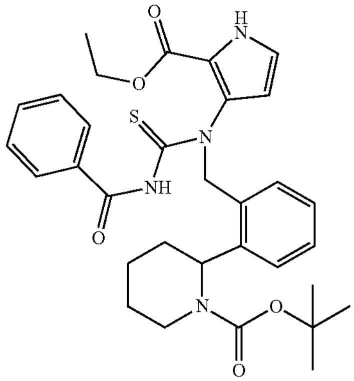 [SMILES: CCOC(=O)c1[nH]ccc1N(Cc1ccccc1C1CCCCN1C(=O)OC(C)(C)C)C(=S)NC(=O)c1ccccc1]

Benzoyl isothiocyanate (0.164 mL, 1.22 mmol) was added to a solution of tert-butyl 2-(2-((2-(ethoxycarbonyl)-1H-pyrrol-3-ylamino)methyl)phenyl)piperidine-1-carboxylate (0.52 g, 1.22 mmol) in DCM (5 mL) and stirred at rt overnight. The solvent was removed in vacuo to afford the crude title compound (0.730 g, 102%) as an orange solid that was used without purification in next step. MS (ESI): m/z $[M+H]^+$591.

Step G. tert-Butyl 2-(2-((4-oxo-2-thioxo-2,3,4,5-tetrahydro-1H-pyrrolo[3,2-d]pyrimidin-1-yl)methyl)phenyl)piperidine-1-carboxylate A mixture of tert-butyl 2-(2-((3-benzoyl-1-(2-(ethoxycarbonyl)-1H-pyrrol-3-yl)thioureido)methyl)phenyl)piperidine-1-carboxylate (15.8 g, 26.75 mmol) in MeOH (80 mL) was treated with $Cs_2CO_3$ (17.43 g, 53.49 mmol) and stirred at 50° C. under $N_2$(g) atmosphere for 3 h. The solvent was removed in vacuo and the residue dissolved in water (150 mL). The pH was adjusted to ~6 with AcOH and extracted with EtOAc (3×150 mL). Solid particles formed which was filtered off to give (3.63 g) the crude title compound. The organics were dried ($MgSO_4$) and evaporated in vacuo to give an additional (10.21 g) the crude title compound as a yellow oil. MS (ESI): m/z $[M+H]^+$ 441.

Intermediate 2

1-(4-Chloro-2-(piperidin-2-yl)benzyl)-2-thioxo-1,2,3,5-tetrahydro-4H-pyrrolo[3,2-d]pyrimidin-4-one

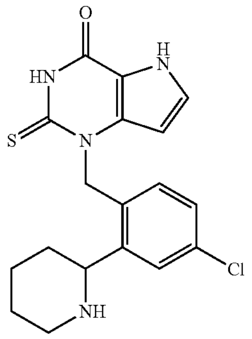 [SMILES: O=c1[nH]c(=S)n(Cc2ccc(Cl)cc2C2CCCCN2)c2cc[nH]c12]

Step A. tert-Butyl 2-(5-chloro-2-(hydroxymethyl)phenyl)piperidine-1-carboxylate

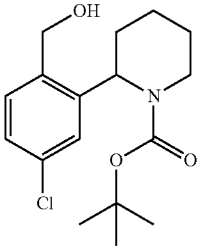 [SMILES: CC(C)(C)OC(=O)N1CCCCC1c1cc(Cl)ccc1CO]

A solution of (4-chloro-2-(piperidin-2-yl)phenyl)methanol hydrochloride (5 g, 19.07 mmol, free base CAS Registry Number 1447109-22-9), DIPEA (6.64 mL, 38.14 mmol) and $Boc_2O$ (4.82 mL, 20.98 mmol) in DCM (100 mL) was stirred at rt for 5 h. The mixture was washed with water (2×200 mL), dried with $MgSO_4$ and evaporated. The crude product was purified by flash chromatography using 100% EtOAc as mobile phase to give (5.61 g, 90%) the title compound. MS (ESI): m/z $[M+H]^+$ 326.

Step B. tert-Butyl 2-(5-chloro-2-formylphenyl)piperidine-1-carboxylate

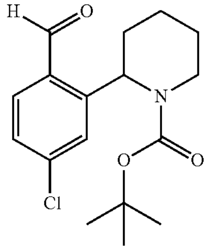 [SMILES: CC(C)(C)OC(=O)N1CCCCC1c1cc(Cl)ccc1C=O]

A mixture of tert-butyl 2-(5-chloro-2-(hydroxymethyl)phenyl)piperidine-1-carboxylate (5.5 g, 16.88 mmol) and pyridinium chlorochromate (5.46 g, 25.32 mmol) in DCM (200 mL) was stirred at rt for 1 h. Celite (10 g) was added followed by $Et_2O$ (100 mL) which gave a black precipitate. The precipitated crude product was purified by flash chromatography using 100% EtOAc as mobile phase followed by a second flash chromatography using 10% EtOAc in heptane as mobile phase to give (3.64 g, 67%) the title compound. MS (ESI): m/z $[M+H]^+$ 324.

Step C. tert-Butyl 2-(5-chloro-2-(((2-(ethoxycarbonyl)-1H-pyrrol-3-yl)amino)methyl)phenyl)piperidine-1-carboxylate

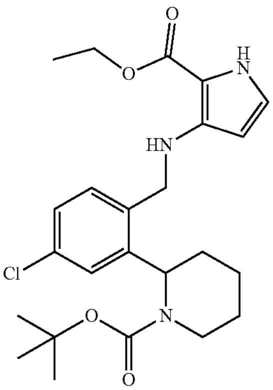 [SMILES: CCOC(=O)c1[nH]ccc1NCc1ccc(Cl)cc1C1CCCCN1C(=O)OC(C)(C)C]

$NaCNBH_3$ (233 mg, 3.71 mmol) was added to a solution of ethyl 3-amino-1H-pyrrole-2-carboxylate hydrochloride (648 mg, 3.40 mmol), DIPEA (0.592 mL, 3.40 mmol), tert-butyl 2-(5-chloro-2-formylphenyl)piperidine-1-carboxylate (1.0 g, 3.09 mmol) and AcOH (0.357 mL, 6.18 mmol) in abs EtOH (100 mL). The reaction was stirred at rt for 3 h, quenched with water and evaporated. The crude product was purified by preparative HPLC on a Kromasil C8 column (10 μm 250×20 mm ID) using a gradient of 30-95% MeCN in a $H_2O$/MeCN/FA (95/5/0.2) buffer system as mobile phase to give (771 mg, 58%) the title compound. $^1H$ NMR (400 MHz, $CDCl_3$) δ 1.22-1.4 (m, 12H), 1.52-1.8 (m, 4H), 1.8-2.02 (m, 2H), 3.03-3.34 (m, 1H), 3.94-4.11 (m, 1H), 4.16-4.57 (m, 4H), 5.21 (t, 1H), 5.63 (t, 1H), 6.68 (s, 1H), 7.16 (dd, 1H), 7.28 (dd, 1H), 7.36 (d, 1H), 8.18 (s, 1H).

Step D. tert-Butyl 2-(2-((3-benzoyl-1-(2-(ethoxycarbonyl)-1H-pyrrol-3-yl)thioureido)methyl)-5-chlorophenyl)piperidine-1-carboxylate

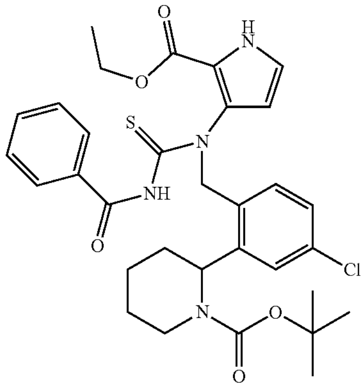 [SMILES: CCOC(=O)c1[nH]ccc1N(Cc1ccc(Cl)cc1C1CCCCN1C(=O)OC(C)(C)C)C(=S)NC(=O)c1ccccc1]

Benzoyl isothiocyanate (0.110 mL, 0.82 mmol) was added to a solution of tert-butyl 2-(5-chloro-2-((2-(ethoxycarbonyl)-1H-pyrrol-3-ylamino)methyl)phenyl)piperidine-1-carboxylate (315 mg, 0.68 mmol) in DCM (50 mL) and the reaction was stirred at rt overnight. The solvent was removed in vacuo to afford (426 mg, 100%) the crude product as an orange gum that was used without purification. MS (ESI): m/z $[M+H]^+$626.

Step E. tert-Butyl 2-(5-chloro-2-((4-oxo-2-thioxo-2,3,4,5-tetrahydro-1H-pyrrolo[3,2-d]pyrimidin-1-yl)methyl)phenyl)piperidine-1-carboxylate

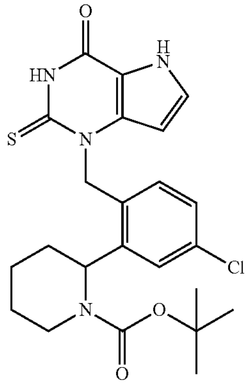 [SMILES: CC(C)(C)OC(=O)N1CCCCC1c1cc(Cl)ccc1Cn1c(=S)[nH]c(=O)c2[nH]ccc21]

$Cs_2CO_3$ (1.605 g, 4.93 mmol) was added to a solution of tert-butyl 2-(2-((3-benzoyl-1-(2-(ethoxycarbonyl)-1H-pyrrol-3-yl)thioureido)methyl)-5-chlorophenyl)piperidine-1-carboxylate (1.54 g, 2.46 mmol) in MeOH (7 mL) and the reaction was stirred at 50° C. under $N_2$(g) atmosphere for 3 h. The solvent was removed in vacuo and the residue dissolved in water (25 mL), pH was adjusted to about 6 with AcOH and then extracted with EtOAc (3×50 mL). The combined organic phase was dried ($MgSO_4$) filtered and evaporated in vacuo. The crude product was purified by preparative HPLC on a Kromasil C8 column (10 μm 250×50 mm ID) using a gradient of 20-70% MeCN in a $H_2O$/MeCN/FA (95/5/0.2) buffer system as mobile phase to give (1.0 g, 85%) the title compound as a yellow/white solid, which was used without purification in next step. MS (ESI): m/z $[M+H]^+$ 475.

Step F. 1-(4-Chloro-2-(piperidin-2-yl)benzyl)-2-thioxo-1,2,3,5-tetrahydro-4H-pyrrolo[3,2-d]pyrimidin-4-one tert-Butyl 2-(5-chloro-2-((4-oxo-2-thioxo-2,3,4,5-tetrahydro-1H-pyrrolo[3,2-d]pyrimidin-1-yl)methyl)phenyl)piperidine-1-carboxylate (215 mg, 0.45 mmol) was added to a mixture of DCM (8 mL) and TFA (2 mL) to give a colorless solution. The reaction was stirred at rt for 1 h. The solvent was evaporated and the crude product was taken up in EtOAc, washed with water, filtred through a phase separator and evaporated to give the title compound in a quantitative yield as a white solid. MS (ESI): m/z $[M+H]^+$ 375.

Intermediate 3 tert-Butyl 2-(5-chloro-2-((4-oxo-2-thioxo-2,3,4,5-tetrahydro-1H-pyrrolo[3,2-d]pyrimidin-1-yl)methyl)phenyl)pyrrolidine-1-carboxylate

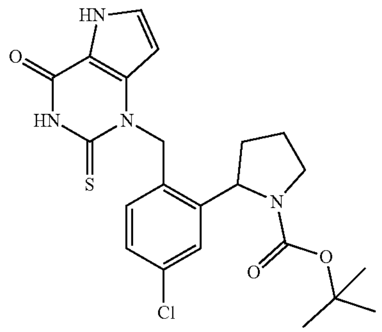 [SMILES: CC(C)(C)OC(=O)N1CCCC1c1cc(Cl)ccc1Cn1c(=S)[nH]c(=O)c2[nH]ccc21]

Step A. tert-Butyl 2-(5-chloro-2-(hydroxymethyl)phenyl)pyrrolidine-1-carboxylate

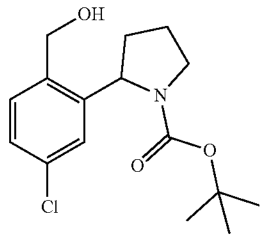 [SMILES: CC(C)(C)OC(=O)N1CCCC1c1cc(Cl)ccc1CO]

DCM (50 mL) and TEA (6.35 mL, 45.83 mmol) were added to a mixture of (4-chloro-2-(pyrrolidin-2-yl)phenyl)methanol (CAS Registry Number 1391024-08-0) (4.62 g, 21.82 mmol) and $Boc_2O$ (5.00 g, 22.92 mmol) and the reaction mixture was stirred at rt overnight. DCM (100 ml) was added and the organic phase was washed with water (40 mL) and dried by passing through a phase separator, and evaporated to give the crude title compound in quantitative yield, which was used without further purification in the next step. MS (ESI): m/z $[M+H]^+$ 312.

Step B. tert-Butyl 2-(5-chloro-2-formylphenyl)pyrrolidine-1-carboxylate

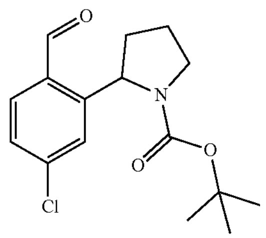 [SMILES: CC(C)(C)OC(=O)N1CCCC1c1cc(Cl)ccc1C=O]

Sulfur trioxide pyridine complex (611 mg, 3.84 mmol) was added in portions to a mixture of tert-butyl 2-(5-chloro-2-(hydroxymethyl)phenyl)pyrrolidine-1-carboxylate (598 mg, 1.92 mmol) and TEA (0.930 mL, 6.71 mmol) in DMSO (5 mL) and the reaction was stirred at rt for 1.5 h. The mixture was diluted with MTBE (100 ml) and washed with sat $NaHCO_3$(aq) (40 mL) and water (40 mL) and dried ($MgSO_4$). Filtration followed by evaporation of the solvent gave (559 mg, 94%) the title compound. MS (ESI): m/z $[M+H]^+$310.

Step C. Ethyl 3-((2-(1-(tert-butoxycarbonyl)pyrrolidin-2-yl)-4-chlorobenzyl)amino)-1H-pyrrole-2-carboxylate

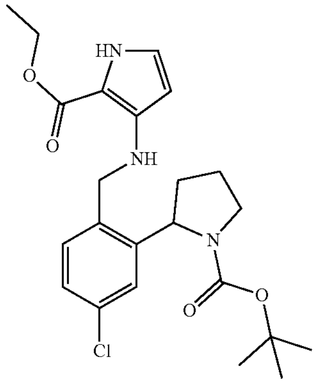 [SMILES: CCOC(=O)c1[nH]ccc1NCc1ccc(Cl)cc1C1CCCN1C(=O)OC(C)(C)C]

A mixture of tert-butyl 2-(5-chloro-2-formylphenyl)pyrrolidine-1-carboxylate (0.552 g, 1.78 mmol), ethyl 3-amino-1H-pyrrole-2-carboxylate hydrochloride (0.375 g, 1.97 mmol) and TEA (0.296 mL, 2.14 mmol) was stirred in MeOH (15 mL) for 30 min. AcOH (0.204 mL, 3.56 mmol) followed by $NaCNBH_3$ (0.112 g, 1.78 mmol) were added at rt and the reaction mixture was stirred at rt for 1 h. The solvent was evaporated, the residue was dissolved in DCM (70 mL) and washed with water (30 mL) and dried by passing through a phase separator. Evaporation of the solvent gave the crude product (0.85 g) which was purified by preparative HPLC on a XBridge C18 column (10 μm, 250×19 ID mm) using a gradient of 30-70% MeCN in $H_2O/MeCN/NH_3$ (95/5/0.2) buffer system as mobile phase to give (380 mg, 48%) the title compound. MS (ESI): m/z $[M+H]^+$448.

Step D. Ethyl 3-(3-benzoyl-1-(2-(1-(tert-butoxycarbonyl)pyrrolidin-2-yl)-4-chlorobenzyl)thioureido)-1H-pyrrole-2-carboxylate

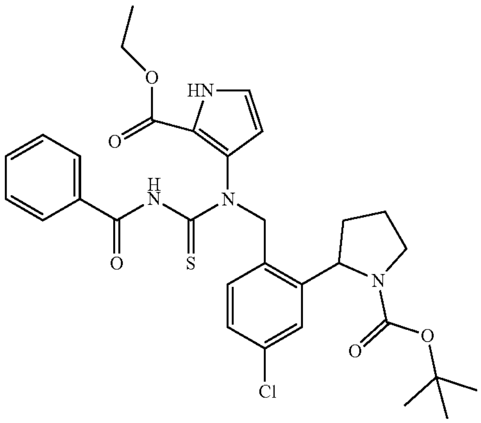 [SMILES: CCOC(=O)c1[nH]ccc1N(Cc1ccc(Cl)cc1C1CCCN1C(=O)OC(C)(C)C)C(=S)NC(=O)c1ccccc1]

Benzoyl isothiocyanate (0.11 mL, 0.81 mmol) was added to a solution of ethyl 3-(2-(1-(tert-butoxycarbonyl)pyrrolidin-2-yl)-4-chlorobenzylamino)-1H-pyrrole-2-carboxylate (365 mg, 0.81 mmol) in DCM (5 mL) and the reaction was stirred at rt for 16 h. The solvent was evaporated to give the crude product (499 mg, 100%) which was used in next step without purification. MS (ESI): m/z $[M+H]^+$ 611.

Step E. tert-Butyl 2-(5-chloro-2-((4-oxo-2-thioxo-2,3,4,5-tetrahydro-1H-pyrrolo[3,2-d]pyrimidin-1-yl)methyl)phenyl)pyrrolidine-1-carboxylate A mixture of ethyl 3-(3-benzoyl-1-(2-(1-(tert-butoxycarbonyl)pyrrolidin-2-yl)-4-chlorobenzyl)thioureido)-1H-pyrrole-2-carboxylate (4.20 g, 6.88 mmol) and $Cs_2CO_3$ (4.48 g, 13.76 mmol) in MeOH (50 mL) was heated to 65° C. for 4 h. The solvent evaporated and water (80 mL) was added to the residue, and pH was adjusted to 6 with AcOH and extracted with EtOAc (4×50 mL). The organic phase was separated and dried ($MgSO_4$). Evaporation of the solvent gave a crude product (3.7 g) which was slurried in DMSO/water. The precipitate was filtered off and washed with water and a small amount of MeOH to give (3.2 g, 100%) the title compound. MS (ESI): m/z $[M+H]^+$ 461.

Intermediate 4 tert-Butyl 3-(5-chloro-2-((4-oxo-2-thioxo-2,3,4,5-tetrahydro-1H-pyrrolo[3,2-d]pyrimidin-1-yl)methyl) phenyl)morpholine-4-carboxylate

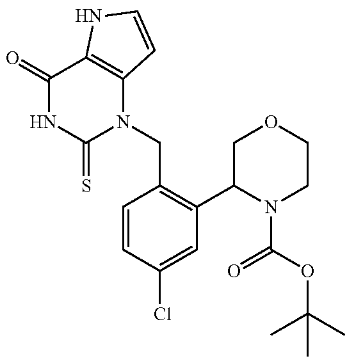 [SMILES: CC(C)(C)OC(=O)N1CCOCC1c1cc(Cl)ccc1Cn1c(=S)[nH]c(=O)c2[nH]ccc21]

Step A. 1-((Allyloxy)methyl)-2-bromo-4-chlorobenzene

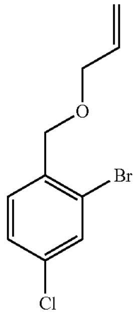

NaH (0.542 g, 22.6 mmol) was added in portions to a solution of (2-bromo-4-chlorophenyl)methanol (CAS Registry Number 143888-84-0) (5 g, 22.6 mmol) and 3-bromoprop-1-ene (2.05 mL, 23.7 mmol) in toluene (50 mL) and THF (50 mL), and the reaction was stirred at rt for 4 h. Additional NaH (0.30 g, 12.5 mmol) was added and the reaction mixture was stirred at rt for 2 days. The reaction mixture was diluted with EtOAc (200 mL) and washed with 0.25 M HCl (aq) (100 mL) and brine (100 mL). The organic phase was dried ($MgSO_4$) and evaporated to give (5.60 g) the crude product, which was purified by flash chromatography using 20% EtOAc in heptane as mobile phase. followed by a second flash chromatography using 10% EtOAc in heptane as mobile phase to give (4.36 g, 74%) the title compound. $^1H$ NMR (500 MHz, $CDCl_3$) δ 4.08-4.13 (2H, m), 4.54 (2H, s), 5.21-5.27 (1H, m), 5.31-5.39 (1H, m), 5.97 (1H, ddt), 7.30 (1H, dd), 7.44 (1H, dt), 7.55 (1H, d).

Step B. (2-((Allyloxy)methyl)-5-chlorophenyl)magnesium chloride

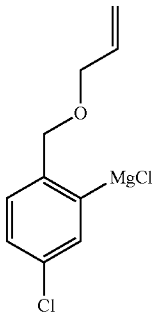

iPrMgCl×LiCl (1.3 M, 18.99 mL, 24.69 mmol) was added to a cool (0° C.) solution of 1-(allyloxymethyl)-2-bromo-4-chlorobenzene (5.87 g, 22.44 mmol) in THF (50 mL) under a $N_2$(g) atmosphere. The reaction mixture was allowed to reach rt during 5 h and was then stirred at rt for 16 h. The solution was stored under a $N_2$(g) atmosphere at −20° C. before use.

Step C. tert-Butyl 3-oxomorpholine-4-carboxylate

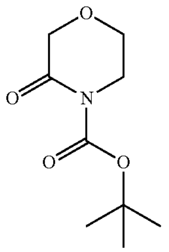

$Boc_2O$ (11.87 g, 54.40 mmol) dissolved in dry THF (30 mL) was added to a solution of morpholin-3-one (CAS Registry Number 109-11-5) (5 g, 49.45 mmol) and DMAP (6.65 g, 54.40 mmol) in dry THF (60 mL) and the reaction mixture was stirred at rt for 3 h. The solvent was removed by evaporation and the crude product was taken up in EtOAc and washed with $NaHCO_3$(aq), and water. The organic phase was dried ($MgSO_4$) and the solvent was removed by evaporation to give the crude product, which was purified by flash chromatography using a gradient of 10-80% EtOAc in heptane as mobile phase to give (8.37 g, 84%) the title compound as a white solid. $^1H$ NMR (400 MHz, CDCl3) δ 1.55 (s, 9H), 3.68-3.81 (m, 2H), 3.83-3.95 (m, 2H), 4.23 (s, 2H).

Step D. tert-Butyl (2-(2-(2-((allyloxy)methyl)-5-chlorophenyl)-2-oxoethoxy)ethyl)carbamate

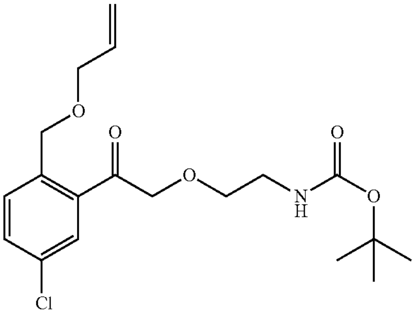 [SMILES: C=CCOCc1ccc(Cl)cc1C(=O)COCCNC(=O)OC(C)(C)C]

(2-((Allyloxy)methyl)-5-chlorophenyl)magnesium chloride (41.3 mL, 12.35 mmol) was cooled to −30° C. and canullated over to a solution of tert-butyl 3-oxomorpholine-4-carboxylate (2.58 g, 12.84 mmol) in THF (30 mL) also at −30° C. The reaction mixture was allowed to reach rt overnight, diluted with DCM (200 mL), and washed with sat $NH_4Cl$ (aq) (80 mL) and brine (80 mL). The organic phase was dried with a phase separator and evaporated. The crude product was purified by flash chromatography using a gradient of 0-40% EtOAc in heptane as mobile phase to give (3.70 g, 78%) the title compound as a yellow oil. MS (ESI): m/z $[M+H]^+$384.

Step E. 3-(2-((Allyloxy)methyl)-5-chlorophenyl)morpholine

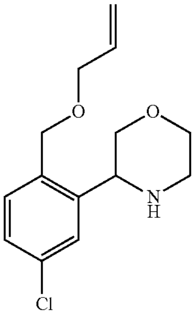 [SMILES: C=CCOCc1ccc(Cl)cc1C1COCCN1]

Acetyl chloride (20.1 mL, 282 mmol) was added dropwise to a cool (0° C.) solution of tert-butyl (2-(2-(2-((allyloxy)methyl)-5-chlorophenyl)-2-oxoethoxy)ethyl)carbamate (5.41 g, 14.09 mmol) in MeOH (120 mL). After stirring at 0° C. for 10 min, the reaction was allowed to reach rt and stirred for 2 h. Additional acetyl chloride (11.1 g, 140 mmol) was added and the reaction was stirred until LCMS showed complete formation of the imine in situ. $NaBH_3CN$ (8.86 g, 141 mmol) was added and the reaction was stirred for 30 min. The reaction was quenched with water and the pH was adjusted to 8 with sat $NaHCO_3$(aq) and the reaction mixture was extracted with DCM. The organic phase was dried using a phase separator and concentrated to give (3.58 g, 95%) the title compound as a yellow oil. MS (ESI): m/z $[M+H]^+$ 268.

Step F. tert-Butyl 3-(2-((allyloxy)methyl)-5-chlorophenyl)morpholine-4-carboxylate

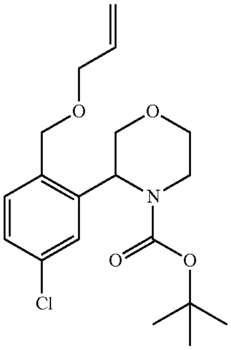 [SMILES: C=CCOCc1ccc(Cl)cc1C1COCCN1C(=O)OC(C)(C)C]

$Boc_2O$ (3.81 g, 17.44 mmol) followed by TEA (4.62 mL, 33.29 mmol) was added to a solution of 3-(2-((Allyloxy)methyl)-5-chlorophenyl)morpholine (4.245 g, 15.85 mmol) in DCM (100 mL) and the reaction was stirred at rt overnight. DCM (50 mL) was added and the organic phase was washed with brine (20 mL) and dried with a phase separator. Evaporation of the solvent gave a crude product which was purified by flash chromatography using a gradient of 0-40% EtOAc in heptane as mobile phase to give (2.70 g, 46%) the title compound as a yellow solid. $^1H$ NMR (400 MHz, CDCl3) δ 1.35 (9H, s), 3.4-3.5 (1H, m), 3.68 (1H, td), 3.73-3.79 (1H, m), 3.87 (1H, dd), 3.95-4.03 (4H, m), 4.37 (1H, d), 4.74 (1H, d), 5.05-5.09 (1H, m), 5.17-5.22 (1H, m), 5.26-5.32 (1H, m), 5.87-5.98 (1H, m), 7.23 (1H, dd), 7.31 (1H, d), 7.66 (1H, d).

Step G. tert-Butyl 3-(5-chloro-2-(hydroxymethyl)phenyl)morpholine-4-carboxylate

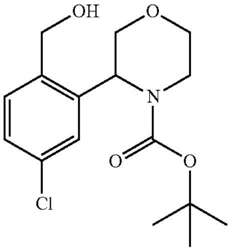 [SMILES: CC(C)(C)OC(=O)N1CCOCC1c1cc(Cl)ccc1CO]

A mixture of tert-butyl 3-(2-(allyloxymethyl)-5-chlorophenyl)morpholine-4-carboxylate (1.226 g, 3.33 mmol), $PdCl_2$ (0.812 g, 4.58 mmol) and NaOAc (0.902 g, 11.00 mmol) were heated at 50° C. in AcOH (20 mL) and water (80 μl) for 3 h. The reaction was diluted with DCM (150 mL) and washed with sat $NaHCO_3$(aq) (3×30 mL). The organic phase was dried using a phase separator and evaporated. The crude product was purified by preparative HPLC on a XBridge C18 column (10 μm 250×50 ID mm) using a gradient of 20-60% MeCN in $H_2O/MeCN/NH_3$ (95/5/0.2) buffer system as mobile phase to give (816 mg, 75%) the title compound. MS (ESI): m/z $[M-H]^+$326

Step H. tert-Butyl 3-(5-chloro-2-formylphenyl)morpholine-4-carboxylate

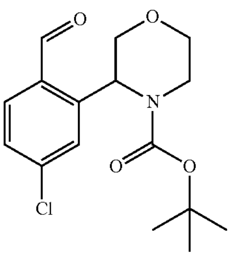 [SMILES: CC(C)(C)OC(=O)N1CCOCC1c1cc(Cl)ccc1C=O]

Sulfur trioxide pyridine complex (792 mg, 4.98 mmol) dissolved in DMSO (3 mL) was added dropwise to a solution of tert-butyl 3-(5-chloro-2-(hydroxymethyl)phenyl) morpholine-4-carboxylate (816 mg, 2.49 mmol) and TEA (1.208 mL, 8.71 mmol) in DMSO (2 mL) at 17° C. and the mixture was stirred for 16 h. The reaction mixture was diluted with MTBE (100 mL) and washed with sat $NaHCO_3$ (aq) (40 mL), water (40 mL) and dried ($MgSO_4$). The solvent was evaporated to give (770 mg, 95%) the title compound. MS (ESI): m/z $[M+H]^+$326.

Step I. tert-Butyl 3-(5-chloro-2-(((2-(ethoxycarbonyl)-1H-pyrrol-3-yl)amino)methyl)phenyl)morpholine-4-carboxylate

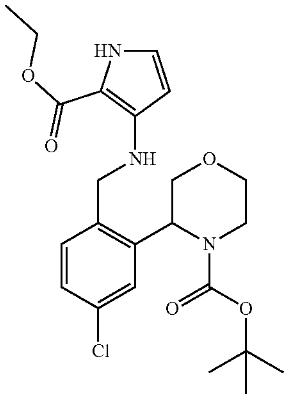 [SMILES: CCOC(=O)c1[nH]ccc1NCc1ccc(Cl)cc1C1COCCN1C(=O)OC(C)(C)C]

tert-Butyl 3-(5-chloro-2-formylphenyl)morpholine-4-carboxylate (770 mg, 2.36 mmol) and ethyl 3-amino-1H-pyrrole-2-carboxylate (451 mg, 2.36 mmol) were dissolved in MeOH (15 mL) and TEA (0.393 mL, 2.84 mmol), and the mixture was stirred at rt for 10 min. AcOH (0.271 mL, 4.73 mmol) was added and the mixture was stirred at rt for an additional 10 min $NaBH_3CN$ (149 mg, 2.36 mmol) was added and the mixture was stirred at rt for 4 h. The solvent was evaporated and the residue was diluted with DCM (100 mL), washed with water (40 mL) and dried with a phase separator. Evaporation gave the crude product (1.2 g) which was purified by preparative HPLC on a XBridge C18 column (10 μm 250×19 ID mm) using a gradient of 35-75% MeCN in $H_2O/MeCN/NH_3$ (95/5/0.2) buffer as mobile phase to give (600 mg, 55%) the title compound. MS (ESI): m/z $[M+H]^+$ 464.

Step J. tert-Butyl 3-(2-((3-benzoyl-1-(2-(ethoxycarbonyl)-1H-pyrrol-3-yl)thioureido)methyl)-5-chlorophenyl)morpholine-4-carboxylate

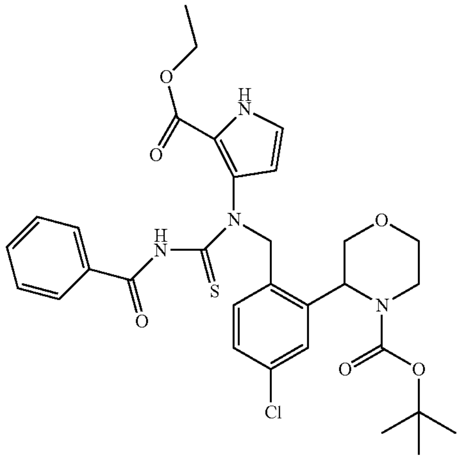 [SMILES: CCOC(=O)c1[nH]ccc1N(Cc1ccc(Cl)cc1C1COCCN1C(=O)OC(C)(C)C)C(=S)NC(=O)c1ccccc1]

Benzoyl isothiocyanate (0.173 mL, 1.28 mmol) was added to a solution of tert-butyl 3-(5-chloro-2-((2-(ethoxycarbonyl)-1H-pyrrol-3-ylamino)methyl)phenyl)morpholine-4-carboxylate (595 mg, 1.28 mmol) in DCM (12 mL) and the reaction was stirred at rt for 3 h. The solvent was evaporated to give (998 mg) the title compound. MS (ESI): m/z $[M+H]^+$627.

Step K. tert-Butyl 3-(5-chloro-2-((4-oxo-2-thioxo-2,3,4,5-tetrahydro-1H-pyrrolo[3,2-d]pyrimidin-1-yl)methyl)phenyl)morpholine-4-carboxylate $Cs_2CO_3$ (834 mg, 2.56 mmol) was added to a solution of tert-butyl 3-(2-((3-benzoyl-1-(2-(ethoxycarbonyl)-1H-pyrrol-3-yl)thioureido)methyl)-5-chlorophenyl)morpholine-4-carboxylate (803 mg, 1.28 mmol) in MeOH (10 mL) and the mixture was heated at 65° C. for 6 h. The solvent was evaporated and water (50 mL) was added to the residue and the aqueous phase was acidified to pH 4 with AcOH and extracted with EtOAc (3×50 mL). The organic phase was dried ($MgSO_4$) and evaporated to give (836 mg) the crude title compound. MS (ESI): m/z $[M+H]^+$ 477.

Intermediate 5 tert-Butyl 3-(5-chloro-2-((6-oxo-2-thioxo-1,2,6,7-tetrahydro-3H-purin-3-yl)methyl)phenyl)morpholine-4-carboxylate

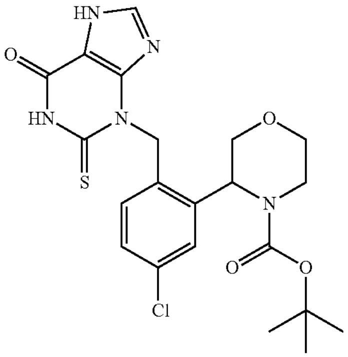 [SMILES: CC(C)(C)OC(=O)N1CCOCC1c1cc(Cl)ccc1Cn1c(=S)[nH]c(=O)c2[nH]cnc21]

Step A. tert-Butyl 3-(2-(((5-carbamoyl-1H-imidazol-4-yl)amino)methyl)-5-chlorophenyl)morpholine-4-carboxylate

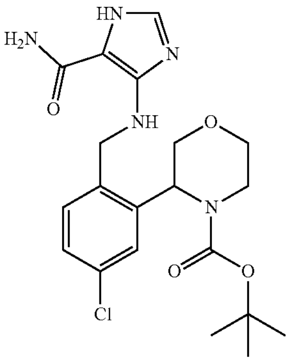 [SMILES: CC(C)(C)OC(=O)N1CCOCC1c1cc(Cl)ccc1CNc1nc[nH]c1C(N)=O]

AcOH (0.054 mL, 0.94 mmol) was added to a solution of tert-butyl 3-(5-chloro-2-formylphenyl)morpholine-4-carboxylate Intermediate 4 step H (305 mg, 0.94 mmol) and 4-amino-1H-imidazole-5-carboxamide (CAS Registry Number 21299-72-9) (118 mg, 0.94 mmol) in EtOH (10 mL) and the reaction was heated at 70° C. for 16 h. The solvent was evaporated and the residue was dissolved in MeOH (20 mL) and cooled on an ice bath. $NaBH_3CN$ (35.4 mg, 0.94 mmol) was added and the reaction was stirred at 0° C. for 2 h and at rt for 16 h. Additional EtOH (20 mL) followed by $NaBH_3CN$ (15 mg, 0.40 mmol) was added and stirring was continued at rt for 3 h. The solvent was evaporated and the residue was partitioned between DCM (40 mL) and brine/sat $NH_4Cl$ solution (1/1) (40 mL). The aqueous layer was extracted with DCM (2×30 ml) and the combined organic phase was evaporated. The crude product was purified by preparative HPLC on a XBridge C18 column (10 μm, 250×50 ID mm) using a gradient of 15-60% MeCN in $H_2O$/MeCN/$NH_3$ (95/5/0.2) buffer as mobile phase to give (343 mg, 84%) the title compound. MS (ESI): m/z $[M+H]^+$ 436.

Step B. tert-Butyl 3-(2-((3-benzoyl-1-(5-carbamoyl-1H-imidazol-4-yl)thioureido)methyl)-5-chlorophenyl)morpholine-4-carboxylate

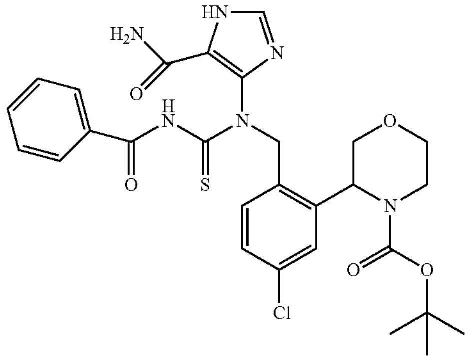 [SMILES: CC(C)(C)OC(=O)N1CCOCC1c1cc(Cl)ccc1CN(C(=S)NC(=O)c1ccccc1)c1nc[nH]c1C(N)=O]

Benzoyl isothiocyanate (0.337 mL, 2.51 mmol) was added to a solution of tert-butyl 3-(2-((5-carbamoyl-1H-imidazol-4-ylamino)methyl)-5-chlorophenyl)morpholine-4-carboxylate (910 mg, 2.09 mmol) in MeCN (30 mL) and the reaction was stirred at rt for 18 h. The solvent evaporated to give the crude product which was used without purification in the next step. MS (ESI): m/z $[M+H]^+$599.

Step C. tert-Butyl 3-(5-chloro-2-((6-oxo-2-thioxo-1,2,6,7-tetrahydro-3H-purin-3-yl)methyl)phenyl)morpholine-4-carboxylate tert-Butyl 3-(2-((3-benzoyl-1-(5-carbamoyl-1H-imidazol-4-yl)thioureido)methyl)-5-chlorophenyl)morpholine-4-carboxylate (1252 mg, 2.09 mmol) was dissolved in a mixture of EtOH (40 mL) and 1 M NaOH (6.27 mL, 6.27 mmol) and the mixture was heated at 78° C. for 16 h. The reaction was quenched with 1 M HCl (5 mL) and concentrated. The crude product was purified by preparative HPLC on a XBridge C18 column (10 μm 250×50 ID mm) using a gradient of 5-50% MeCN in $H_2O$/MeCN/$NH_3$ (95/5/0.2) buffer as mobile phase to give (566 mg, 57%) the title compound. MS (ESI): m/z $[M+H]^+$478.

Intermediate 6 tert-Butyl 2-(2-((4-oxo-2-thioxo-2,3,4,5-tetrahydro-1H-pyrrolo[3,2-d]pyrimidin-1-yl)methyl)phenyl)azepane-1-carboxylate

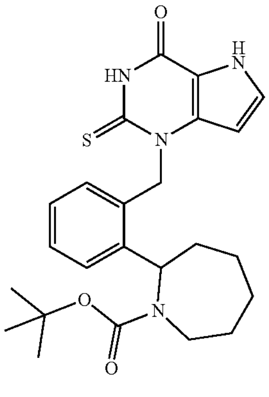 [SMILES: CC(C)(C)OC(=O)N1CCCCCC1c1ccccc1Cn1c(=S)[nH]c(=O)c2[nH]ccc21]

Step A. (2-((Allyloxy)methyl)phenyl)magnesium chloride

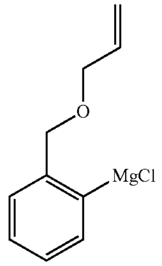

iPrMgCl×LiCl (1.3 M, 130 mL, 169.5 mmol) was added to a cold (0° C.) solution of 1-(allyloxymethyl)-2-bromobenzene (CAS Registry Number 1447109-22-9) (35 g, 154.1 mmol) in THF (100 mL). The reaction mixture was allowed to reach rt during 5 h and was then stirred at rt for 16 h. The reagent was used as such in the next step.

Step B. tert-Butyl (6-(2-((allyloxy)methyl)phenyl)-6-oxohexyl)carbamate

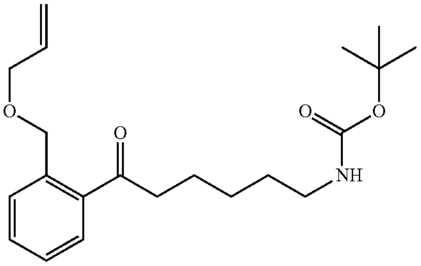 [SMILES: C=CCOCc1ccccc1C(=O)CCCCCNC(=O)OC(C)(C)C]

(2-((Allyloxy)methyl)phenyl)magnesium chloride (25 g, 145.77 mmol) (the reaction mixture from above) was cooled to −5° C. and canulated over to a solution of tert-butyl 2-oxoazepane-1-carboxylate (CAS Registry (Number 106412-36-6) (40.4 g, 189.51 mmol) in THF (100 mL) at −5° C. and the temperature was not allowed exceed −3° C. The reaction mixture was allowed to reach rt over 6 h and was then stirred for 16 h at rt. The reaction was quenched by addition of $NH_4Cl$ (aq) (20 mL). EtOAc (200 mL) was added and the phases were separated. The organic phase was dried ($MgSO_4$) and the solvent was removed by evaporation. The crude product was purified by flash chromatography using a gradient of 5-20% EtOAc in heptane as mobile phase to give (16 g, 30%) the title compound. MS (ESI): m/z $[M+H]^+$362.

Step C. 2-(2-((Allyloxy)methyl)phenyl)azepane

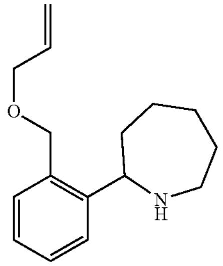 [SMILES: C=CCOCc1ccccc1C1CCCCCN1]

TFA (2.131 mL, 27.66 mmol) was added to a solution of tert-butyl 6-(2-(allyloxymethyl)phenyl)-6-oxohexylcarbamate (1 g, 2.77 mmol) in DCM (10 mL) and the mixture was stirred at rt for 30 min. The solvent was removed by evaporation and co-evaporated with toluene (3×50 mL). The residue was taken up in MeOH (10 mL) and $NaBH_3CN$ (0.191 g, 3.04 mmol) was added. The mixture was stirred at rt for 20 h. DIPEA (0.580 mL, 3.32 mmol) was added and the mixture was stirred for an additional 20 h. Only the intermediate imine was observed in LCMS. $H_2SO_4$ (0.147 mL, 2.77 mmol) was added dropwise, effervesce occurred, and the reaction was complete in 30 min. The crude product was purified by flash chromatography using a gradient of heptane/EtOAc/sat $NH_3$ in MeOH (50/50/0 to 0/90/10) to give (0.52 g, 77%) the title compound as a colour less oil. MS (ESI): m/z $[M+H]^+$246.

Step D. tert-Butyl 2-(2-((allyloxy)methyl)phenyl) azepane-1-carboxylate

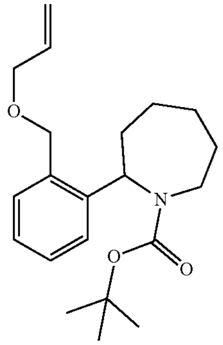 [SMILES: C=CCOCc1ccccc1C1CCCCCN1C(=O)OC(C)(C)C]

$Boc_2O$ (1.06 g, 4.84 mmol) was added to a solution of 2-(2-(allyloxymethyl)phenyl)azepane (1.08 g, 4.40 mmol) and DIPEA (0.923 mL, 5.28 mmol) in DCM (10 mL) at 0° C., and the mixture was allowed to reach rt over 30 min. The reaction mixture was concentrated and the crude product was purified by flash chromatography using a gradient of 10-70% EtOAc in heptane as mobile phase to give (0.96 g, 63%) the title compound. MS (ESI): m/z $[M+H]^+$346.

Step E. tert-Butyl 2-(2-(hydroxymethyl)phenyl)azepane-1-carboxylate

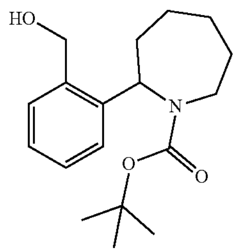 [SMILES: CC(C)(C)OC(=O)N1CCCCCC1c1ccccc1CO]

$PdCl_2$ (2.66 g, 15.02 mmol) and NaOAc (2.71 g, 33.05 mmol) were added to a solution of tert-butyl 2-(2-(allyloxymethyl)phenyl)azepane-1-carboxylate (3.46 g, 10.02 mmol) in AcOH (20 mL) and 20 drops of water. The mixture was stirred at 50° C. for 2 h. DCM (130 mL) was added and the organic phase was washed with sat $NaHCO_3$(aq) (3×30 mL). The organic phase was dried ($MgSO_4$) and the solvent was removed by evaporation. The crude product was purified by flash chromatography using a gradient of 10-90% EtOAc in heptane as mobile phase to give (2.26 g, 74%) the title compound. MS (ESI): m/z [M+H]+ 306.

Step F. tert-Butyl 2-(2-formylphenyl)azepane-1-carboxylate

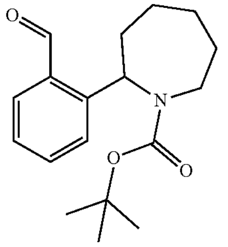 [SMILES: CC(C)(C)OC(=O)N1CCCCCC1c1ccccc1C=O]

DIPEA (4.38 ml, 25.05 mmol) was added to a solution of tert-butyl 2-(2-(hydroxymethyl)phenyl)azepane-1-carboxylate (2.186 g, 7.16 mmol) in DMSO (4.4 mL) followed by dropwise addition (5 min) sulfur trioxide pyridine complex (2.278 g, 14.32 mmol) dissolved in DMSO (6.7 mL). The mixture was stirred at rt for 2 h. MTBE (100 mL) was added and the organic phase was washed with sat $NaHCO_3$(aq) (40 mL) and water (40 mL). The organic phase was dried ($MgSO_4$) and evaporated to give (82.6 g) the crude title compound.

Step G. tert-Butyl 2-(2-(((2-(ethoxycarbonyl)-1H-pyrrol-3-yl)amino)methyl)phenyl)azepane-1-carboxylate

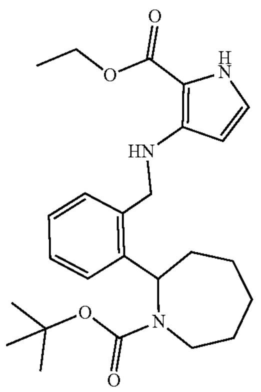 [SMILES: CCOC(=O)c1[nH]ccc1NCc1ccccc1C1CCCCCN1C(=O)OC(C)(C)C]

A mixture of ethyl 3-amino-1H-pyrrole-2-carboxylate hydrochloride (1.960 g, 10.28 mmol), DIPEA (1.79 mL, 10.3 mmol), AcOH (1.09 mL, 18.85 mmol) in 99.5% EtOH (20 mL) was added to tert-butyl 2-(2-formylphenyl) azepane-1-carboxylate (2.6 g, 8.57 mmol) to give a brownish solution. The solution was stirred for 15 min before addition of $NaBH_3CN$ (0.727 g, 11.57 mmol) over 5 min. The mixture was stirred at rt for 2 h. The reaction was quenched with water (30 mL) and MTBE (100 mL) was added. The layers were separated and the organic phase was dried ($MgSO_4$) and evaporated. The crude product was purified by flash chromatography using a gradient of 10-80% EtOAc in heptane as mobile phase to give (2.58 g, 68%) the title compound. MS (ESI): m/z $[M+H]^+$ 441.

Step H. tert-Butyl 2-(2-((3-benzoyl-1-(2-(ethoxycarbonyl)-1H-pyrrol-3-yl)thioureido)methyl)phenyl) azepane-1-carboxylate

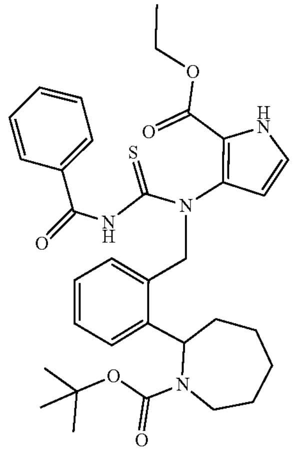 [SMILES: CCOC(=O)c1[nH]ccc1N(Cc1ccccc1C1CCCCCN1C(=O)OC(C)(C)C)C(=S)NC(=O)c1ccccc1]

Benzoyl isothiocyanate (0.947 mL, 7.05 mmol) was added to a solution of tert-butyl 2-(2-((2-(ethoxycarbonyl)-1H-pyrrol-3-ylamino)methyl)phenyl)azepane-1-carboxylate (2.58 g, 5.84 mmol) in DCM (50 mL) and the reaction was stirred at rt for 4 h. The solvent was removed in vacuo to afford (3.5 g, 99%) the crude product that was used without purification in next step. MS (ESI): m/z $[M+H]^+$ 605.

Step I. tert-butyl 2-(2-((4-oxo-2-thioxo-2,3,4,5-tetrahydro-1H-pyrrolo[3,2-d]pyrimidin-1-yl)methyl)phenyl)azepane-1-carboxylate $Cs_2CO_3$ (2.263 g, 6.94 mmol) was added (slightly exothermic) to a solution of tert-butyl 2-(2-((3-benzoyl-1-(2-(ethoxycarbonyl)-1H-pyrrol-3-yl)thioureido)methyl)phenyl)azepane-1-carboxylate (3.5 g, 5.79 mmol) in MeOH (100 mL) and the reaction was stirred at 50° C. under $N_2$(g) atmosphere for 3 h. The mixture was concentrated in vacuo and the crude product was purified by flash chromatography using a gradient of 10-80% EtOAc in heptane to give (1.70 g, 65%) the title compound. MS (ESI): m/z $[M+H]^+$455.

Intermediate 7 tert-Butyl (R)-2-(5-chloro-2-((6-oxo-2-thioxo-1,2,6,7-tetrahydro-3H-purin-3-yl)methyl)phenyl)azepane-1-carboxylate

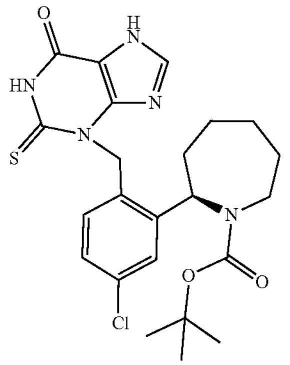 [SMILES: CC(C)(C)OC(=O)N1CCCCC[C@@H]1c1cc(Cl)ccc1Cn1c(=S)[nH]c(=O)c2[nH]cnc21]

Step A. (S,E)-N-(2-Bromo-5-chlorobenzylidene)-2-methylpropane-2-sulfinamide

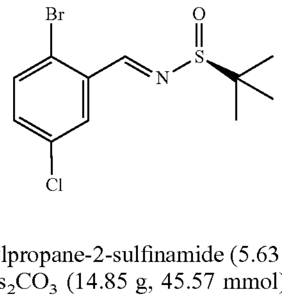

(S)-2-Methylpropane-2-sulfinamide (5.63 g, 46.48 mmol) followed by $Cs_2CO_3$ (14.85 g, 45.57 mmol) were added to a solution of 2-bromo-5-chlorobenzaldehyde (10 g, 45.57 mmol) in DCM (300 mL). The mixture was refluxed until LC-MS shows full conversion. The mixture was diluted with brine and DCM. The DCM layer was dried through a phase-separator and then evaporated to give (14.77 g, 100%) the title compound as a yellow oil. MS (ESI): m/z $[M+H]^+$ 322.

Step B. (S)—N-(1-(2-Bromo-5-chlorophenyl)pent-4-en-1-yl)-2-methylpropane-2-sulfinamide

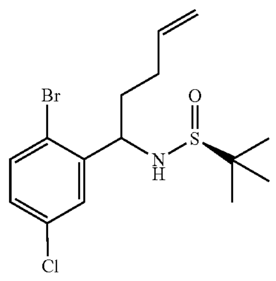 [SMILES: C=CCCC(N[S@@](=O)C(C)(C)C)c1cc(Cl)ccc1Br]

Flask 1: cerium (III) chloride (99 mg, 0.40 mmol) was added to a roundbottomed flask then dried with heating gun under vacuum. THF (4 mL) was added and the mixture was cooled to −78° C. But-3-enylmagnesium bromide (2.42 mL, 1.21 mmol) was added dropwise during 15 min (a white suspension is seen). The mixture was stirred at −78° C. for 30 min, and then allowed to reach rt. Flask 2: (S,E)-N-(2-bromo-5-chlorobenzylidene)-2-methylpropane-2-sulfinamide (100 mg, 0.29 mmol) was dissolved into THF (1 mL) and cooled to −78° C. The solution in flask 1 was added in one portion. The resulting mixture was stirred at −78° C. for 2 min. The reaction was quenched with sat $NH_4Cl$ (aq) in an ice bath and extracted with EtOAc. The solvent was evaporated and the residue was co-evaporated with DCM to give (110 mg, 94%) the title compound as a colourless oil (mixture of diastereomers). MS (ESI): m/z $[M+H]^+$378.

Step C. (S)—N-Allyl-N-(1-(2-bromo-5-chlorophenyl)pent-4-en-1-yl)-2-methylpropane-2-sulfinamide

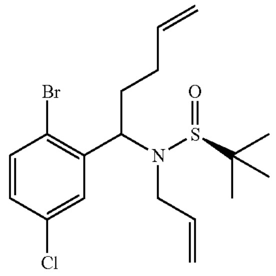 [SMILES: C=CCCC(c1cc(Cl)ccc1Br)N(CC=C)[S@@](=O)C(C)(C)C]

Allyl bromide (6.85 mL, 79.21 mmol) was added to a solution of (S)—N-(1-(2-bromo-5-chlorophenyl)pent-4-enyl)-2-methylpropane-2-sulfinamide (6.0 g, 15.84 mmol) in THF (40 mL) followed by LiHMDS (63.4 mL, 63.37 mmol) and the reaction was stirred at rt overnight followed by heating at 40° C. overnight. The reaction was cooled in on ice bath and quenched with sat $NH_4Cl$ (aq). The mixture was extracted with DCM and evaporated. The crude product was purified by flash chromatography using a gradient of 0-20% EtOAc in heptane as mobile phase to give (4.0 g, 60%) the title compound (mixture of diastereomers). MS (ESI): m/z $[M+H]^+$418.

Step D. (R)-2-(2-Bromo-5-chlorophenyl)-1-((S)-tert-butylsulfinyl)-2,3,4,7-tetrahydro-1H-azepine

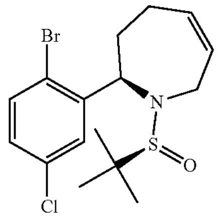 [SMILES: CC(C)(C)[S@](=O)N1CC=CCC[C@@H]1c1cc(Cl)ccc1Br]

The GrubbsII catalyst (0.231 g, 0.27 mmol, CAS Registry Number 246047-72-3) was added to a solution of (S)—N-allyl-N-(1-(2-bromo-5-chlorophenyl)pent-4-enyl)-2-methylpropane-2-sulfinamide (3.8 g, 9.07 mmol) in DCM (800 ml) under $N_2$(g) atmosphere. The reaction mixture was refluxed for 6 h and the solvent was evaporated leaving the crude title compound as a slightly brown oil (mixture of two diastereomers). The crude product was purified by flash chromatography using a gradient of 0-25% of EtOAc in heptane to give the second eluting compound (R)-2-(2-Bromo-5-chlorophenyl)-1-((S)-tert-butylsulfinyl)-2,3,4,7-tetrahydro-1H-azepine as an oil (1.47 g, 42%) as an oil. MS (ESI): m/z $[M+H]^+$390.

Step E. (R)-2-(2-Bromo-5-chlorophenyl)-2,3,4,7-tetrahydro-1H-azepine hydrochloride

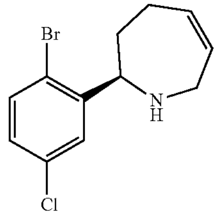 [SMILES: Clc1ccc(Br)c([C@H]2CCC=CCN2)c1]

HCl in dioxane (4 M) (8.83 mL, 35.32 mmol) was added to a solution of (R)-2-(2-bromo-5-chlorophenyl)-1-((S)-tert-butylsulfinyl)-2,3,4,7-tetrahydro-1H-azepine (1.38 g, 3.53 mmol) in MeOH (10 mL) and the resulting mixture was stirred at rt for 1 h. The volatiles were evaporated to give (1.26 g) the crude title compound as a slightly brown solid. MS (ESI): m/z $[M+H]^+$286.

Step F. tert-Butyl (R)-2-(2-bromo-5-chlorophenyl)-2,3,4,7-tetrahydro-1H-azepine-1-carboxylate

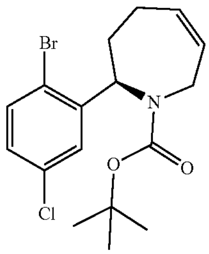 [SMILES: CC(C)(C)OC(=O)N1CC=CCC[C@@H]1c1cc(Cl)ccc1Br]

$Boc_2O$ (1.54 g, 7.06 mmol) and TEA (1.52 mL, 10.94 mmol) was added to a solution of (R)-2-(2-bromo-5-chlorophenyl)-2,3,4,7-tetrahydro-1H-azepine hydrochloride (1.14 g, 3.53 mmol) dissolved in DCM (25 mL) and the reaction was stirred at rt overnight. The reaction mixture was diluted with DCM and washed with brine and dried through a phase separator. The solvents were evaporated and the crude product was purified by flash chromatography using a gradient of 0-20% EtOAc in heptane as mobile phase. Unreacted $Boc_2O$ co-eluted on the column so the product mixture was redissolved into DCM (20 mL), then DEA (5 mL) was added and the mixture was stirred at rt 3 h. The solvents were evaporated and the crude product was purified by flash chromatography using a gradient of 0-10% EtOAc in heptane as mobile phase to give (1.31 g, 96%) the title compound.

Step G. tert-Butyl (R)-2-(5-chloro-2-formylphenyl)-2,3,4,7-tetrahydro-1H-azepine-1-carboxylate

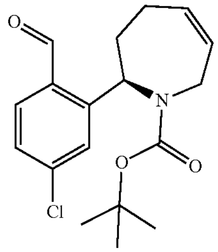 [SMILES: CC(C)(C)OC(=O)N1CC=CCC[C@@H]1c1cc(Cl)ccc1C=O]

tert-Butyl (R)-2-(2-bromo-5-chlorophenyl)-2,3,4,7-tetrahydro-1H-azepine-1-carboxylate (100 mg, 0.26 mmol), $Pd(OAc)_2$ (2.90 mg, 0.01 mmol), CataCXium A (13.91 mg, 0.04 mmol), and TMEDA (0.029 mL, 0.19 mmol) dissolved in toluene (1 mL) were added to a vessel and placed in an autoclave. The autoclave was purged with CO(g) several times, then synthesis gas ($CO:H_2$, 1:1, 5 bar) was filled into the autoclave. The autoclave was heated in an oilbath at 100° C. for 18 h. The solvents were evaporated and the crude product was purified by flash chromatography using a gradient of 0-25% of EtOAc in heptane as mobile phase to give (80 mg, 92%) the title compound. MS (ESI): m/z $[M+H]^+$ 236.

Step H. tert-Butyl (R)-2-(5-chloro-2-formylphenyl) azepane-1-carboxylate

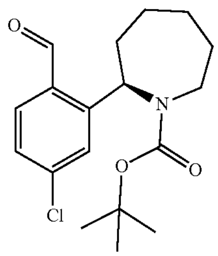 [SMILES: CC(C)(C)OC(=O)N1CCCCC[C@@H]1c1cc(Cl)ccc1C=O]

Pd/C (16.31 mg, 0.12 mmol) was added to a solution of tert-butyl (R)-2-(5-chloro-2-formylphenyl)-2,3,4,7-tetrahydro-1H-azepine-1-carboxylate (390 mg, 1.16 mmol) in MeOH (10 mL) and the resulting mixture was hydrogenated at 1 bar for 2 h. The catalysts was filtered off through Celite and washed with MeOH. The solvents were evaporated. The crude product was re-dissolved into DCM and the remaining solvents were evaporated to give (400 mg) the crude title compound as a yellow viscous oil. MS (ESI): m/z $[M+H]^+$ 238.

Step I. tert-Butyl (R)-2-(2-(((5-carbamoyl-1H-imidazol-4-yl)amino)methyl)-5-chlorophenyl)azepane-1-carboxylate

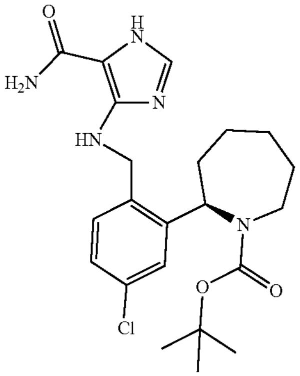 [SMILES: CC(C)(C)OC(=O)N1CCCCC[C@@H]1c1cc(Cl)ccc1CNc1nc[nH]c1C(N)=O]

AcOH (0.068 mL, 1.18 mmol) was added to a solution of tert-butyl (R)-2-(5-chloro-2-formylphenyl)azepane-1-carboxylate (400 mg, 1.18 mmol) and 4-amino-1H-imidazole-5-carboxamide (194 mg, 1.54 mmol) in EtOH (10 mL) and the reaction was heated at 40° C. for 16 h. The reaction mixture was diluted with EtOH (10 mL) and $NaBH_3CN$ (134 mg, 3.55 mmol) was added at rt and the reaction mixture was stirred at rt for 1 h. The reaction was quenched with water (4 mL) and concentrated. The residue was diluted with DCM (100 ml) and washed with brine (20 mL). The crude product was purified by preparative HPLC on a XBridge C18 column (10 μm 250×50 ID mm) using a gradient of 10-70% MeCN in $H_2O$/MeCN/$NH_3$ (95/5/0.2) as buffer system to give (63 mg, 12%) the title compound. MS (ESI): m/z $[M+H]^+$448.

Step J. tert-Butyl (R)-2-(2-((3-benzoyl-1-(5-carbamoyl-1H-imidazol-4-yl)thioureido)methyl)-5-chlorophenyl)azepane-1-carboxylate

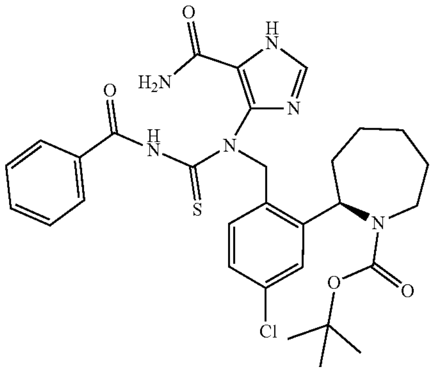 [SMILES: CC(C)(C)OC(=O)N1CCCCC[C@@H]1c1cc(Cl)ccc1CN(C(=S)NC(=O)c1ccccc1)c1nc[nH]c1C(N)=O]

tert-Butyl (R)-2-(2-(((5-carbamoyl-1H-imidazol-4-yl)amino)methyl)-5-chlorophenyl)azepane-1-carboxylate (63 mg, 0.14 mmol) was dissolved in MeCN (2 mL) and benzoyl isothiocyanate (0.023 mL, 0.17 mmol) was added. The reaction was stirred at rt for 18 h and the solvent was evaporated to give the title compound in quantitative yield. MS (ESI): m/z [M+H]+ 611.

Step K. tert-Butyl (R)-2-(5-chloro-2-((6-oxo-2-thioxo-1,2,6,7-tetrahydro-3H-purin-3-yl)methyl)phenyl)azepane-1-carboxylate tert-Butyl (R)-2-(2-((3-benzoyl-1-(5-carbamoyl-1H-imidazol-4-yl)thioureido)methyl)-5-chlorophenyl)azepane-1-carboxylate (86 mg, 0.14 mmol) was dissolved in a mixture of EtOH (2 mL) and 3.8 M NaOH (aq) (0.11 mL, 0.42 mmol) and the mixture was heated at 78° C. for 16 h. The reaction was quenched with 1 M HCl (5 mL) until pH 7, then the solvents were evaporated. The crude product was purified by preparative HPLC on a Kromasil C8 column (10 μm 250×20 ID mm) using a gradient of 10-60% MeCN in $H_2O$/MeCN/FA (95/5/0.2) buffer as mobile phase to give (34 mg, 50%) the title compound. MS (ESI): m/z $[M+H]^+$488.

Intermediate 8 tert-Butyl (R)-3-(2-((4-oxo-2-thioxo-2,3,4,5-tetrahydro-1H-pyrrolo[3,2-d]pyrimidin-1-yl)methyl)phenyl)morpholine-4-carboxylate

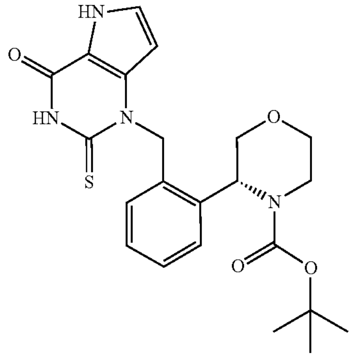 [SMILES: CC(C)(C)OC(=O)N1CCOC[C@H]1c1ccccc1Cn1c(=S)[nH]c(=O)c2[nH]ccc21]

Step A. (S,E)-N-(2-bromobenzylidene)-4-methylbenzenesulfinamide

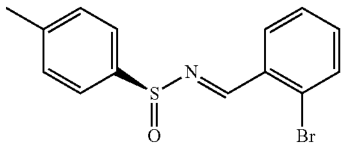 [SMILES: Cc1ccc([S@](=O)/N=C/c2ccccc2Br)cc1]

$Ti(OEt)_4$ (13.3 mL, 64.0 mmol) followed by (S)-4-methylbenzenesulfinamide (2.03 g, 13.1 mmol) were added to a solution of 2-bromobenzaldehyde (2.37 g, 12.81 mmol) in dry DCM (150 mL) and the reaction was refluxed for 4 h. The reaction was quenched with sat $NH_4Cl$ (aq) (300 mL) and stirred for 10 min. The reaction mixture was extracted with DCM and dried with a phase separator. The solvent was evaporated and EtOAc and heptane was added to give a white solid which was filtered off and dried to give (3.29 g, 80%) the title compound. MS (ESI): m/z $[M+H]^+$322.

Step B. (S)—N—((R)-(2-Bromophenyl)(1,3-dithian-2-yl)methyl)-4-methylbenzenesulfinamide

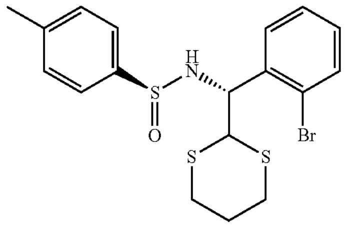 [SMILES: Cc1ccc([S@](=O)N[C@H](c2ccccc2Br)C2SCCCS2)cc1]

n-BuLi (2.5 M) (3.50 mL, 8.76 mmol) was added slowly to a solution of 1,3-dithiane (1.13 g, 9.37 mmol) in dry THF (33 mL) at −20° C. After 1.5 h, the resulting solution was cooled to −78° C. and added via a syringe to a—solution of (S,E)-N-(2-bromobenzylidene)-4-methylbenzenesulfinamide (2.019 g, 6.27 mmol) in dry THF (39 mL) at 78° C. The reaction was stirred for 20 min and quenched at −78° C. by the addition of sat $NH_4Cl$ (aq). The mixture was extracted with EtOAc, and the organic layer was dried ($MgSO_4$) and concentrated. The crude product was purified by flash chromatography using a gradient of 0-45% EtOAc in heptane as mobile phase to give (2.011 g, 72.5%) the title compound as a white solid. MS (ESI): m/z $[M+H]^+$442.

Step C. (R)—N-(1-(2-bromophenyl)-2-hydroxyethyl)-4-methylbenzenesulfonamide

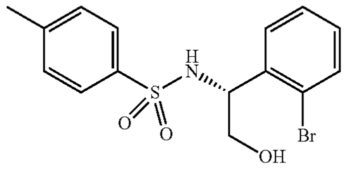 [SMILES: Cc1ccc(S(=O)(=O)N[C@@H](CO)c2ccccc2Br)cc1]

A solution of (S)—N—((R)-(2-bromophenyl)(1,3-dithian-2-yl)methyl)-4-methylbenzenesulfinamide (3.261 g, 7.37 mmol) in acetone (90 mL) was added dropwise to a solution of 1,3-dibromo-5,5-dimethylimidazolidine-2,4-dione (7.59 g, 26.53 mmol) in 80% acetone (aq) (70 mL) at −20° C. and the reaction was stirred for 12 min at −20° C. followed by 10 min at rt. The reaction was quenched with $Na_2SO_3$ (18 mL) and heptane/DCM (1/1, 18 mL). The organic phase was separated and washed with $NaHCO_3$(aq) (25 mL), water (25 mL) and brine (25 mL), and then dried with a phase separator and concentrated to give the intermediate aldehyde. The intermediate aldehyde was dissolved in EtOH (150 mL) and THF (4 mL) and cooled in an ice-bath. $NaBH_4$ (1.39 g, 36.8 mmol) was added and the mixture was stirred at rt for 30 min. The reaction was quenched by addition of sat $NH_4Cl$ (aq) and extracted with EtOAc. The combined organic extract was washed with brine, dried with a phase separator, and concentrated under reduced pressure to give (1.867 g, 68%) the title compound. MS (ESI): m/z $[M+H]^+$370.

Step D. (R)-3-(2-Bromophenyl)-4-tosylmorpholine

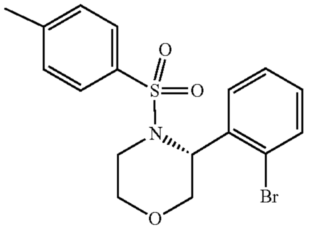 [SMILES: Cc1ccc(S(=O)(=O)N2CCOC[C@H]2c2ccccc2Br)cc1]

TEA (1.414 mL, 10.20 mmol) was added to a stirred solution of (R)—N-(1-(2-bromophenyl)-2-hydroxyethyl)-4-methylbenzenesulfonamide (1.87 g, 5.04 mmol) in DCM (85 mL) at 0° C. under $N_2$(g) atmosphere. After 10 min a solution of diphenyl(vinyl)sulfonium trifluoromethanesulfonate (2.193 g, 6.05 mmol, CAS Registry Number 247129-29-88) in DCM (45 mL) was added dropwise and the reaction was stirred for 3 h at 0° C., followed at rt overnight. The reaction was then quenched with sat $NH_4Cl$ (aq), and the mixture was extracted with DCM. The organic layer was washed with water, dried using a phase separator and concentrated under vacuum. The crude product was purified by flash chromatography using a gradient of 0-35% EtOAc in heptane as mobile phase to give (0.676 g, 33.8%) the title compound. MS (ESI): m/z $[M+H]^+$396.

Step E. (R)-3-(2-Bromophenyl)morpholine hydrobromide

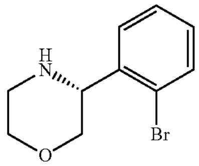 [SMILES: Brc1ccccc1[C@@H]1COCCN1]

A solution of (R)-3-(2-bromophenyl)-4-tosylmorpholine (0.676 g, 1.71 mmol), phenol (0.304 ml, 3.41 mmol) and 33% HBr in AcOH (4.9 mL) was stirred at rt overnight. The reaction mixture was poured into anhydrous $Et_2O$ (13 mL) to give a precipitate. The precipitate was removed by filtration, washed with $Et_2O$ and dried under vacuum to give (0.452 g, 82%) the title compound as a white solid. MS (ESI): m/z $[M+H]^+$ 242.

Step F. tert-Butyl (R)-3-(2-bromophenyl)morpholine-4-carboxylate

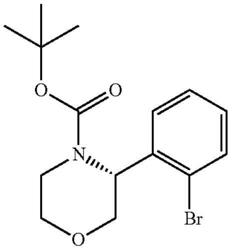 [SMILES: CC(C)(C)OC(=O)N1CCOC[C@H]1c1ccccc1Br]

$Boc_2O$ (0.336 g, 1.54 mmol) followed by TEA (0.601 mL, 4.34 mmol) was added to a solution of (R)-3-(2-Bromophenyl)morpholine hydrobromide (0.452 g, 1.40 mmol) in DCM (12 mL) and the reaction was stirred at rt overnight. DCM was added and the organic phase was washed with brine and dried with a phase separator and evaporated. The crude product was purified by flash chromatography using a gradient of 0-30% EtOAc in heptane to give (0.470 g, 98%) the title compound as a colourless oil. $^1H$ NMR (400 MHz, CDCl3) δ 1.31 (9H, s), 3.55-3.72 (2H, m), 3.85-3.91 (2H, m), 3.99-4.05 (1H, m), 4.08 (1H, dd), 5.22 (1H, dd), 7.13 (1H, td), 7.30 (1H, dd), 7.40 (1H, dd), 7.56 (1H, dd).

Step G. tert-Butyl (R)-3-(2-formylphenyl)morpholine-4-carboxylate

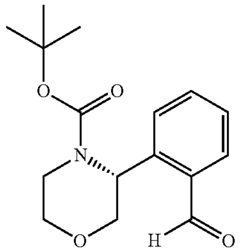 [SMILES: CC(C)(C)OC(=O)N1CCOC[C@H]1c1ccccc1C=O]

tert-Butyl (R)-3-(2-bromophenyl)morpholine-4-carboxylate (0.441 g, 1.29 mmol), $Pd(OAc)_2$ (0.014 g, 0.06 mmol), CataCXium A (0.069 g, 0.19 mmol) and TMEDA (0.145 mL, 0.97 mmol) were dissolved in toluene (2.5 mL) and sealed in an autoclave. The autoclave was filled with synthesis gas ($CO:H_2$, 1:1, 5 bar) and heated in an oilbath for at 100° C. for 6 h. The reaction was concentrated and the crude product was purified by flash chromatography using a gradient of 0-35% EtOAc in heptane as mobile phase to give (0.235 g, 62.6%) the title compound as yellow oil. MS (ESI): m/z $[M-Boc+H]^+$192.

Step H. tert-Butyl (R)-3-(2-(((2-(ethoxycarbonyl)-1H-pyrrol-3-yl)amino)methyl)phenyl)morpholine-4-carboxylate

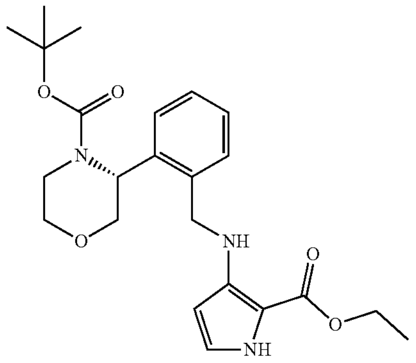 [SMILES: CCOC(=O)c1[nH]ccc1NCc1ccccc1[C@@H]1COCCN1C(=O)OC(C)(C)C]

tert-Butyl (R)-3-(2-formylphenyl)morpholine-4-carboxylate (0.220 g, 0.76 mmol) and ethyl 3-amino-1H-pyrrole-2-carboxylate hydrochloride (0.144 g, 0.76 mmol) were dissolved in MeOH (5.5 mL) and TEA (0.126 mL, 0.91 mmol) and the mixture was stirred at rt for 10 min. AcOH (0.086 mL, 1.51 mmol) was added and the mixture was stirred at rt for 10 min. $NaBH_3CN$ (0.040 mL, 0.76 mmol) was added and the mixture was stirred at rt for 4 h. The solvent was evaporated and the residue was dissolved in DCM and washed with water and dried with a phase separator. The solvent was evaporated and the crude product was purified by flash chromatography using a gradient of 0-20% EtOAc in DCM as mobile phase to give (0.124 g, 38%) the title compound. MS (ESI): m/z $[M-Boc+H]^+$430.

Step I. tert-Butyl (R)-3-(2-((3-benzoyl-1-(2-(ethoxycarbonyl)-1H-pyrrol-3-yl)thioureido)methyl)phenyl)morpholine-4-carboxylate

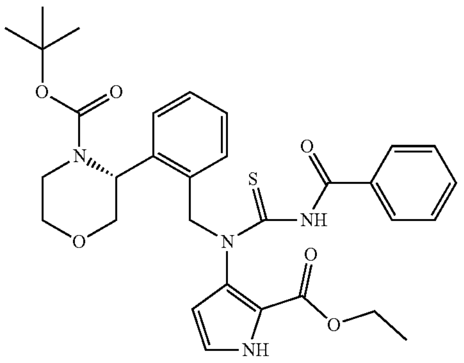 [SMILES: CCOC(=O)c1[nH]ccc1N(Cc1ccccc1[C@@H]1COCCN1C(=O)OC(C)(C)C)C(=S)NC(=O)c1ccccc1]

Benzoyl isothiocyanate (0.039 mL, 0.29 mmol) was added to a solution of tert-butyl (R)-3-(2-(((2-(ethoxycarbonyl)-1H-pyrrol-3-yl)amino)methyl)phenyl)morpholine-4-carboxylate (0.124 g, 0.29 mmol) in DCM (3 mL) and the reaction was stirred at rt overnight. The solvent was evaporated to give the title compound assuming a quantitative yield. MS (ESI): m/z $[M-Boc+H]^+$593.

Step J. tert-Butyl (R)-3-(2-((4-oxo-2-thioxo-2,3,4,5-tetrahydro-1H-pyrrolo[3,2-d]pyrimidin-1-yl)methyl)phenyl)morpholine-4-carboxylate $Cs_2CO_3$ (0.188 g, 0.58 mmol) was added to a solution of tert-butyl (R)-3-(2-((3-benzoyl-1-(2-(ethoxycarbonyl)-1H-pyrrol-3-yl)thioureido)methyl)phenyl)morpholine-4-carboxylate (0.171 g, 0.29 mmol) in MeOH (2.5 mL) and the mixture was heated at 65° C. for 5 h. The solvent was evaporated and the residue was diluted with water (10 mL) and acidified to pH 4 with AcOH and extracted with EtOAc (3×10 mL). The organic phase was and dried (MgSO4) filtered and evaporated to give (0.169 g) the crude title compound. MS (ESI): m/z $[M+H]^+$ 443.

Intermediate 9

Benzyl 4-methyl-2-(2-((4-oxo-2-thioxo-2,3,4,5-tetrahydro-1H-pyrrolo[3,2-d]pyrimidin-1-yl)methyl)phenyl)piperazine-1-carboxylate

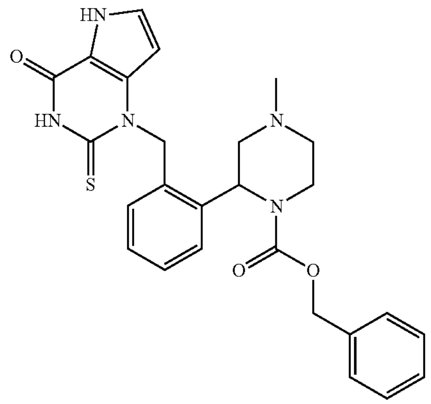 [SMILES: CN1CCN(C(=O)OCc2ccccc2)C(c2ccccc2Cn2c(=S)[nH]c(=O)c3[nH]ccc32)C1]

Step A. tert-Butyl 3-(2-bromophenyl)piperazine-1-carboxylate

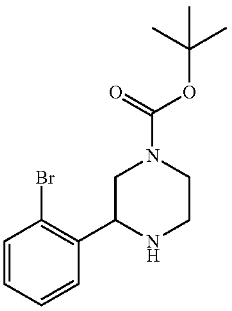 [SMILES: CC(C)(C)OC(=O)N1CCNC(c2ccccc2Br)C1]

A mixture of 2-(2-bromophenyl)piperazine (CAS Registry Number 910444-36-9) (4.172 g, 17.30 mmol), $Boc_2O$ (3.78 g, 17.30 mmol) and TEA (2.63 mL, 19.00 mmol) in DCM (65 mL) was stirred at rt for 1 h and then partitioned between water and DCM. The organic layer was washed with water, dried with a phase separator and evaporated in vacuo. The crude product was purified by flash chromatography using a gradient system of DCM/MeOH/$NH_4OH$ (99/1/0.2 to 9/1/0.2) to give the title compound in quantitative yield a as yellow oil. MS (ESI): m/z $[M+H]^+$341.

Step B. 1-Benzyl 4-(tert-butyl) 2-(2-bromophenyl)piperazine-1,4-dicarboxylate

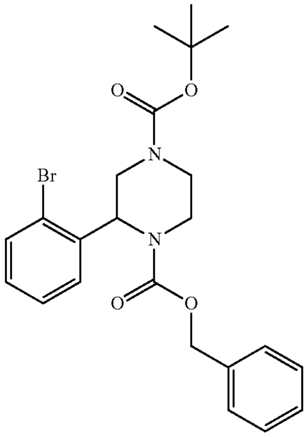 [SMILES: CC(C)(C)OC(=O)N1CCN(C(=O)OCc2ccccc2)C(c2ccccc2Br)C1]

A mixture of tert-butyl 3-(2-bromophenyl)piperazine-1-carboxylate (2.457 g, 7.2 mmol), benzyl carbonochloridate (1.71 g, 10.0 mmol) and DIPEA (2.68 mL, 15.4 mmol) in dioxane (40 mL) was heated at 95° C. for 4 h. After cooling, the reaction mixture was diluted with EtOAc (200 mL) and washed with sat $NaHCO_3$(aq) (100 mL) and brine (50 mL). The solvent was evaporated and the crude product was purified by flash chromatography using a gradient of 0-55% EtOAc in hepatene as mobile phase to give (2.84 g, 83%) the title compound as an oil.

Step C. 1-Benzyl 4-(tert-butyl) 2-(2-formylphenyl)piperazine-1,4-dicarboxylate

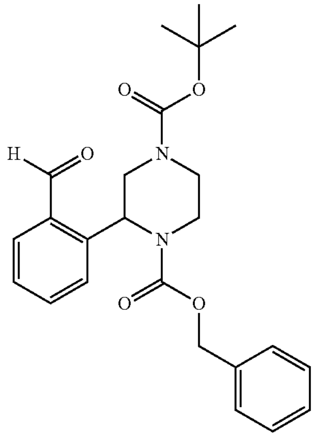 [SMILES: CC(C)(C)OC(=O)N1CCN(C(=O)OCc2ccccc2)C(c2ccccc2C=O)C1]

1-Benzyl 4-(tert-butyl) 2-(2-bromophenyl)piperazine-1,4-dicarboxylate (2.69 g, 5.66 mmol), $Pd(OAc)_2$ (0.064 g, 0.28 mmol), CataCXium A (0.304 g, 0.85 mmol), TMEDA (0.64 mL, 4.24 mmol) were dissolved in toluene (11 mL) and sealed in an autoclave. The autoclave was filled with synthesis gas ($CO:H_2$, 1:1, 5 bar) and heated in an oilbath for 18 h at 100° C. The solvent was evaporated an the crude product was purified by flash chromatography using a gradient of 0-38% EtOAc in heptane as mobile phase to give (1.46 g, 61%) the title compound. MS (ESI): m/z $[M+H]^+$ 425.

Step D. 1-Benzyl 4-(tert-butyl) 2-(2-(((2-(ethoxycarbonyl)-1H-pyrrol-3-yl)amino)methyl)phenyl) piperazine-1,4-dicarboxylate

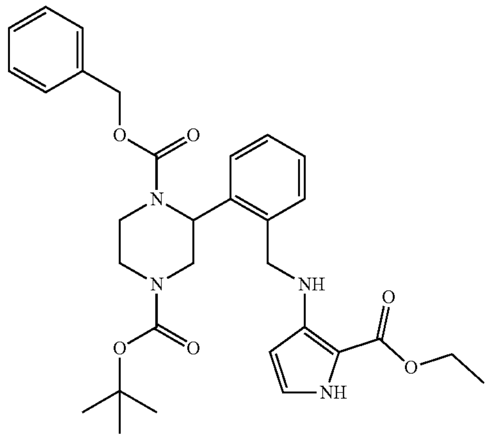 [SMILES: CCOC(=O)c1[nH]ccc1NCc1ccccc1C1CN(C(=O)OC(C)(C)C)CCN1C(=O)OCc1ccccc1]

1-Benzyl 4-(tert-butyl) 2-(2-formylphenyl)piperazine-1,4-dicarboxylate (1.46 g, 3.45 mmol), ethyl 3-amino-1H-pyrrole-2-carboxylate hydrochloride (0.69 g, 3.62 mmol) and TEA (0.573 mL, 4.14 mmol) were dissolved in EtOH (29 mL). The mixture was stirred at rt for 10 min. AcOH (0.395 mL, 6.89 mmol) was added and the reaction mixture was heated at 40° C. for 16 h. The reaction was allowed to cool to rt and $NaBH_4$ (0.287 g, 7.58 mmol) was added in portions and the reaction stirred at rt for 3.5 h. An additional $NaBH_4$ (0.287 g, 7.58 mmol) was added and the stirring was continued at rt for 2 h. The reaction was quenched with water (5 mL) and concentrated. The residue was diluted with DCM (100 mL) and washed with brine (25 mL). The solvent was evaporated and the crude product was purified by flash chromatography using a gradient of 0-18% EtOAc in DCM as mobile phase to give (0.85 g, 44%) the title compound. MS (ESI): m/z $[M+H]^+$563.

Step E. 1-Benzyl 4-(tert-butyl) 2-(2-((3-benzoyl-1-(2-(ethoxycarbonyl)-1H-pyrrol-3-yl)thioureido) methyl)phenyl)piperazine-1,4-dicarboxylate

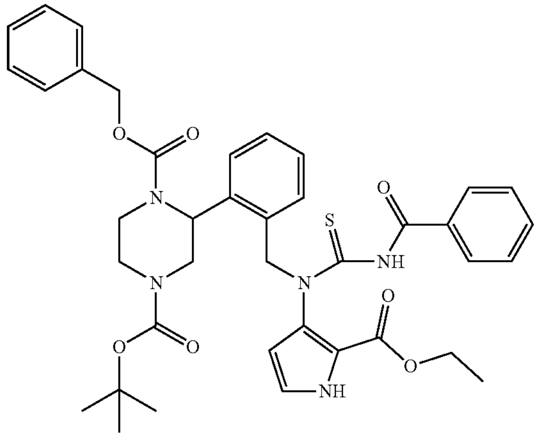 [SMILES: CCOC(=O)c1[nH]ccc1N(Cc1ccccc1C1CN(C(=O)OC(C)(C)C)CCN1C(=O)OCc1ccccc1)C(=S)NC(=O)c1ccccc1]

Benzoyl isothiocyanate (0.204 mL, 1.52 mmol) was added to a solution of 1-benzyl 4-(tert-butyl) 2-(2-(((2-(ethoxycarbonyl)-1H-pyrrol-3-yl)amino)methyl)phenyl) piperazine-1,4-dicarboxylate (0.853 g, 1.52 mmol) in DCM (16 mL) and the reaction was stirred at rt for 4 h. The solvent was evaporated to give the crude product assuming quantitative yield. MS (ESI): m/z $[M+H]^+$726

Step F. 1-Benzyl 4-(tert-butyl) 2-(2-((4-oxo-2-thioxo-2,3,4,5-tetrahydro-1H-pyrrolo[3,2-d]pyrimidin-1-yl)methyl)phenyl)piperazine-1,4-dicarboxylate

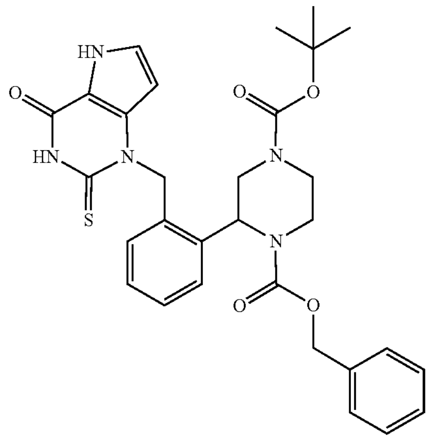 [SMILES: CC(C)(C)OC(=O)N1CCN(C(=O)OCc2ccccc2)C(c2ccccc2Cn2c(=S)[nH]c(=O)c3[nH]ccc32)C1]

$Cs_2CO_3$ (0.99 g, 3.03 mmol) was added to a solution of 1-benzyl 4-(tert-butyl) 2-(2-((3-benzoyl-1-(2-(ethoxycarbonyl)-1H-pyrrol-3-yl)thioureido)methyl)phenyl)piperazine-1,4-dicarboxylate (1.1 g, 1.52 mmol) in MeOH (12 mL) and the mixture was heated at 65° C. for 3.5 h. The solvent was evaporated and the residue was diluted with water (10 mL) and acidified to pH 4 with AcOH. The mixture was extracted with EtOAc (×3) and the combined organic layer was dried ($MgSO_4$). The solvent was evaporate to give (0.75 g, 86%) the title compound. MS (ESI): m/z $[M+H]^+$574.

Step G. Benzyl 2-(2-((4-oxo-2-thioxo-2,3,4,5-tetrahydro-1H-pyrrolo[3,2-d]pyrimidin-1-yl)methyl)phenyl)piperazine-1-carboxylate 2,2,2-trifluoroacetate

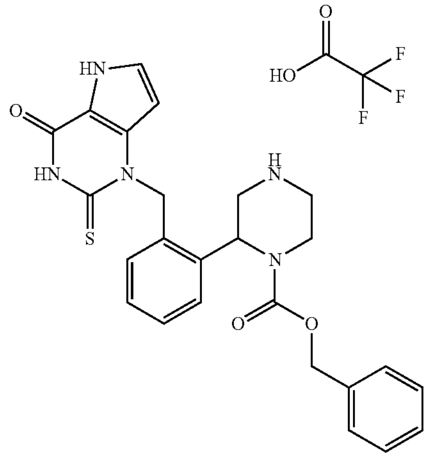 [SMILES: O=C(OCc1ccccc1)N1CCNCC1c1ccccc1Cn1c(=S)[nH]c(=O)c2[nH]ccc21 ; O=C(O)C(F)(F)F]

TFA (3.3 mL) was added to a solution of 1-benzyl 4-(tert-butyl) 2-(2-((4-oxo-2-thioxo-2,3,4,5-tetrahydro-1H- pyrrolo[3,2-d]pyrimidin-1-yl)methyl)phenyl)piperazine-1,4-dicarboxylate (0.746 g, 1.30 mmol) in DCM (20 mL) and the mixture was stirred at rt for 1.5 h. The solvents were evaporated to give (0.77 g, 10%) the title compound. MS (ESI): m/z $[M+H]^+$476.

Step H. Benzyl 4-methyl-2-(2-((4-oxo-2-thioxo-2,3,4,5-tetrahydro-1H-pyrrolo[3,2-d]pyrimidin-1-yl)methyl)phenyl)piperazine-1-carboxylate Formaldehyde (33 weight % in $H_2O$) (0.668 mL, 6.53 mmol) followed by $NaBH(OAc)_3$ (0.415 g, 1.96 mmol) was added to a solution of benzyl 2-(2-((4-oxo-2-thioxo-2,3,4,5-tetrahydro-1H-pyrrolo[3,2-d]pyrimidin-1-yl)methyl)phenyl)piperazine-1-carboxylate 2,2,2-trifluoroacetate (0.77 g, 1.31 mmol) in DCM (10 mL) and the reaction was stirred at rt for 2 h. The reaction was diluted with DCM and washed with sat $NaHCO_3$(aq) and brine. The organic phase was filtered in a phase separator and the solvent was evaporated to give (0.590 g, 92%) the title compound as a solid. MS (ESI): m/z $[M+H]^+$490.

Intermediate 10

2-Thioxo-1-(2-(1-tosyl-4-(trifluoromethyl)piperidin-2-yl)benzyl)-1,2,3,5-tetrahydro-4H-pyrrolo[3,2-d]pyrimidin-4-one

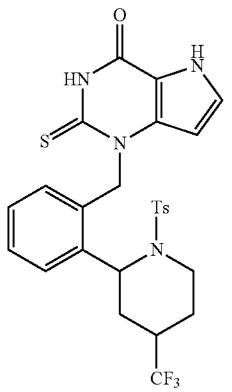 [SMILES: Cc1ccc(S(=O)(=O)N2CCC(C(F)(F)F)CC2c2ccccc2Cn2c(=S)[nH]c(=O)c3[nH]ccc32)cc1]

Step A. 2-(2-(Methoxymethyl)phenyl)-4-(trifluoromethyl)pyridine

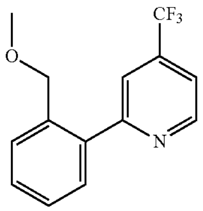 [SMILES: COCc1ccccc1-c1cc(C(F)(F)F)ccn1]

2-Chloro-4-(trifluoromethyl)pyridine (12.06 g, 66.4 mmol) was added to a solution of [2-(methoxymethyl)phenyl]boronic acid (10 g, 60.2 mmol) in dioxane-$H_2O$ (10/1) (264 mL) and the flask was purged and maintained with an inert atmosphere of $N_2$(g). $Na_2CO_3$ (6.36 g, 60.0 mmol) and $Pd(dppf)Cl_2 \times CH_2Cl_2$ (1.32 g, 1.44 mmol) were added and the resulting solution was stirred at 100° C. for 16 h. The resulting solids were filtered off, and the solvents removed in vaccuo. The crude product was purified by flash chromatography using heptane/EtOAc (9/1) as mobile phase to give (13 g, 75%) the title compound as a light brown liquid. MS (ESI): m/z $[M+H]^+$268.

Step B. 2-(2-(Methoxymethyl)phenyl)-4-(trifluoromethyl)piperidine

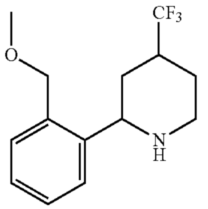 [SMILES: COCc1ccccc1C1CC(C(F)(F)F)CCN1]

A solution of 2-[2-(methoxymethyl)phenyl]-4-(trifluoromethyl)pyridine (2.3 g, 8.61 mmol) in MeOH (50 mL) was placed into a round-bottom flask under $N_2$(g) atmosphere followed by 12 M HCl (2.88 mL) and $PtO_2$ (230 mg, 1.01 mmol). The mixture was evacuated and back-filled with $H_2$(g) (×3), and then hydrogenated at 1 bar and rt for 3 h. The reaction was filtered and concentrated under vacuum. The residue was diluted with water (40 mL) and the pH was adjusted to 10 with sat $Na_2CO_3$ (aq). The resulting aqueous solution was extracted with DCM (2×30 mL) and the organic layers combined and concentrated under vacuum. The crude product was purified by flash chromatography using heptane/EtOAc (6/1) as mobile phase to give (1.2 g, 51%) the title compound as a light yellow solid. MS (ESI): m/z $[M+H]^+$ 274.

Step C. 2-(2-(Methoxymethyl)phenyl)-1-tosyl-4-(trifluoromethyl)piperidine

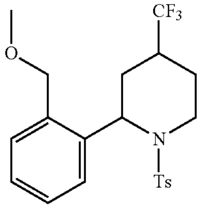 [SMILES: COCc1ccccc1C1CC(C(F)(F)F)CCN1S(=O)(=O)c1ccc(C)cc1]

TsCl (1.68 g, 8.81 mmol, 1.20 equiv) was added to a solution of 2-[2-(methoxymethyl)phenyl]-4-(trifluoromethyl)piperidine (2.0 g, 7.32 mmol) and TEA (2.22 g, 21.9 mmol) in DCM (4.0 mL). The resulting solution was stirred at rt for 4 h, and then diluted with DCM (40 mL) and water (40 mL). The organic layer was washed with water (2×40 mL) and brine (40 mL), dried ($Na_2SO_4$) and concentrated under vacuum. The crude product was purified by flash chromatography using heptane/EtOAc (6/1) as mobile phase to give (2.95 g, 94%) the title compound as a light yellow solid. MS (ESI): m/z $[M+H]^+$ 274.

Step D. 2-(2-(Bromomethyl)phenyl)-1-tosyl-4-(trifluoromethyl)piperidine

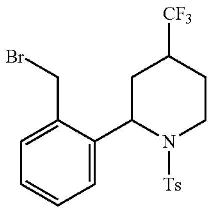 [SMILES: Cc1ccc(S(=O)(=O)N2CCC(C(F)(F)F)CC2c2ccccc2CBr)cc1]

A solution of $BBr_3$ (492 mg, 1.97 mmol) in DCM (1.0 mL) was added dropwise to a solution of 2-[2-(methoxymethyl)phenyl]-1-[(4-methylbenzene)sulfonyl]-4-(trifluoromethyl)piperidine (280 mg, 0.66 mmol) in DCM (4.0 mL) at 0° C. The resulting solution was stirred for 30 min at 0° C., then water (2.0 mL) was added dropwise at 0° C. The resulting aqueous solution was extracted with DCM (2×20 mL). The combined organic layer was washed with water (2×10 mL) and brine (10 mL), dried ($Na_2SO_4$), and concentrated under vacuum give (250 mg, 80%) the title compound as a light brown oil. MS (ESI): m/z $[M+H]^+$ 476.

Step E. (2-(1-Tosyl-4-(trifluoromethyl)piperidin-2-yl)phenyl)methanol

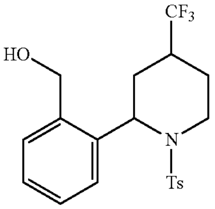 [SMILES: Cc1ccc(S(=O)(=O)N2CCC(C(F)(F)F)CC2c2ccccc2CO)cc1]

KOH (710 mg, 12.6 mmol) was added to a solution of 2-(2-(bromomethyl)phenyl)-1-tosyl-4-(trifluoromethyl)piperidine (3.0 g, 6.3 mmol) in dioxane/water (1/1) (80 mL) and the resulting solution was stirred at 50° C. for 5 h and then cooled to rt. The reaction was diluted with EtOAc (60 mL) and water (40 mL). The organic layer was washed with water (40 mL) and brine (40 mL), dried ($Na_2SO_4$), and concentrated under vacuum. The residue was purified by flash chromatography using 5% EtOAc in heptane as mobile phase to give (1.8 g, 69%) the title compound as a light yellow solid. MS (ESI): m/z $[M+H]^+$414.

Step F. 2-(1-Tosyl-4-(trifluoromethyl)piperidin-2-yl) benzaldehyde

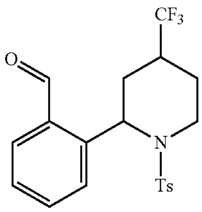 [SMILES: Cc1ccc(S(=O)(=O)N2CCC(C(F)(F)F)CC2c2ccccc2C=O)cc1]

DMP (3.7 g, 8.72 mmol) was added to a solution of (2-(1-tosyl-4-(trifluoromethyl)piperidin-2-yl)phenyl)methanol (1.8 g, 4.35 mmol) in DCM (40 mL) at 0° C. The resulting solution was stirred at 0-20° C. for 2 h. 1 M NaOH (aq) was added dropwise at 0° C., and the resulting aqueous solution was diluted with DCM (40 mL) and water (40 mL). The organic layer was washed with water (2×40 mL) and brine (40 mL), dried ($Na_2SO_4$), and concentrated under vacuum. The crude product was purified by flash chromatography using 14% EtOAc in heptane as mobile phase to give (1.75 g, 98%) the title compound as a red oil. MS (ESI): m/z $[M+H]^+$412.

Step G. Ethyl 3-((2-(1-tosyl-4-(trifluoromethyl)piperidin-2-yl)benzyl)amino)-1H-pyrrole-2-carboxylate

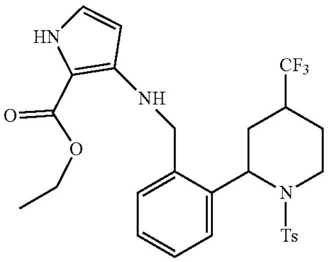 [SMILES: CCOC(=O)c1[nH]ccc1NCc1ccccc1C1CC(C(F)(F)F)CCN1S(=O)(=O)c1ccc(C)cc1]

AcOH (225 mg, 3.76 mmol) and $NaBH(OAc)_3$ (2.71 g, 12.79 mmol) were added to a solution of 2-(1-tosyl-4-(trifluoromethyl)piperidin-2-yl)benzaldehyde (1.75 g, 4.25 mmol) and ethyl 3-amino-1H-pyrrole-2-carboxylate hydrochloride (970 mg, 6.29 mmol) in DCE (40 mL). The resulting solution was stirred for 16 h at rt, and then quenched by the addition of sat $NaHCO_3$(aq) (20 mL). The resulting aqueous solution was diluted with DCM (40 mL) and water (30 mL), and the organic layer was washed with water (40 mL) and brine (40 mL), dried ($Na_2SO_4$), and concentrated under vacuum. The crude product was purified by flash chromatography using 17% EtOAc in heptane as mobile phase to give (2.0 g, 86%) the title compound as a white solid. MS (ESI): m/z $[M+H]^+$ 550.

Step H. Ethyl 3-(3-benzoyl-1-(2-(1-tosyl-4-(trifluoromethyl)piperidin-2-yl)benzyl)thioureido)-1H-pyrrole-2-carboxylate

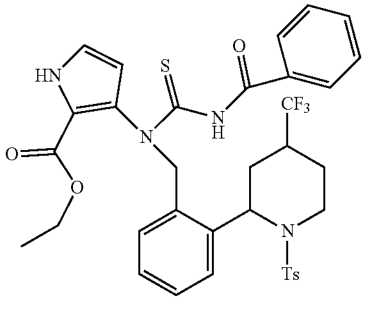 [SMILES: CCOC(=O)c1[nH]ccc1N(Cc1ccccc1C1CC(C(F)(F)F)CCN1S(=O)(=O)c1ccc(C)cc1)C(=S)NC(=O)c1ccccc1]

Benzoyl isothiocyanate (579 mg, 3.55 mmol) was added to a solution of ethyl 3-((2-(1-tosyl-4-(trifluoromethyl)piperidin-2-yl)benzyl)amino)-1H-pyrrole-2-carboxylate (1.5 g, 2.73 mmol) in MeCN (40 mL). The resulting solution was stirred for 4 h at rt and concentrated under vacuum to give (2.1 g) the crude title compound as a yellow solid. MS (ESI): m/z [M+H]+ 713.

Step I. 2-Thioxo-1-(2-(1-tosyl-4-(trifluoromethyl)piperidin-2-yl)benzyl)-1,2,3,5-tetrahydro-4H-pyrrolo[3,2-d]pyrimidin-4-one $Cs_2CO_3$ (1.72 g, 5.28 mmol, 1.94 equiv) was added to a solution of ethyl 3-[[(2-[1-[(4-methylbenzene)sulfonyl]-4-(trifluoro-methyl)piperidin-2-yl]phenyl)methyl][(phenylformamido)methanethioyl]amino]-1H-pyrrole-2-carboxylate (1.94 g, 2.72 mmol) in MeOH (50 mL), and the reaction was stirred for 4 h at 50° C. and then concentrated under vacuum. The residue was dissolved in water (80 mL) and AcOH (737 mg). The pH value of the solution was adjusted to 6 with 3 M HCl (aq) The resulting aqueous solution was extracted with DCM (2×50 mL). The combined organic layer was washed with water (2×50 mL) and brine (50 mL). The organic layer was dried ($Na_2SO_4$) and concentrated under vacuum. The crude product was purified by flash chromatography using DCM/MeOH (20/1) as mobile phase to give (1.35 g, 88%) the title compound as a light yellow solid. MS (ESI): m/z $[M+H]^+$563.

Intermediate 11 tert-Butyl 2-(2-((3-benzoyl-1-(2-(ethoxycarbonyl)-1H-pyrrol-3-yl)thioureido)methyl)phenyl)-5-(trifluoromethyl)piperidine-1-carboxylate

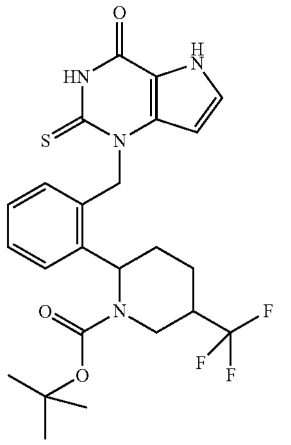 [SMILES: CC(C)(C)OC(=O)N1CC(C(F)(F)F)CCC1c1ccccc1Cn1c(=S)[nH]c(=O)c2[nH]ccc21]

Step A. tert-Butyl 2-oxo-5-(trifluoromethyl)piperidine-1-carboxylate

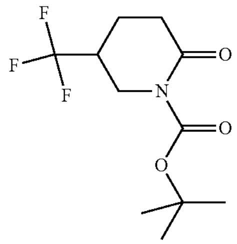 [SMILES: CC(C)(C)OC(=O)N1CC(C(F)(F)F)CCC1=O]

DMAP (1.61 g, 13.2 mmol) and $Boc_2O$ (3.13 g, 14.36 mmol) was added to a solution of 5-(trifluoromethyl)piperidin-2-one (CAS Registry Number 50549-24-1) (2 g, 11.97 mmol) in 2-methyltetrahydrofuran (50 mL). The mixture was stirred at rt for 2.5 h. 1 M $KHSO_4$ (30 mL) was added and the layers were separated and the aqueous phase was extracted with methyltetrahydrofuran (50 mL). The combined organic layer was washed with water (40 mL) and brine (40 mL), dried ($Na_2SO_4$) and concentrated in vacuo to give (3.18 g, 99%) the title compound. $^1H$ NMR (400 MHz, CDCl3) δ 1.53 (9H, s), 1.84-1.98 (1H, m), 2.13 (1H, qd), 2.42-2.56 (1H, m), 2.57-2.74 (2H, m), 3.74 (1H, dd), 3.99 (1H, ddd).

Step B. (2-Bromophenyl)magnesium chloride

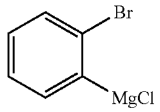

A solution of 1,2-dibromobenzene (1.204 mL, 10 mmol) in THF (10 mL) in an oven-dried flask and under $N_2$(g) atmosphere was cooled to −40° C. iPrMgCl×LiCl (1.3 M, 7.69 mL, 10.00 mmol) was added dropwise during 2 min. The mixture was stirred at −40° C. for 10 min, then the reaction was allowed to reach 0° C. over 2 h. The reaction mixture was used directly in the next step.

Step C. tert-Butyl (5-(2-bromophenyl)-5-oxo-2-(trifluoromethyl)pentyl)carbamate

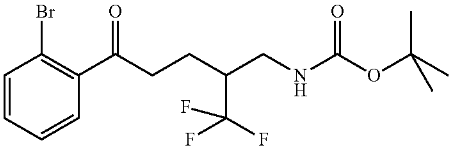 [SMILES: CC(C)(C)OC(=O)NCC(CCC(=O)c1ccccc1Br)C(F)(F)F]

(2-Bromophenyl)magnesium chloride (18.9 mL, 10.00 mmol) was added dropwise via syringe at −40° C. to a solution of tert-butyl 2-oxo-5-(trifluoromethyl)piperidine-1-carboxylate (891 mg, 3.33 mmol) in dry THF (15 mL) in an oven-dried flask under $N_2$-atmosphere. The mixture was allowed to slowly reach rt and stirred for 15 h. Sat $NH_4Cl$ (aq) (30 mL) was added and the layers were separated. The aqueous phase was extracted with DCM (30 mL) and the combined organic layer was dried ($Na_2SO_4$), filtered and concentrated in vacuo to give (2.3 g) the title compound. MS (ESI): m/z $[M+H]^+$324.

Step D. 2-(2-Bromophenyl)-5-(trifluoromethyl)piperidine

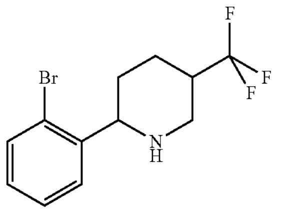 [SMILES: FC(F)(F)C1CCC(c2ccccc2Br)NC1]

HCl (1.25 M in MeOH) (25 mL, 31.25 mmol) was added to tert-butyl (5-(2-bromophenyl)-5-oxo-2-(trifluoromethyl) pentyl)carbamate (1.41 g, 3.33 mmol), and the mixture was stirred at rt for 1.5 h, 65° C. for 1 h, and at 40° C. for 16 h. The mixture was concentrated in vacuo and the residue was dissolved in MeOH (20 mL). $NaBH_3CN$ (0.42 g, 6.67 mmol) was added and the mixture was stirred at rt for 2 h. Water (10 mL) was added and the mixture was concentrated in vacuo. DCM (25 mL) was added to the residue and the organic layer was washed with sat $NaHCO_3$(aq) (20 mL) using a phase separator. The aqueous layer was extracted with DCM (3×25 mL) and the combined organic layer was concentrated in vacuo. The crude product was purified by flash chromatography using a gradient of 40-100% EtOAc in heptane as mobile phase to give (0.245 g, 24%) the title compound. MS (ESI): m/z $[M+H]^+$308.

Step E. tert-Butyl 2-(2-bromophenyl)-5-(trifluoromethyl)piperidine-1-carboxylate

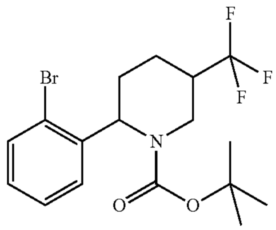 [SMILES: CC(C)(C)OC(=O)N1CC(C(F)(F)F)CCC1c1ccccc1Br]

DIPEA (0.17 mL, 0.95 mmol) and $Boc_2O$ (208 mg, 0.95 mmol) was added to a solution of 2-(2-bromophenyl)-5-(trifluoromethyl)piperidine (245 mg, 0.80 mmol) in DCM (5 mL. The mixture was stirred at rt for 22 h. 1 M $KHSO_4$ (aq) (4 mL) was added and the layers were separated and the aqueous phase was extracted with DCM (5 mL) using a phase separator. The organic layers were combined and washed with brine (5 mL) and concentrated in vacuo to give (330 mg, 102%) the title compound which was used without further purification.

Step F. tert-Butyl 2-(2-formylphenyl)-5-(trifluoromethyl)piperidine-1-carboxylate

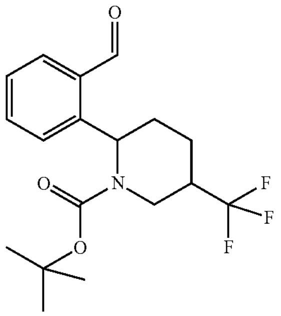 [SMILES: CC(C)(C)OC(=O)N1CC(C(F)(F)F)CCC1c1ccccc1C=O]

tert-Butyl 2-(2-bromophenyl)-5-(trifluoromethyl)piperidine-1-carboxylate (330 mg, 0.81 mmol), $Pd(OAc)_2$ (9.07 mg, 0.04 mmol), CataCXium A (43.5 mg, 0.12 mmol), TMEDA (0.091 mL, 0.61 mmol) were dissolved in toluene (1.5 mL) and sealed in an autoclave. The autoclave was filled with synthesis gas ($CO:H_2$, 1:1, 5 bar). The mixture was stirred in an oil bath at 100° C. for 17 h and was then concentrated in vacuo. The crude product was purified by flash chromatography using a gradient of 10-50% EtOAc in heptane as mobile phase to give (127 mg, 44%) the title compound. $^1H$ NMR (400 MHz, CDCl3) δ 1.23 (9H, s), 1.38-1.58 (1H, m), 1.66-1.8 (1H, m), 1.95-2.07 (1H, m), 2.17-2.35 (1H, m), 2.48-2.65 (1H, m), 3.53 (1H, ddd), 4.40 (1H, dd), 5.73 (1H, dd), 7.38 (1H, ddd), 7.44 (1H, td), 7.56 (1H, td), 7.81 (1H, dd), 10.17 (1H, s).

Step G. tert-Butyl 2-(2-(((2-(ethoxycarbonyl)-1H-pyrrol-3-yl)amino)methyl)phenyl)-5-(trifluoromethyl)piperidine-1-carboxylate

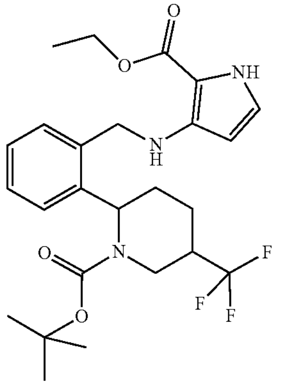 [SMILES: CCOC(=O)c1[nH]ccc1NCc1ccccc1C1CCC(C(F)(F)F)CN1C(=O)OC(C)(C)C]

DIPEA (0.068 mL, 0.39 mmol), AcOH (0.041 mL, 0.71 mmol) and tert-butyl 2-(2-formylphenyl)-5-(trifluoromethyl)piperidine-1-carboxylate (127 mg, 0.36 mmol) was added to a solution of ethyl 3-amino-1H-pyrrole-2-carboxylate hydrochloride (74.5 mg, 0.39 mmol) in EtOH (10 mL) and the mixture was stirred at 40° C. for 15 h. $NaBH_3CN$ (67.0 mg, 1.07 mmol) was added in one portion and the mixture was stirred rt for 4.5 h. An additional $NaBH_3CN$ (0.037 mL, 0.71 mmol) was added and the reaction mixture was stirred at rt for 1 h. Water (10 mL) was added and the reaction mixture was concentrated in vacuo. The residue was dissolved in DCM (10 mL) and the resulting mixture was washed with brine (5 mL) using a phase separator. The aqueous layer was washed with DCM (10 mL) and the combined organic layer was concentrated in vacuo. The crude product was purified by preparative HPLC on a Kromasil C8 column (10 μm 250×50 mm ID) using a gradient of 40-85% MeCN in $H_2O$/MeCN/AcOH (95/5/0.2) buffer system as mobile phase to give (110 mg, 62%) the title compound. MS (ESI): m/z $[M+H]^+$308.

Step H. tert-Butyl 2-(2-((3-benzoyl-1-(2-(ethoxycarbonyl)-1H-pyrrol-3-yl)thioureido)methyl)phenyl)-5-(trifluoromethyl)piperidine-1-carboxylate

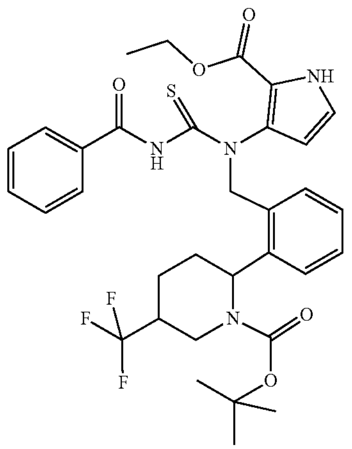 [SMILES: CCOC(=O)c1[nH]ccc1N(Cc1ccccc1C1CCC(C(F)(F)F)CN1C(=O)OC(C)(C)C)C(=S)NC(=O)c1ccccc1]

Bensoyl isothiocyante (43.5 mg, 0.27 mmol) was added to a solution of tert-butyl 2-(2-(((2-(ethoxycarbonyl)-1H-pyrrol-3-yl)amino)methyl)phenyl)-5-(trifluoromethyl)piperidine-1-carboxylate (110 mg, 0.22 mmol) in MeCN (5 mL). The mixture was stirred at rt for 18 h and was then concentrated in vacuo to give the title compound. MS (ESI): m/z $[M+H]^+$496.

Step I. tert-Butyl 2-(2-((3-benzoyl-1-(2-(ethoxycarbonyl)-1H-pyrrol-3-yl)thioureido)methyl)phenyl)-5-(trifluoromethyl)piperidine-1-carboxylate $Cs_2CO_3$ (144 mg, 0.44 mmol) was added to a solution of tert-butyl 2-(2-((3-benzoyl-1-(2-(ethoxycarbonyl)-1H-pyrrol-3-yl)thioureido)methyl)phenyl)-5-(trifluoromethyl)piperidine-1-carboxylate (146 mg, 0.22 mmol) in MeOH (2 mL). The mixture was stirred at 65° C. for 3 h and then concentrated in vacuo. DCM (5 mL) and water (5 mL) was added to the residue and the layers were separated using a phase separator. 1 M HCl was added to the aqueous phase until pH 6-7 was reached, and the aqueous phase was extracted with an additional DCM (3×5 mL). The combined organic layer was concentrated in vacuo to give (175 mg) the title compound. MS (ESI): m/z $[M+H]^+$ 509.

Intermediate 12

1-(2-(4,4-Difluoropiperidin-2-yl)benzyl)-2-thioxo-1,2,3,5-tetrahydro-4H-pyrrolo[3,2-d]pyrimidin-4-one

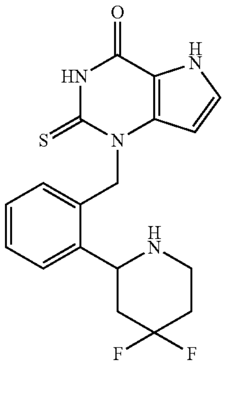 [SMILES: O=c1[nH]c(=S)n(Cc2ccccc2C2CC(F)(F)CCN2)c2cc[nH]c12]

Step A. Benzyl 4,4-difluoro-2-(2-(methoxymethyl)phenyl)piperidine-1-carboxylate

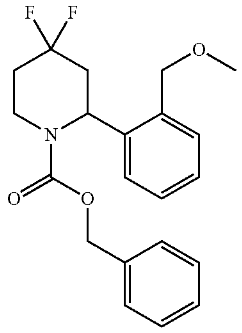 [SMILES: COCc1ccccc1C1CC(F)(F)CCN1C(=O)OCc1ccccc1]

DAST (3.3 g, 20.5 mmol) was added to a solution of benzyl 2-[2-(methoxymethyl)phenyl]-4-oxopiperidine-1-carboxylate (1.8 g, 5.09 mmol) in DCM (50 mL) at 0° C. The resulting solution was stirred for 48 h at rt and the reaction was quenched with $NH_4Cl$ (aq) (10 mL). The resulting organic layer was washed with water (3×20 mL) and brine (3×20 mL), dried ($Na_2SO_4$) and concentrated under vacuum. The crude product was purified by flash chromatography using a gradient of 0-5% EtOAc in petroleum ether to give (800 mg, 42%) the title compound as light yellow oil. MS (ESI): m/z $[M+H]^+$ 376.

Step B. Benzyl 4,4-difluoro-2-(2-formylphenyl)piperidine-1-carboxylate

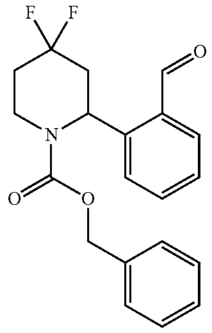 [SMILES: O=Cc1ccccc1C1CC(F)(F)CCN1C(=O)OCc1ccccc1]

$HNO_3$ (202 mg, 2.20 mmol) was added dropwise to a solution of benzyl 4,4-difluoro-2-[2-(methoxymethyl)phenyl]piperidine-1-carboxylate (300 mg, 0.80 mmol) in DCM (10 mL). The resulting solution was stirred for 3 days at rt and diluted with EtOAc (50 mL). The resulting organic layer was washed with water (3×20 mL) and brine (3×20 mL), dried over anhydrous ($Na_2SO_4$) and concentrated under vacuum. The crude product was purified by flash chromatography using a gradient of 0-15% EtOAc in petroleum ether to give (138 mg, 48%) the title compound as a brown oil. MS (ESI): m/z $[M+H]^+$360.

Step C. Benzyl 2-(2-(((2-(ethoxycarbonyl)-1H-pyrrol-3-yl)amino)methyl)phenyl)-4,4-difluoropiperidine-1-carboxylate

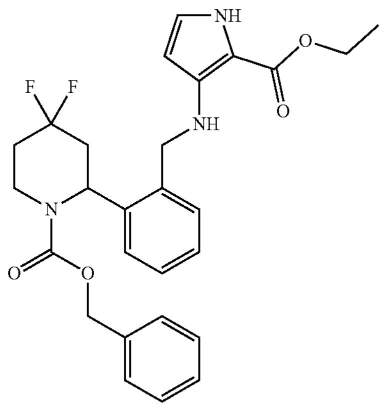 [SMILES: CCOC(=O)c1[nH]ccc1NCc1ccccc1C1CC(F)(F)CCN1C(=O)OCc1ccccc1]

TEA (2.5 g, 24.7 mmol) and $NaBH(OAc)_3$ (3.2 g, 15.1 mmol) was added to a suspension of benzyl 4,4-difluoro-2-(2-formylphenyl)piperidine-1-carboxylate (1.8 g, 5.01 mmol) and ethyl 3-amino-1H-pyrrole-2-carboxylate (950 mg, 6.16 mmol) in DCM (50 mL). The resulting solution was stirred for 48 h at rt and the reaction was quenched by the addition of water (20 mL). The resulting aqueous solution was extracted with DCM (3×30 mL), washed with brine (2×20 mL), dried ($Na_2SO_4$) and concentrated under vacuum. The crude product was purified by flash chromatography using a gradient of 0-20% EtOAc in petroleum ether to give (1.9 g, 76%) the title compound as a brown oil. MS (ESI): m/z $[M+H]^+$498.

Step D. Benzyl 2-(2-((3-benzoyl-1-(2-(ethoxycarbonyl)-1H-pyrrol-3-yl)thioureido)methyl)phenyl)-4,4-difluoropiperidine-1-carboxylate

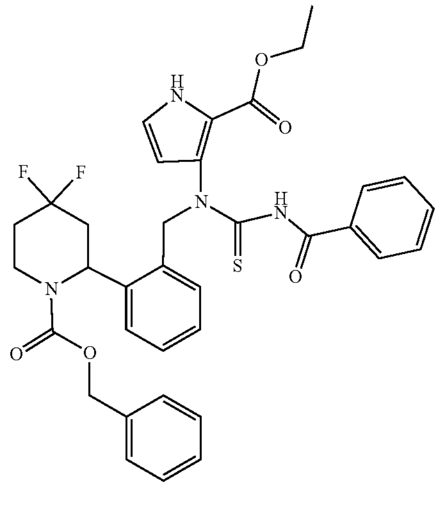 [SMILES: CCOC(=O)c1[nH]ccc1N(Cc1ccccc1C1CC(F)(F)CCN1C(=O)OCc1ccccc1)C(=S)NC(=O)c1ccccc1]

Benzoyl isothiocyanate (2 g, 12.3 mmol) was added dropwise to a solution of benzyl 2-(2-(((2-(ethoxycarbonyl)-1H-pyrrol-3-yl)amino)methyl)phenyl)-4,4-difluoropiperidine-1-carboxylate (2 g, 4.02 mmol) in MeCN (50 mL) at 0° C. The resulting solution was stirred for 4 h at rt and then concentrated under vacuum. The crude product was purified by flash chromatography using a gradient of 0-20% EtOAc in petroleum ether to give (1.8 g, 68%) the title compound as a brown oil. MS (ESI): m/z $[M+H]^+$661.

Step E. benzyl 4,4-difluoro-2-(2-((4-oxo-2-thioxo-2,3,4,5-tetrahydro-1H-pyrrolo[3,2-d]pyrimidin-1-yl)methyl)phenyl)piperidine-1-carboxylate

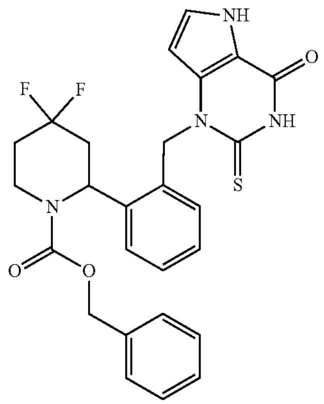 [SMILES: O=C(OCc1ccccc1)N1CCC(F)(F)CC1c1ccccc1Cn1c(=S)[nH]c(=O)c2[nH]ccc21]

$Cs_2CO_3$ (1.8 g, 5.54 mmol) was added in portions to a solution of benzyl 2-(2-((3-benzoyl-1-(2-(ethoxycarbonyl)-1H-pyrrol-3-yl)thioureido)methyl)phenyl)-4,4-difluoropiperidine-1-carboxylate (1.8 g, 2.72 mmol) in MeOH (50 mL). The resulting solution was stirred for 2 h at 50° C. and concentrated under vacuum. The crude product was purified by flash chromatography using a gradient of 0-10% MeOH in DCM to give (1.2 g, 86%) the title compound as a white solid. MS (ESI): m/z $[M+Na]^+$533.

Step F. 1-(2-(4,4-Difluoropiperidin-2-yl)benzyl)-2-thioxo-1,2,3,5-tetrahydro-4H-pyrrolo[3,2-d]pyrimidin-4-one Benzyl 4,4-difluoro-2-(2-((4-oxo-2-thioxo-2,3,4,5-tetrahydro-1H-pyrrolo[3,2-d]pyrimidin-1-yl)methyl)phenyl)piperidine-1-carboxylate (500 mg, 0.98 mmol) was added to a suspension of HBr in AcOH(40% w/w) (5 mL, 87.8 mmol) and PhOH (460 mg, 4.90 mmol) and the resulting solution was stirred for 1 h at rt and then concentrated under vacuum. The crude product was purified by preparative HPLC on a XBridge C18 OBD Column (5 μm, 150×19 mm ID) using a gradient of 0-100% MeCN in $H_2O/NH_3$ (100/0.03) to give (190 mg, 52%) the title compound as a white solid.

Intermediate 13

2-Thioxo-3-(2-(1-tosyl-4-(trifluoromethyl)piperidin-2-yl)benzyl)-1,2,3,7-tetrahydro-6H-purin-6-one

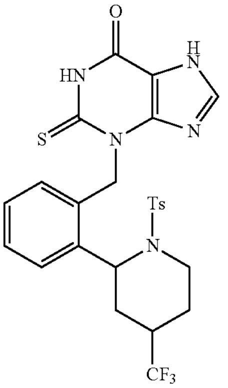 [SMILES: Cc1ccc(S(=O)(=O)N2CCC(C(F)(F)F)CC2c2ccccc2Cn2c(=S)[nH]c(=O)c3[nH]cnc32)cc1]

Step A. 4-((2-(1-Tosyl-4-(trifluoromethyl)piperidin-2-yl)benzyl)amino)-1H-imidazole-5-carboxamide

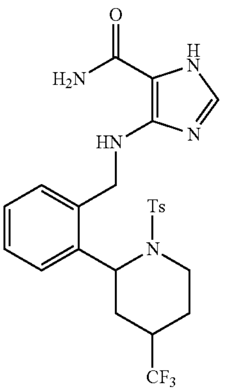 [SMILES: Cc1ccc(S(=O)(=O)N2CCC(C(F)(F)F)CC2c2ccccc2CNc2nc[nH]c2C(N)=O)cc1]

AcOH (270 mg, 4.5 mmol) was added to a solution of 2-(1-tosyl-4-(trifluoromethyl)piperidin-2-yl)benzaldehyde Intermediate 10 step F (3.7 g, 8.99 mmol) and 4-amino-1H-imidazole-5-carboxamide (1.25 g, 9.92 mmol) in EtOH (50 mL). The resulting solution was stirred overnight at 75° C. and then cooled to 0° C. $NaBH_4$ (680 mg, 18.0 mmol) was added and the reaction mixture was stirred for 1 h at rt. The reaction was quenched by the addition of water (20 mL) and then concentrated under vacuum. The residue was diluted with water (30 mL) and extracted with DCM (3×30 mL). The combined organic layer was washed with brine (40 mL), dried ($Na_2SO_4$) and concentrated under vacuum. The crude product was purified by flash chromatography using a gradient of 0-15% EtOAc in petroleum ether to give (3.6 g 77%) the title compound as a white solid. MS (ESI): m/z $[M+Na]^+$522.

Step B. 4-(3-Benzoyl-1-(2-(1-tosyl-4-(trifluoromethyl)piperidin-2-yl)benzyl)thioureido)-1H-imidazole-5-carboxamide

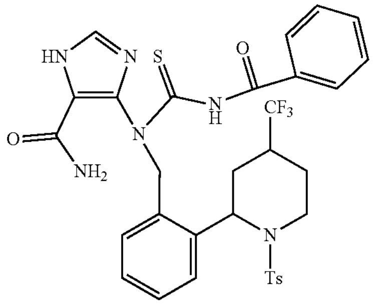 [SMILES: Cc1ccc(S(=O)(=O)N2CCC(C(F)(F)F)CC2c2ccccc2CN(C(=S)NC(=O)c2ccccc2)c2nc[nH]c2C(N)=O)cc1]

Benzoyl isothiocyanate (465 mg, 2.85 mmol) was added to a solution of 4-(2-(1-tosyl-4-(trifluoromethyl)piperidin-2-yl)benzylamino)-1H-imidazole-5-carboxamide (1.35 g, 2.59 mmol) in MeCN (40 mL). The resulting solution was stirred for 4 h at rt and concentrated under vacuum to give (1.8 g) the crude title compound as a yellow solid. MS (ESI): m/z $[M+Na]^+$685.

Step C. 2-Thioxo-3-(2-(1-tosyl-4-(trifluoromethyl)piperidin-2-yl)benzyl)-1,2,3,7-tetrahydro-6H-purin-6-one NaOH (1.72 g, 5.28 mmol) was added to a solution of 4-(3-benzoyl-1-(2-(1-tosyl-4-(trifluoromethyl)piperidin-2-yl)benzyl)thioureido)-1H-imidazole-5-carboxamide (640 mg, 2.72 mmol) in MeOH (50 mL). The resulting solution was stirred for 8 h at 55° C. and then concentrated under vacuum. The crude product was purified by flash chromatography using a gradient of 0-10% MeOH in DCM to give (400 mg, 88%) the title compound as a light yellow solid. MS (ESI): m/z $[M+Na]^+$564.

Intermediate 14

2-Thioxo-3-(2-((2R,4S)-1-tosyl-4-(trifluoromethyl)piperidin-2-yl)benzyl)-1,2,3,7-tetrahydro-6H-purin-6-one

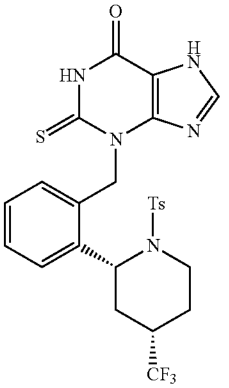 [SMILES: Cc1ccc(S(=O)(=O)N2CC[C@H](C(F)(F)F)C[C@@H]2c2ccccc2Cn2c(=S)[nH]c(=O)c3[nH]cnc32)cc1]

Step A. 2-((2R,4S)-1-Tosyl-4-(trifluoromethyl)piperidin-2-yl)benzaldehyde

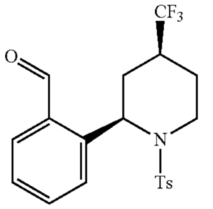 [SMILES: Cc1ccc(S(=O)(=O)N2CC[C@H](C(F)(F)F)C[C@@H]2c2ccccc2C=O)cc1]

$HNO_3$ (10 mL, 75 mmol) was added to a solution of (2R,4S)-2-(2-(methoxymethyl)phenyl)-1-tosyl-4-(trifluoromethyl)piperidine (Intermediate 15) (4.0 g, 9.37 mmol) in DCM (80 mL) at 0° C. and the mixture was stirred overnight at 0-20° C. The resulting solution was washed with water (2×40 mL) and brine (40 mL), dried ($Na_2SO_4$) and concentrated under vacuum. The crude product was purified by flash chromatography using a gradient of 0-15% EtOAc in petroleum ether to give (1.36 g, 83%) the title compound as yellow solid. MS (ESI): m/z $[M+Na]^+$412.

Step B. 4-((2-((2R,4S)-1-Tosyl-4-(trifluoromethyl)piperidin-2-yl)benzyl)amino)-1H-imidazole-5-carboxamide

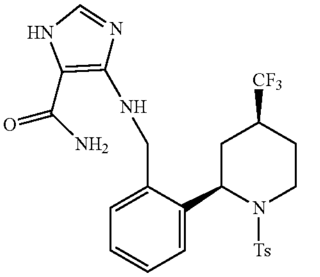 [SMILES: Cc1ccc(S(=O)(=O)N2CC[C@H](C(F)(F)F)C[C@@H]2c2ccccc2CNc2nc[nH]c2C(N)=O)cc1]

AcOH (183 mg, 3.04 mmol) was added to a solution of 2-((2R,4S)-1-tosyl-4-(trifluoromethyl)piperidin-2-yl)benzaldehyde (2.5 g, 6.08 mmol,) and ethyl 3-amino-1H-pyrrole-2-carboxylate (920 mg, 7.30 mmol) in EtOH (50 mL). The resulting solution was stirred overnight at 75° C., and then cooled to rt. $NaBH_4$ (460 mg, 12.16 mmol) was added and the reaction mixture was stirred for 1 h at rt. The reaction mixture was concentrated under vacuum and diluted with DCM (50 mL) and water (30 mL). The separated organic layer was washed with water (40 mL) and brine (40 mL), dried ($Na_2SO_4$) and concentrated under vacuum. The crude product was purified by flash chromatography using a gradient of 0-15% EtOAc in petroleum ether to give (2.5 g, 79%) the title compound as a white solid. MS (ESI): m/z $[M+Na]^+$522.

Step C. 4-(3-Benzoyl-1-(2-((2R,4S)-1-tosyl-4-(trifluoromethyl)piperidin-2-yl)benzyl)thioureido)-1H-imidazole-5-carboxamide

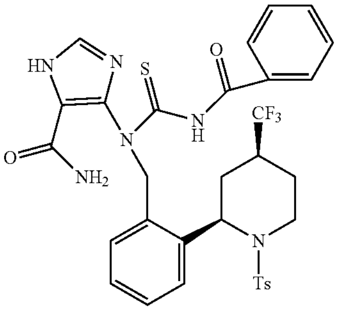 [SMILES: Cc1ccc(S(=O)(=O)N2CC[C@H](C(F)(F)F)C[C@@H]2c2ccccc2CN(C(=S)NC(=O)c2ccccc2)c2nc[nH]c2C(N)=O)cc1]

Benzoyl isothiocyanate (1.08 g, 6.62 mmol, 1.50) was added to a solution of 4-((2-((2R,4S)-1-tosyl-4-(trifluoromethyl)piperidin-2-yl)benzyl)amino)-1H-imidazole-5-carboxamide (2.3 g, 4.41 mmol) in MeCN (30 mL) and the resulting solution was stirred for at rt for 4 h and concentrated under vacuum to give (3.3 g, crude) the crude title compound as a yellow solid. MS (ESI): m/z $[M+Na]^+$ 685.

Step D. 2-Thioxo-3-(2-((2R,4S)-1-tosyl-4-(trifluoromethyl)piperidin-2-yl)benzyl)-1,2,3,7-tetrahydro-6H-purin-6-one A solution of 4-(3-benzoyl-1-(2-((2R,4S)-1-tosyl-4-(trifluoromethyl)piperidin-2-yl)benzyl)thioureido)-1H-imidazole-5-carboxamide (3 g, crude) in 33% $NH_3$ (aq)/EtOH (2/1, 30 mL) was stirred at 50° C. overnight and then concentrated under vacuum. The crude product was purified by flash chromatography using DCM/MeOH (15/1) as mobile phase to give (1.8 g, 72%) the title compound as a light yellow solid. MS (ESI): m/z $[M+Na]^+$564.

Intermediate 15

(2R,4S)-2-(2-(Methoxymethyl)phenyl)-1-tosyl-4-(trifluoromethyl)piperidine

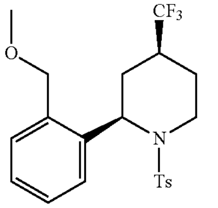 [SMILES: COCc1ccccc1[C@H]1C[C@@H](C(F)(F)F)CCN1S(=O)(=O)c1ccc(C)cc1]

Obtained by chiral separation of Intermediate 10 step C. $[\alpha]_D$=−87 (c=1 g/100 mL, MeCN).

Intermediate 16

2-Thioxo-3-(2-((2S,4R)-1-tosyl-4-(trifluoromethyl) piperidin-2-yl)benzyl)-1,2,3,7-tetrahydro-6H-purin-6-one

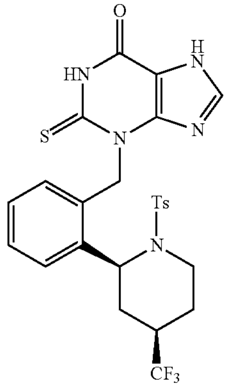 [SMILES: Cc1ccc(S(=O)(=O)N2CC[C@@H](C(F)(F)F)C[C@H]2c2ccccc2Cn2c(=S)[nH]c(=O)c3[nH]cnc32)cc1]

Prepared as described for Intermediate 14 using Intermediate 17 (2S,4R)-2-(2-(methoxymethyl)phenyl)-1-tosyl-4-(trifluoromethyl)piperidine as starting material. MS (ESI): m/z $[M+Na]^+$564.

Intermediate 17

(2S,4R)-2-(2-(Methoxymethyl)phenyl)-1-tosyl-4-(trifluoromethyl)piperidine

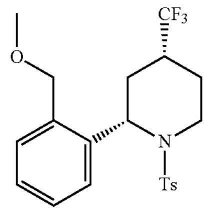

Obtained by chiral separation of Intermediate 10 step C. $[\alpha]_D$=+78 (c=1 g/100 mL, MeCN).

Intermediate 18

Benzyl 4,4-difluoro-2-(2-((6-oxo-2-thioxo-1,2,6,7-tetrahydro-3H-purin-3-yl)methyl)phenyl)piperidine-1-carboxylate

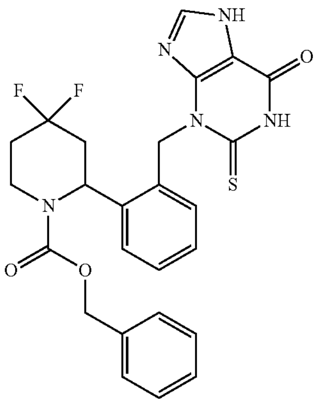 [SMILES: O=C(OCc1ccccc1)N1CCC(F)(F)CC1c1ccccc1Cn1c(=S)[nH]c(=O)c2[nH]cnc21]

Step A. Benzyl 2-(2-(((5-carbamoyl-1H-imidazol-4-yl)amino)methyl)phenyl)-4,4-difluoropiperidine-1-carboxylate

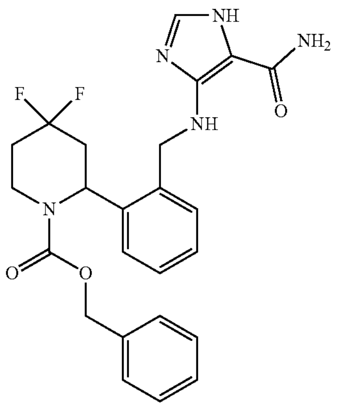 [SMILES: NC(=O)c1[nH]cnc1NCc1ccccc1C1CC(F)(F)CCN1C(=O)OCc1ccccc1]

AcOH (80 mg, 1.33 mmol) was added to a solution of benzyl 4,4-difluoro-2-(2-formylphenyl)piperidine-1-carboxylate Intermediate 12 step B (940 mg, 2.62 mmol) and 4-amino-1H-imidazole-5-carboxamide (330 mg, 2.62 mmol) in EtOH (20 mL) and the resulting solution was stirred at 70° C. for 16 h. $NaBH_4$ (100 mg, 2.64 mmol) was added and the resulting solution was stirred for another 4 h at 20° C., and then the reaction was quenched by the addition of water. The resulting mixture was concentrated under vacuum. The crude product aws purified by flsah chromatography using a gradient of 0-5% MeOH in DCM to give (790 mg, 66%) the title compound as a white solid. MS (ESI): m/z $[M+Na]^+$470

Step B. Benzyl 2-(2-((3-benzoyl-1-(5-carbamoyl-1H-imidazol-4-yl)thioureido)methyl)phenyl)-4,4-difluoropiperidine-1-carboxylate

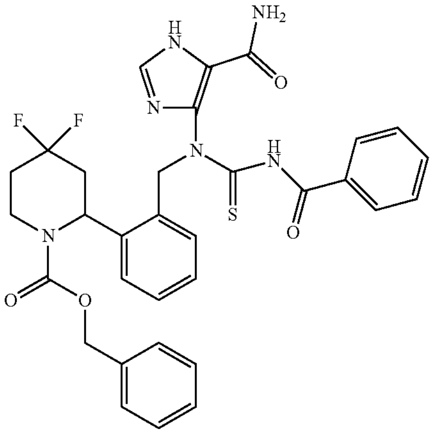 [SMILES: NC(=O)c1[nH]cnc1N(Cc1ccccc1C1CC(F)(F)CCN1C(=O)OCc1ccccc1)C(=S)NC(=O)c1ccccc1]

Benzoyl isothiocyanate (105 mg, 0.64 mmol) was added to a solution of benzyl 2-(2-(((5-carbamoyl-1H-imidazol-4-yl)amino)methyl)phenyl)-4,4-difluoropiperidine-1-carboxylate (300 mg, 0.64 mmol) in MeCN (20 mL) and the resulting solution was stirred for 48 h at 20° C. The formed solid was collected by filtration and washed with MeCN (3×1 mL) and dried to give (230 mg, 57%) the title compound as a light yellow solid. MS (ESI): m/z $[M+Na]^+$633.

Step C. Benzyl 4,4-difluoro-2-(2-((6-oxo-2-thioxo-1,2,6,7-tetrahydro-3H-purin-3-yl)methyl)phenyl) piperidine-1-carboxylate 28% $NH_3$ (aq) (2 mL) was added dropwise to a solution of benzyl 2-(2-((3-benzoyl-1-(5-carbamoyl-1H-imidazol-4-yl)thioureido)methyl)phenyl)-4,4-difluoropiperidine-1-carboxylate (100 mg, 0.16 mmol) in EtOH (1 mL). The resulting solution was stirred for 24 h at 50° C. and then concentrated under vacuum. The residue was purified by preparative TLC using DCM/MeOH (20/1) as mobile phase to give (80 mg, 98%) the title compound as an off-white solid. MS (ESI): m/z $[M+Na]^+$512.

Intermediate 19

3-(2-(5-Fluoro-1-(4-methoxybenzyl)piperidin-2-yl) benzyl)-2-thioxo-1,2,3,7-tetrahydro-6H-purin-6-one

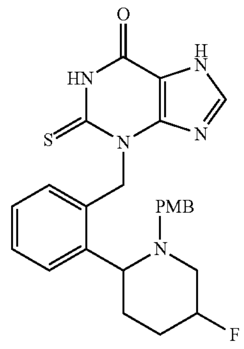

Step A. Methyl 3-(2-bromophenyl)-3-oxopropanoate

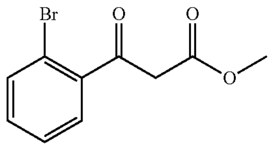

NaH (60% by weight) (24 g, 600 mmol) was added to a s solution of 1-(2-bromophenyl)ethan-1-one (100 g, 502.40 mmol) in dimethyl carbonate (600 mL) and the resulting solution was stirred for 1 h at 90° C., cooled to rt and diluted with water (700 mL). The pH was adjusted to 4 with 12 M HCl and the resulting acidic aqueous solution was extracted with EtOAc (3×300 mL). The combined organic layer was washed with water (2×800 mL) and brine (800 mL), then dried ($Na_2SO_4$) and concentrated under vacuum to give (120 g, 93%) the crude title compound as a red liquid which was used without further purification. MS (ESI): m/z $[M+H]^+$ 257.

Step B. Methyl 2-(2-bromobenzoyl)pent-4-enoate

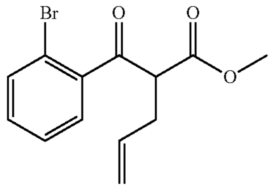 [SMILES: C=CCC(C(=O)OC)C(=O)c1ccccc1Br]

NaH (60% by weight) (14 g, 350 mmol) was added in portions to a solution of methyl 3-(2-bromophenyl)-3-oxopropanoate (70 g, 272 mmol) in THF (600 mL) at 0° C. The mixture was stirred for 1 h at rt. 3-Bromoprop-1-ene (35.7 g, 295 mmol) and NaI (12.67 g, 84.47 mmol) were added and the resulting solution was stirred for 15 h at rt and then concentrated under vacuum. The residue was diluted with water (600 mL) and the pH was adjusted to 7 with 2 M HCl (aq). The resulting aqueous solution was extracted with DCM (3×100 mL), dried ($Na_2SO_4$) and concentrated under vacuum to give (78 g, 97%) the crude title compound as light brown liquid. MS (ESI): m/z $[M+H]^+$ 297.

Step C. 1-(2-Bromophenyl)pent-4-en-1-one

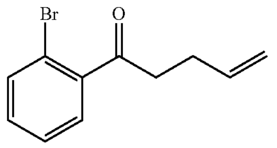

KOH (37.1 g, 661.8 mmol) was added to a solution of methyl 2-(2-bromobenzoyl)pent-4-enoat (65.52 g, 220.50 mmol) in dioxane/water (1/2) and the resulting solution was heated to reflux for 2.5 h and then cooled to rt. The pH of the solution was adjusted to 6 with 4 M HCl (aq). The resulting aqueous solution was extracted with DCM (2×400 mL). The combined organic layer was washed with water (400 mL) and brine (400 mL), dried ($Na_2SO_4$) and concentrated under vacuum. The crude product was purified by flash chromatography using 0-5% EtOAc in petroleum ether to give (36 g, 60%, yield for three steps) the title compound as yellow liquid. MS (ESI): m/z $[M+H]^+$ 239.

Step D. 1-(2-Bromophenyl)-N-(4-methoxybenzyl) pent-4-en-1-amine

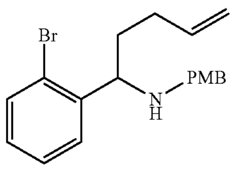

$TiCl_4$ (23 g, 121 mmol) was added dropwise to a solution of 1-(2-bromophenyl)pent-4-en-1-one (29 g, 121 mmol), 4-methoxyaniline (19.95 g, 161.99 mmol) and TEA (36.75 g, 363.2 mmol) in THF (400 mL) at −78° C. under $N_2$(g) atmosphere. The mixture was stirred for 5 h at −78° C. to 20°

C. A solution of $NaBH_3CN$ (33.85 g, 545.9 mmol) in MeOH (150 mL) was added at 0° C. The resulting solution was stirred for 15 h at 20° C. and the reaction was quenched with sat $K_2CO_3$ (aq) (80 mL). The resulting solution was extracted with $Et_2O$ (2×400 mL), and the combined organic layer was washed with water (2×400 mL) and brine (400 mL), dried ($Na_2SO_4$), and concentrated under vacuum. The crude product was purified by flash chromatography using a gradient of 0-10% EtOAc in petroleum ether to give (27.7 g, 66%) the title compound as a light yellow oil. MS (ESI): m/z $[M+H]^+$ 360.

Step E. 2-(2-Bromophenyl)-5-iodo-1-(4-methoxy-benzyl)piperidine

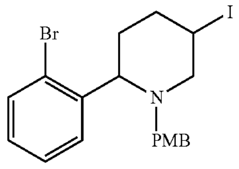

NIS (17.7 g, 81.6 mmol) was added in portions to a solution of 1-(2-bromophenyl)-N-(4-methoxybenzyl)pent-4-en-1-amine (28.2 g, 81.6 mmol) in DCM (300 mL) at 0° C. The resulting solution was stirred for 30 min at 0° C. and the reaction was quenched with water (100 mL). The resulting organic layer was separated and washed with water (100 mL), brine (100 mL), then dried ($Na_2SO_4$) and concentrated under vacuum to give (40 g) the crude title compound as a black oil. MS (ESI): m/z $[M+H]^+$486.

Step F. 6-(2-Bromophenyl)-1-(4-methoxybenzyl) piperidin-3-ol

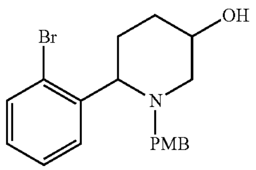

AgOAc (82.2 g, 492 mmol) was added in portions to a solution of 2-(2-bromophenyl)-5-iodo-1-(4-methoxybenzyl) piperidine (40 g, 82 mmol) in toluene (400 mL) and the mixture was stirred for 1.5 h at 25° C. The resulting solids were filtered off and the filtrate was concentrated under vacuum. The residue was dissolved in MeOH (400 mL) and $K_2CO_3$ (17 g, 123 mmol) was added and the resulting solution was stirred at rt until completion of the reaction. The reaction was quenched by the addition of sat $NH_4Cl$ (aq) (50 mL) and extracted with DCM (2×200 mL). The combined organic layer was washed with water (2×300 mL), and brine (300 mL), then dried ($Na_2SO_4$) and concentrated under vacuum. The crude product was purified by flash chromatography using a gradient of 0-20% EtOAc in petroleum ether to give (9.62 g, 32% two steps) the title compound as a light yellow solid. MS (ESI): m/z $[M+H]^+$376.

Step G. 2-(2-Bromophenyl)-5-fluoro-1-(4-methoxy-benzyl)piperidine

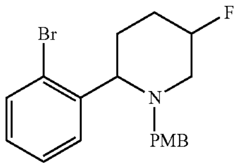

DAST (1.67 g, 10.37 mmol) was added dropwise to a solution of 6-(2-bromophenyl)-1-(4-methoxybenzyl)piperidin-3-ol (3.0 g, 7.97 mmol) in DCM (50 mL) at 0° C. and the resulting solution was stirred for 4 h at 0° C. and the reaction was quenched with water (4 mL). The resulting aqueous solution was diluted with DCM (50 mL), and the organic layer was washed with sat $NaHCO_3$(aq) (50 mL), and brine (50 mL), then dried ($Na_2SO_4$) and concentrated under vacuum. The crude product was purified by flash chromatography using a gradient of 0-10% EtOAc in petroleum ether to give (2.45 g, 81%) the title compound as a light yellow solid. MS (ESI): m/z $[M+H]^+$378.

Step H. 2-(5-Fluoro-1-(4-methoxybenzyl)piperidin-2-yl)benzaldehyde

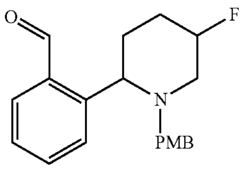

A solution of n-BuLi (2.5 M in hexane) (2.34 mL, 5.84 mmol) was added to a solution of 2-(2-bromophenyl)-5-fluoro-1-(4-methoxybenzyl)piperidine (2.21 g, 5.84 mmol) in THF (40 mL) at −78° C. under $N_2$(g) atmosphere. The mixture was stirred for 45 min at −78° C. and DMF (1.28 g, 3.00 equiv) was added dropwise at −78° C. The resulting solution was stirred for 1 h at −70° C. to −60° C. and the reaction was quenched with water (2 mL). The resulting aqueous solution was extracted with DCM (3×100 mL), the combined organic layer ws washed with water (2×40 mL) and brine (40 mL), then dried ($Na_2SO_4$) and concentrated under vacuum. The crude product was purified by flash chromatography using a gradient of 0-15% EtOAc in petroleum ether to give (1.6 g, 84%) the title compound as a light yellow solid. MS (ESI): m/z $[M+H]^+$328.

Step I. 4-((2-(5-Fluoro-1-(4-methoxybenzyl)piperidin-2-yl)benzyl)amino)-1H-imidazole-5-carboxamide

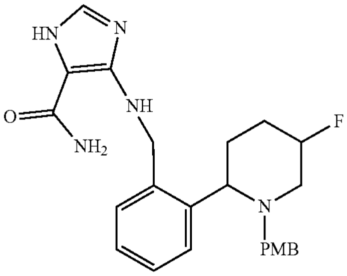

AcOH (293 mg, 4.89 mmol) was added to a solution of 2-(5-fluoro-1-(4-methoxybenzyl)piperidin-2-yl)benzaldehyde (1.6 g, 4.89 mmol) and 4-amino-1H-imidazole-5-carboxamide (616 mg, 4.8 mmol) in EtOH (20 mL). The mixture was stirred for 6 h at reflux and then cooled to rt. The precipitated solids were collected by filtration and dissolved in EtOH (20 mL) and $NaBH_4$(181 mg, 4.89 mmol) was added in portions. The resulting solution was stirred for 1 h at rt and the reaction was quenched by dropwise addition of water (10 mL) at 0° C. The resulting solids were collected by filtration and dried under vacuum to give (2.0 g, 94%) the title compound as an off-white solid. MS (ESI): m/z $[M+H]^+$ 438.

Step J. 4-(3-Benzoyl-1-(2-(5-fluoro-1-(4-methoxybenzyl)piperidin-2-yl)benzyl)thioureido)-1H-imidazole-5-carboxamide

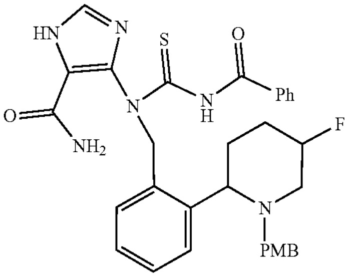

Benzoyl isothiocyanate (1.12 g, 6.86 mmol) was added to a solution of 4-((2-(5-fluoro-1-(4-methoxybenzyl)piperidin-2-yl)benzyl)amino)-1H-imidazole-5-carboxamide (2.0 g, 4.57 mmol) in DCM (40 mL). The resulting solution was stirred for 15 h at rt and concentrated under vacuum. The crude product was purified by flash chromatography using a gradient of 0-5% MeOH in DCM to give (2.24 g, 82%) the title compound as a light yellow solid. MS (ESI): m/z $[M+H]^+$601.

Step K. 3-(2-(5-Fluoro-1-(4-methoxybenzyl)piperidin-2-yl)benzyl)-2-thioxo-1,2,3,7-tetrahydro-6H-purin-6-one 4 M NaOH (aq) (4.16 mL, 16.6 mmol) was added to a solution of 4-(3-benzoyl-1-(2-(5-fluoro-1-(4-methoxybenzyl)piperidin-2-yl)benzyl)thioureido)-1H-imidazole-5-carboxamide (2.0 g, 3.33 mmol) in MeOH (30 mL) and the resulting solution was stirred at 50° C. for 10 h and then the reaction was quenched with AcOH (2.0 mL). The resulting mixture was concentrated under vacuum and diluted with DCM (150 mL), washed with brine (2×70 mL), then dried ($Na_2SO_4$) and concentrated under vacuum. The crude product was purified by flash chromatography using a gradient of 0-5% MeOH in DCM to give (1.2 g, 75%) the title compound as a an off-white solid. MS (ESI): m/z $[M+H]^+$ 480.

Intermediate 20 tert-Butyl 2-(3-((4-oxo-2-thioxo-2,3,4,5-tetrahydro-1H-pyrrolo[3,2-d]pyrimidin-1-yl)methyl)pyridin-2-yl)-4-trifluoromethyl)piperidine-1-carboxylate

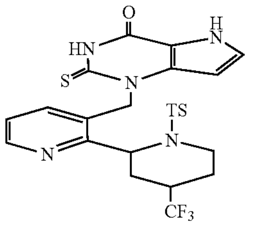

Step A. 2-Bromo-3-(1,3-dioxolan-2-yl)pyridine

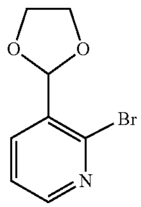 [SMILES: Brc1ncccc1C1OCCO1]

TsOH (1.852 g, 10.75 mmol) was added to 2-bromonicotinaldehyde (10 g, 53.8 mmol) and ethane-1,2-diol (6.67 g, 107.5 mmol) in toluene (80 mL) at rt. The resulting solution was stirred at 130° C. for 15 h. The solvent was removed under reduced pressure and the residue was poured into sat $NaHCO_3$(aq) (300 mL). The mixture was extracted with EtOAc (3×150 mL), and the combined organic layer was dried ($Na_2SO_4$), filtered, and evaporated to give (11.00 g, 89%) the title compound as a yellow liquid which was used in the next step directly without further purification. MS (ESI): m/z $[M+H]^+$230.

Step B. tert-Butyl (5-(3-(1,3-dioxolan-2-yl)pyridin-2-yl)-5-oxo-3-(trifluoromethyl)pentyl)carbamate

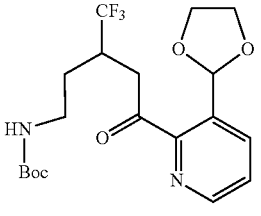 [SMILES: CC(C)(C)OC(=O)NCCC(CC(=O)c1ncccc1C1OCCO1)C(F)(F)F]

n-BuLi (2.5 M in hexane) (12.2 mL, 30.4 mmol) was added dropwise to a solution of 2-bromo-3-(1,3-dioxolan-2-yl)pyridine (6.36 g, 27.6 mmol) in THF (180 mL) under $N_2$(g) atmosphere at −78° C. and the mixture was stirred for 0.5 h at −78° C. A solution of tert-butyl 2-oxo-4-(trifluoromethyl)piperidine-1-carboxylate (CAS Registry Number 911634-72-5) (7.45 g, 27.9 mmol) in THF (20 mL) was added dropwise keeping the temperature below −78° C. The solution was allowed to reach rt and stirred for another 2 h. The reaction was quenched by the addition of sat $NH_4Cl$(aq) (2 mL) and the resulting mixture was concentrated under vacuum. The residue was dissolved in DCM (300 mL), washed with water (2×200 mL) and brine (2×300 mL), then dried ($Na_2SO_4$) and evaporated to dryness. The crude product was purified by flash chromatography using a gradient of 0-20% EtOAc in petroleum ether to give (6.87 g, 59%) the title compound as a yellow solid. MS (ESI): m/z $[M+H]^+$ 419.

Step C. tert-Butyl 3'-(1,3-dioxolan-2-yl)-4-(trifluoromethyl)-5,6-dihydro-[2,2'-bipyridine]-1(4H)-carboxylate

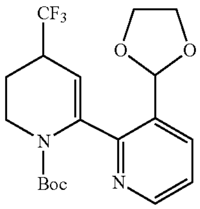 [SMILES: CC(C)(C)OC(=O)N1CCC(C(F)(F)F)C=C1c1ncccc1C1OCCO1]

TFA (4.64 g, 40.7 mmol) was added to a solution of tert-butyl (5-(3-(1,3-dioxolan-2-yl)pyridin-2-yl)-5-oxo-3-(trifluoromethyl)pentyl)carbamate (5.67 g, 13.6 mmol) in DCM (200 mL) and the reaction mixture was stirred for 4 h at rt. The mixture was washed with sat $NaHCO_3$(aq) (3×300 mL) and brine (2× 200 mL). The combined organic layer was dried ($Na_2SO_4$) and evaporated to dryness. The crude product was purified by flash chromatography using a gradient of 0-10% EtOAc in petroleum ether to give (3.17 g, 58%) the title compound as a yellow solid. MS (ESI): m/z $[M+H]^+$ 401.

Step D. tert-Butyl 2-(3-(1,3-dioxolan-2-yl)pyridin-2-yl)-4-(trifluoromethyl)piperidine-1-carboxylate

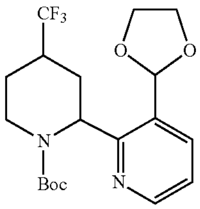 [SMILES: CC(C)(C)OC(=O)N1CCC(C(F)(F)F)CC1c1ncccc1C1OCCO1]

Pd/C (10% Pd w/w, 650 mg) was added to a solution of TEA (2.40 g, 23.7 mmol) and tert-butyl 3'-(1,3-dioxolan-2-yl)-4-(trifluoromethyl)-5,6-dihydro-[2,2'-bipyridine]-1(4H)-carboxylate (3.17 g, 7.92 mmol) in EtOAc (50 mL) under $N_2$(g) atmosphere in a flask. The flask was evacuated and backfilled with $H_2$(g) three times and hydrogenated at 1 bar for 36 h at rt. The catalyst was filtered off and the filtrate was concentrated under vacuum. The crude product was purified by flash chromatography using a gradient of 0-20% EtOAc in petroleum ether to give (2.53 g, 79%) the title compound as a white solid. MS (ESI): m/z $[M+H]^+$ 403.

Step E. tert-Butyl 2-(3-formylpyridin-2-yl)-4-(trifluoromethyl)piperidine-1-carboxylate

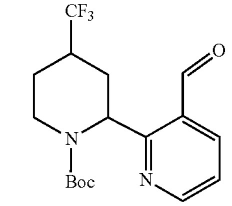 [SMILES: CC(C)(C)OC(=O)N1CCC(C(F)(F)F)CC1c1ncccc1C=O]

A solution of tert-butyl 2-(3-(1,3-dioxolan-2-yl)pyridin-2-yl)-4-(trifluoromethyl)piperidine-1-carboxylate (1.6 g, 3.98 mmol), TsOH (0.068 g, 0.40 mmol), water (1.074 g, 59.64 mmol) in acetone (20 mL) was stirred at 60° C. for 16 h. The solvent was removed under vacuum. The crude product was purified by flash chromatography using a gradient of 0-20% EtOAc in petroleum ether to give (1.00 g, 70%) the title compound as a white solid. MS (ESI): m/z $[M+H]^+$259.

Step F. tert-Butyl 2-(3-(((2-(ethoxycarbonyl)-1H-pyrrol-3-yl)amino)methyl)pyridin-2-yl)-4-(trifluoromethyl)piperidine-1-carboxylate

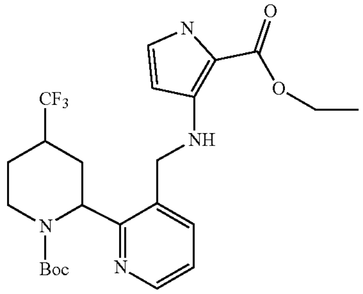

AcOH (215 mg, 3.58 mmol) and $NaBH(OAc)_3$ (2.28 g, 10.75 mmol) were added to a solution of ethyl 3-amino-1H-pyrrole-2-carboxylate hydrochloride (820 mg, 4.30 mmol) and tert-butyl 2-(3-formylpyridin-2-yl)-4-(trifluoromethyl) piperidine-1-carboxylate (1.28 g, 3.57 mmol) in DCE (10 mL). The resulting solution was stirred for 2 h at rt and the reaction was quenched by the addition of water (20 mL). The organic layer was separated and washed with brine (2×20 mL), then dried ($Na_2SO_4$) and concentrated under vacuum. The crude product was purified by flash chromatography using a gradient of 0-10% MeOH in DCM to give (0.9 g, 79%) the title compound as an off-white solid. MS (ESI): m/z $[M+H]^+$497.

Step G. tert-Butyl 2-(3-((3-benzoyl-1-(2-(ethoxycarbonyl)-1H-pyrrol-3-yl)thioureido)methyl)pyridin-2-yl)-4-(trifluoromethyl)piperidine-1-carboxylate

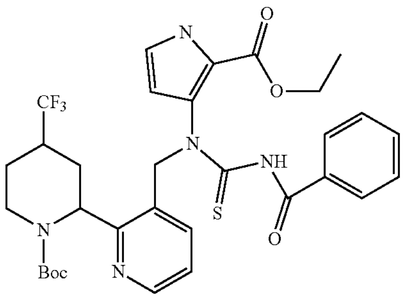

Benzoyl isothiocyanate (726 mg, 4.45 mmol) was added to a solution of tert-butyl 2-(3-(((2-(ethoxycarbonyl)-1H-pyrrol-3-yl)amino)methyl)pyridin-2-yl)-4-(trifluoromethyl) piperidine-1-carboxylate (1.84 g, 3.71 mmol) in DCM (20 mL). The resulting solution was stirred for 16 h at rt and then concentrated under vacuum. The crude product was purified by flash chromatography using a gradient of 0-20% EtOAc in petroleum ether to give (2.05 g, 84%) the title compound as a light yellow solid. MS (ESI): m/z $[M+H]^+$ 660.

Step H. tert-Butyl 2-(3-((4-oxo-2-thioxo-2,3,4,5-tetrahydro-1H-pyrrolo[3,2-d]pyrimidin-1-yl)methyl) pyridin-2-yl)-4-(trifluoromethyl)piperidine-1-carboxylate A suspension of tert-butyl 2-(3-((3-benzoyl-1-(2-(ethoxycarbonyl)-1H-pyrrol-3-yl)thioureido)methyl)pyridin-2-yl)-4-(trifluoromethyl)piperidine-1-carboxylate (2.05 g, 3.11 mmol) and $Cs_2CO_3$ (2.03 g, 6.21 mmol) in MeOH (20 mL) was stirred for 16 h at 50° C., and then cooled to rt. AcOH (900 mg, 15.0 mmol) was added and the mixture was diluted with DCM (50 mL) and filtered. The filtrate was concentrated under vacuum and triturated with $Et_2O$ (100 mL). The resulting solid was collected by filtration and dried under vacuum to give (1.2 g, 76%) the title compound as a yellow solid. MS (ESI): m/z $[M+H]^+$510.

Intermediate 21 rac-1-(2-((2R,4S)-4-(Difluoromethyl)piperidin-2-yl) benzyl)-2-thioxo-1,2,3,5-tetrahydro-4H-pyrrolo[3,2-d]pyrimidin-4-one

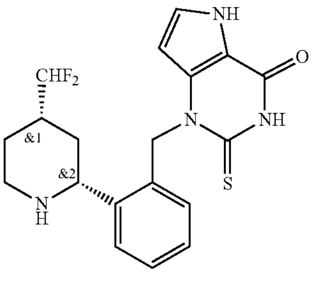

Step A. tert-Butyl 4-(difluoromethyl)piperidine-1-carboxylate

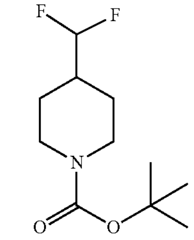 [SMILES: CC(C)(C)OC(=O)N1CCC(C(F)F)CC1]

DAST (11.3 g, 49.5 mmol) was added dropwise to a solution of tert-butyl 4-formylpiperidine-1-carboxylate (5.0 g, 23.4 mmol) in DCM at 0° C. during 15 min. The resulting solution was stirred for another 15 min at 0° C., and the reaction was quenched by the addition of $NaHCO_3$(aq) (100 mL). The resulting aqueous solution was extracted with DCM (2×100 mL). The combined organic layer was washed with brine (2×100 mL), then dried ($Na_2SO_4$) and concentrated under vacuum. The crude product was purified by flash chromatography using a gradient of 0-5% EtOAc in petroleum ether as mobile phase to give (3.6 g, 65%) the title compound as an off-white solid. MS (ESI): m/z $[M+H]^+$180.

Step B. tert-Butyl 4-(difluoromethyl)-2-oxopiperidine-1-carboxylate

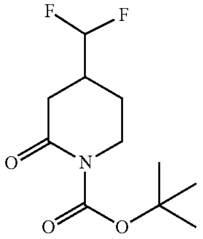 [SMILES: CC(C)(C)OC(=O)N1CCC(C(F)F)CC1=O]

$RuO_2$(890 mg, 5.24 mmol) was added to a solution of tert-butyl 4-(difluoromethyl)pi-peridine-1-carboxylate (3.6 g, 15.30 mmol) in EtOAc (63 mL), followed by a solution of $NaIO_4$ (9.84 g, 46.0 mmol) in water (36 mL) that was added in several batches at 0° C. The resulting solution was stirred for 15 h at 25° C. The solids were filtered off. The filtrate was extracted with EtOAc (3×50 mL). The combined organic layer was washed with brine (3×5 0 mL), then dried ($Na_2SO_4$) and concentrated under vacuum. The crude product was purified by flash chromatography using a gradient of 0-5% EtOAc in petroleum ether as mobile phase to give (2.5 g, 66%) the title compound as a white solid. MS (ESI): m/z $[M+H]^+$194

Step C. tert-Butyl (3-(difluoromethyl)-5-(2-(methoxymethyl)phenyl)-5-oxopentyl)carbamate

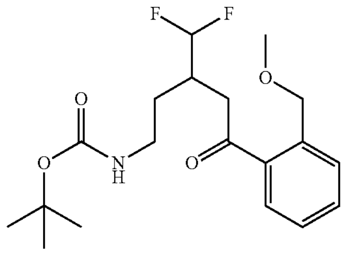 [SMILES: COCc1ccccc1C(=O)CC(CCNC(=O)OC(C)(C)C)C(F)F]

n-BuLi (2.2 M, 2 mL, 4.4 mmol) was added dropwise to a solution of 1-bromo-2-(methoxymethyl)benzene (800 mg, 4.00 mmol) in THF (15 mL) at −78° C. under $N_2$(g) atmosphere, and the mixture was stirred for 30 min at −78° C. A solution of tert-butyl 4-(difluoromethyl)-2-oxopiperidine-1-carboxylate (1.0 g, 4.01 mmol) in THF (5 mL) was added dropwise at −100° C. to the reaction mixture, and the resulting solution was stirred for 2 h at −78° C. The reaction was quenched by the addition of $NH_4Cl$ (aq) (15 mL). The resulting mixture was extracted with EtOAc (3×30 mL), and the organic layers combined and concentrated under vacuum. The crude product was purified by flash chromatography using a gradient of 0-5% MeOH in DCM as mobile phase to give (1.0 g, 67%) the title compound as a light yellow oil. MS (ESI): m/z $[M+H]^+$372.

Step D. 4-(Difluoromethyl)-6-(2-(methoxymethyl)phenyl)-1,2,3,4-tetrahydropyridine

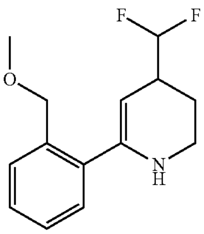 [SMILES: COCc1ccccc1C1=CC(C(F)F)CCN1]

TFA (4.0 mL) was added to a solution of tert-butyl (3-(difluoromethyl)-5-(2-(methoxymethyl)phenyl)-5-oxopentyl)carbamate (2.8 g, 7.54 mmol) in DCM (40 mL). The resulting solution was stirred for 30 min at 100° C. in a microwave reactor and concentrated under vacuum. The residue was diluted with DCM (50 mL) and washed with sat $Na_2CO_3$ (aq) (2×70 mL). The organic layer was dried ($Na_2SO_4$) and concentrated under vacuum to give (2.0 g, 70%) the title compound as a yellow oil. MS (ESI): m/z $[M+H]^+$254.

Step E. 4-(Difluoromethyl)-6-(2-(methoxymethyl)phenyl)-1-tosyl-1,2,3,4-tetrahydropyridine

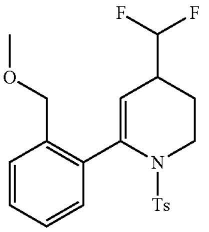 [SMILES: COCc1ccccc1C1=CC(C(F)F)CCN1S(=O)(=O)c1ccc(C)cc1]

TsCl (2.24 g, 26.4 mmol) was added in portions to a solution of 4-(difluoromethyl)-6-[2-(methoxymethyl)phenyl]-1,2,3,4-tetrahydropyridine (1.99 g, 7.84 mmol) and TEA (2.38 g, 23.5 mmol) in DCM (40 mL) at 0° C. The resulting solution was stirred for 20 h at 20° C. and then diluted with DCM (80 mL). The resulting mixture was washed with water (2×50 mL) and brine (60 mL), then dried ($Na_2SO_4$) and concentrated under vacuum. The crude product was purified by flash chromatography using a gradient of 0-10% EtOAc in petroleum ether as mobile phase to give (2.0 g, 63%) the title compound as a light yellow solid. MS (ESI): m/z $[M+H]^+$408.

Step F. 4-(Difluoromethyl)-2-(2-(methoxymethyl)phenyl)-1-tosylpiperidine

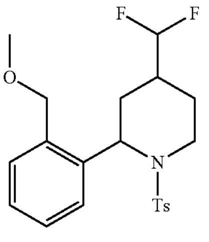 [SMILES: COCc1ccccc1C1CC(C(F)F)CCN1S(=O)(=O)c1ccc(C)cc1]

$PtO_2$ (300 mg, 1.32 mmol) was added to a solution of 4-(difluoromethyl)-6-(2-(methoxymethyl)phenyl)-1-tosyl-1,2,3,4-tetrahydropyridine (2.0 g, 4.91 mmol) in AcOH (40 mL). The reaction flask was evacuated and backfilled with $N_2$(g) twice and then evacuated and backfilled with $H_2$(g) twice and then stirred for 2 days at 30° C. under an atmosphere of $H_2$(g). The solids were filtered off, and the filtrate was concentrated under vacuum. The crude product was purified by flash chromatography using a gradient of 0-15% EtOAc in petroleum ether as mobile phase to give (1.1 g, 55%) the title compound as a light yellow oil. MS (ESI): m/z $[M+H]^+$410.

Step G. 2-(4-(Difluoromethyl)-1-tosylpiperidin-2-yl) benzaldehyde

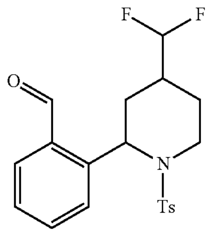 [SMILES: Cc1ccc(S(=O)(=O)N2CCC(C(F)F)CC2c2ccccc2C=O)cc1]

$HNO_3$ (1.0 mL, 22.30 mmol) was added dropwise to a solution of 4-(difluoromethyl)-2-(2-(methoxymethyl)phenyl)-1-tosylpiperidine (1.1 g, 2.70 mmol) in DCM (20 mL) at 0° C. The resulting solution was stirred for 15 h at rt and diluted with DCM (60 mL). The resulting mixture was washed with water (2×40 mL) and brine (40 mL), then dried ($Na_2SO_4$) and concentrated under vacuum. The crude product was purified by flash chromatography using a gradient of 0-15% EtOAc in petroleum ether as mobile phase to give (770 mg, 72%) the title compound as a light yellow solid.

Step H. Ethyl 3-((2-(4-(difluoromethyl)-1-tosylpiperidin-2-yl)benzyl)amino)-1H-pyrrole-2-carboxylate

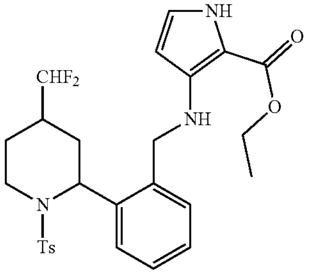 [SMILES: CCOC(=O)c1[nH]ccc1NCc1ccccc1C1CC(C(F)F)CCN1S(=O)(=O)c1ccc(C)cc1]

A solution of 2-(4-(difluoromethyl)-1-tosylpiperidin-2-yl) benzaldehyde (770 mg, 1.96 mmol), ethyl 2-amino-1H-pyrrole-3-carboxylate hydrochloride (411 mg, 2.15 mmol), AcOH (118 mg, 1.96 mmol) and $NaBH(OAc)_3$ (1.25 g, 5.90 mmol) in DCE (30 mL) was stirred for 15 h at 20° C., and then diluted with DCM (30 mL). The resulting mixture was washed with water (2×30 mL) and brine (30 mL), then dried ($Na_2SO_4$) and concentrated under vacuum. The crude product was purified by flash chromatography using EtOAc/petroleum ether (1/2) as mobile phase to give (867 mg, 83%) the title compound as a light yellow solid. MS (ESI): m/z $[M+H]^+$532.

Step I. Ethyl 3-(3-benzoyl-1-(2-(4-(difluoromethyl)-1-tosylpiperidin-2-yl)benzyl)thioureido)-1H-pyrrole-2-carboxylate

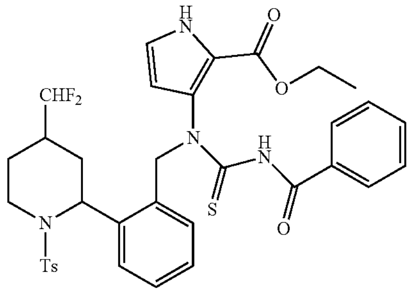 [SMILES: CCOC(=O)c1[nH]ccc1N(Cc1ccccc1C1CC(C(F)F)CCN1S(=O)(=O)c1ccc(C)cc1)C(=S)NC(=O)c1ccccc1]

Benzoyl isothiocyanate (346 mg, 2.12 mmol) was added to a solution of ethyl 3-((2-(4-(difluoromethyl)-1-tosylpiperidin-2-yl)benzyl)amino)-1H-pyrrole-2-carboxylate (867 mg, 1.63 mmol) in DCM (25 mL) and the resulting solution was stirred for 15 h at rt, and then concentrated under vacuum to give (1.2 g) the crude title compound as a light yellow solid. MS (ESI): m/z $[M+H]^+$ 695.

Step J. 1-(2-(4-(Difluoromethyl)-1-tosylpiperidin-2-yl)benzyl)-2-thioxo-1,2,3,5-tetrahydro-4H-pyrrolo[3,2-d]pyrimidin-4-one

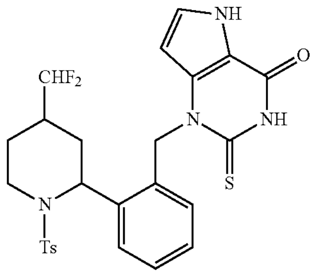 [SMILES: Cc1ccc(S(=O)(=O)N2CCC(C(F)F)CC2c2ccccc2Cn2c(=S)[nH]c(=O)c3[nH]ccc32)cc1]

$Cs_2CO_3$ (1.12 g, 3.45 mmol) was added to a solution of ethyl 3-(3-benzoyl-1-(2-(4-(difluoromethyl)-1-tosylpiperidin-2-yl)benzyl)thioureido)-1H-pyrrole-2-carboxylate (1.2 g, 1.73 mmol) in MeOH (30 mL), and the resulting solution was stirred for 5 h at 50° C., and then cooled to rt. AcOH (4.5 eq) was added dropwise and the resulting mixture was concentrated under vacuum. The residue was dissolved in DCM (30 mL) and water (30 mL) and the pH value of the mixture was adjusted to 6 with 2 M HCl. The resulting mixture was extracted with DCM (2×30 mL), and the combined organic layer was dried over ($Na_2SO_4$) and concentrated under vacuum to give (680 mg, 72%) the title compound as a light yellow solid. MS (ESI): m/z $[M+H]^+$ 545.

Step K. rac-1-(2-((2R,4S)-4-(difluoromethyl)piperidin-2-yl)benzyl)-2-thioxo-1,2,3,5-tetrahydro-4H-pyrrolo[3,2-d]pyrimidin-4-one Phenol (225 mg, 2.39 mmol) was added to a solution of 1-(2-(4-(difluoromethyl)-1-tosylpiperidin-2-yl)benzyl)-2-thioxo-1,2,3,5-tetrahydro-4H-pyrrolo[3,2-d]pyrimidin-4-one (650 mg, 1.19 mmol) in HBr—AcOH (15 mL) and the resulting solution was stirred for 4 h at 25° C. and then concentrated under vacuum. The crude product was purified by preparative HPLC on a XSelect CSH Prep C18 OBD Column (5 μm, 150×19 mm ID) using a gradient of 10-85% MeCN in a $H_2O/NH_3$ (95/5/0.03) buffer system as mobile phase to give (320 mg, 69%) the title compound as a light yellow solid. MS (ESI): m/z $[M+H]^+$391.

Intermediate 22 tert-Butyl 2-(3-((4-oxo-2-thioxo-2,3,4,5-tetrahydro-1H-pyrrolo[3,2-d]pyrimidin-1-yl)methyl)pyridin-2-yl)piperidine-1-carboxylate

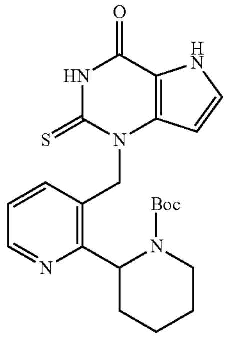 [SMILES: CC(C)(C)OC(=O)N1CCCCC1c1ncccc1Cn1c(=S)[nH]c(=O)c2[nH]ccc21]

Step A. tert-Butyl 3'-(1,3-dioxolan-2-yl)-5,6-dihydro-[2,2'-bipyridine]-1(4H)-carboxylate

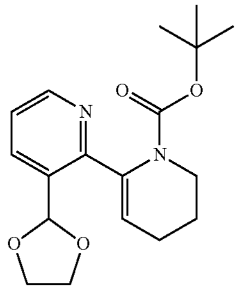 [SMILES: CC(C)(C)OC(=O)N1CCCC=C1c1ncccc1C1OCCO1]

CataCXium A Pd G3 (CAS Registry Number 1651823-59-4) (0.317 g, 0.43 mmol) and CataCXium A (0.156 g, 0.43 mmol) were added to a mixture of 2-bromo-3-(1,3-dioxolan-2-yl)pyridine (1.0 g, 4.35 mmol), tert-butyl 6-(4,4,5,5-tetramethyl-1,3,2-dioxaborolan-2-yl)-3,4-dihydropyridine-1(2H)-carboxylate (CAS Registry No 865245-32-5) (1.075 g, 3.48 mmol) and $Cs_2CO_3$ (3.12 g, 9.56 mmol) in 1,4-dioxane (30 mL) and water (6 mL) at rt and the resulting suspension was stirred at 80° C. for 15 h under $N_2$(g) atmosphere. The reaction mixture was dried ($Na_2SO_4$), filtered and evaporated. The crude product was purified by flash chromatography using a gradient of 5-25% EtOAc in petroleum ether to give (1.0 g, 69%) the title compound as a yellow solid. MS (ESI): m/z $[M+H]^+$333.

Step B. tert-Butyl 2-(3-(1,3-dioxolan-2-yl)-1,2-dihydropyridin-2-yl)piperidine-1-carboxylate

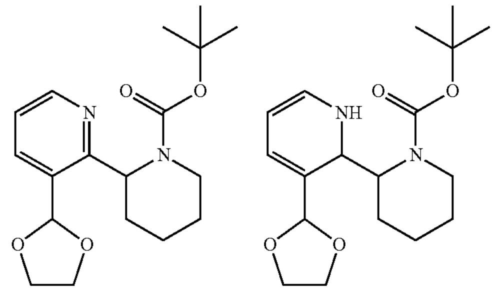

minor (30%)

INTTA144
Major (70%)

$Pd(OH)_2/C$ (10% Pd, 1014 mg, 0.72 mmol,) was added to tert-butyl 3'-(1,3-dioxolan-2-yl)-5,6-dihydro-[2,2'-bipyridine]-1(4H)-carboxylate (800 mg, 2.41 mmol) in MeOH (80 mL) at rt. The reaction mixture was evacuated and back-filled with $H_2$(g) five times. The resulting suspension was stirred at 25° C. for 16 h under $H_2$(g) atmosphere. The reaction mixture was filtered through Celite, and the filter cake was washed with MeOH (50 mL). The filtrate was concentrated under reduced pressure to afford a mixture of tert-butyl 2-(3-(1,3-dioxolan-2-yl)-1,2-dihydropyridin-2-yl)piperidine-1-carboxylateand and tert-butyl 2-(3-(1,3-dioxolan-2-yl)pyridin-2-yl)piperidine-1-carboxylate and (7:3, 600 mg, 74%) as a pale yellow gum which was used directly in the next step without further purification. MS (ESI): m/z [M+H]+ 337 and 335 respectively.

Step C. tert-Butyl 2-(3-(1,3-dioxolan-2-yl)pyridin-2-yl)piperidine-1-carboxylate

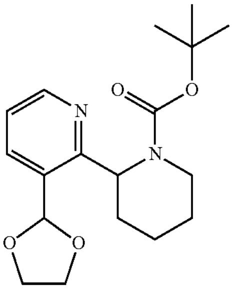 [SMILES: CC(C)(C)OC(=O)N1CCCCC1c1ncccc1C1OCCO1]

$MnO_2$ (3.62 g, 41.6 mmol) was added to the mixture of products obtained in Step B (700 mg, 2.08 mmol) in chloroform (20 mL) at rt and the resulting suspension was stirred at 80° C. for 16 h. The reaction mixture was filtered through Celite, and the filter cake was washed with EtOAc (50 mL). The filtrate was concentrated under reduced pressure to afford a yellow gum. The crude product was purified by preparative TLC (EtOAc:petroleum ether=1:5) to give the title compound (240 mg, 34%) as a pale yellow gum. MS (ESI): m/z $[M+H]^+$ 335.

Step D. tert-Butyl 2-(3-formylpyridin-2-yl)piperidine-1-carboxylate

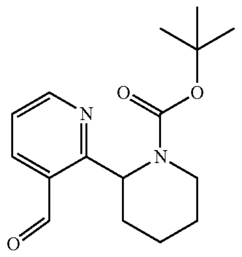 [SMILES: CC(C)(C)OC(=O)N1CCCCC1c1ncccc1C=O]

pTsOH×$H_2O$ (25.03 mg, 0.13 mmol) was added to tert-butyl 2-(3-(1,3-dioxolan-2-yl)pyridin-2-yl)piperidine-1-carboxylate (220 mg, 0.66 mmol) and water (0.178 mL, 9.87 mmol) in acetone (20 mL) at rt. The resulting suspension was stirred at 60° C. for 16 h. The reaction mixture was poured into brine (100 mL), extracted with EtOAc (3×50 mL), and the organic layer was dried ($Na_2SO_4$), filtered and evaporated to afford a yellow gum. The crude product was purified by preparative TLC (EtOAc:petroleum ether=1:2) to give (135 mg, 71%) the title compound as a pale yellow gum. MS (ESI): m/z $[M+H]^+$335.

Step E. tert-Butyl 2-(3-(((2-(ethoxycarbonyl)-1H-pyrrol-3-yl)amino)methyl)pyridin-2-yl)piperidine-1-carboxylate

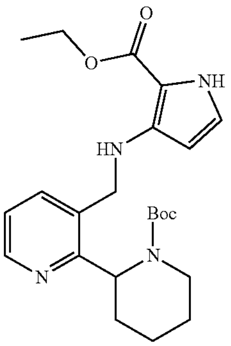 [SMILES: CCOC(=O)c1[nH]ccc1NCc1cccnc1C1CCCCN1C(=O)OC(C)(C)C]

AcOH (2.0 mL, 34.9 mmol) was added to tert-butyl 2-(3-formylpyridin-2-yl)piperidine-1-carboxylate (600 mg, 2.07 mmol), ethyl 3-amino-1H-pyrrole-2-carboxylate hydrochloride (473 mg, 2.48 mmol) in MeOH (25 mL) at rt and the resulting solution was stirred at 60° C. for 2 h. $NaBH_4$ (260 mg, 4.13 mmol) was added into the reaction mixture at rt and the resulting solution was stirred at 60° C. for 5 h. The reaction mixture was poured into sat $NaHCO_3$ (aq) (125 mL), and extracted with EtOAc (3×75 mL). The combined organic layer was dried ($Na_2SO_4$), filtered and evaporated to afford yellow gum. The crude product was purified by preparative TLC (EtOAc: petroleum ether=1:3) to give (100 mg, 11%) the title compound as a pale yellow gum. MS (ESI): m/z $[M+H]^+$ 429.

Step F. tert-Butyl 2-(3-((4-oxo-2-thioxo-2,3,4,5-tetrahydro-1H-pyrrolo[3,2-d]pyrimidin-1-yl)methyl)pyridin-2-yl)piperidine-1-carboxylate Benzoyl isothiocyanate (76 mg, 0.47 mmol) was added to tert-butyl 2-(3-(((2-(ethoxycarbonyl)-1H-pyrrol-3-yl)amino)methyl)pyridin-2-yl)piperidine-1-carboxylate (100 mg, 0.23 mmol) in DCM (10 mL) at 20° C. The resulting solution was stirred at rt for 5 h. The solvent was removed under reduced pressure, and the residue was dissolved in MeOH (10 mL). $Cs_2CO_3$ (152 mg, 0.47 mmol) was added and the resulting solution was stirred at 50° C. for 15 h. The solvent was removed under reduced pressure and the crude product was purified by preparative TLC (EtOAc:petroleum ether=1:2) to give (90 mg, 87%) the title compound as a pale yellow oil which solidified on standing. MS (ESI): m/z $[M+H]^+$442.

Intermediate 23

(9H-Fluoren-9-yl)methyl 2-(2-(((2-(ethoxycarbonyl)-1H-pyrrol-3-yl)amino)methyl)pyridin-3-yl)-4-(trifluoromethyl)piperidine-1-carboxylate

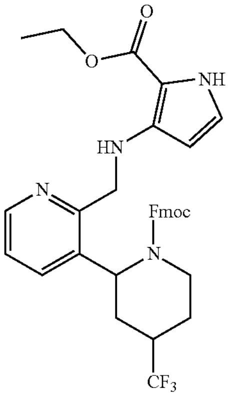

Step A. 3-Bromo-2-(1,3-dioxolan-2-yl)pyridine

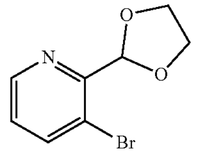 [SMILES: Brc1cccnc1C1OCCO1]

pTsOH (1.85 g, 10.8 mmol) was added to 3-bromopicolinaldehyde (10.0 g, 53.8 mmol) and ethane-1,2-diol (6.67 g, 107.5 mmol) in toluene (80 mL) at rt. The resulting solution was stirred at 130° C. for 15 h. The solvent was removed under reduced pressure, the residue was poured into sat $NaHCO_3$(aq) (300 mL), and extracted with EtOAc (3×150 mL). The combined organic layer was dried ($Na_2SO_4$), filtered and evaporated to afford (9.50 g, 77%) the title compound as a yellow liquid which was used directly in the next step without further purification. MS (ESI): m/z $[M+H]^+$ 230/232.

Step B. tert-Butyl (5-(2-(1,3-dioxolan-2-yl)pyridin-3-yl)-5-oxo-3-(trifluoromethyl)pentyl)carbamate

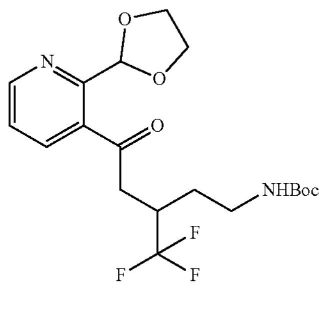 [SMILES: CC(C)(C)OC(=O)NCCC(CC(=O)c1cccnc1C1OCCO1)C(F)(F)F]

n-BuLi (2.5 M in hexane, 3.6 mL, 9.0 mmol) was added to 3-bromo-2-(1,3-dioxolan-2-yl)pyridine (1.894 g, 8.23 mmol) in THF (10 mL) at −78° C. The resulting solution was stirred at −78° C. for 15 min under $N_2$(g) atmosphere. A solution of tert-butyl 2-oxo-4-(trifluoromethyl)piperidine-1-carboxylate(CAS registry No. 911634-72-5) (2.0 g, 7.48 mmol) in THF (10 mL) was added dropwise to the stirred solution at −78° C. under $N_2$(g) atmosphere. The resulting solution was then stirred at −78° C. for 1 h. The reaction mixture was poured into brine (200 mL), extracted with EtOAc (3×100 mL), and the combined organic layer was dried ($Na_2SO_4$), filtered and evaporated to afford a yellow gum. The crude product was purified by flash chromatography using a gradient of 10-30% EtOAc in petroleum ether as mobile phase to give (2.2 g, 70%) the title compound as a pale yellow gum. MS (ESI): m/z $[M+H]^+$419.

Step C. 2'-(1,3-Dioxolan-2-yl)-4-(trifluoromethyl)-1,4,5,6-tetrahydro-2,3'-bipyridine

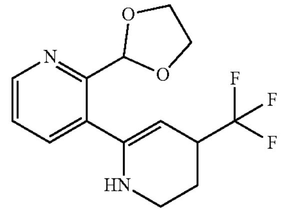 [SMILES: FC(F)(F)C1C=C(c2cccnc2C2OCCO2)NCC1]

TFA (0.81 mL, 10.5 mmol) was added to tert-butyl (5-(2-(1,3-dioxolan-2-yl)pyridin-3-yl)-5-oxo-3-(trifluoromethyl)pentyl)carbamate (2.2 g, 5.26 mmol) in DCM (40 mL) at rt and the resulting solution was stirred for 20 h. The solvent was removed under reduced pressure, the residue was poured into brine (150 mL), and extracted with EtOAc (3×100 mL). The combined organic layer was dried ($Na_2SO_4$), filtered and evaporated to give (1.5 g, 95%) the title compound as a yellow gum which. MS (ESI): m/z $[M+H]^+$301.

Step D. 2-(1,3-Dioxolan-2-yl)-3-(4-(trifluoromethyl)piperidin-2-yl)pyridine

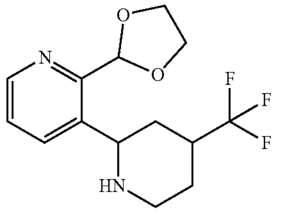 [SMILES: FC(F)(F)C1CCNC(c2cccnc2C2OCCO2)C1]

$Pd(OH)_2/C$ (0.81 g, 0.87 mmol) was added to 2'-(1,3-dioxolan-2-yl)-4-(trifluoromethyl)-1,4,5,6-tetrahydro-2,3'-bipyridine (1.30 g, 4.33 mmol) in MeOH (20 mL) and AcOH (2.0 mL) at rt. The reaction mixture was evacuated and back-filled with $H_2$(g) five times. The resulting suspension was stirred at rt for 8 h under $H_2$(g) atmosphere. The reaction mixture was filtered through Celite and the solvent was removed under reduced pressure to give (1.0 g, 76%) the title compound as a yellow gum. MS (ESI): m/z $[M+H]^+$303.

Step E. (9H-Fluoren-9-yl)methyl 2-(2-(1,3-dioxolan-2-yl)pyridin-3-yl)-4-(trifluoromethyl)piperidine-1-carboxylate

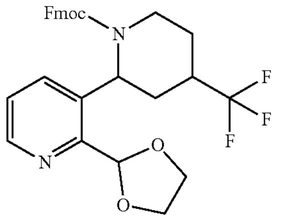

Fmoc-Cl (1.03 g, 3.97 mmol) was added to 2-(1,3-dioxolan-2-yl)-3-(4-(trifluoromethyl)piperidin-2-yl)pyridine (1.0 g, 3.31 mmol) and TEA (1.38 mL, 9.92 mmol) in THF (25 mL) at rt and the resulting solution was stirred for 15 h. The reaction mixture was poured into brine (200 mL), and extracted with EtOAc (3×100 mL). The combined organic layer was dried ($Na_2SO_4$), filtered and evaporated to afford yellow gum. The crude product was purified by flash chromatography using a gradient of 5-50% EtOAc in petroleum ether as mobile phase to give (1.05 g, 60%) the title compound as a white solid. MS (ESI): m/z $[M+H]^+$525.

Step F. (9H-Fluoren-9-yl)methyl 2-(2-formylpyridin-3-yl)-4-(trifluoromethyl)piperidine-1-carboxylate

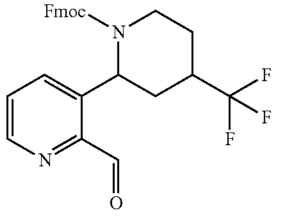

6 M HCl (aq.) (50 mL, 300 mmol) was added to (9H-fluoren-9-yl)methyl 2-(2-(1,3-dioxolan-2-yl)pyridin-3-yl)-4-(trifluoromethyl)piperidine-1-carboxylate (1.05 g, 2.00 mmol) in MeCN (50 mL) at rt. The resulting solution was stirred at 90° C. for 15 h. The reaction mixture was poured into sat $NaHCO_3$(aq) (250 mL), and extracted with EtOAc (3×125 mL). The combined organic layer was dried ($Na_2SO_4$), filtered and evaporated to give (0.7 g, 73%) the title compound as a brown gum. MS (ESI): m/z $[M+H]^+$ 481.

Step G. (9H-fluoren-9-yl)methyl 2-(2-(((2-(ethoxycarbonyl)-1H-pyrrol-3-yl)amino)methyl)pyridin-3-yl)-4-(trifluoromethyl)piperidine-1-carboxylate $NaBH_4$ (137 mg, 2.19 mmol) was added to (9H-fluoren-9-yl)methyl 2-(2-formylpyridin-3-yl)-4-(trifluoromethyl)piperidine-1-carboxylate (700 mg, 1.46 mmol) and ethyl 3-amino-1H-pyrrole-2-carboxylate (270 mg, 1.75 mmol) in MeOH (20 mL) and AcOH (4.00 mL) at rt and the resulting solution was stirred at 60° C. for 3 h. The reaction mixture was poured into sat $NaHCO_3$(aq) (100 mL), and extracted with EtOAc (3×50 mL). The combined organic layer was dried ($Na_2SO_4$), filtered and evaporated to afford a yellow gum. The crude product was purified by flash chromatography using a gradient of 5-30% EtOAc in petroleum ether as mobile phase to give (660 mg, 73%) the title compound as a pale yellow oil which solidified on standing. MS (ESI): m/z $[M+H]^+$ 481.

Intermediate 24

(9H-Fluoren-9-yl)methyl 2-(4-(((2-(ethoxycarbonyl)-1H-pyrrol-3-yl)amino)methyl)pyridin-3-yl)-4-(trifluoromethyl)piperidine-1-carboxylate

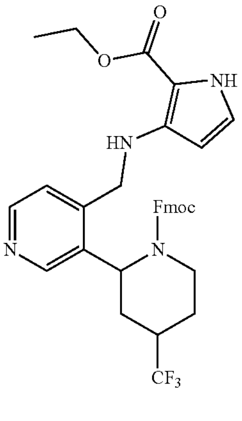

Step A. 3-Bromo-4-(1,3-dioxolan-2-yl)pyridine

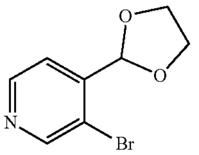 [SMILES: Brc1cnccc1C1OCCO1]

pTsOH (1.85 g, 10.8 mmol) was added to 3-bromoisonicotinaldehyde (10 g, 53.8 mmol) and ethane-1,2-diol (6.67 g, 107.5 mmol) in toluene (80 mL) at rt, and the mixture was stirred at 130° C. for 15 h. The solvent was removed under reduced pressure, the residue was poured into sat $NaHCO_3$ (aq) (300 mL), and extracted with EtOAc (3×150 mL). The combined organic layer was dried ($Na_2SO_4$), filtered and evaporated to give (10.0 g, 81%) the title compound as a yellow liquid. MS (ESI): m/z $[M+H]^+$230/232.

Step B. tert-Butyl (5-(4-(1,3-dioxolan-2-yl)pyridin-3-yl)-5-oxo-3-(trifluoromethyl)pentyl)carbamate

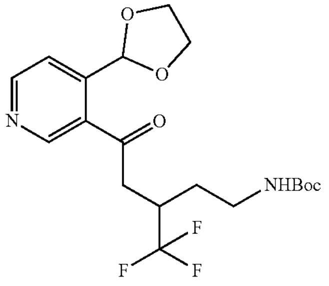 [SMILES: CC(C)(C)OC(=O)NCCC(CC(=O)c1cnccc1C1OCCO1)C(F)(F)F]

n-BuLi (2.5 M in hexane, 9.0 mL, 22.5 mmol) was added to 3-bromo-4-(1,3-dioxolan-2-yl)pyridine (4.95 g, 21.52 mmol) in THF (30 mL) at −78° C. The resulting solution was stirred at −78° C. for 15 min under $N_2$(g) atmosphere. A solution of tert-butyl 2-oxo-4-(trifluoromethyl)piperidine-1-carboxylate (5.0 g, 18.71 mmol) in THF (30 mL) was added dropwise to the stirred solution at −78° C. under $N_2$(g) atmosphere. The resulting solution was stirred at −78° C. for 1 h. The reaction mixture was poured into brine (200 mL), and extracted with EtOAc (3×100 mL). The combined organic layer was dried ($Na_2SO_4$), filtered and evaporated to afford yellow gum. The crude product was purified by flash chromatography using a gradient of 10-50% EtOAc in petroleum ether as mobile phase to give (4.60 g, 59%) the title compound as a pale yellow gum. MS (ESI): m/z $[M+H]^+$ 419.

Step C. 4'-(1,3-Dioxolan-2-yl)-4-(trifluoromethyl)-1,4,5,6-tetrahydro-2,3'-bipyridine

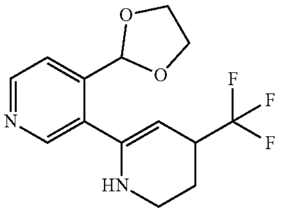 [SMILES: FC(F)(F)C1C=C(c2cnccc2C2OCCO2)NCC1]

TFA (14.4 mL, 186.9 mmol) was added to tert-butyl (5-(4-(1,3-dioxolan-2-yl)pyridin-3-yl)-5-oxo-3-(trifluoromethyl)pentyl)carbamate (4.6 g, 10.99 mmol) in DCM (60 mL) at rt and stirred at 20° C. for 15 h. The solvent was removed under reduced pressure. The residue was poured into sat $NaHCO_3$(aq) (150 mL), and extracted with EtOAc (3×100 mL). The combined organic layer was dried ($Na_2SO_4$), filtered and evaporated to give (3.20 g, 97%) the title compound as a brown. MS (ESI): m/z $[M+H]^+$ 301.

Step D. 4-(1,3-Dioxolan-2-yl)-3-(4-(trifluoromethyl)piperidin-2-yl)pyridine

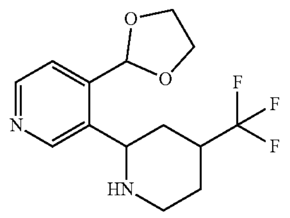 [SMILES: FC(F)(F)C1CCNC(c2cnccc2C2OCCO2)C1]

Lithium triethylborohydride (1 M in THF) (22 mL, 22 mmol) was added to 4'-(1,3-dioxolan-2-yl)-4-(trifluoromethyl)-1,4,5,6-tetrahydro-2,3'-bipyridine (2.2 g, 7.33 mmol) in THF (10 mL) cooled to 0° C. The resulting solution was stirred at rt for 2 h. The solvent was removed under reduced pressure. The residue was poured into sat $NaHCO_3$(aq) (150 mL), and extracted with EtOAc (3×100 mL). The combined organic layer was dried ($Na_2SO_4$), filtered and evaporated to give (2.0 g, 90%) the title compound as a yellow gum. MS (ESI): m/z $[M+H]^+$ 303.

Step E. (9H-Fluoren-9-yl)methyl 2-(4-(1,3-dioxolan-2-yl)pyridin-3-yl)-4-(trifluoromethyl)piperidine-1-carboxylate

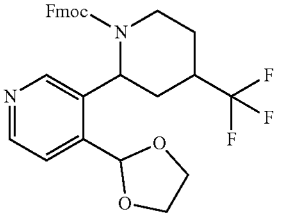

Fmoc-Cl (2.05 g, 7.94 mmol) was added to 4-(1,3-dioxolan-2-yl)-3-(4-(trifluoromethyl)piperidin-2-yl)pyridine (2.0 g, 6.62 mmol) and TEA (2.77 mL, 19.85 mmol) in THF (10 mL) and the resulting solution was stirred at rt for 15 h. The reaction mixture was poured into brine (200 mL), and extracted with EtOAc (3×100 mL). The combined organic layer was dried ($Na_2SO_4$), filtered and evaporated to afford a yellow gum. The crude product was purified by flash chromatography using a gradient 5-50% EtOAc in petroleum ether as mobile phase to give (1.15 g, 33%) the title compound as a white solid. MS (ESI): m/z $[M+H]^+$ 525.

Step F. (9H-Fluoren-9-yl)methyl 2-(4-formylpyridin-3-yl)-4-(trifluoromethyl)piperidine-1-carboxylate

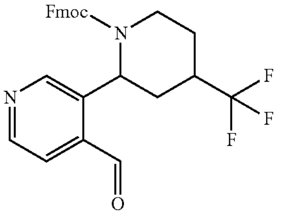

HCl (6 M, aq) (15 mL, 90.0 mmol) was added to (9H-fluoren-9-yl)methyl 2-(4-(1,3-dioxolan-2-yl)pyridin-3-yl)-4-(trifluoromethyl)piperidine-1-carboxylate (1.1 g, 2.10 mmol) in MeCN (30 mL) and the resulting solution was stirred at 90° C. for 15 h. The reaction mixture was poured into sat $NaHCO_3$(250 mL), and extracted with EtOAc (3×125 mL). The combined organic layer was dried ($Na_2SO_4$), filtered and evaporated to give (0.95 g, 94%) the title compound as a brown gum which. MS (ESI): m/z $[M+H]^+$481.

Step G. (9H-Fluoren-9-yl)methyl 2-(4-(((2-(ethoxycarbonyl)-1H-pyrrol-3-yl)amino)methyl)pyridin-3-yl)-4-(trifluoromethyl)piperidine-1-carboxylate $NaBH_4$ (177 mg, 2.81 mmol) was added to (9H-fluoren-9-yl)methyl 2-(4-formylpyridin-3-yl)-4-(trifluoromethyl)piperidine-1-carboxylate (900 mg, 1.87 mmol) and ethyl 3-amino-1H-pyrrole-2-carboxylate (347 mg, 2.25 mmol) in MeOH (20 mL) and AcOH (4.00 mL) at rt and the resulting solution was stirred at 60° C. for 3 h. The reaction mixture was poured into sat $NaHCO_3$(aq) (100 mL), and extracted with EtOAc (3×50 mL). The combined organic layer was dried ($Na_2SO_4$), filtered and evaporated to afford a yellow gum. The crude product was purified by preparative TLC (EtOAc:petroleum ether=1:2), to give (550 mg, 47.5%) the title compound as a pale yellow oil which solidified on standing. MS (ESI): m/z $[M+H]^+$619.

Intermediate 25 rac-(2R,4R)-2-(2-(Methoxymethyl)phenyl)-1-tosyl-4-(trifluoromethyl)piperidine

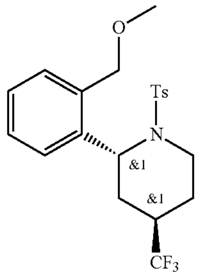 [SMILES: COCc1ccccc1[C@H]1C[C@H](C(F)(F)F)CCN1S(=O)(=O)c1ccc(C)cc1]

The isomeric mixture from Intermediate 10 step B was subjected to chromatography on a ChiralPak-AD-H column (5 μm, 250×20 mm ID) using Hexane/IPA 95/5 as mobile phase to give the title compound.

Intermediate 26 rac-2-((2R,4R)-1-Tosyl-4-(trifluoromethyl)piperidin-2-yl)benzaldehyde

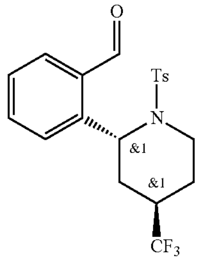 [SMILES: Cc1ccc(S(=O)(=O)N2CC[C@@H](C(F)(F)F)C[C@@H]2c2ccccc2C=O)cc1]

The title compound was prepared in essentially the same way as described for Intermediate 21 step G from Intermediate 25 rac-(2R,4R)-2-(2-(methoxymethyl)phenyl)-1-tosyl-4-(trifluoromethyl)piperidine.

Intermediate 27 rac-2-Thioxo-1-(2-((2R,4R)-1-tosyl-4-(trifluoromethyl)piperidin-2-yl)benzyl)-1,2,3,5-tetrahydro-4H-pyrrolo[3,2-d]pyrimidin-4-one

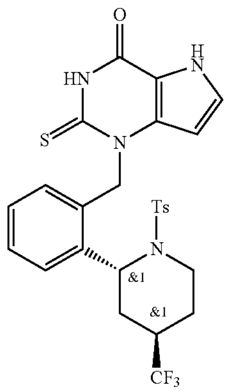 [SMILES: Cc1ccc(S(=O)(=O)N2CC[C@@H](C(F)(F)F)C[C@@H]2c2ccccc2Cn2c(=S)[nH]c(=O)c3[nH]ccc32)cc1]

The title compound was prepared in essentially the same way as described for Intermediate 10 from Intermediate 26 rac-2-((2R,4R)-1-tosyl-4-(trifluoromethyl)piperidin-2-yl) benzaldehyde. MS (ESI): m/z $[M+H]^+$ 619.

Intermediate 28 rac-2-Thioxo-3-(2-((2R,4R)-1-tosyl-4-(trifluoromethyl)piperidin-2-yl)benzyl)-1,2,3,7-tetrahydro-6H-purin-6-one

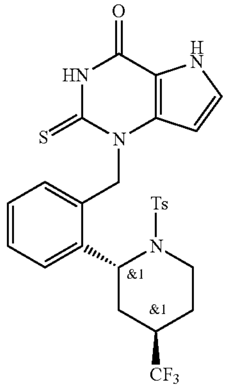 [SMILES: Cc1ccc(S(=O)(=O)N2CC[C@@H](C(F)(F)F)C[C@@H]2c2ccccc2Cn2c(=S)[nH]c(=O)c3[nH]ccc32)cc1]

The title compound ws prepared in essentially the same way as described for Intermediate 27 from rac-2-((2R,4R)-1-tosyl-4-(trifluoromethyl)piperidin-2-yl)benzaldehyde Intermediate 26 and 4-amino-1H-imidazole-5-carboxamide. MS (ESI): m/z $[M+H]^+$564.

Intermediate 29

1-(Isoquinolin-8-ylmethyl)-2-thioxo-1,2,3,5-tetrahydro-4H-pyrrolo[3,2-d]pyrimidin-4-one

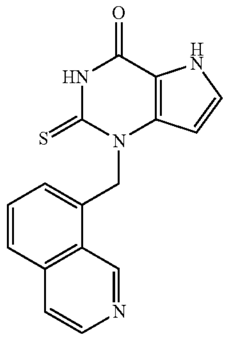 [SMILES: O=c1[nH]c(=S)n(Cc2cccc3ccncc23)c2cc[nH]c12]

Step A. Ethyl 3-((isoquinolin-8-ylmethyl)amino)-1H-pyrrole-2-carboxylate

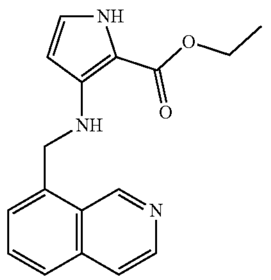 [SMILES: CCOC(=O)c1[nH]ccc1NCc1cccc2ccncc12]

Ethyl 3-amino-1H-pyrrole-2-carboxylate (0.364 g, 1.91 mmol) was suspended in EtOH (12 mL) and DIPEA (0.315 mL, 1.91 mmol) and stirred for 10 min. AcOH (0.219 mL, 3.82 mmol) and $NaBH_3CN$ (0.360 g, 5.73 mmol) was added and the reaction mixture was stirred for 5 min. A solution of isoquinoline-8-carbaldehyde (0.300 g, 1.91 mmol) in EtOH (15 mL) was added dropwise over 15 min, and the reaction was stirred overnight, and then poured into aq 1M HCl (100 mL). The acidic water phase was washed with $Et_2O$ (3×30 mL), and then the aqueous layer was basified with NaOH and extracted with $Et_2O$ (3×50 mL). The combined organic layer was washed with water (30 mL), dried ($Na_2SO_4$), filtered and evaporated to give the title compound as a brown gum. MS (ESI): m/z $[M+H]^+$295.

Step B. Ethyl 3-(3-benzoyl-1-(isoquinolin-8-ylmethyl)thioureido)-1H-pyrrole-2-carboxylate

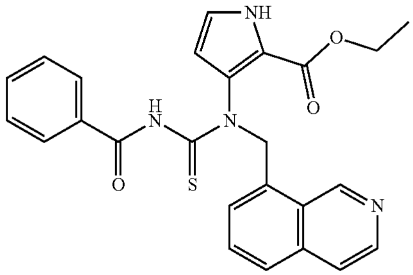 [SMILES: CCOC(=O)c1[nH]ccc1N(Cc1cccc2ccncc12)C(=S)NC(=O)c1ccccc1]

Benzoyl isothiocyanate (0.191 mL, 1.42 mmol) was added dropwise to a solution of ethyl 3-((isoquinolin-8-ylmethyl)amino)-1H-pyrrole-2-carboxylate (0.420 g, 1.42 mmol) and DIPEA (0.235 mL, 1.42 mmol) in DCM (20 mL) and the reaction was stirred overnight. The reaction was filtered and the filtrate was evaporated to give (0.5 g, 77%) the title compound.

Step C. 1-(Isoquinolin-8-ylmethyl)-2-thioxo-1,2,3,5-tetrahydro-4H-pyrrolo[3,2-d]pyrimidin-4-one NaOH (0.218 g, 5.45 mmol) was added to a solution of ethyl 3-(3-benzoyl-1-(isoquinolin-8-ylmethyl)thioureido)-1H-pyrrole-2-carboxylate (0.500 g, 1.09 mmol) in MeOH (20 mL) and the reaction was gently refluxed for 6 h then allowed to cool to rt. The solvent was removed in vacuo and the residue partitioned between water and EtOAc. After shaking and allowing to settle the mixture was filtered and the collected solid was washed with a little EtOAc, collected and dried to give (105 mg, 31%) the title compound. MS (ESI): m/z $[M+H]^+$309.

Intermediate 30 tert-Butyl (1-(4-((4-oxo-2-thioxo-2,3,4,5-tetrahydro-1H-pyrrolo[3,2-d]pyrimidin-1-yl)methyl)phenyl)cyclobutyl)carbamate

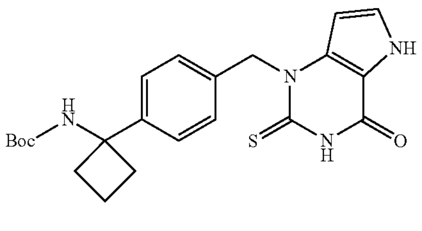 [SMILES: CC(C)(C)OC(=O)NC1(c2ccc(Cn3c(=S)[nH]c(=O)c4[nH]ccc43)cc2)CCC1]

Step A. Ethyl 3-((4-(1-((tert-butoxycarbonyl)amino)cyclobutyl)benzyl)amino)-1H-pyrrole-2-carboxylate

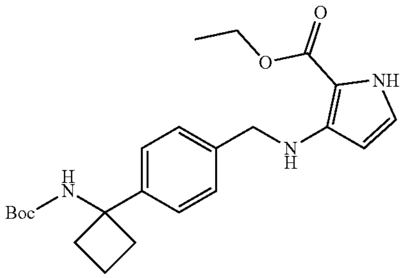 [SMILES: CCOC(=O)c1[nH]ccc1NCc1ccc(C2(NC(=O)OC(C)(C)C)CCC2)cc1]

AcOH (212 mg, 3.52 mmol) and $NaBH(OAc)_3$ (1.49 g, 7.05 mmol) was aded to a solution of tert-butyl (1-(4-formylphenyl)cyclobutyl)carbamate (970 mg, 3.52 mmol) and ethyl 3-amino-1H-pyrrole-2-carboxylate (736 mg, 3.88 mmol) in DCE (40 mL) and the resulting solution was stirred for 16 h at rt. The reaction was quenched with sat $NaHCO_3$ (aq) (20 mL), and the resulting aqueous solution was extracted with (3×30 mL) DCM. The combined organic layer was washed with water (40 mL), dried ($Na_2SO_4$), and concentrated under vacuum to give (1.39 g, 95%) the title compound as a white solid. MS (ESI): m/z $[M+H]^+$414.

Step B. Ethyl 3-(3-benzoyl-1-(4-(1-((tert-butoxycarbonyl)amino)cyclobutyl)benzyl)thioureido)-1H-pyrrole-2-carboxylate

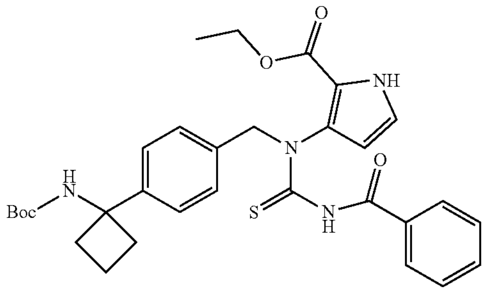 [SMILES: CCOC(=O)c1[nH]ccc1N(Cc1ccc(C2(NC(=O)OC(C)(C)C)CCC2)cc1)C(=S)NC(=O)c1ccccc1]

Benzoyl isothiocyanate (677 mg, 4.15 mmol) was added to a solution of ethyl 3-((4-(1-((tert-butoxycarbonyl)amino)cyclobutyl)benzyl)amino)-1H-pyrrole-2-carboxylate (1.56 g, 3.77 mmol) in MeCN (40 mL) and the resulting solution was stirred for 4 h at rt and then concentrated under vacuum to give (2.1 g) the crude title compound as a yellow solid. MS (ESI): m/z $[M+H]^+$577.

Step C. tert-Butyl (1-(4-((4-oxo-2-thioxo-2,3,4,5-tetrahydro-1H-pyrrolo[3,2-d]pyrimidin-1-yl)methyl)phenyl)cyclobutyl)carbamate $Cs_2CO_3$ (2.46 g, 7.54 mmol) was added to a solution of ethyl 3-(3-benzoyl-1-(4-(1-((tert-butoxycarbonyl)amino)cyclobutyl)benzyl)thioureido)-1H-pyrrole-2-carboxylate (2.1 g, 3.77 mmol) in MeOH (50 mL) and the resulting solution was stirred for 4 h at 50° C. and then concentrated under vacuum. The crude product was purified by flash chromatography using a gradient of 0-5% MeOH in DCM as mobile phase to give (1.4 g, 88%) the title compound as a light yellow solid. MS (ESI): m/z $[M+H]^+427$.

Intermediate 31 tert-Butyl 5-((4-oxo-2-thioxo-2,3,4,5-tetrahydro-1H-pyrrolo[3,2-d]pyrimidin-1-yl)methyl)isoindoline-2-carboxylate

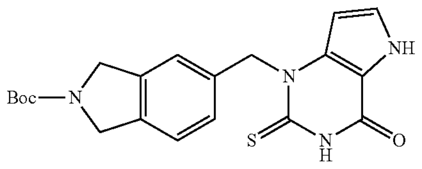 [SMILES: CC(C)(C)OC(=O)N1Cc2ccc(Cn3c(=S)[nH]c(=O)c4[nH]ccc43)cc2C1]

Step A. tert-Butyl 5-(((2-(ethoxycarbonyl)-1H-pyrrol-3-yl)amino)methyl)isoindoline-2-carboxylate

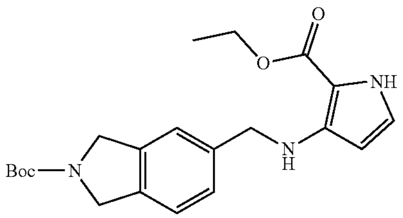 [SMILES: CCOC(=O)c1[nH]ccc1NCc1ccc2c(c1)CN(C(=O)OC(C)(C)C)C2]

AcOH (236 mg, 3.92 mmol) and $NaBH(OAc)_3$ (1.66 g, 7.85 mmol) was added to a solution of tert-butyl 5-formylisoindoline-2-carboxylate (CAS Registry Number 253801-15-9) (970 mg, 3.92 mmol) and ethyl 3-amino-1H-pyrrole-2-carboxylate (823 mg, 4.32 mmol) in DCE (40 mL) and the resulting solution was stirred for 16 h at rt. The reaction was quenched by the addition of sat $NaHCO_3$(aq) (20 mL). The resulting aqueous solution was diluted with DCM (40 mL) and water (30 mL). The separated organic layer was washed with water (40 mL) and brine (40 mL), then dried ($Na_2SO_4$) and concentrated under vacuum to give (1.4 g, 92%) the title compound as a white solid. MS (ESI): m/z $[M+H]^+386$.

Step B. tert-Butyl 5-((3-benzoyl-1-(2-(ethoxycarbonyl)-1H-pyrrol-3-yl)thioureido)methyl)isoindoline-2-carboxylate

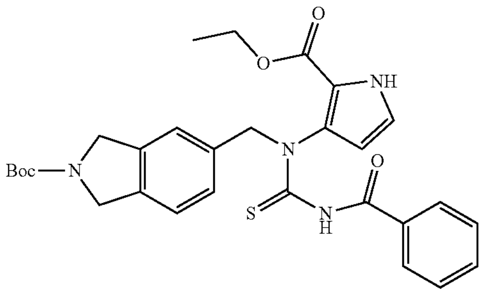 [SMILES: CCOC(=O)c1[nH]ccc1N(Cc1ccc2c(c1)CN(C(=O)OC(C)(C)C)C2)C(=S)NC(=O)c1ccccc1]

Benzoyl isothiocyanate (754 mg, 4.62 mmol) was added to a solution of tert-butyl 5-(((2-(ethoxycarbonyl)-1H-pyrrol-3-yl)amino)methyl)isoindoline-2-carboxylate (1.62 g, 4.20 mmol) in MeCN (40 mL). The resulting solution was stirred for 4 h at rt and then concentrated under vacuum to give (2.3 g) the crude title compound as a yellow solid. MS (ESI): m/z $[M+H]^+549$.

Step C. tert-Butyl 5-((4-oxo-2-thioxo-2,3,4,5-tetrahydro-1H-pyrrolo[3,2-d]pyrimidin-1-yl)methyl)isoindoline-2-carboxylate $Cs_2CO_3$ (2.74 g, 8.4 mmol) was added to a solution of tert-butyl 5-((3-benzoyl-1-(2-(ethoxycarbonyl)-1H-pyrrol-3-yl)thioureido)methyl)isoindoline-2-carboxylate (2.3 g, 4.2 mmol) in MeOH (50 mL) and the resulting solution was stirred for 4 h at 50° C. and then concentrated under vacuum. The crude product was purified by flash chromatography using a gradient of 0-5% MeOH in DCM as mobile phase to give (1.4 g, 88%) the title compound as a light yellow solid. MS (ESI): m/z $[M-56+H]^+343$.

Intermediate 32 tert-Butyl 4-((4-oxo-2-thioxo-2,3,4,5-tetrahydro-1H-pyrrolo[3,2-d]pyrimidin-1-yl)methyl)isoindoline-2-carboxylate

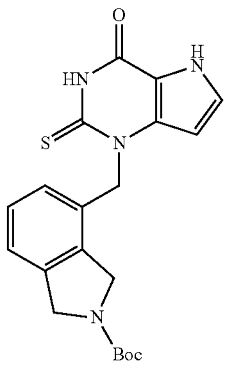 [SMILES: CC(C)(C)OC(=O)N1Cc2cccc(Cn3c(=S)[nH]c(=O)c4[nH]ccc43)c2C1]

Step A. tert-Butyl 4-(((2-(ethoxycarbonyl)-1H-pyrrol-3-yl)amino)methyl)isoindoline-2-carboxylate

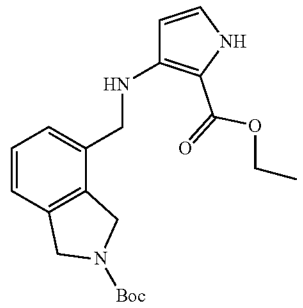 [SMILES: CCOC(=O)c1[nH]ccc1NCc1cccc2c1CN(C(=O)OC(C)(C)C)C2]

AcOH (236 mg, 3.92 mmol) and $NaBH(OAc)_3$ (1.66 g, 7.85 mmol) were added to a solution of tert-butyl 4-formylisoindoline-2-carboxylate (970 mg, 3.92 mmol) and ethyl 3-amino-1H-pyrrole-2-carboxylate hydrochloride (823 mg, 4.32 mmol) in DCE (40 mL) and the resulting solution was stirred for 16 h at rt and then quenched by the addition of sat $NaHCO_3$(aq) (20 mL). The resulting aqueous solution was diluted with DCM (40 mL) and water (30 mL). The separated organic layer was washed with water (40 mL) and brine (40 mL), then dried ($Na_2SO_4$), filtered and concentrated under vacuum to give (1.6 g) the crude title compound as a white solid. MS (ESI): m/z $[M-56+H]^+$ 386.

Step B. tert-Butyl 4-((3-benzoyl-1-(2-(ethoxycarbonyl)-1H-pyrrol-3-yl)thioureido)methyl)isoindoline-2-carboxylate Benzoyl isothiocyanate (640 mg, 3.92 mmol) was added dropwise to a solution of tert-butyl 4-(((2-(ethoxycarbonyl)-1H-pyrrol-3-yl)amino)methyl)isoindoline-2-carboxylate (1.0 g, 2.6 mmol) in MeCN (20 mL) and the resulting solution was stirred for 16 h at rt and then concentrated under vacuum. The crude product was purified by flash chromatography using a gradient of 0-30% EtOAc in petroleum ether as mobile phase to give (1.2 g, 84%) the title compound as a yellow solid. MS (ESI): m/z $[M+H]^+$549.

Step C. tert-Butyl 4-((4-oxo-2-thioxo-2,3,4,5-tetrahydro-1H-pyrrolo[3,2-d]pyrimidin-1-yl)methyl)isoindoline-2-carboxylate A solution of tert-butyl 4-((3-benzoyl-1-(2-(ethoxycarbonyl)-1H-pyrrol-3-yl)thioureido)methyl)isoindoline-2-carboxylate (600 mg, 1.09 mmol) in sat $NH_3$/MeOH (5 mL) was stirred for 16 h at rt and then concentrated under vacuum. The crude product was purified by flash chromatography using a gradient of 0-5% MeOH in DCM as mobile phase to give (400 mg, 92%) the title compound as a white solid. MS (ESI): m/z $[M-56+H]^+$399.

Intermediate 33 tert-Butyl (1-(3-((4-oxo-2-thioxo-2,3,4,5-tetrahydro-1H-pyrrolo[3,2-d]pyrimidin-1-yl)methyl)phenyl)cyclobutyl)carbamate

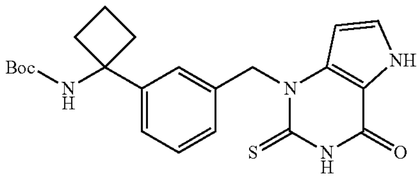 [SMILES: CC(C)(C)OC(=O)NC1(c2cccc(Cn3c(=S)[nH]c(=O)c4[nH]ccc43)c2)CCC1]

Step A. 1-(3-Bromophenyl)cyclobutane-1-carbonitrile

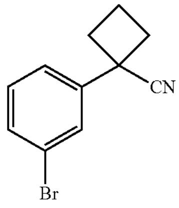 [SMILES: N#CC1(c2cccc(Br)c2)CCC1]

2-(3-Bromophenyl)acetonitrile (400 g, 2.04 mol) was added to a mixture of NaH (180 g, 4.5 mol) in DMF (4 L) at 0° C. The mixture was stirred at rt for 1 h, then 1,3-dibromo-propane (450 g, 2.24 mol) was added to the mixture at 0° C. The mixture was stirred at rt for 1 h. The mixture was poured into water (4 L) and extracted with n-heptane (3×2 L). The combined organic layer was washed with brine (2×1 L), dried and concentrated to give (400 g, 83%) the title compound as a yellow oil. $^1H$ NMR (400 MHz, CDCl3) δ 2.03-2.13 (1H, m), 2.40-2.50 (1H, m), 2.56-2.64 (2H, m), 2.79-2.86 (2H, m), 7.27 (1H, t), 7.34-7.36 (1H, m), 7.45 (1H, d), 7.55 (1H, t).

Step B. 1-(3-Bromophenyl)cyclobutane-1-carboxylic acid

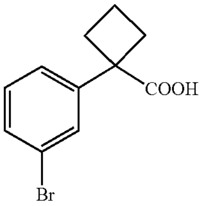 [SMILES: O=C(O)C1(c2cccc(Br)c2)CCC1]

KOH (320 g, 5.7 mol) was added to a mixture of compound 1-(3-bromophenyl)cyclobutane-1-carbonitrile (270 g, 1.14 mol) in n-BuOH (3 L). The mixture was heated to reflux for 16 h. The solvent was evaporated, the residue was dissolved in water (3 L) and the pH was adjusted to 6 with 3 M HCl. A solid formed was collected by filtration and dried to give (200 g, yield 68.5%) the title compound as a white solid. $^1H$ NMR (400 MHz, CDCl3) δ 1.84-1.92 (1H, m), 2.05-2.14 (m, 1H), 2.46-2.53 (2H, m), 2.80-2.86 (2H, m), 6.90-6.30 (1H br s), 7.17-7.24 (2H, m), 7.38 (1H, dd), 7.44 (1H, s).

Step C. tert-Butyl (1-(3-bromophenyl)cyclobutyl)carbamate

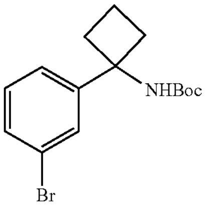 [SMILES: CC(C)(C)OC(=O)NC1(c2cccc(Br)c2)CCC1]

TEA (103 g, 1.02 mol) and DPPA (168 g, 0.61 mol) was added to a mixture of 1-(3-bromophenyl)cyclobutane-1-carboxylic acid (130 g, 0.50 mol) in tert-BuOH (1.5 L). The mixture was heated to reflux for 16 h. The solvent was evaporated. The crude product was purified by flash chromatography using a gradient of 5-10% EtOAc in petroleum ether as mobile phase to give (140 g, 84%) the title compound as a white solid. MS (ESI): m/z $[M-56+H]^+$569.

Step D. tert-Butyl (1-(3-formylphenyl)cyclobutyl)carbamate

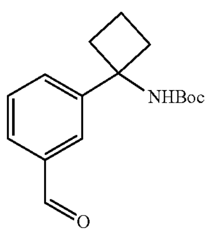 [SMILES: CC(C)(C)OC(=O)NC1(c2cccc(C=O)c2)CCC1]

n-BuLi (2.5M in THF, 272 mL, 0.68 mol) was added dropwise to a solution of tert-butyl (1-(3-bromophenyl) cyclobutyl)carbamate (100 g, 0.31 mol) in THF (1 L) at −78° C. over 30 min. DMF (50 g, 0.68 mol) was added and the reaction mixture was stirred at −78° C. for another 30 min. The mixture was poured into water (0.5 L) and extracted with EtOAc (3×200 mL). The combined organic layer was washed with brine (2×200 mL), dried and concentrated. The crude product was purified by flash chromatography using a gradient of 5-15% EtOAc in petroleum ether as mobile phase to give (38 g, 45%) the title compound as a white solid. MS (ESI): m/z $[M+Na]^+$298.

Step E. Ethyl 3-((3-(1-((tert-butoxycarbonyl)amino) cyclobutyl)benzyl)amino)-1H-pyrrole-2-carboxylate

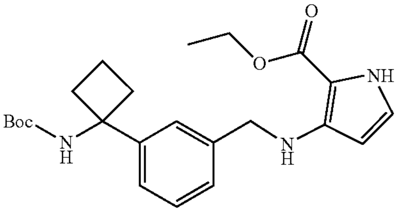 [SMILES: CCOC(=O)c1[nH]ccc1NCc1cccc(C2(NC(=O)OC(C)(C)C)CCC2)c1]

AcOH (212 mg, 3.52 mmol) and $NaBH(OAc)_3$ (1.49 g, 7.05 mmol) was added to a solution of tert-butyl 1-(3-formylphenyl)cyclobutylcarbamate (970 mg, 3.52 mmol) and ethyl 3-amino-1H-pyrrole-2-carboxylate (736 mg, 3.88 mmol) in DCE (40 mL) and the resulting solution was stirred for 16 h at rt. The reaction was quenched by the addition of sat $NaHCO_3$(aq) (20 mL). The resulting aqueous solution was extracted with DCM (3×50 mL). The combined organic layer was washed with water (40 mL) and brine (40 mL), dried ($Na_2SO_4$) and concentrated under vacuum. The crude product was purified by flash chromatography using a gradient of 0-10% MeOH in DCM as mobile phase to give (1.2 g, 82%) the title compound as a white solid. MS (ESI): m/z $[M+Na]^+$414.

Step F. Ethyl 3-(3-benzoyl-1-(3-(1-((tert-butoxycarbonyl)amino)cyclobutyl)benzyl)thioureido)-1H-pyrrole-2-carboxylate

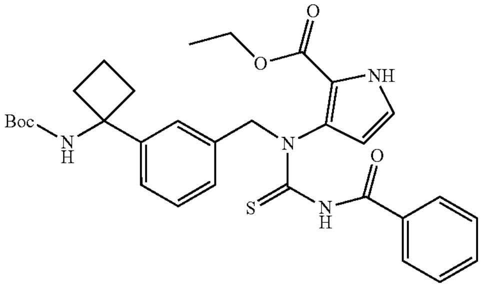 [SMILES: CCOC(=O)c1[nH]ccc1N(Cc1cccc(C2(NC(=O)OC(C)(C)C)CCC2)c1)C(=S)NC(=O)c1ccccc1]

Benzoyl isothiocyanate (520 mg, 3.2 mmol) was added to a solution of ethyl 3-((3-(1-((tert-butoxycarbonyl)amino) cyclobutyl)benzyl)amino)-1H-pyrrole-2-carboxylate (1.2 g, 2.9 mmol) in MeCN (40 mL) and the resulting solution was stirred for 4 h at rt and then concentrated under vacuum. The crude product was purified by flash chromatography using a gradient of 0-10% MeOH in DCM as mobile phase to give (1.4 g, 79%) the title compound as a yellow solid. MS (ESI): m/z $[M+H]^+$577.

Step G. tert-Butyl (1-(3-((4-oxo-2-thioxo-2,3,4,5-tetrahydro-1H-pyrrolo[3,2-d]pyrimidin-1-yl)methyl) phenyl)cyclobutyl)carbamate $Cs_2CO_3$ (2.52 g, 7.74 mmol) was added to a solution of ethyl 3-(3-benzoyl-1-(3-(1-((tert-butoxycarbonyl)amino)cyclobutyl)benzyl)thioureido)-1H-pyrrole-2-carboxylate (2.3 g, 3.87 mmol) in MeOH (50 mL) and the resulting solution was stirred for 4 h at 50° C. and then concentrated under vacuum. The crude product was purified by flash chromatography using a gradient of 0-10% MeOH in DCM as mobile phase to give (1.4 g, 85%) the title compound as a light yellow solid. MS (ESI): m/z $[M-56+H]^+$399.

Intermediate 34 tert-Butyl 3-(2-((4-oxo-2-thioxo-2,3,4,5-tetrahydro-1H-pyrrolo[3,2-d]pyrimidin-1-yl)methyl)phenyl) piperidine-1-carboxylate

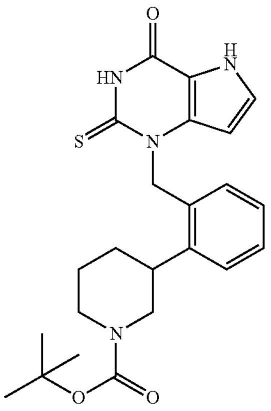 [SMILES: CC(C)(C)OC(=O)N1CCCC(c2ccccc2Cn2c(=S)[nH]c(=O)c3[nH]ccc32)C1]

Step A. (2-(Pyridin-3-yl)phenyl)methanol

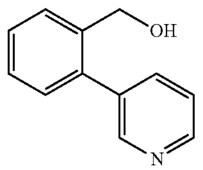 [SMILES: OCc1ccccc1-c1cccnc1]

A mixture of (2-bromophenyl)methanol (1 g, 5.35 mmol), 3-(diethylboraneyl)pyridine (CAS Reg No 89878-14-8) (0.786 g, 5.35 mmol), tetrabutylammonium bromide (1.724 g, 5.35 mmol), $Na_2CO_3$ (2.153 g, 20.32 mmol) and tetrakis (triphenylphosphine)palladium(0) (0.185 g, 0.16 mmol) in water (15 mL) was heated at 150° C. in a microwave reactor for 15 min. The reaction was cooled to rt, diluted with water (100 mL) and extracted with EtOAc (2×100 mL). The combined organic layer was dried ($Na_2SO_4$), evaporated in vacuo, and the residue was purified by flash chromatography using EtOAc as mobile phase, followed by flash chromatography using 4% MeOH in DCM as mobile phase to give (0.564 g, 57%) the title compound as a yellow oil. $^1H$ NMR (400 MHz, $CDCl_3$) δ 2.29 (s, 1H), 4.59 (2H, s), 7.24-7.29 (1H, m), 7.32-7.48 (3H, m), 7.61 (1H, ddd), 7.75 (1H, ddd), 8.58 (2H, ddd).

Step B. (2-(Piperidin-3-yl)phenyl)methanol hydrochloride

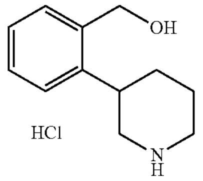 [SMILES: OCc1ccccc1C1CCCNC1 ; Cl]

A stirred suspension of (2-(pyridin-3-yl)phenyl)methanol (1.5 g, 8.10 mmol) and platinum (IV) oxide (0.129 g, 0.57 mmol) in a mixture of HCl (2 M, aq) (4.05 mL, 8.10 mmol) and EtOH (50 mL) was hydrogenated at 3 atm for 24 h. The mixture was filtered through Celite and the filtrate was evaporated in vacuo to afford (1.950 g) the title compound. MS (ESI): m/z $[M+H]^+$ 192.

Step C. tert-Butyl 3-(2-(hydroxymethyl)phenyl) piperidine-1-carboxylate

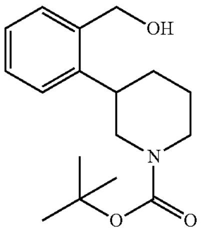 [SMILES: CC(C)(C)OC(=O)N1CCCC(c2ccccc2CO)C1]

$Boc_2O$ (2.131 mL, 9.18 mmol) was added to a solution of (2-(piperidin-3-yl)phenyl)methanol hydrochloride (1.9 g, 8.34 mmol) and DIPEA (4.37 mL, 25.03 mmol) in DCM (40 mL) at rt under $N_2$(g) atmosphere and the reaction mixture was stirred for 2 h at rt. The reaction was diluted with DCM (100 mL) and washed with water (2×100 mL). The organic layer was dried ($MgSO_4$), and evaporated in vacuo. The crude product was purified by flash chromatography using 30% EtOAc in isohexane as mobile phase to give (1.850 g, 76%) the title compound as a colorless oil. MS (ESI): m/z $[M-Boc+H]^+$192.

Step D. tert-Butyl 3-(2-formylphenyl)piperidine-1-carboxylate

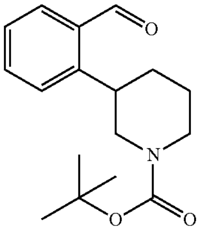 [SMILES: CC(C)(C)OC(=O)N1CCCC(c2ccccc2C=O)C1]

$MnO_2$ (activated) (3.07 g, 31.74 mmol) was added to a solution of tert-butyl 3-(2-(hydroxymethyl)phenyl)piperidine-1-carboxylate (1.85 g, 6.35 mmol) in DCM (20 mL) and the reaction was stirred at rt overnight. $MnO_2$ (activated) (1.104 g, 12.70 mmol) was added and stirring continued for a further 24 h. The mixture was filtered through Celite and the filtrate was evaporated in vacuo to give (1.57 g, 85%) the title compound as a pale yellow oil. MS (ESI): m/z $[M-Boc+H]^+$ 190.

Step E. tert-Butyl 3-(2-(((2-(ethoxycarbonyl)-1H-pyrrol-3-yl)amino)methyl)phenyl)piperidine-1-carboxylate

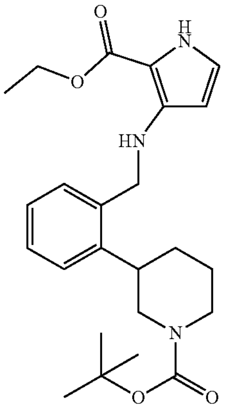 [SMILES: CCOC(=O)c1[nH]ccc1NCc1ccccc1C1CCCN(C(=O)OC(C)(C)C)C1]

DIPEA (0.362 mL, 2.07 mmol) was added to a solution of ethyl 3-amino-1H-pyrrole-2-carboxylate hydrochloride (329 mg, 1.73 mmol) in EtOH (20 mL) and the mixture was stirred for 10 min. AcOH (0.237 mL, 4.15 mmol) and $NaBH_3CN$ (163 mg, 2.59 mmol) was added. A solution of tert-butyl 3-(2-formylphenyl)piperidine-1-carboxylate (500 mg, 1.73 mmol) in EtOH (15 mL) was then added dropwise over 15 min and the resultant suspension was stirred at rt for 2 h. The mixture was evaporated in vacuo, and the residue was treated with water (100 mL) and extracted with DCM (2×100 mL). The combined organic layer was dried ($Na_2SO_4$) and evaporated in vacuo. The crude product was purified by flash chromatography using 20% EtOAc in isohexane as mobile phase to give (630 mg, 85%) the title compound as a colourless oil. MS (ESI): m/z $[M+H]^+$428.

Step F. tert-Butyl 3-(2-((3-benzoyl-1-(2-(ethoxycarbonyl)-1H-pyrrol-3-yl)thioureido)methyl)phenyl) piperidine-1-carboxylate

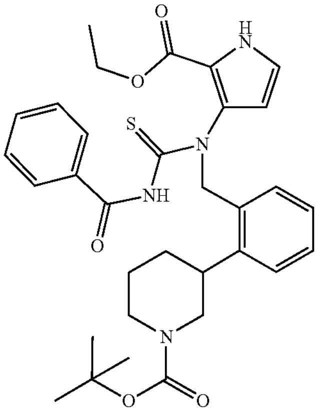 [SMILES: CCOC(=O)c1[nH]ccc1N(Cc1ccccc1C1CCCN(C(=O)OC(C)(C)C)C1)C(=S)NC(=O)c1ccccc1]

Benzoyl isothiocyanate (0.40 mL, 2.99 mmol) was added to a solution of tert-butyl 3-(2-((2-(ethoxycarbonyl)-1H-pyrrol-3-ylamino)methyl)phenyl)piperidine-1-carboxylate (1.28 g, 2.99 mmol) in DCM (10 mL) and the mixture was stirred at rt for 1 h. The solvent was removed in vacuo to afford (1.71 g, 97%) the title compound as an orange gum. MS (ESI): m/z $[M+H]^+$589.

Step G. tert-Butyl 3-(2-((4-oxo-2-thioxo-2,3,4,5-tetrahydro-1H-pyrrolo[3,2-d]pyrimidin-1-yl)methyl) phenyl)piperidine-1-carboxylate NaOH (298 mg, 7.45 mmol) was added to a solution of tert-butyl 3-(2-((3-benzoyl-1-(2-(ethoxycarbonyl)-1H-pyrrol-3-yl)thioureido)methyl)phenyl)piperidine-1-carboxylate (880 mg, 1.49 mmol) in MeOH (20 mL) and stirred under reflux and $N_2$(g) atmosphere for 2 h. The solvent was removed in vacuo and the residue was dissolved in water (50 mL), neutralised with AcOH and extracted with EtOAc (2×75 mL). The combined organic layer was dried ($MgSO_4$) and evaporated in vacuo. The crude product was purified by flash chromatography using 70% EtOAc in isohexane as mobile phase to give (640 mg, 98%) the title compound as a brown gum. MS (ESI): m/z $[M-56+H]^+$ 441.

Intermediate 35

1-2-(Morpholin-2-yl)benzyl)-2-thioxo-1,2,3,5-tetrahydro-4H-pyrrolo[3,2-d]pyrimidin-4-one

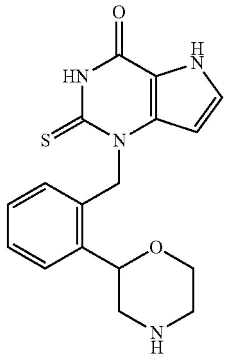 [SMILES: O=c1[nH]c(=S)n(Cc2ccccc2C2CNCCO2)c2cc[nH]c12]

Step A. tert-Butyl 2-(2-bromophenyl)morpholine-4-carboxylate

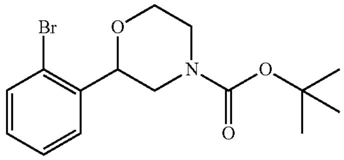 [SMILES: CC(C)(C)OC(=O)N1CCOC(c2ccccc2Br)C1]

TEA (3.44 mL, 24.78 mmol) was added to a solution of 2-(2-bromophenyl)morpholine (5 g, 20.65 mmol) and $Boc_2O$ (4.51 g, 20.65 mmol) in DCM (200 mL) and the reaction was stirred at rt for 3 h. The mixture was washed with brine (50 mL), dried using a phase separator, and evaporated to give (7.94 g) the crude title compound. $^1H$ NMR (500 MHz, $CDCl_3$) δ 1.50 (9H, s), 2.51-2.68 (2H, m), 3.03 (1H, s), 3.75 (1H, td), 4.05 (1H, d), 4.33 (1H, d), 4.72 (1H, d), 7.17 (1H, td), 7.35 (1H, t), 7.52-7.58 (2H, m).

Step B. tert-Butyl 2-(2-formylphenyl)morpholine-4-carboxylate

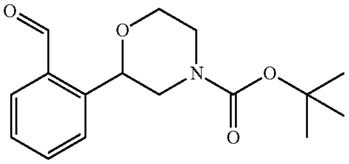 [SMILES: CC(C)(C)OC(=O)N1CCOC(c2ccccc2C=O)C1]

tert-Butyl 2-(2-bromophenyl)morpholine-4-carboxylate (1 g, 2.92 mmol), $Pd(OAc)_2$ (33 mg, 0.15 mmol), CataCXium A (157 mg, 0.44 mmol), and TMEDA (0.328 mL, 2.19 mmol) in toluene (1 mL) were added to a vessel and placed in an autoclave. Synthesis gas ($CO:H_2$, 1:1, 5 bar) was filled into the autoclave. The autoclave was heated in an oil bath at 100° C. for 16 h. The reaction mixture was filtered and concentrated to give (1.04 g) the crude title compound. MS (ESI): m/z $[M+H]^+$ 292.

Step C. tert-Butyl 2-(2-(((2-(ethoxycarbonyl)-1H-pyrrol-3-yl)amino)methyl)phenyl)morpholine-4-carboxylate

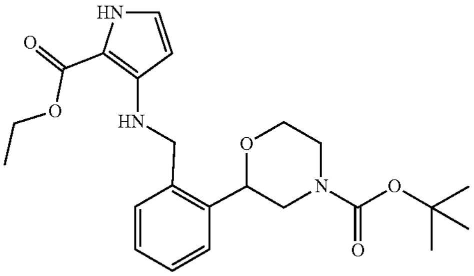 [SMILES: CCOC(=O)c1[nH]ccc1NCc1ccccc1C1CN(C(=O)OC(C)(C)C)CCO1]

A solution of tert-butyl 2-(2-formylphenyl)morpholine-4-carboxylate (0.851 g, 2.92 mmol), ethyl 3-amino-1H-pyrrole-2-carboxylate hydrochloride (0.584 g, 3.07 mmol), TEA (0.405 mL, 2.92 mmol) and AcOH (0.334 mL, 5.84 mmol) in EtOH (15 mL) was heated at 40° C. for 16 h. The heating was removed and $NaBH_4$ (0.25 g, 6.61 mmol) was added in portions and the reaction mixture was stirred at rt for 4 h. The reaction was quenched with water (5 mL) and concentrated in vacuo. The residue was diluted with DCM (100 mL) and the organic layer was washed with brine (25 mL) and concentrated. The compound was purified by preparative HPLC on an XBridge C18 column (10 μm, 250×50 mm ID) using a gradient of 25-70% MeCN in $H_2O$/MeCN/$NH_3$ (95/5/0.2) buffer as mobile phase to give (583 mg, 46%) the title compound. MS (ESI): m/z $[M+H]^+$ 430.

Step D. tert-Butyl 2-(2-((4-oxo-2-thioxo-2,3,4,5-tetrahydro-1H-pyrrolo[3,2-d]pyrimidin-1-yl)methyl)phenyl)morpholine-4-carboxylate

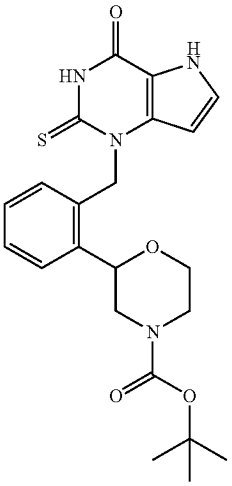 [SMILES: CC(C)(C)OC(=O)N1CCOC(c2ccccc2Cn2c(=S)[nH]c(=O)c3[nH]ccc32)C1]

Benzoyl isothiocyanate (0.22 mL, 1.62 mmol) was added to a solution of tert-butyl 2-(2-((2-(ethoxycarbonyl)-1H-pyrrol-3-ylamino)methyl)phenyl)morpholine-4-carboxylate (580 mg, 1.35 mmol) in MeCN (13 mL) and the reaction was stirred at rt for 16 h. The reaction was concentrated and the residue was dissolved in EtOH (26 mL) and refluxed with 1 M NaOH (4.05 mL, 4.05 mmol) for 3 h. The reaction was quenched with 1 M HCl (4 mL) and concentrated. The crude product was purified by preparative HPLC on a XBridge C18 column (10 μm 250×50 ID mm) using a gradient of 15-55% MeCN in $H_2O$/MeCN/$NH_3$ (95/5/0.2) to give (291 mg, 49%) the title compund. MS (ESI): m/z $[M+H]^+$ 443.

Step E. 1-(2-(Morpholin-2-yl)benzyl)-2-thioxo-1,2,3,5-tetrahydro-4H-pyrrolo[3,2-d]pyrimidin-4-one tert-Butyl 2-(2-((4-oxo-2-thioxo-2,3,4,5-tetrahydro-1H-pyrrolo[3,2-d]pyrimidin-1-yl)methyl)phenyl)morpholine-4-carboxylate (291 mg, 0.66 mmol) was refluxed in HCl (1.25 M in MeOH) (10 mL, 12.50 mmol) for 1 h and then concentrated to give (300 mg) the crude title compound. MS (ESI): m/z $[M-56+H]^+$ 441.

Intermediate 36 tert-Butyl 4-(2-((4-oxo-2-thioxo-2,3,4,5-tetrahydro-1H-pyrrolo[3,2-d]pyrimidin-1-yl)methyl)phenyl)piperidine-1-carboxylate

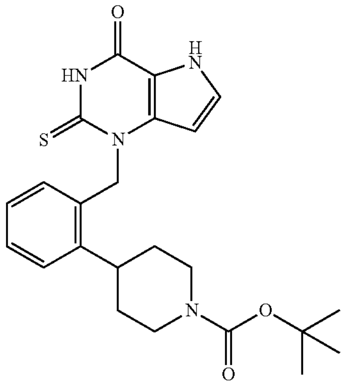 [SMILES: CC(C)(C)OC(=O)N1CCC(c2ccccc2Cn2c(=S)[nH]c(=O)c3[nH]ccc32)CC1]

Step A. tert-Butyl 4-(2-(methoxy(methyl)carbamoyl)phenyl)piperidine-1-carboxylate

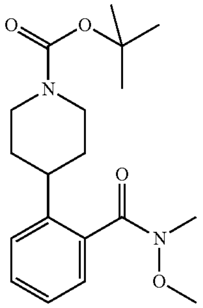 [SMILES: CON(C)C(=O)c1ccccc1C1CCN(C(=O)OC(C)(C)C)CC1]

DIPEA (3.2 ml, 18.37 mmol) was added to a slurry of 2-(1-(tert-butoxycarbonyl)piperidin-4-yl)benzoic acid (4.65 g, 15.23 mmol), N,O-dimethylhydroxylamine hydrochloride (1.636 g, 16.77 mmol) and DMAP (0.186 g, 1.52 mmol) in DCM (19 mL) under $N_2(g)$ atmosphere and stirred for 10 min. EDC hydrochloride (3.643 g, 19.00 mmol) was added and the reaction mixture was stirred at rt for 5 h and 45 min.

The reaction mixture wa diluted with DCM (50 mL) and water (25 mL). The layers were separated and the organic layer was washed with 1 M citric acid solution (25 mL) followed by sat $NaHCO_3$(aq) (25 mL) and brine (25 mL). The organic layer was dried using a phase separator and concentrated. The crude product was purified by flash chromatography using a gradient of 0-50% EtOAc in heptane as mobile phase to give (4.71 g, 89%) the title compound as a colorless foam. MS (ESI): m/z $[M+H]^+$349.

Step B. tert-Butyl 4-(2-formylphenyl)piperidine-1-carboxylate

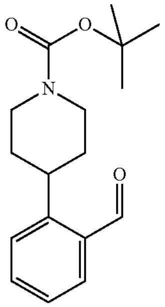 [SMILES: CC(C)(C)OC(=O)N1CCC(c2ccccc2C=O)CC1]

1 M $LiAlH_4$ (16 ml, 16.00 mmol) was added to a solution tert-butyl 4-(2-(methoxy(methyl)carbamoyl)phenyl)piperidine-1-carboxylate (4.58 g, 13.14 mmol) in dry THF (50 mL) at −74° C. under $N_2$(g) atmosphere and stirring. The reaction mixture was stirred for 3.5 h. EtOAc (70 mL) was added dropwise, keeping the temperature below −66° C. during the addition. The reaction mixture was stirred for 30 min and then 1 M citric acid (25 mL) was added and the cooling was removed. 1 M citric acid (115 mL) was added at 0° C. and the reaction mixture was stirred at 0° C. for 10 min, and then the temperature was allowed to reach 10° C. over 30 min. EtOAc (100 mL) was added, and the phases were separated. The aqueous phase was extracted with EtOAc (2×100 mL). The combined organic layer was washed with $NaHCO_3$(aq) (100 mL+50 mL). The combined organic layer was dried ($MgSO_4$), filtered through a phase separator, and the solvent was removed in vacuo. The crude product was purified by flash chromatography using a gradient of 0-30% EtOAc in DCM as mobile phase to give (3.05 g, 80%) the title compound as a colorless oil. MS (ESI): m/z $[M-Boc+H]^+$190.

Step C. tert-Butyl 4-(2-(((2-(ethoxycarbonyl)-1H-pyrrol-3-yl)amino)methyl)phenyl)piperidine-1-carboxylate

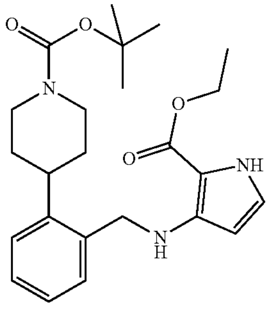 [SMILES: CCOC(=O)c1[nH]ccc1NCc1ccccc1C1CCN(C(=O)OC(C)(C)C)CC1]

A solution of ethyl 3-amino-1H-pyrrole-2-carboxylate hydrochloride (0.682 g, 3.58 mmol) in EtOH (99.5%) (35 mL) was treated with DIPEA (0.748 ml, 4.29 mmol) and then stirred for 10 min before the addition of AcOH (0.491 ml, 8.58 mmol) and $NaBH_3CN$ (0.337 g, 5.37 mmol). A solution of tert-butyl 4-(2-formylphenyl)piperidine-1-carboxylate (1.04 g, 3.58 mmol) in EtOH (99.5%) (53 mL) was then added over 6 min and the reaction was stirred at rt over night. The reaction was quenched with water (65 mL) and evaporated. The crude product was taken up in a mixture of DCM (100 mL) and sat $NaHCO_3$(aq.) (60 mL). The phases were separated and the organic layer was washed with $NaHCO_3$ (2×25 mL) and evaporated to give an orange oil. The crude product was dissolved in DCM (75 mL) and washed with HCl (aq) (2×25 mL, pH 5) and (25 mL, pH 4). The organic layer was dried through a phase separator and evaporated. The crude product was purified by flash chromatography using a gradient of 0-20% EtOAc in heptane as mobile phase to give (0.86 g, 56%) the title compound as a white solid. MS (ESI): m/z $[M+H]^+$ 428.

Step D. tert-Butyl 4-(2-((3-benzoyl-1-(2-(ethoxycarbonyl)-1H-pyrrol-3-yl)thioureido)methyl)phenyl)piperidine-1-carboxylate

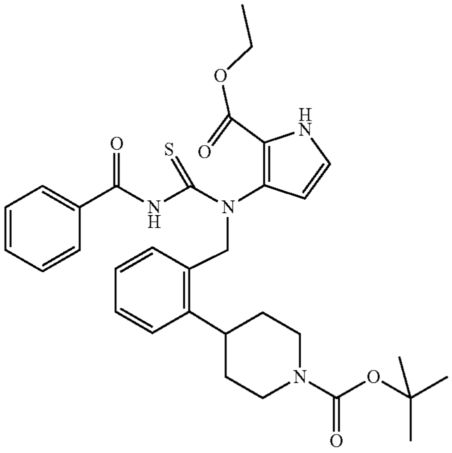 [SMILES: CCOC(=O)c1[nH]ccc1N(Cc1ccccc1C1CCN(C(=O)OC(C)(C)C)CC1)C(=S)NC(=O)c1ccccc1]

Benzoyl isothiocyanate (0.251 mL, 1.87 mmol) was added to a solution of tert-butyl 4-(2-(((2-(ethoxycarbonyl)-1H-pyrrol-3-yl)amino)methyl)phenyl)piperidine-1-carboxylate (973 mg, 1.87 mmol) in DCM (20 mL) was stirred at rt for 17 h. The solvent was removed in vacuo to give (1.56 g) the crude product as an bright yellow foam.

Step E. tert-Butyl 4-(2-((4-oxo-2-thioxo-2,3,4,5-tetrahydro-1H-pyrrolo[3,2-d]pyrimidin-1-yl)methyl)phenyl)piperidine-1-carboxylate $Cs_2CO_3$ (1.35 g, 4.16 mmol) was added to a solution of tert-butyl 4-(2-((3-benzoyl-1-(2-(ethoxycarbonyl)-1H-pyrrol-3-yl)thioureido)methyl)phenyl)piperidine-1-carboxylate (1.55 g, 1.84 mmol) in MeOH (10 mL) and the reaction was stirred at 50° C. under $N_2$(g) atmosphere over night. The solvent was removed in vacuo and the residue was dissolved in water (130 mL), pH was adjusted to ~6 with AcOH and the aqeous layer was extracted with EtOAc (2×100 mL). The combined organic layer was washed with water (50 mL), and concentrated to give (711 mg, 88%) the crude title compound as an off-white solid. MS (ESI): m/z [M-56+H]$^+$ 439.

Intermediate 37 rac-tert-Butyl (2R,4R)-2-(3-((4-oxo-2-thioxo-2,3,4,5-tetrahydro-1H-pyrrolo[3,2-d]pyrimidin-1-yl)methyl)pyridin-2-yl)-4-(trifluoromethyl)piperidine-1-carboxylate

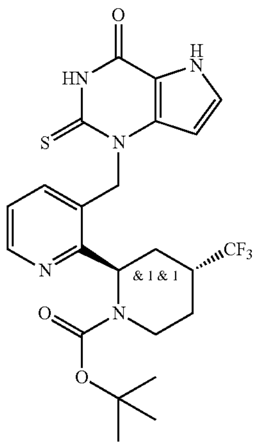 [SMILES: CC(C)(C)OC(=O)N1CC[C@@H](C(F)(F)F)C[C@@H]1c1ncccc1Cn1c(=S)[nH]c(=O)c2[nH]ccc21]

Step A: 1-Benzyl-4-(trifluoromethyl)pyridin-1-ium bromide

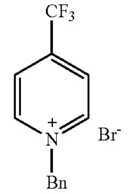

(Bromomethyl)benzene (1000 g, 5.85 mol) and 4-(trifluoromethyl)pyridine (903 g, 6.14 mol) were charged into a 2 L reactor. MeCN (2 L) was added and the solution was stirred at 80° C. for 2 h. Upon reaction completion, the mixture was cooled to 50° C. and toluene (5 L) was added to the vessel. The solution was concentrated under reduced pressure to ~3 volumes. MTBE (5 L) was charged to the reactor at 20° C. and the resulting suspension was filtered under an atmosphere of $N_2$(g) and dried under vacuum to give a white solid in 95% isolated yield. $^1$H NMR (500 MHz, MeOD) δ 6.03 (s, 2H), 7.56-7.45 (m, 3H), 7.61 (dd, 2H), 8.53 (d, 2H), 9.41 (d, 2H); $^{19}$F NMR (471 MHz, MeOD) δ -66.71.

Step B: 2-Bromo-3-(1,3-dioxolan-2-yl)pyridine

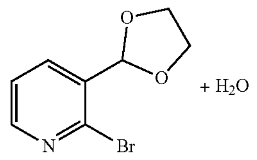 [SMILES: Brc1ncccc1C1OCCO1]

2-Bromonicotinaldehyde (1000 g, 5.36 mol, 1 equiv.) and TsOH hydrate (10.2 g, 53.6 mmol, 0.01 equiv.) were charged into a 10 L reactor. Toluene (10 L) was added, followed by ethane-1,2-diol (0.448 L, 8.04 mol, 1.5 equiv.). The reaction mixture was stirred for 1 h at reflux then concentrated to ~5 volumes at atmospheric pressure. The mixture was washed with 5% $K_2CO_3$ (aq, 5 L), then with water (5 L). The organic layer was concentrated under reduced pressure to ~3 L and the product was precipitated from toluene/heptane (5 L) at 5° C. to give an off-white solid in 82% isolated yield. $^1$H NMR (400 MHz, DMSO) δ 4.43-3.64 (m, 4H), 5.92 (s, 1H), 7.50 (m, 1H), 7.94 (d, 1H), 8.71-8.22 (m, 1H).

Step C: 3-(1,3-Dioxolan-2-yl)-2-(4-(trifluoromethyl)piperidin-2-yl)pyridine

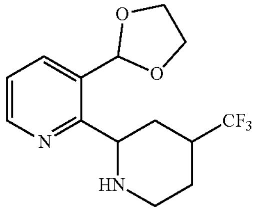 [SMILES: FC(F)(F)C1CCNC(c2ncccc2C2OCCO2)C1]

A solution of BuLi (2.5 M in hexanes) (94 mL, 235 mmol, 1.2 equiv.) was slowly added to a −75° C. solution of 2-bromo-3-(1,3-dioxolan-2-yl)pyridine (from Step A) (45 g, 195.6 mmol, 1 equiv.) in dry THF (450 mL) under an atmosphere of $N_2$(g). 1-Benzyl-4-(trifluoromethyl)pyridin-1-ium bromide (from Step B, 0.12% water w/w) (62.2 g, 195.6 mmol, 1 equiv.) was charged to the reaction mixture under an atmosphere of $N_2$(g), keeping the internal temperature below 60° C. At the end of the addition, the reaction was allowed to reach −20° C. after which the reaction was quenched by addition of MeOH (450 mL) and the reaction mixture was warmed up to 20° C. About 500 mL of the solvent was removed under reduced pressure and the remaining solution (~500 mL) was hydrogenated under 4 bar pressure of $H_2$(g) at 40° C. with palladium (10% on charcoal) (8.33 g, 7.82 mmol, 10 mol %) as catalyst. Upon reaction completion, the reaction mixture was filtered through a celite filter. The crude mixture was used as such in next step (Step D) without further purification (58% over 2 steps by quantitative NMR).

Step D: rac-tert-Butyl (2R,4R)-2-(3-(1,3-dioxolan-2-yl)pyridin-2-yl)-4-(trifluoromethyl)piperidine-1-carboxylate

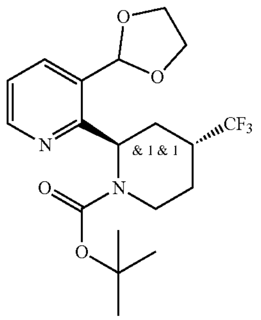 [SMILES: CC(C)(C)OC(=O)N1CC[C@@H](C(F)(F)F)C[C@@H]1c1ncccc1C1OCCO1]

$Boc_2O$ (6.8 kg, 30.7 mol) was added to a crude mixture of 3-(1,3-dioxolan-2-yl)-2-(4-(trifluoromethyl)piperidin-2-yl)pyridine from Step C (6.22 kg, 20.6 mol) in MeOH (250 L) at 15-30° C., and the resulting mixture was stirred at 15-30° C. for 16 h. The mixture was concentrated, EtOAc (70 L) was added and the resulting mixture was washed with aqueous citric acid (5%, 35 L), aqueous $NaHCO_3$ (sat, 35 L) and brine (35 L). The organic layer was concentrated until 20 L remained. Heptane (150 L) was added and the resulting mixture was filtered through silica and washed with heptane/EtOAc (7:1). After evaporation of solvents, the residue was dissolved in heptane (40 L) and the solvent evaporated at 45° C. to half of the original volume. The mixture was stirred at −5° C. for 16 h and the solids where filtered off. The mother liquor was concentrated to yield a brown syrup (1.1 kg) containing ~10% of the desired trans isomer. 29 g of this brown syrup was purified by preparative HPLC at pH11 on a XBridge C8-column, (50×250 mm) (15×2 g injections in DMSO); eluted with a gradient of 70-85% MeCN in $H_2O$/MeCN/$NH_3$ (95/5/0.2) over 20 min. The product was recrystallized from heptane (~12-13 mL) to yield the product as a white solid (2.05 g); MS (ESI) m/z $[M+H]^+$ 403.

Step E. rac-tert-Butyl (2R,4R)-2-(3-formylpyridin-2-yl)-4-(trifluoromethyl)piperidine-1-carboxylate

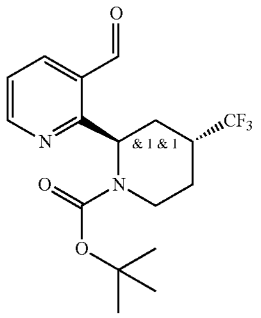 [SMILES: CC(C)(C)OC(=O)N1CC[C@@H](C(F)(F)F)C[C@@H]1c1ncccc1C=O]

A mixture of rac-tert-butyl (2R,4R)-2-(3-(1,3-dioxolan-2-yl)pyridin-2-yl)-4-(trifluoromethyl)piperidine-1-carboxylate (2.04 g, 5.07 mmol) StepD and $NaHSO_4$ (0.304 g, 2.53 mmol) in MeCN (13 mL) and $H_2O$ (5 mL) was stirred at 55° C. for 20 h. The mixture was diluted with DCM and washed with 8% aqueous $NaHCO_3$. The organic layer was concentrated, and the residue purified by straight phase flash chromatography on silica (gradient: 0-50% EtOAc in heptane) to give the title compound (1.68 g, 90%) as a colorless solid; MS (ESI) m/z $[M-H]^-$ 357.

Step F. rac-tert-Butyl (2R,4R)-2-(3-(((2-(ethoxycarbonyl)-1H-pyrrol-3-yl)amino)methyl)pyridin-2-yl)-4-(trifluoromethyl)piperidine-1-carboxylate

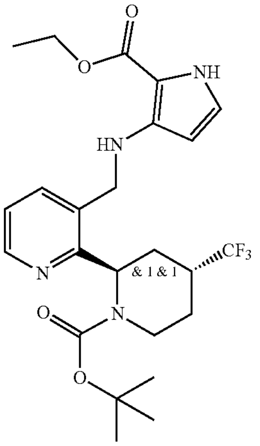 [SMILES: CCOC(=O)c1[nH]ccc1NCc1cccnc1[C@H]1C[C@H](C(F)(F)F)CCN1C(=O)OC(C)(C)C]

Aqueous $K_3PO_3$ (2M, 10 mL) was added to a stirred suspension of ethyl 3-amino-1H-pyrrole-2-carboxylate hydrochloride (1.78 g, 9.32 mmol) in 2-MeTHF (25 mL). The phases were separated, and the organic layer was added to rac-tert-butyl (2R,4R)-2-(3-formylpyridin-2-yl)-4-(trifluoromethyl)piperidine-1-carboxylate (1.67 g, 4.66 mmol) from Step E. Toluene (100 mL) was added and the mixture was concentrated at 75° C. The residue was coevaporated with 2-MeTHF (3×25 mL) and toluene (100 mL) at 75° C. The residue was dissolved in THF (25 mL). AcOH (0.533 mL, 9.32 mmol) and $NaBH(OAc)_3$ (1.58 g, 7.45 mmol) were added, and the resulting mixture was stirred at rt for 20 h. AcOH (0.093 mL, 1.63 mmol) and $NaBH(OAc)_3$ (0.296 g, 1.40 mmol) were added and the stirring was continued for 1 h. The reaction mixture was diluted with DCM and washed with 8% aqueous $NaHCO_3$. The organic layer was concentrated, and the residue was purified by straight phase flash chromatography on silica (gradient: 0-70% EtOAc in heptane) to give the title compound (1.81 g, 78%) as a white solid; MS (ESI) m/z $[M+H]^+$497.

Step G. rac-tert-Butyl (2R,4R)-2-(3-((4-oxo-2-thioxo-2,3,4,5-tetrahydro-1H-pyrrolo[3,2-d]pyrimidin-1-yl)methyl)pyridin-2-yl)-4-(trifluoromethyl)piperidine-1-carboxylate Benzoyl isothiocyanate (0.536 mL, 3.99 mmol) was added to a stirred solution of rac-tert-butyl (2R,4R)-2-(3-(((2-(ethoxycarbonyl)-1H-pyrrol-3-yl)amino)methyl)pyridin-2-yl)-4-(trifluoromethyl)piperidine-1-carboxylate (1.80 g, 3.63 mmol) from Step F in 2-MeTHF (20 mL), and the reaction mixture was heated to 30° C. for 1 h. Aqueous NaOH (50%) (0.229 mL, 4.35 mmol) and MeOH (20 mL) were added and the reaction mixture was heated to 50° C. for 20 h. The reaction mixture was diluted with DCM and washed with 8% aqueous $NaHCO_3$. The organic layer was concentrated, and the resulting white solid triturated with DCM to yield the title compound (1.58 g, 85%) as an off-white solid; MS (ESI) m/z $[M+H]^+$510

Example 1. 1-(2-(Piperidin-2-yl)benzyl)-2-thioxo-1,2,3,5-tetrahydro-4H-pyrrolo[3,2-d]pyrimidin-4-one

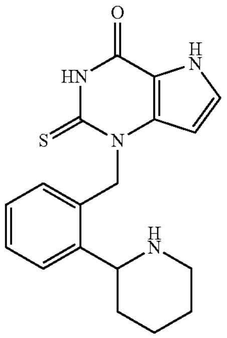 [SMILES: O=c1[nH]c(=S)n(Cc2ccccc2C2CCCCN2)c2cc[nH]c12]

TFA (40 mL) was added to a solution of tert-butyl 2-(2-((4-oxo-2-thioxo-2,3,4,5-tetrahydro-1H-pyrrolo[3,2-d] pyrimidin-1-yl)methyl)phenyl)piperidine-1-carboxylate Intermediate 1 (3.50 g, 7.94 mmol) in DCM (80 mL) and the reaction was stirred at rt for 2 h. The solvent was removed in vacuo and the crude product was purified by preparative HPLC on an XBridge C18 column (10 μm, 250×50 mm ID) using a gradient of MeCN (0-30%) in $H_2O$/MeCN/AcOH (95/5/0.2) buffer system as mobile phase to give (2.13 g, 79%) the title compound as a white solid. $^1H$ NMR (400 MHz, DMSO) δ 1.33-1.64 (4H, m), 1.72-1.9 (2H, m), 2.73 (1H, t), 3.08 (1H, d), 3.86 (1H, d), 5.76 (1H, d), 5.90 (1H, d), 6.00 (1H, d), 6.61 (1H, d), 7.07 (1H, t), 7.20 (1H, t), 7.28 (1H, d), 7.55 (1H, d). HRMS (ESI) m/z $[M+H]^+$ calcd for $C_{18}H_{21}N_4OS$: 341.1430, found: 341.1410.

Example 1a. rel-(R)-1-(2-(piperidin-2-yl)benzyl)-2-thioxo-1,2,3,5-tetrahydro-4H-pyrrolo[3,2-d]pyrimidin-4-one (Isomer 1) & Example 1b. rel-(R)-1-(2-(piperidin-2-yl)benzyl)-2-thioxo-1,2,3,5-tetrahydro-4H-pyrrolo[3,2-d]pyrimidin-4-one (Isomer 2)

Example 1a (Isomer 1)

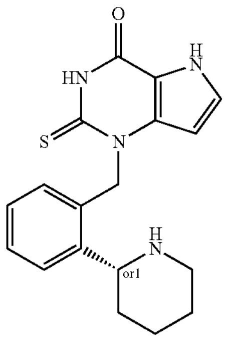

-continued

Example 1b (Isomer 2)

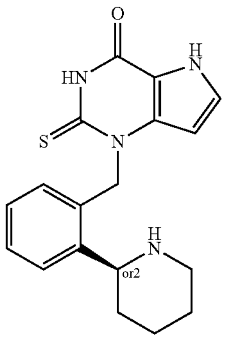

The isomers of 1-(2-(piperidin-2-yl)benzyl)-2-thioxo-1,2,3,5-tetrahydro-4H-pyrrolo[3,2-d]pyrimidin-4-one (1.6 g, 4.7 mmol) Example 1 were separated by preparative chiral SFC on a Chiralpak AD column (5 μm, 250×30 mm ID) using 35% IPA/DEA (100/0.5) in $CO_2$ as mobile phase to give the first eluting compound Isomer 1: rel-(R)-1-(2-(piperidin-2-yl)benzyl)-2-thioxo-1,2,3,5-tetrahydro-4H-pyrrolo[3,2-d]pyrimidin-4-one Example 1a (0.78 g, 49%). $^1H$ NMR (400 MHz, DMSO) δ 1.33-1.65 (4H, m), 1.75-1.9 (2H, m), 2.73 (1H, t), 3.08 (1H, d), 3.86 (1H, d), 5.76 (1H, d), 5.90 (1H, d), 6.00 (1H, d), 6.58-6.64 (1H, m), 7.07 (1H, td), 7.20 (1H, td), 7.28 (1H, d), 7.55 (1H, dd). HRMS (ESI) m/z $[M+H]^+$ calcd for $C_{18}H_{21}N_4OS$: 341.1430, found: 341.1430. % ee=99.9. $[\alpha]_D$=−69.2 (c=0.3, MeOH) and the second eluting compound Isomer 2: rel-(R)-1-(2-(piperidin-2-yl)benzyl)-2-thioxo-1,2,3,5-tetrahydro-4H-pyrrolo[3,2-d] pyrimidin-4-one Example 1b (0.79 g, 49%). $^1H$ NMR (500 MHz, $CD_3OD$) δ 1.79-2.06 (6H, m), 3.31-3.36 (1H, m), 3.54 (1H, d), 4.73-4.8 (1H, m), 5.58 (1H, d), 6.06 (1H, d), 6.17 (1H, d), 7.04 (1H, d), 7.24 (1H, d), 7.31 (1H, t), 7.41 (1H, t), 7.59 (1H, d). HRMS (ESI) m/z $[M+H]^+$ calcd for $C_{18}H_{21}N_4OS$: 341.1430, found: 341.1434. % ee=99.6. $[\alpha]_D$=+71.6 (c=0.5, MeOH).

Example 2a. rel-(R)-1-(4-Chloro-2-(piperidin-2-yl)benzyl)-2-thioxo-1,2,3,5-tetrahydro-4H-pyrrolo[3,2-d]pyrimidin-4-one (Isomer 1) & Example 2b. rel-(R)-1-(4-Chloro-2-(piperidin-2-yl)benzyl)-2-thioxo-1,2,3,5-tetrahydro-4H-pyrrolo[3,2-d]pyrimidin-4-one (Isomer 2)

Example 2a (Isomer 1)

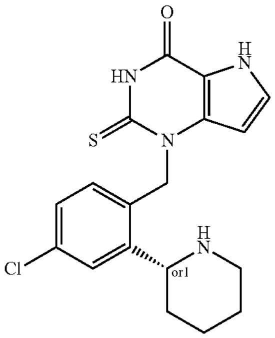

-continued

Example 2b (Isomer 2)

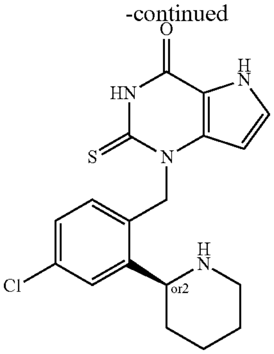

The isomers of 1-(4-chloro-2-(piperidin-2-yl)benzyl)-2-thioxo-1,2,3,5-tetrahydro-4H-pyrrolo[3,2-d]pyrimidin-4-one Intermediate 2 (980 mg, 2.61 mmol) were separated by preparative chiral chromatography on a Chiralpak IA column (20 μm, 250×50 mm ID) using heptane/EtOH/TEA (80/20/0.1) as mobile phase to give the first eluting compound Isomer 1: rel-(R)-1-(4-chloro-2-(piperidin-2-yl)benzyl)-2-thioxo-1,2,3,5-tetrahydro-4H-pyrrolo[3,2-d]pyrimidin-4-one Example 2a (456 mg). % ee=98.9. $[\alpha]_D$=−59 (c=1, MeOH) which was further purified by preparative HPLC on a XBridge C18 column (10 μm 250×50 mm ID) using a gradient of 10-55% MeCN in a $H_2O$/MeCN/$NH_3$ (95/5/0.2) buffer system as mobile phase to give (261 mg, 27%) Example 2a. $^1$H NMR (400 MHz, DMSO) δ 1.27-1.62 (4H, m), 1.73-1.84 (2H, m), 2.71 (1H, t), 3.08 (1H, d), 3.13-3.2 (1H, m), 3.86 (1H, d), 5.68 (1H, d), 5.84 (1H, d), 6.01 (1H, d), 6.62 (1H, d), 7.14 (1H, d), 7.30 (1H, d), 7.58 (1H, s). HRMS (ESI) m/z $[M+H]^+$ calcd for $C_{18}H_{20}ClN_4OS$: 375.1040, found: 375.1058; and the second eluting compound Isomer 2: rel-(R)-1-(4-chloro-2-(piperidin-2-yl)benzyl)-2-thioxo-1,2,3,5-tetrahydro-4H-pyrrolo[3,2-d]pyrimidin-4-one Example 2b (338 mg). % ee=94.8. $[\alpha]_D$=+29 (c=1, MeOH) which was further purified by preparative HPLC on an XBridge C18 column (10 μm, 250×50 mm ID) using a gradient of 10-55% MeCN in a $H_2O$/MeCN/$NH_3$ (95/5/0.2) buffer system as mobile phase to give (80 mg, 8%) Example 2b. $^1$H NMR (400 MHz, DMSO) δ 1.31-1.62 (4H, m), 1.77-1.89 (2H, m), 2.66-2.76 (1H, m), 3.04-3.11 (1H, m), 3.14-3.2 (1H, m), 3.83-3.9 (1H, m), 5.68 (1H, d), 5.84 (1H, d), 6.01 (1H, s), 6.62 (1H, d), 7.14 (1H, d), 7.30 (1H, s), 7.58 (1H, s). HRMS (ESI) m/z $[M+H]^+$ calcd for $C_{18}H_{20}ClN_4OS$: 375.1040, found: 375.1074.

Example 3. 1-(4-Chloro-2-(pyrrolidin-2-yl)benzyl)-2-thioxo-1,2,3,5-tetrahydro-4H-pyrrolo[3,2-d]pyrimidin-4-one

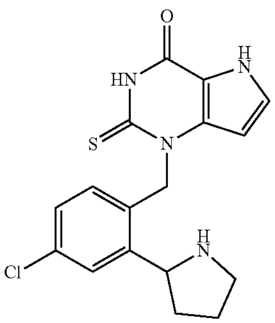 [SMILES: O=c1[nH]c(=S)n(Cc2ccc(Cl)cc2C2CCCN2)c2cc[nH]c12]

tert-Butyl 2-(5-chloro-2-((4-oxo-2-thioxo-2,3,4,5-tetrahydro-1H-pyrrolo[3,2-d]pyrimidin-1-yl)methyl)phenyl)pyrrolidine-1-carboxylate Intermediate 3 (369 mg, 0.8 mmol) was added to a mixture of DCM (5 mL) and TFA (1 mL) and the reaction was stirred at rt for 16 h. The solvents were evaporated and the crude product was purified by preparative HPLC on an XBridge C18 column (10 μm, 250×19 mm ID) using a gradient of 5-55% MeCN in a $H_2O$/MeCN/$NH_3$ (95/5/0.2) buffer system as mobile phase to give (139 mg, 48%) the title compound. $^1$H NMR (500 MHz, DMSO) δ 1.51 (1H, dq), 1.78 (2H, ddd), 2.23-2.33 (1H, m), 2.96 (1H, dt), 3.04 (1H, ddd), 4.43 (1H, t), 5.65 (1H, d), 5.76 (1H, d), 6.00 (1H, d), 6.62 (1H, d), 7.12 (1H, dd), 7.31 (1H, d), 7.66 (1H, d). HRMS (ESI) m/z $[M+H]^+$ calcd for $C_{17}H_{18}ClN_4OS$: 361.0884, found: 361.0878.

Example 3a. rel-(R)-1-(4-Chloro-2-(pyrrolidin-2-yl)benzyl)-2-thioxo-1,2,3,5-tetrahydro-4H-pyrrolo[3,2-d]pyrimidin-4-one (acetate salt) (Isomer 1) & Example 3b. rel-(R)-1-(4-Chloro-2-(pyrrolidin-2-yl)benzyl)-2-thioxo-1,2,3,5-tetrahydro-4H-pyrrolo[3,2-d]pyrimidin-4-one (Isomer 2)

Example 3a (Isomer 1)

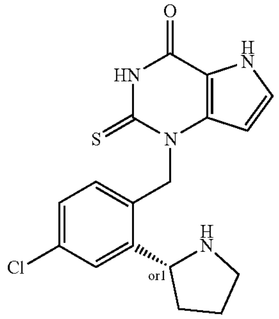

Example 3b (Isomer 2)

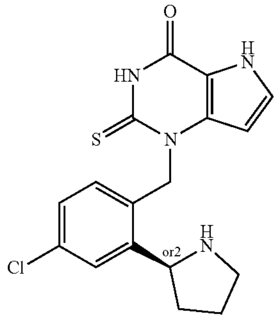

The isomers of 1-(4-chloro-2-(pyrrolidin-2-yl)benzyl)-2-thioxo-1,2,3,5-tetrahydro-4H-pyrrolo[3,2-d]pyrimidin-4-one Example 3 (6.88 mmol from a crude product) were separated by preparative chiral preparative SFC on a (S,S) Whelk-O1 column (5 μm, 250×30 mm ID) using 30% MeOH/DEA (100/0.5) in $CO_2$ as mobile phase to give the first eluting compound Isomer 1: rel-(R)-1-(4-chloro-2-(pyrrolidin-2-yl)benzyl)-2-thioxo-1,2,3,5-tetrahydro-4H-pyrrolo[3,2-d]pyrimidin-4-one Example 3a (1.52 g). % ee=98.3, which was further purified by preparative HPLC on a Kromasil C8 column (10 μm, 250×50 ID mm) using a gradient of 0-30% MeCN in $H_2O$/MeCN/AcOH (95/5/0.2) buffer system as mobile phase to give (688 mg, 30%) Example 3a. $[\alpha]_D$=+39 (c=1, MeOH). $^1$H NMR (400 MHz, DMSO) δ 1.51 (1H, dq), 1.73-1.85 (2H, m), 2.28 (1H, dq), 2.91-3.09 (2H, m), 4.43 (1H, t), 5.64 (1H, d), 5.77 (1H, d), 6.00 (1H, d), 6.62 (1H, d), 7.11 (1H, dd), 7.30 (1H, d), 7.66 (1H, d). HRMS (ESI) m/z [M+H]+ calcd for $C_{17}H_{18}ClN_4OS$: 361.0884, found: 361.0896 and the second eluting compound Isomer 2: rel-(R)-1-(4-chloro-2-(pyrrolidin-2-yl)benzyl)-2-thioxo-1,2,3,5-tetrahydro-4H-pyrrolo[3,2-d]pyrimidin-4-one Example 3b (3.36 g). % ee=99.2, which was further purified by preparative HPLC on a Kromasil C8 column (10 μm, 250×50 mm ID) using a gradient of 0-30% MeCN in $H_2O$/MeCN/AcOH (95/5/0.2) buffer system as mobile phase to give (300 mg, 12%) Example 3b. $[\alpha]_D$=−29 (c=1, MeOH). $^1$H NMR (600 MHz, DMSO) δ 1.94-2.15 (3H, m), 2.34-2.41 (1H, m), 3.36-3.43 (2H, m), 4.81-4.86 (1H, m), 5.73 (1H, d), 5.79 (1H, d), 6.03 (1H, s), 6.71 (1H, d), 7.30 (1H, d), 7.35 (1H, s), 7.72 (1H, s). HRMS (ESI) m/z $[M+H]^+$ calcd for $C_{17}H_{18}ClN_4O$ S: 361.0884, found: 361.0900.

Example 4. 1-(4-Chloro-2-(morpholin-3-yl)benzyl)-2-thioxo-1,2,3,5-tetrahydro-4H-pyrrolo[3,2-d]pyrimidin-4-one

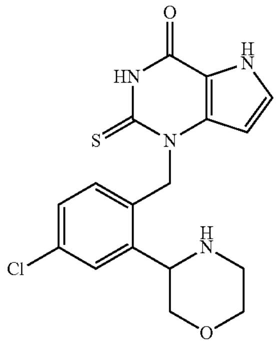 [SMILES: O=c1[nH]c(=S)n(Cc2ccc(Cl)cc2C2COCCN2)c2cc[nH]c12]

tert-Butyl 3-(5-chloro-2-((4-oxo-2-thioxo-2,3,4,5-tetrahydro-1H-pyrrolo[3,2-d]pyrimidin-1-yl)methyl)phenyl) morpholine-4-carboxylate Intermediate 4 (611 mg, 1.28 mmol) was dissolved in DCM (20 mL) and TFA (4 mL) and the mixture was stirred at rt for 16 h. The solvents were evaporated. and the crude product was purified by preparative HPLC on a Kromasil C8 column (10 μm, 250×20 mm ID) using a gradient of 0-25% MeCN in $H_2O$/MeCN/FA (95/5/0.2) buffer as mobile phase to give (437 mg, 81%) the title compound. $^1$H NMR (500 MHz, DMSO) δ 3.27-3.38 (2H, m), 3.63-3.71 (1H, m), 3.74-3.82 (1H, m), 3.98-4.07 (2H, m), 4.67-4.72 (1H, m), 5.74 (1H, d), 5.86 (1H, d), 6.07 (1H, d), 6.72 (1H, d), 7.3-7.38 (2H, m), 7.78 (1H, d), 12.42 (1H, s), 12.53 (1H, s). HRMS (ESI) m/z $[M+H]^+$ calcd for $C_{17}H_{18}ClN_4O_2S$: 377.0834, found: 377.0836.

Example 4a. rel-(R)-1-(4-Chloro-2-(morpholin-3-yl)benzyl)-2-thioxo-1,2,3,5-tetrahydro-4H-pyrrolo[3,2-d]pyrimidin-4-one (Isomer 2) & Example 4b. rel-(R)-1-(4-chloro-2-(morpholin-3-yl)benzyl)-2-thioxo-1,2,3,5-tetrahydro-4H-pyrrolo[3,2-d]pyrimidin-4-one (Isomer 1)

Example 4a (Isomer 2)

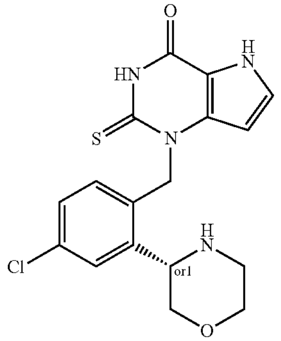

Example 4b (Isomer 1)

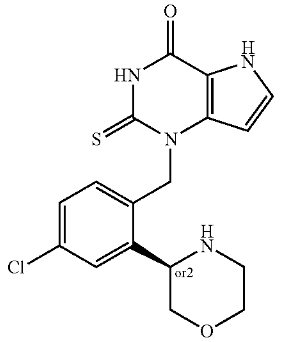

The isomers of 1-(4-chloro-2-(pyrrolidin-2-yl)benzyl)-2-thioxo-1,2,3,5-tetrahydro-4H-1-(4-chloro-2-(morpholin-3-yl)benzyl)-2-thioxo-1,2,3,5-tetrahydro-4H-pyrrolo[3,2-d]pyrimidin-4-one Example 4 (417 mg, 1.11 mmol) were separated by preparative chiral cromatography on a Chiralpak AD column (5 μm, 250×20 mm ID) using heptane/IPA/TEA (40/60/0.1) as mobile phase to give the first eluting compound Isomer 1: rel-(R)-1-(4-chloro-2-(morpholin-3-yl)benzyl)-2-thioxo-1,2,3,5-tetrahydro-4H-pyrrolo[3,2-d]pyrimidin-4-one Example 4b (138 mg, 33%). % ee=98.6. $^1$H NMR (400 MHz, DMSO) δ 2.87-3.02 (2H, m), 3.19-3.3 (1H, m), 3.51 (1H, td), 3.78 (1H, d), 3.88 (1H, dd), 4.14 (1H, dd), 5.69 (1H, d), 5.84 (1H, d), 6.06 (1H, d), 6.62 (1H, d), 7.18 (1H, dd), 7.32 (1H, d), 7.66 (1H, d), 12.37 (1H, s), 12.49 (1H, s). HRMS (ESI) m/z $[M+H]^+$ calcd for $C_{17}H_{18}ClN_4O_2S$: 377.0834, found: 377.0826; and the second eluting compound Isomer 2:rel-(R)-1-(4-chloro-2-(morpholin-3-yl)benzyl)-2-thioxo-1,2,3,5-tetrahydro-4H-pyrrolo[3,2-d]pyrimidin-4-one Example 4a (135 mg, 32%). % ee=97.6. $[\alpha]_D$=+27 (c=0.5, MeOH). $^1$H NMR (400 MHz, DMSO) δ 2.83-3.06 (2H, m), 3.17-3.28 (1H, m), 3.51 (1H, td), 3.78 (1H, d), 3.88 (1H, dd), 4.14 (1H, dd), 5.69 (1H, d), 5.84 (1H, d), 6.06 (1H, d), 6.62 (1H, d), 7.18 (1H, dd), 7.32 (1H, d), 7.66 (1H, d), 12.37 (1H, s), 12.49 (1H, s). HRMS (ESI) m/z $[M+H]^+$ calcd for $C_{17}H_{18}ClN_4O_2S$: 377.0834, found: 377.0810.

Example 5. 3-(4-Chloro-2-(morpholin-3-yl)benzyl)-2-thioxo-1,2,3,7-tetrahydro-6H-purin-6-one

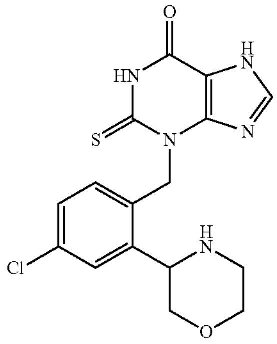 [SMILES: O=c1[nH]c(=S)n(Cc2ccc(Cl)cc2C2COCCN2)c2nc[nH]c12]

A mixture of tert-butyl 3-(5-chloro-2-((6-oxo-2-thioxo-1,2,6,7-tetrahydro-3H-purin-3-yl)methyl)phenyl)morpholine-4-carboxylate Intermediate 5 (116 mg, 0.24 mmol) and HCl (1.25 M in MeOH) (10 mL, 12.50 mmol) was refluxed at 65° C. for 1 h. The solvent was evaporated and the residue was coevaporated with MeOH and with water to give (100 mg, 91%) the title compound as an HCl salt. 1H NMR (500 MHz, $CD_3OD$) δ 3.48 (1H, d), 3.55-3.63 (1H, m), 3.93-4.04 (2H, m), 4.14 (1H, dd), 4.28 (1H, dd), 5.16 (1H, dd), 5.80 (1H, d), 6.06 (1H, d), 7.31-7.37 (2H, m), 7.68 (1H, d), 8.06 (1H, s). HRMS (ESI) m/z $[M+H]^+$ calcd for $C_{16}H_{17}ClN_5O_2S$: 378.0786, found: 378.0796.

Example 6. 1-(2-(Azepan-2-yl)benzyl)-2-thioxo-1,2,3,5-tetrahydro-4H-pyrrolo[3,2-d]pyrimidin-4-one

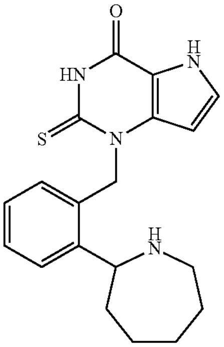 [SMILES: O=c1[nH]c(=S)n(Cc2ccccc2C2CCCCCN2)c2cc[nH]c12]

TFA (2.88 mL, 37.40 mmol) was added to a solution of tert-butyl 2-(2-((4-oxo-2-thioxo-2,3,4,5-tetrahydro-1H-pyrrolo[3,2-d]pyrimidin-1-yl)methyl)phenyl)azepane-1-carboxylate Intermediate 6 (1.7 g, 3.74 mmol) in DCM (100 mL) and the reaction was stirred at rt for 2 h. The solvent was removed in vacuo and the residue was co-evaporated with DCM (3×100 mL). The crude product was purified twice with preparative HPLC on an XBridge C18 column (10 μm 250×50 mm ID) using a gradient of 0-50% MeCN in $H_2O$/MeCN/HOAc (95/5/0.2) buffer system as mobile phase to give (475 mg, 36%) the title compound. $^1H$ NMR (400 MHz, DMSO) δ 1.49-1.76 (6H, m), 1.76-1.86 (1H, m), 1.89-1.99 (1H, m), 2.74-2.87 (1H, m), 2.97-3.1 (1H, m), 3.96-4.06 (1H, m), 5.64-5.92 (2H, m), 5.99-6.05 (1H, m), 6.58-6.65 (1H, m), 7-7.09 (1H, m), 7.15-7.22 (1H, m), 7.26-7.33 (1H, m), 7.47-7.54 (1H, m), 12.17-12.73 (1H, m). HRMS (ESI) m/z $[M+H]^+$ calcd for $C_{19}H_{23}N_4OS$: 355.1586, found: 355.1612.

Example 6a. rel-(R)-1-(2-(Azepan-2-yl)benzyl)-2-thioxo-1,2,3,5-tetrahydro-4H-pyrrolo[3,2-d]pyrimidin-4-one (Isomer 1) & Example 6b. rel-(R)-1-(2-(Azepan-2-yl)benzyl)-2-thioxo-1,2,3,5-tetrahydro-4H-pyrrolo[3,2-d]pyrimidin-4-one (Isomer 2)

Example 6a (Isomer 1)

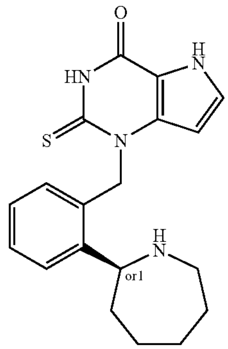

Example 6b (Isomer 2)

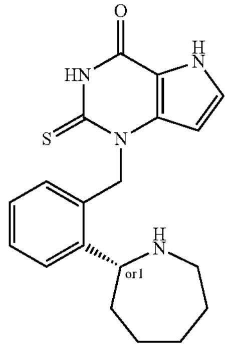

The isomers of 1-(2-(azepan-2-yl)benzyl)-2-thioxo-1,2,3,5-tetrahydro-4H-pyrrolo[3,2-d]pyrimidin-4-one Example 6 (462 mg, 1.3 mmol) were separated by preparative chiral chromatography on a Chiralpak IA column (5 μm, 250×50 mm ID) using heptane/EtOH/TEA (40/60/1) as mobile phase to give the first eluting compound Isomer 1: rel-(R)-1-(2-(azepan-2-yl)benzyl)-2-thioxo-1,2,3,5-tetrahydro-4H-pyrrolo[3,2-d]pyrimidin-4-one Example 6a. % ee=99.2%, which was further purified by preparative HPLC on a Kromasil C8 column (10 μm, 250×50 mm ID) using a gradient of 0-30% MeCN in $H_2O$/MeCN/AcOH (95/5/0.2) buffer system as mobile phase to give (148 mg, 32%) Example 6a. $^1H$ NMR (400 MHz, MeOD) δ 1.63-1.89 (8H, m), 2.91-3 (1H, m), 3.11-3.2 (1H, m), 4.12-4.22 (1H, m), 5.65-5.73 (1H, m), 5.95-6.04 (1H, m), 6.04-6.08 (1H, m), 6.81-6.88 (1H, m), 7.08-7.16 (1H, m), 7.21-7.31 (2H, m), 7.45-7.52 (1H, m). HRMS (ESI) m/z $[M+H]^+$ calcd for $C_{19}H_{23}N_4OS$: 355.1586, found: 355.1596, and the second eluting compound Isomer 2: rel-(R)-1-(2-(azepan-2-yl)benzyl)-2-thioxo-1,2,3,5-tetrahydro-4H-pyrrolo[3,2-d]pyrimidin-4-one Example 6b. % ee=98.9, which was further purified by preparative HPLC on a Kromasil C8 column (10 μm 250×50 mm ID) using a gradient of 0-70% MeCN in $H_2O$/MeCN/AcOH (95/5/0.2) buffer system as mobile phase to give (109 mg, 24%) Example 6b. $^1$H NMR (400 MHz, MeOD) δ 1.63-1.89 (8H, m), 2.91-3 (1H, m), 3.11-3.2 (1H, m), 4.12-4.22 (1H, m), 5.65-5.73 (1H, m), 5.95-6.04 (1H, m), 6.04-6.08 (1H, m), 6.81-6.88 (1H, m), 7.08-7.16 (1H, m), 7.21-7.31 (2H, m), 7.45-7.52 (1H, m). HRMS (ESI) m/z $[M+H]^+$ calcd for $C_{19}H_{23}N_4OS$: 355.1586, found: 355.1592.

Example 7. (R)-3-(2-(Azepan-2-yl)-4-chlorobenzyl)-2-thioxo-1,2,3,7-tetrahydro-6H-purin-6-one

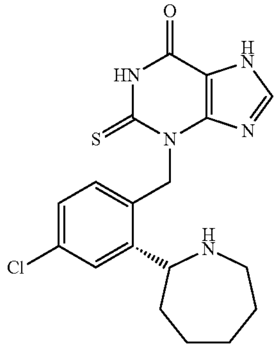

tert-Butyl (R)-2-(5-chloro-2-((6-oxo-2-thioxo-1,2,6,7-tetrahydro-3H-purin-3-yl)methyl)phenyl)azepane-1-carboxylate Intermediate 7 (34 mg, 0.07 mmol) was dissolved in HCl (1.25 M in MeOH) (1 mL, 1.25 mmol) and the mixture was heated at reflux for 1 h. The solvent was evaporated to give (30 mg, 100%) the title compound as an HCl salt. $^1$H NMR (400 MHz, $CD_3OD$) δ 1.77-1.93 (2H, m), 1.99-2.14 (4H, m), 2.21-2.29 (2H, m), 3.42-3.58 (2H, m), 5.01-5.16 (1H, m), 5.71 (1H, d), 6.14 (1H, d), 7.33 (1H, dd), 7.38 (1H, d), 7.61 (1H, d), 8.10 (1H, s). HRMS (ESI) m/z $[M+H]^+$ calcd for $C_{18}H_{21}ClN_5OS$: 390.1150, found: 390.1156.

Example 8. (R)-1-(2-(Morpholin-3-yl)benzyl)-2-thioxo-1,2,3,5-tetrahydro-4H-pyrrolo[3,2-d]pyrimidin-4-one

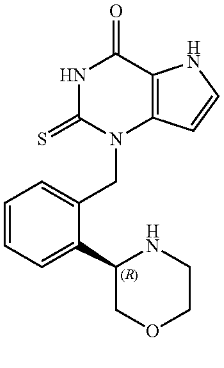

tert-Butyl (R)-3-(2-((4-oxo-2-thioxo-2,3,4,5-tetrahydro-1H-pyrrolo[3,2-d]pyrimidin-1-yl)methyl)phenyl)morpholine-4-carboxylate Intermediate 8 (0.128 g, 0.29 mmol) was dissolved in DCM (5 mL) and TFA (0.9 mL) and the mixture was stirred at rt for 4.5 h. The solvents were evaporated and the crude product was purified by preparative HPLC on a Kromasil C8 column (10 μm, 250×20 mm ID) using a gradient of 0-25% MeCN in $H_2O$/MeCN/AcOH (95/5/0.2) buffer as mobile phase to give (0.045 g, 45%) the title compound as a white solid. $^1$H NMR (400 MHz, DMSO) δ 3.66 (1H, t), 3.72-3.81 (1H, m), 3.96-4.04 (2H, m), 4.57-4.82 (1H, m), 5.82 (2H, dd), 6.03 (1H, d), 6.69 (1H, d), 7.25 (1H, t), 7.28-7.37 (2H, m), 7.65 (1H, d), 12.38 (1H, bs), 12.50 (1H, s). (3 protons are hidden under the solvent peak). HRMS (ESI) m/z $[M+H]^+$ calcd for $C_{17}H_{19}N_4O_2S$: 343.1224, found: 343.1238.

Example 9. 1-(2-(4-Methylpiperazin-2-yl)benzyl)-2-thioxo-1,2,3,5-tetrahydro-4H-pyrrolo[3,2-d]pyrimidin-4-one

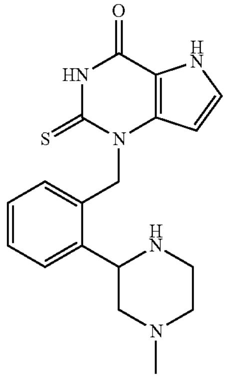 [SMILES: CN1CCNC(c2ccccc2Cn2c(=S)[nH]c(=O)c3[nH]ccc32)C1]

A solution of benzyl 4-methyl-2-(2-((4-oxo-2-thioxo-2,3,4,5-tetrahydro-1H-pyrrolo[3,2-d]pyrimidin-1-yl)methyl)phenyl)piperazine-1-carboxylate Intermediate 9 (0.565 g, 1.15 mmol), phenol (0.205 mL, 2.31 mmol) and 33% HBr in AcOH (1.283 mL) was stirred at rt overnight. The reaction mixture was poured into anhydrous $Et_2O$ and a yellow precipitate formed. The precipitate was collected by filtration, washed with $Et_2O$, and dried under vacum to give (0.483 g) a crude product. The crude product was purified by preparative HPLC on an XBridge C18 column (10 μm, 250×5 0 mm ID) using a gradient of 0-30% MeCN in $H_2O$/MeCN/$NH_3$ (95/5/0.2) buffer as mobile phase to give (0.223 g, 54%) the title compound as a white solid. $^1$H NMR (400 MHz, DMSO) δ 1.90 (1H, d), 1.93-2.02 (1H, m), 2.18 (3H, s), 2.69 (1H, d), 2.78-2.98 (3H, m), 4-4.06 (1H, m), 5.71 (1H, d), 5.89 (1H, d), 6.01 (1H, d), 6.58 (1H, d), 7.08 (1H, t), 7.19 (1H, t), 7.28 (1H, d), 7.56 (1H, d). HRMS (ESI) m/z $[M+H]^+$ calcd for $C_{118}H_{22}N_5OS$: 356.1540, found: 356.1534.

Example 10a. rel-2-Thioxo-1-(2-((2R,4S)-4-(trifluoromethyl)piperidin-2-yl)benzyl)-1,2,3,5-tetrahydro-4H-pyrrolo[3,2-d]pyrimidin-4-one (Isomer 1) & Example 10b. rel-2-Thioxo-1-(2-((2R,4S)-4-(trifluoromethyl)piperidin-2-yl)benzyl)-1,2,3,5-tetrahydro-4H-pyrrolo[3,2-d]pyrimidin-4-one (Isomer 2)

Example 10a (Isomer 1)

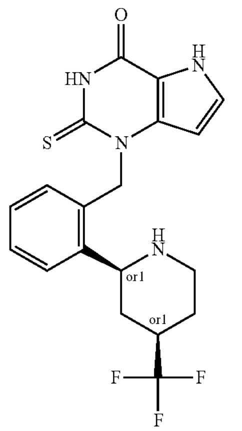

Example 10b (Isomer 2)

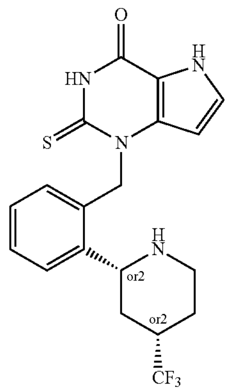

Phenol (451.2 mg, 4.80 mmol) was added to a solution of 2-thioxo-1-(2-(1-tosyl-4-(trifluoromethyl)piperidin-2-yl)benzyl)-1,2,3,5-tetrahydro-4H-pyrrolo[3,2-d]pyrimidin-4-one Intermediate 10 (1.35 g, 2.40 mmol) in 33% HBr in AcOH (20 mL) and the resulting solution was stirred for 3 h at rt and then concentrated under vacuum. The residue was purified by preparative HPLC on a Naminix C18 column (150x19 mm ID) using a gradient of 0-100% MeCN in $H_2O/NH_3$ (0.1%) as mobile phase to give (250 mg, 26%) 2-thioxo-1-(2-(4-(trifluoromethyl)piperidin-2-yl)benzyl)-1,2,3,5-tetrahydro-4H-pyrrolo[3,2-d]pyrimidin-4-one. The isomers of 2-thioxo-1-(2-(4-(trifluoromethyl)piperidin-2-yl)benzyl)-1,2,3,5-tetrahydro-4H-pyrrolo[3,2-d]pyrimidin-4-one were separated by chiral preparative chiral SFC on a Chiralpak AD-H column (5 μm, 250×20 mm ID) using 40% MeOH/DEA (100/0.1) in $CO_2$ as mobile phase to give (92 mg, 9%) the first eluting compound Isomer 1: rel-2-thioxo-1-(2-((2R,4S)-4-(trifluoromethyl)piperidin-2-yl)benzyl)-1,2,3,5-tetrahydro-4H-pyrrolo[3,2-d]pyrimidin-4-one Example 10a. $^1$H NMR (300 MHz, DMSO): δ 1.30-1.54 (2H, m), 1.78-1.82 (1H, m), 1.93-1.97 (1H, m), 2.62-2.66 (1H, m), 2.74-2.81 (1H, m), 3.17-3.20 (1H, m), 3.98-4.01 (1H, m), 5.70-5.75 (1H, d), 5.92-6.02 (2H, m), 6.66-6.68 (2H, d), 7.09-7.30 (3H, m), 7.54-7.56 (1H, d), 12.19-12.50 (1H, m). HRMS (ESI) m/z $[M+H]^+$ calcd for $C_{19}H_{20}F_3N_4OS$: 409.1304, found: 409.1304; and (98 mg, 10%) the second eluting compound Isomer 2:rel-2-thioxo-1-(2-((2R,4S)-4-(trifluoromethyl)piperidin-2-yl)benzyl)-1,2,3,5-tetrahydro-4H-pyrrolo[3,2-d]pyrimidin-4-one Example 10b as an off-white solid. $^1$H NMR (300 MHz, DMSO): δ 1.30-1.54 (2H, m), 1.78-1.82 (1H, m), 1.93-1.97 (1H, m), 2.62-2.66 (1H, m), 2.74-2.81 (1H, m), 3.17-3.20 (1H, m), 3.98-4.01 (1H, m), 5.70-5.75 (1H, d), 5.92-6.02 (2H, m), 6.66-6.68 (2H, d), 7.09-7.30 (3H, m), 7.54-7.56 (1H, d), 12.19-12.50 (1H, m). HRMS (ESI) m/z $[M+H]^+$ calcd for $C_{19}H_{20}F_3N_4OS$: 409.1304, found: 409.1294.

Example 11. 2-Thioxo-1-(2-(5-(trifluoromethyl)piperidin-2-yl)benzyl)-1,2,3,5-tetrahydro-4H-pyrrolo[3,2-d]pyrimidin-4-one

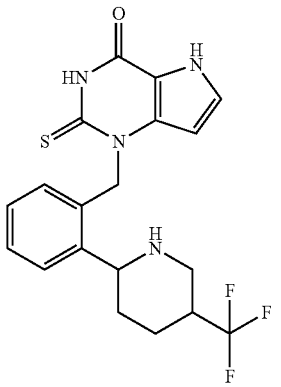 [SMILES: O=c1[nH]c(=S)n(Cc2ccccc2C2CCC(C(F)(F)F)CN2)c2cc[nH]c12]

HCl (1.25 M in MeOH) (5 mL, 6.25 mmol) was added to tert-butyl 2-(2-((4-oxo-2-thioxo-2,3,4,5-tetrahydro-1H-pyrrolo[3,2-d]pyrimidin-1-yl)methyl)phenyl)-5-(trifluoromethyl)piperidine-1-carboxylate Intermediate 11 (113 mg, 0.22 mmol). The mixture was stirred at 50° C. for 1.5 h and then concentrated in vacuo. The crude product was purified by preparative HPLC on a Kromasil C8 column (10 μm, 250×50 mm ID) using a gradient of 10-60% MeCN in $H_2O$/MeCN/AcOH (95/5/0.2) buffer system as mobile phase to give (75 mg, 83%) the title compound. $^1$H NMR (400 MHz, DMSO) δ 1.46-1.7 (2H, m), 1.90 (1H, d), 2.03 (1H, d), 2.35-2.44 (1H, m), 2.74 (1H, t), 3.23 (1H, d), 3.88 (1H, d), 5.75 (1H, d), 5.87 (1H, d), 5.93-6.04 (1H, m), 6.63 (1H, d), 7-7.15 (1H, m), 7.15-7.33 (2H, m), 7.43-7.56 (1H, m), 12.33 (1H, bs), 12.43 (1H, bs). HRMS (ESI) m/z $[M+H]^+$ calcd for $C_{19}H_{20}F_3N_4OS$: 409.1304, found: 409.1304.

Example 12a. rel-(R)-1-(2-(4,4-Difluoropiperidin-2-yl)benzyl)-2-thioxo-1,2,3,5-tetrahydro-4H-pyrrolo[3,2-d]pyrimidin-4-one (Isomer 2) & Example 12b. rel-(R)-1-(2-(4,4-Difluoropiperidin-2-yl)benzyl)-2-thioxo-1,2,3,5-tetrahydro-4H-pyrrolo[3,2-d]pyrimidin-4-one (Isomer 1)

Example 12a (Isomer 2)

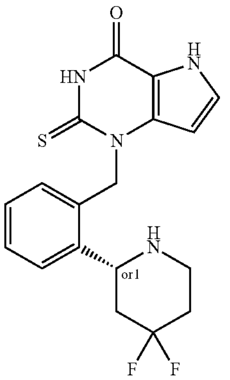

Example 12b (Isomer 1)

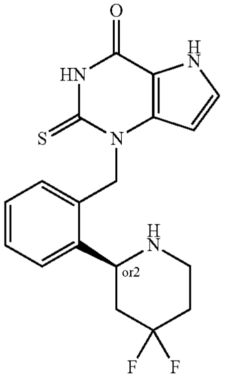

The isomers of 1-(2-(4,4-difluoropiperidin-2-yl)benzyl)-2-thioxo-1,2,3,5-tetrahydro-4H-pyrrolo[3,2-d]pyrimidin-4-one Intermediate 12 (190 mg, 0.5 mmol) were separated by preparative chiral cromatography on a Chiralpak IA column (5 μm, 250×20 mm ID) using hexane/EtOH/TEA (70/30/0.1) as mobile phase to give the first eluting compound Isomer 1: rel-(R)-1-(2-(4,4-difluoropiperidin-2-yl)benzyl)-2-thioxo-1,2,3,5-tetrahydro-4H-pyrrolo[3,2-d]pyrimidin-4-one Example 12b (67 mg, 25%). % ee=100. $^1$H NMR (300 MHz, DMSO) δ 1.84-2.07 (3H, m), 2.29 (1H, m), 2.80-2.83 (1H, m), 3.16-3.32 (1H, m), 4.03-4.07 (1H, m), 5.71-5.89 (2H, m), 6.08 (1H, s), 6.63-6.65 (1H, d), 7.11-7.30 (3H, m), 7.52-7.54 (1H, m), 12.34-12.48 (2H, m). HRMS (ESI) m/z $[M+H]^+$ calcd for $C_{18}H_{19}F_2N_4OS$: 377.1242, found: 377.1250; and the second eluting compound Isomer 2:rel-(R)-1-(2-(4,4-difluoropiperidin-2-yl)benzyl)-2-thioxo-1,2,3,5-tetrahydro-4H-pyrrolo[3,2-d]pyrimidin-4-one Example 12a (59 mg, 31%). % ee=99.6. $^1$H NMR (300 MHz, DMSO) δ 1.84-2.07 (3H, m), 2.30-2.34 (1H, m), 2.8-2.89 (1H, m), 3.17-3.20 (1H, m), 4.05-4.08 (1H, m), 5.71-5.89 (2H, m), 6.08 (1H, s), 6.63-6.66 (1H, d), 7.12-7.30 (3H, m), 7.52-7.55 (1H, m), 12.34-12.46 (2H, m). HRMS (ESI) m/z $[M+H]^+$ calcd for $C_{18}H_{19}F_2N_4OS$: 377.1242, found: 377.1254.

Example 13. rac-2-Thioxo-3-(2-((2R,4S)-4-(trifluoromethyl)piperidin-2-yl)benzyl)-1,2,3,7-tetrahydro-6H-purin-6-one

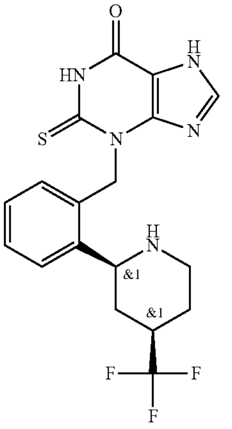 [SMILES: O=c1[nH]c(=S)n(Cc2ccccc2[C@@H]2C[C@H](C(F)(F)F)CCN2)c2nc[nH]c12]

Phenol (94 mg, 1.74 mmol) was added to a solution of 2-thioxo-3-(2-(1-tosyl-4-(trifluoromethyl)piperidin-2-yl)benzyl)-1,2,3,7-tetrahydro-6H-purin-6-one Intermediate 13 (490 mg, 0.87 mmol) in 33% HBr in AcOH (6 mL) and the resulting solution was stirred for 3 h at rt and then concentrated under vacuum. The crude product was purified by preparative HPLC on an XBridge Prep C18 OBD Column (5 um, 150×19 mm ID) using a gradient of 25-95% MeCN in $H_2O/NH_4HCO_3$ (10 mM) buffer system as mobile phase to give (37 mg, 10%) the title compound as a white solid. $^1$H NMR (400 MHz, DMSO) δ 1.46-1.54 (2H, m), 1.85-1.87 (1H, m), 2.08-2.11 (1H, m), 2.70-2.81 (1H, m), 2.85-2.96 (1H, m), 3.04-3.08 (1H, m), 4.17-4.19 (1H, m), 5.78-5.91 (2H, m), 6.81 (1H, d), 7.11-7.15 (1H, m), 7.23-7.26 (1H, m), 7.56-7.58 (1H, m). HRMS (ESI) m/z $[M+H]^+$ calcd for $C_{18}H_{19}F_3N_5OS$: 410.1256, found: 410.1272

Example 13a. 2-Thioxo-3-(2-((2R,4S)-4-(trifluoromethyl)piperidin-2-yl)benzyl)-1,2,3,7-tetrahydro-6H-purin-6-one

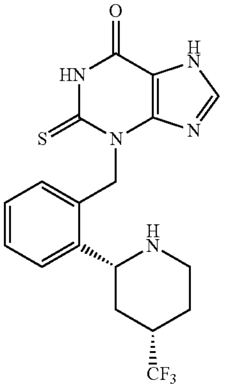 [SMILES: O=c1[nH]c(=S)n(Cc2ccccc2[C@H]2C[C@@H](C(F)(F)F)CCN2)c2nc[nH]c12]

Phenol (284 mg, 3.02 mmol) was added to a solution of 2-thioxo-3-(2-((2R,4S)-1-tosyl-4-(trifluoromethyl)-yl)benzyl)-1,2,3,7-tetrahydro-6H-purin-6-one Intermediate 14 (850 mg, 1.51 mmol) in 33% HBr in AcOH (20 mL). The resulting solution was stirred for 3 h at rt and then concentrated under vacuum. The crude product was washed with $Et_2O$/MeOH (10:1) to give (500 mg, 82%) the title compound as a dihydrobromide salt as a white solid. $^1H$ NMR (400 MHz, DMSO) δ 1.87-1.93 (2H, m), 2.13-2.16 (1H, m), 2.34-2.45 (1H, m), 3.11-3.12 (1H, m), 3.35 (1H, m), 3.43-3.47 (1H, m), 4.94-4.97 (1H, m), 5.78-5.99 (2H, m), 6.95-7.02 (1H, m), 7.30-7.45 (2H, m), 7.70-7.72 (1H, m), 8.18 (1H, s), 8.89 (1H, s), 9.17 (1H, s), 12.72 (1H, s), 13.87 (1H, s). HRMS (ESI) m/z $[M+H]^+$ calcd for $C_{18}H_{19}F_3N5OS$: 410.1256, found: 410.1256

Example 13b. 2-Thioxo-3-(2-((2S,4R)-4-(trifluoromethyl)piperidin-2-yl)benzyl)-1,2,3,7-tetrahydro-6H-purin-6-one

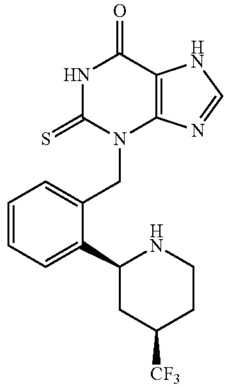 [SMILES: O=c1[nH]c(=S)n(Cc2ccccc2[C@@H]2C[C@H](C(F)(F)F)CCN2)c2nc[nH]c12]

The title compound was prepared in essentially the same way as Example 13a from Intermediate 16 2-thioxo-3-(2-((2S,4R)-1-tosyl-4-(trifluoromethyl)piperidin-2-yl)benzyl)-1,2,3,7-tetrahydro-6H-purin-6-one to give the title compound as a dihydrobromide salt. $^1H$ NMR (300 MHz, DMSO) δ 1.83-1.95 (2H, m), 2.09-2.13 (1H, m), 2.30-2.35 (1H, m), 3.07-3.32 (1H, m), 3.55-3.95 (1H, m), 4.91-4.95 (1H, m), 5.74-5.79 (1H, d), 5.92-5.97 (1H, d), 6.97-6.99 (1H, m), 7.26-7.31 (1H, m), 7.37-7.42 (1H, m). HRMS (ESI) m/z $[M+H]^+$ calcd for $C_{18}H_{19}F_3N_5OS$: 410.1256, found: 410.1242.

Example 14. 3-(2-(4,4-Difluoropiperidin-2-yl)benzyl)-2-thioxo-1,2,3,7-tetrahydro-6H-purin-6-one

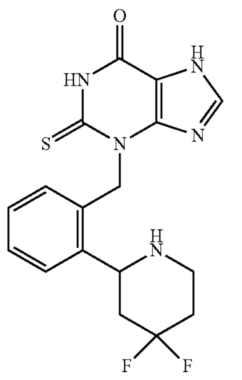 [SMILES: O=c1[nH]c(=S)n(Cc2ccccc2C2CC(F)(F)CCN2)c2nc[nH]c12]

A suspension of benzyl 4,4-difluoro-2-(2-((6-oxo-2-thioxo-1,2,6,7-tetrahydro-3H-purin-3-yl)methyl)phenyl)piperidine-1-carboxylate Intermediate 18 (250 mg, 0.49 mmol) and 40% HBr in AcOH (2 mL, 68.5 mmol) was stirred for 1 h at rt. The reaction mixtuer was diluted with MeOH (2 mL) and concentrated under vacuum. The crude product was purified by preparative TLC using DCM/MeOH (10:1) as mobile phase to give (200 mg, 92%) the title compound as a white solid. $^1H$ NMR (300 MHz, DMSO) δ 1.85-2.05 (3H, m), 2.34 (1H, m), 2.78-2.86 (1H, m), 3.15-3.19 (1H, m), 4.10-4.13 (1H, m), 5.70-5.75 (1H, d), 5.84-5.89 (d, 1H), 6.73-6.75 (1H, d), 7.09-7.14 (1H, t), 7.21-7.26 (1H, t), 7.51-7.54 (1H, d), 8.09 (1H, s), 12.60 (1H, bs), HRMS (ESI) m/z $[M+H]^+$ calcd for $C_{17}H_{18}F_2N_5OS$: 378.1194, found: 378.1216.

Example 15. 3-(2-(5-Fluoropiperidin-2-yl)benzyl)-2-thioxo-1,2,3,7-tetrahydro-6H-purin-6-one

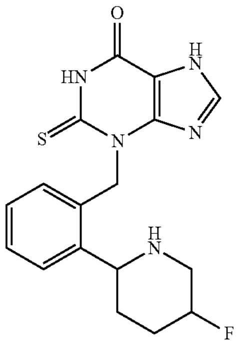 [SMILES: O=c1[nH]c(=S)n(Cc2ccccc2C2CCC(F)CN2)c2nc[nH]c12]

A solution of 3-(2-(5-fluoro-1-(4-methoxybenzyl)piperidin-2-yl)benzyl)-2-thioxo-1,2,3,7-tetrahydro-6H-purin-6-one Intermediate 19 (1.0 g, 2.09 mmol) in TFA (30 mL) was heated to 120° C. for 3 h in a microwave reactor. The solvent was evaporated and the residue was triturated with EtOAc (10 mL) and MeOH (6 mL) to give (380 mg, 51%) the title compound as a light green solid. $^1H$ NMR (300 MHz, DMSO) δ 1.94-2.04 (2H, m), 2.21-2.35 (2H, m), 3.33-3.39 (1H, m), 3.62-3.72 (1H, m), 4.87-5.10 (2H, m), 5.77 (1H, d), 5.97 (1H, d), 6.99 (1H, d), 7.30-7.58 (2H, m), 7.61-7.68 (2H, m), 8.17 (1H, s), 9.00-10.00 (1H, m), 12.72 (1H, s). HRMS (ESI) m/z $[M+H]^+$ calcd for $C_{17}H_{19}FN_5OS$: 360.1288, found: 360.1296.

Example 16. rac-2-Thioxo-1-((2-((2R,4S)-4-(trifluoromethyl)piperidin-2-yl)pyridin-3-yl)methyl)-1,2,3,5-tetrahydro-4H-pyrrolo[3,2-d]pyrimidin-4-one

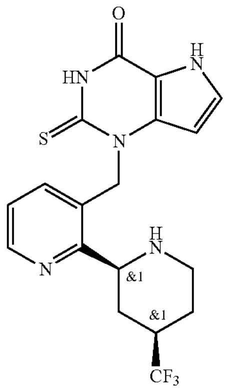 [SMILES: O=c1[nH]c(=S)n(Cc2cccnc2[C@@H]2C[C@H](C(F)(F)F)CCN2)c2cc[nH]c12]

TFA (10 mL) was added to a solution of tert-butyl 2-(3-((4-oxo-2-thioxo-2,3,4,5-tetrahydro-1H-pyrrolo[3,2-d]pyrimidin-1-yl)methyl)pyridin-2-yl)-4-(trifluoromethyl)piperidine-1-carboxylate Intermediate 20 (1.2 g, 2.36 mmol) DCM (10 mL) and the resulting solution was stirred for 2 h at rt and then concentrated under vacuum. The residue was dissolved in MeOH/water (5:1) (10 mL) and $Na_2CO_3$ (625 mg, 5.90 mmol) was added and the mixture was stirred for 0.5 h at rt and then evaporated to dryness. The residue was dissolved in water (10 mL) and extracted with DCM (3×20 mL). The combined organic layer was dried ($Na_2SO_4$) and evaporated to dryness. The residue was triturated with $Et_2O$ (50 mL) and the resulting solid was collected by filtration and dried under vacuum to give (310 mg, 32%) the title compound as an off-white solid. $^1H$ NMR (300 MHz, DMSO) δ 1.32-1.34 (1H, m), 1.70-1.81 (2H, m), 1.97-2.01 (1H, m), 2.63-2.82 (2H, m), 3.17-3.22 (1H, m), 4.14 (1H, d), 5.78-5.90 (2H, m), 6.15 (1H, d), 7.08 (1H, d), 7.11-7.16 (1H, m), 7.29-7.30 (1H, d), 8.41-8.43 (1H, m), 12.45 (2H, s). HRMS (ESI) m/z $[M+H]^+$ calcd for $C_{18}H_{19}F_3N_5OS$: 410.1256, found: 410.1260.

Example 16a. rel-2-Thioxo-1-((2-((2R,4S)-4-(trifluoromethyl)piperidin-2-yl)pyridin-3-yl)methyl)-1,2,3,5-tetrahydro-4H-pyrrolo[3,2-d]pyrimidin-4-one (Isomer 1) & Example 16b. rel-2-Thioxo-1-((2-((2R,4S)-4-(trifluoromethyl)piperidin-2-yl)pyridin-3-yl)methyl)-1,2,3,5-tetrahydro-4H-pyrrolo[3,2-d]pyrimidin-4-one (Isomer 2)

Example 16a (Isomer 1)

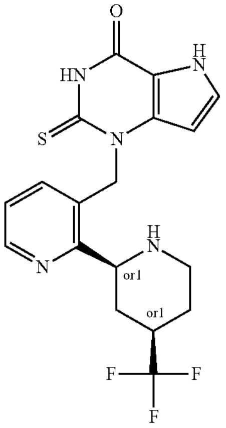

Example 16b (Isomer 2)

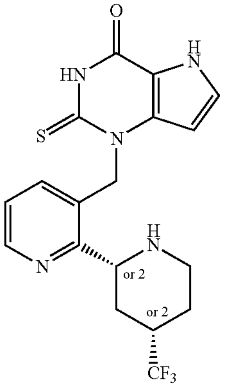

The isomers of rac-2-thioxo-1-((2-((2R,4S)-4-(trifluoromethyl)piperidin-2-yl)pyridin-3-yl)methyl)-1,2,3,5-tetrahydro-4H-pyrrolo[3,2-d]pyrimidin-4-one Example 16 (250 mg, 0.61 mmol) were separated by preparative chiral chromatography on a Chiralpak IA column (5 μm, 250×30 mm ID) using heptane/EtOH/TEA (70/30/0.1) as mobile phase to give the first eluting compound Isomer 1: rel-2-thioxo-1-((2-((2R,4S)-4-(trifluoromethyl)piperidin-2-yl)pyridin-3-yl)methyl)-1,2,3,5-tetrahydro-4H-pyrrolo[3,2-d]pyrimidin-4-one Example 16a (143 mg). % ee=96.9, which was further purified firstly by preparative HPLC on a Kromasil C8 column (10 μm, 250×20 mm ID) using a gradient of 5-45% MeCN in $H_2O$/MeCN/AcOH (95/5/0.2) buffer system as mobile phase, secondly by preparative HPLC on an XBridge C18 column (10 μm, mm 250×19 ID) using a gradient of 10-50% MeCN in $H_2O$/MeCN/$NH_3$ (95/5/0.2) buffer system as mobile phase, and finally by flash chromatography using gradient of (19:1 to 9:1) DCM/MeOH (2 M $NH_3$) as mobile phase to give (46 mg, 18%) the title compound as a solid. Example 16a. $[\alpha]_D$=−63 (c=0.5, MeOH). $^1H$ NMR (400 MHz, MeOD) δ 1.45-1.7 (2H, m), 1.92 (1H, d), 2.04 (1H, dt), 2.66 (1H, dtp), 2.92 (1H, td), 3.31-3.4 (1H, m), 4.32 (1H, dd), 5.61 (1H, d), 5.99-6.18 (2H, m), 7.09-7.34 (3H, m), 8.47 (1H, dd). HRMS (ESI) m/z $[M+H]^+$ calcd for $C_{18}H_{19}F_3N_5OS$: 410.1256, found: 410.1252, and the second eluting compound Isomer 2:rel-2-thioxo-1-((2-((2R,4S)-4-(trifluoromethyl)piperidin-2-yl)pyridin-3-yl)methyl)-1,2,3,5-tetrahydro-4H-pyrrolo[3,2-d]pyrimidin-4-one Example 16b (116 mg). % ee=96.4, which was further purified firstly by preparative HPLC on a Kromasil C8 column (10 μm, 250×20 mm ID) using a gradient of 5-45% MeCN in $H_2O$/MeCN/AcOH (95/5/0.2) buffer system as mobile phase, secondly by preparative HPLC on an XBridge C18 column (10 μm, mm 250×19 ID) using a gradient of 10-50% MeCN in $H_2O$/MeCN/$NH_3$ (95/5/0.2) buffer system as mobile phase and finally by flash chromatography using gradient of (19:1 to 9:1) DCM/MeOH (2 M $NH_3$) to give (34 mg, 14%) the title compound as a solid. Example 16b. $[\alpha]_D$=+58 (c=0.5, MeOH). $^1H$ NMR (600 MHz, MeOD) δ 1.54 (1H, qd), 1.63 (1H, td), 1.89-1.93 (1H, m), 2-2.06 (1H, m), 2.65 (1H, dqq), 2.90 (1H, td), 3.31-3.38 (1H, m), 4.29 (1H, dd), 5.62 (1H, d), 6.08-6.15 (2H, m), 6.84-7.56 (3H, m), 8.47 (1H, dd). HRMS (ESI) m/z $[M+H]^+$ calcd for $C_{18}H_{19}F_3N_5OS$: 410.1256, found: 410.1256.

Example 17a. rel-2-Thioxo-1-(2-((2R,4R)-4-(trifluoromethyl)piperidin-2-yl)benzyl)-1,2,3,5-tetrahydro-4H-pyrrolo[3,2-d]pyrimidin-4-one Example 17a

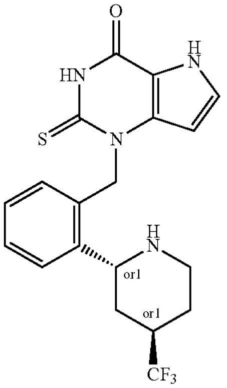

Phenol (83.7 mg, 0.89 mmol) was added to a solution of rel-2-thioxo-1-(2-((2R,4R)-1-tosyl-4-(trifluoromethyl)piperidin-2-yl)benzyl)-1,2,3,5-tetrahydro-4H-pyrrolo[3,2-d]pyrimidin-4-one (250 mg, 0.44 mmol) in HBr in AcOH (3.0 mL) and the resulting solution was stirred for 2 h at rt, and then concentrated under vacuum. The crude product was first washed with $Et_2O$-MeOH (2.0 mL/0.2 mL) and then purified by preparative HPLC on an IntelFlash-1 column usind a gradient of 5-70% MeCN in $H_2O/NH_3$ (0.5%) buffer system as mobile phase to give 60 mg, 33%) the title compound as a white solid. $[\alpha]_D=-27$ (c=0.046 g/100 mL, MeOH). % ee=100. $^1H$ NMR (400 mHz, DMSO) δ 1.78-1.91 (3H, m), 2.08 (1H, m), 2.83-2.91 (3H, m), 4.17-4.20 (1H, m), 5.77 (2H, dd), 6.03 (1H, d), 6.61 (1H, d), 7.11 (1H, t), 7.31-7.23 (2H, m), 7.56 (1H, d), 12.28-12.47 (m, 2H), HRMS (ESI) m/z $[M+H]^+$ calcd for $C_{19}H_{20}F_3N_4OS$: 409.1304, found: 409.1294

Example 17b. rac-2-Thioxo-1-(2-((2R,4R)-4-(trifluoromethyl)piperidin-2-yl)benzyl)-1,2,3,5-tetrahydro-4H-pyrrolo[3,2-d]pyrimidin-4-one Example 17b

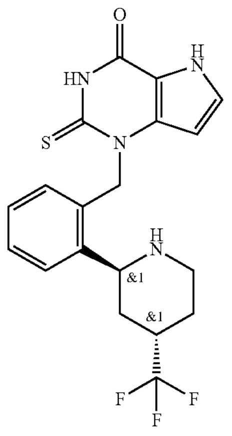

Phenol (670 mg, 7.12 mmol) was added to a solution of rac-2-thioxo-1-(2-((2R,4R)-1-tosyl-4-(trifluoromethyl)piperidin-2-yl)benzyl)-1,2,3,5-tetrahydro-4H-pyrrolo[3,2-d]pyrimidin-4-one Intermediate 27 (2.0 g, 3.55 mmol) in HBr in AcOH (50 mL) and the resulting solution was stirred for 2 h at rt and then concentrated under vacuum. The crude product was purified by preparative HPLC on an X Bridge C18 (5 μM, 150×19 mm ID) using a gradient of 30-70% MeCN in $H_2O$/TFA (0.05%) to give (72 mg, 4%) the title compound as an off-white solid. $^1H$ NMR (400 MHz, DMSO): δ 1.72-1.87 (3H, m), 1.97-2.05 (1H, m), 2.73-2.90 (3H, m), 4.16-4.19 (1H, m), 5.78 (2H, dd), 6.03 (1H, d), 6.65 (1H, d), 7.10 (1H, t), 7.22-7.31 (2H, m), 7.56 (1H, d), 12.0-12.77 (2H, m), HRMS (ESI) m/z $[M+H]^+$ calcd for $C_{19}H_{20}F_3N_4OS$: 409.1304, found: 409.1296.

Example 18a. rel-2-Thioxo-3-(2-((2R,4R)-4-(trifluoromethyl)piperidin-2-yl)benzyl)-1,2,3,7-tetrahydro-6H-purin-6-one (Isomer 1) & Example 18b. rel-2-Thioxo-3-(2-((2R,4R)-4-(trifluoromethyl)piperidin-2-yl)benzyl)-1,2,3,7-tetrahydro-6H-purin-6-one (Isomer 2)

Example 18a (Isomer 1)

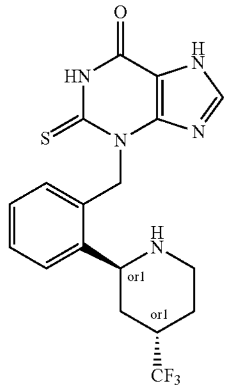

Example 18b (Isomer 2)

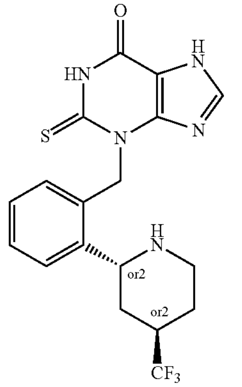

Phenol (227 mg, 2.42 mmol) was added to solution of rac-2-thioxo-3-(2-((2R,4R)-1-tosyl-4-(trifluoromethyl)piperidin-2-yl)benzyl)-1,2,3,7-tetrahydro-6H-purin-6-one Intermediate 28 (680 mg, 1.21 mmol) in HBr-in AcOH (20 mL) and the resulting solution was stirred for 15 h at rt and then concentrated under vacuum. The crude product was purified by preparative HPLC on an X Bridge C18 (5 μM, 150×19 mm ID) using a gradient of 30-70% MeCN in $H_2O$/TFA (0.05%) to give (290 mg, 42%) rac-2-thioxo-3-(2-((2R,4R)-4-(trifluoromethyl)piperidin-2-yl)benzyl)-1,2,3,7-tetrahydro-6H-purin-6-one dihydrobromide as a light yellow solid. The isomers of rac-2-thioxo-3-(2-((2R,4R)-4-(trifluoromethyl)piperidin-2-yl)benzyl)-1,2,3,7-tetrahydro-6H-purin-6-one (300 mg, 0.73 mmol) were separated by preparative chiral HPLC on a Chiralpak AD-H, (250×20 mm ID) using hexane (0.1% DEA)/EtOH (0.1% DEA) (50/50) as mobile phase to give the first eluting compound Isomer 1: rel-2-thioxo-3-(2-((2R,4R)-4-(trifluoromethyl)piperidin-2-yl)benzyl)-1,2,3,7-tetrahydro-6H-purin-6-one Example 18a (65 mg, 22%). $[\alpha]_D=-23$ (c=0.09 g/100 mL, DMSO). % ee=100. $^1H$ NMR (400 MHz, DMSO): δ 1.75-1.91 (3H, m), 2.16-2.19 (1H, m), 2.81-2.99 (3H, m), 4.24-4.27 (1H, m), 5.72-5.78 (2H, m), 6.70 (1H, d), 7.07-7.11 (1H, m), 7.21-7.25 (1H, m), 7.56 (1H, d), 7.83 (1H, s). HRMS (ESI) m/z $[M+H]^+$ calcd for $C_{18}H_{19}F_3N_5OS$: 410.1256, found: 410.1264; and the second eluting compound Isomer 2: rel-2-thioxo-3-(2-((2R,4R)-4-(trifluoromethyl)piperidin-2-yl)benzyl)-1,2,3,7-tetrahydro-6H-purin-6-one Example 18b (75 mg, 25%). $[\alpha]_D$=+19 (c=0.122 g/100 mL, DMSO). % ee=98. $^1H$ NMR (400 MHz, DMSO): δ 1.75-1.91 (3H, m), 2.16-2.19 (1H, m), 2.81-2.99 (3H, m), 4.24-4.27 (1H, m), 5.72-5.78 (2H, m), 6.70 (1H, d), 7.07-7.11 (1H, m), 7.21-7.25 (1H, m), 7.56 (1H, d), 7.83 (1H, s). HRMS (ESI) m/z $[M+H]^+$ calcd for $C_{18}H_{19}F_3N_5OS$: 410.1256, found: 410.1248.

Example 19a rel-1-(2-((2R,4S)-4-(Difluoromethyl) piperidin-2-yl)benzyl)-2-thioxo-1,2,3,5-tetrahydro-4H-pyrrolo[3,2-d]pyrimidin-4-one (Isomer 1) & Example 19b. rel-1-(2-((2R,4S)-4-(difluoromethyl) piperidin-2-yl)benzyl)-2-thioxo-1,2,3,5-tetrahydro-4H-pyrrolo[3,2-d]pyrimidin-4-one (Isomer 2)

Example 19a (Isomer 1)

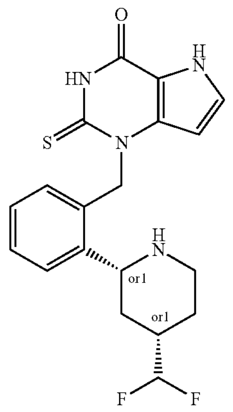

Example 19b (Isomer 2)

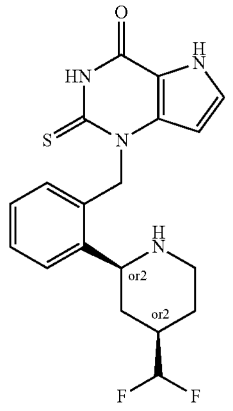

The isomers of rac-1-(2-((2R,4S)-4-(difluoromethyl)piperidin-2-yl)benzyl)-2-thioxo-1,2,3,5-tetrahydro-4H-pyrrolo [3,2-d]pyrimidin-4-one Intermediate 21 (2.5 g, 4.53 mmol) were separated by preparative chiral SFC on a on a Chiralpak AD-H column (5 μm, 250×50 mm ID) using 50% EtOH/DEA (100/0.2) in $CO_2$ as mobile phase to give the first eluting compound Isomer 1: rel-1-(2-((2R,4S)-4-(difluoromethyl)piperidin-2-yl)benzyl)-2-thioxo-1,2,3,5-tetrahydro-4H-pyrrolo[3,2-d]pyrimidin-4-one Example 19a (500 mg, 28%) as an off white solid. % ee=98.4. $[\alpha]_D$=+85 (c=0.104 g/100 mL, MeOH). $^1H$ NMR (300 MHz, $CD_3OD$) 1.45-1.60 (2H, m), 1.84-1.91 (2H, m), 2.18-2.35 (1H, m), 2.93-3.07 (1H, m), 4.22 (1H, d), 5.53-5.95 (1H, m), 6.01-6.1 (2H, m), 6.91 (1H, d), 7.16-7.24 (2H, m), 7.32 (1H, t), 7.50 (1H, d). HRMS (ESI) m/z $[M+H]^+$ calcd for $C_{19}H_{21}F_2N_4OS$: 391.1398, found: 391.1414; and the second eluting compound Isomer 2: rel-1-(2-((2R,4S)-4-(difluoromethyl)piperidin-2-yl)benzyl)-2-thioxo-1,2,3,5-tetrahydro-4H-pyrrolo[3,2-d]pyrimidin-4-one Example 19b (720 mg, 41%). $[\alpha]_D$=−81 (c=0.091 g/100 mL, MeOH). $^1H$ NMR (300 MHz, $CD_3OD$) 1.45-1.60 (2H, m), 1.84-1.91 (2H, m), 2.18-2.35 (1H, m), 2.93-3.07 (1H, m), 4.22 (1H, d), 5.53-5.95 (1H, m), 6.01-6.1 (2H, m), 6.91 (1H, d), 7.16-7.24 (2H, m), 7.32 (1H, t), 7.50 (1H, d). HRMS (ESI) m/z $[M+H]^+$ calcd for C19 H21 F2 N4 O S: 391.1398, found: 391.1396.

Example 20. 1-((2-(Piperidin-2-yl)pyridin-3-yl) methyl)-2-thioxo-1,2,3,5-tetrahydro-4H-pyrrolo[3,2-d]pyrimidin-4-one

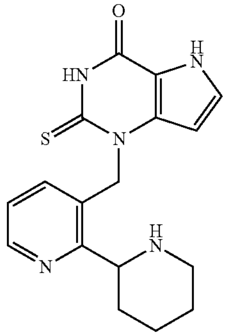 [SMILES: O=c1[nH]c(=S)n(Cc2cccnc2C2CCCCN2)c2cc[nH]c12]

TFA (2 mL, 25.96 mmol) was added to tert-butyl 2-(3-((4-oxo-2-thioxo-2,3,4,5-tetrahydro-1H-pyrrolo[3,2-d]pyrimidin-1-yl)methyl)pyridin-2-yl)piperidine-1-carboxylate Intermediate 22 (80 mg, 0.18 mmol) in DCM (10 mL) at 20° C. The resulting solution was stirred at 20° C. for 15 h. The solvent was removed under reduced pressure. The crude product was purified by preparative HPLC on an YMC-Actus Triart C18 ExRS column (5 μm, 150×30 mm ID) using a gradient of 10-32% MeCN in 10 mM $NH_4HCO_3$/$NH_3$ (0.1%) buffer system as mobile phase to give (45 mg, 73%) the title compound as a white solid. $^1H$ NMR (300 MHz, DMSO): δ 1.36 (1H, d), 1.49-1.69 (3H, m), 1.77-1.99 (2H, m), 2.70 (1H, t), 3.08 (1H, d), 4.01 (1H, d), 5.72-5.96 (2H, m), 6.06 (1H, d), 7.03 (1H, dd), 7.12 (1H, dd), 7.28 (1H, d), 8.38 (1H, dd). HRMS (ESI) m/z $[M+H]^+$ calcd for $C_{17}H_{20}N_5OS$: 342.1384, found: 342.1378.

Example 21. rac-2-Thioxo-1-((3-((2R,4S)-4-(trifluoromethyl)piperidin-2-yl)pyridin-2-yl)methyl)-1,2,3,5-tetrahydro-4H-pyrrolo[3,2-d]pyrimidin-4-one

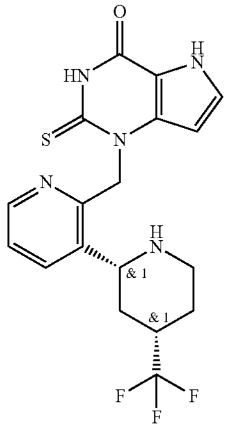 [SMILES: O=c1[nH]c(=S)n(Cc2ncccc2[C@H]2C[C@@H](C(F)(F)F)CCN2)c2cc[nH]c12]

Benzoyl isothiocyanate (332 mg, 2.04 mmol) was added to (9H-fluoren-9-yl)methyl 2-(2-(((2-(ethoxycarbonyl)-1H-pyrrol-3-yl)amino)methyl)pyridin-3-yl)-4-(trifluoromethyl)piperidine-1-carboxylate Intermediate 23 (600 mg, 0.97 mmol) in DCM (20 mL) at rt and the resulting solution was stirred for 15 h. The solvent was removed under reduced pressure, and the residue was dissolved in MeOH (20 mL). $Cs_2CO_3$ (632 mg, 1.94 mmol) was added into the solution and the resulting solution was stirred at 65° C. for 5 h. The solvent was removed under reduced pressure. The crude product was purified by preparative HPLC on an YMC-Actus Triart C18 ExRS column (5 μm, 150×30 mm ID) using a gradient of 26-41% MeCN in 10 mM $NH_4HCO_3$/$NH_3$ (0.1%) buffer system as mobile phase to give (45 mg, 11%) the title compound as a white solid. $^1$H NMR (300 MHz, DMSO) δ 1.17-1.40 (2H, m), 1.69 (1H, d), 1.89 (1H, d), 2.54 (1H, d), 2.66 (1H, t), 3.06 (1H, d), 3.92 (1H, d), 5.66 (1H, d), 5.88 (1H, d), 5.93 (1H, d), 7.13 (2H, dd), 7.78 (1H, dd), 8.12 (1H, dd), 12.17 (2H, s). HRMS (ESI) m/z $[M+H]^+$ calcd for $C_{18}H_{19}F_3N_5OS$: 410.1256, found: 410.1258.

Example 22. rac-2-Thioxo-1-((3-((2R,4S)-4-(trifluoromethyl)piperidin-2-yl)pyridin-4-yl)methyl)-1,2,3,5-tetrahydro-4H-pyrrolo[3,2-d]pyrimidin-4-one

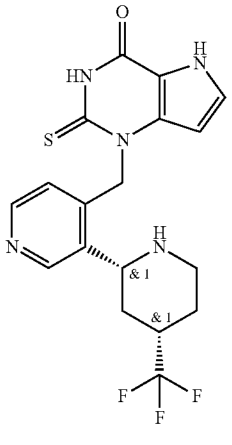 [SMILES: O=c1[nH]c(=S)n(Cc2ccncc2[C@H]2C[C@@H](C(F)(F)F)CCN2)c2cc[nH]c12]

Benzoyl isothiocyanate (185 mg, 1.13 mmol) was added to (9H-fluoren-9-yl)methyl 2-(4-(((2-(ethoxycarbonyl)-1H-pyrrol-3-yl)amino)methyl)pyridin-3-yl)-4-(trifluoromethyl)piperidine-1-carboxylate Intermediate 24 (500 mg, 0.81 mmol) in DCM (5 mL) at rt and the resulting solution was stirred for 15 h. The solvent was removed under reduced pressure, and the residue was dissolved in MeOH (5 mL). $Cs_2CO_3$ (527 mg, 1.62 mmol) was added and the resulting solution was stirred at 65° C. for 5 h. The solvent was removed under reduced pressure and the residue was first purified by preparative TLC (MeOH:DCM, 1:20), to afford crude product. The crude product was finally purified by preparative HPLC on an XBridge Shield RP18 OBD column (5 μm, 150×30 mm ID) using a gradient of 10-47% MeCN in 10 mM $NH_4HCO_3$/$NH_3$ (0.1%) buffer system as mobile phase to give (70 mg, 21%) the title compound as a white solid. $^1$H NMR (300 MHz, DMSO) δ 1.25-1.50 (2H, m), 1.70 (1H, d), 1.84-1.99 (1H, m), 2.62 (2H, dd), 3.08 (1H, d), 3.91 (1H, d), 5.60-5.87 (2H, m), 5.95 (1H, d), 6.52 (1H, d), 7.21 (1H, d), 8.18 (1H, d), 8.55 (1H, s), 12.35 (2H, s). HRMS (ESI) m/z $[M+H]^+$ calcd for $C_{18}H_{19}F_3N_5OS$: 410.1256, found: 410.1260.

Example 23. 1-((1,2,3,4-Tetrahydroisoquinolin-8-yl)methyl)-2-thioxo-1,2,3,5-tetrahydro-4H-pyrrolo[3,2-d]pyrimidin-4-one

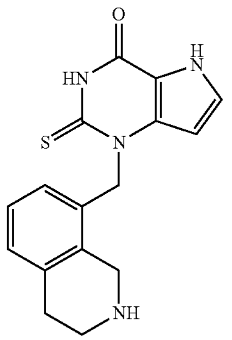 [SMILES: O=c1[nH]c(=S)n(Cc2cccc3c2CNCC3)c2cc[nH]c12]

Methanesulfonic acid (0.021 mL, 0.32 mmol) was added to a suspension of 1-(isoquinolin-8-ylmethyl)-2-thioxo-1,2,3,5-tetrahydro-4H-pyrrolo[3,2-d]pyrimidin-4-one Intermediate 29 (0.100 g, 0.32 mmol) in DCM (10 mL) and the reaction was stirred for 2 h at rt. AcOH (0.187 mL, 3.24 mmol) and MeOH (1 mL) were added, and the suspension was treated with $NaBH_3CN$ (0.102 g, 1.62 mmol) and stirred overnight. The reaction was filtered and the solid was washed with a little DCM/MeOH, collected, dried and purified using standard procedures. $^1$H NMR (500 MHz, DMSO) δ 3.04 (2H, t), 3.40 (2H, t), 4.43 (2H, s), 5.57 (2H, s), 6.03 (1H, t), 6.53-6.59 (1H, m), 7.1-7.18 (2H, m), 7.33 (1H, t), 9.17 (1H, s), 12.39 (1H, s), 12.51 (1H, s). HRMS (ESI) m/z $[M+H]^+$ calcd for $C_{16}H_{17}N_4OS$: 313.1118, found: 313.1122.

Example 24. 1-(4-(1-Aminocyclobutyl)benzyl)-2-thioxo-1,2,3,5-tetrahydro-4H-pyrrolo[3,2-d]pyrimidin-4-one

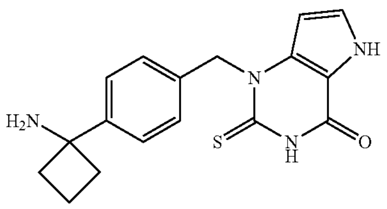 [SMILES: NC1(c2ccc(Cn3c(=S)[nH]c(=O)c4[nH]ccc43)cc2)CCC1]

A suspension of tert-butyl (1-(4-((4-oxo-2-thioxo-2,3,4,5-tetrahydro-1H-pyrrolo[3,2-d]pyrimidin-1-yl)methyl)phenyl)cyclobutyl)carbamate Intermediate 30 (300 mg, 0.70 mmol) in concentrated HCl (20 mL) was stirred for 3 h at rt and then concentrated under vacuum. The residue was triturated with DCM to provide (200 mg, 78%) the title compound as an HCl salt as a white solid. $^1$H NMR (300 MHz, DMSO) δ 1.23-1.25 (1H, m), 1.70-1.82 (1H, m), 2.08-2.22 (4H, m), 5.73-5.74 (2H, m), 6.15-6.16 (1H, m), 7.31-7.40 (3H, m), 7.48-7.51 (2H, m), 8.68-8.72 (2H, br). HRMS (ESI) m/z $[M+H]^+$ calcd for $C_{17}H_{19}N_4OS$: 325.1118, found: 325.1148.

Example 25. 1-(Isoindolin-5-ylmethyl)-2-thioxo-1,2,3,5-tetrahydro-4H-pyrrolo[3,2-d]pyrimidin-4-one

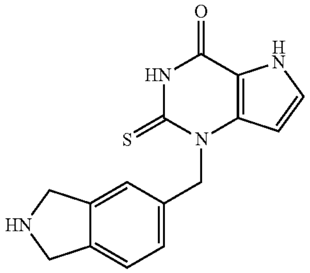 [SMILES: O=c1[nH]c(=S)n(Cc2ccc3c(c2)CNC3)c2cc[nH]c12]

tert-Butyl 5-((4-oxo-2-thioxo-2,3,4,5-tetrahydro-1H-pyrrolo[3,2-d]pyrimidin-1-yl)methyl)isoindoline-2-carboxylate Intermediate 31 (500 mg, 1.25 mmol) was dissolved in DCM/TFA (4/1) (20 mL) and the mixture was stirred at rt for 3 h and then concentrated under vacuum. The residue was triturated with DCM and the resulting solid was collected by filtration and dried under vacuum to give (380 mg, 74%) the title compound as a TFA salt. $^1$H NMR (400 MHz, DMSO) δ 4.45 (4H, s), 5.66 (1H, s), 6.09 (1H, d), 7.27-7.41 (4H, m). HRMS (ESI) m/z $[M+H]^+$ calcd for $C_{15}H_{15}N_4OS$: 299.0960, found: 299.0976

Example 26. 1-(Isoindolin-4-ylmethyl)-2-thioxo-1,2,3,5-tetrahydro-4H-pyrrolo[3,2-d]pyrimidin-4-one

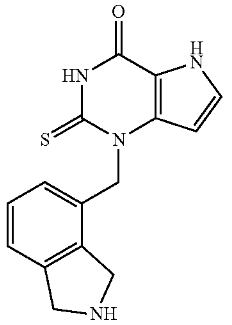 [SMILES: O=c1[nH]c(=S)n(Cc2cccc3c2CNC3)c2cc[nH]c12]

Concentrated HCl (2 mL, 54.8 mmol) was added to a suspension of tert-butyl 4-((4-oxo-2-thioxo-2,3,4,5-tetrahydro-1H-pyrrolo[3,2-d]pyrimidin-1-yl)methyl)isoindoline-2-carboxylate Intermediate 32 (300 mg, 0.75 mmol) in DCM (2 mL) and MeOH (2 mL) and the resulting solution was stirred for 8 h at rt and then concentrated under vacuum. The residue was triturated with MeOH (20 mL). The resulting solids were collected by filtration and dried in an oven under reduced pressure to provide (200 mg, 79%) the title compound as an HCl salt as a white solid. $^1$H NMR (300 MHz, DMSO) δ 4.53-4.60 (4H, m), 5.69 (2H, s), 6.09 (1H, t), 6.89-6.92 (1H, m), 7.26-7.35 (3H, m), 9.79 (2H, m), 12.41 (1H, s), 12.52 (1H, s). HRMS (ESI) m/z $[M+H]^+$ calcd for $C_{15}H_{15}N_4OS$: 299.0960, found: 299.0986.

Example 27. 1-(3-(1-Aminocyclobutyl)benzyl)-2-thioxo-1,2,3,5-tetrahydro-4H-pyrrolo[3,2-d]pyrimidin-4-one

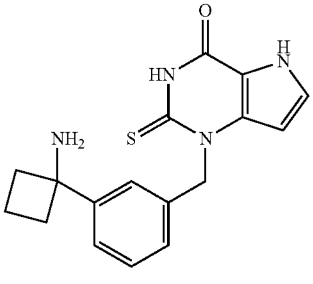 [SMILES: NC1(c2cccc(Cn3c(=S)[nH]c(=O)c4[nH]ccc43)c2)CCC1]

A suspension of tert-butyl (1-(3-((4-oxo-2-thioxo-2,3,4,5-tetrahydro-1H-pyrrolo[3,2-d]pyrimidin-1-yl)methyl)phenyl)cyclobutyl)carbamate Intermediate 33 (300 mg, 0.70 mmol) in concentrated HCl (20 mL) and dioxane (20 mL) was stirred for 3 h at rt and then concentrated under vacuum. The residue was triturated with DCM (30 mL) to provide (200 mg, 79%) the title compound as an HCl salt as a white solid. $^1$H NMR (300 MHz, DMSO) δ 1.52-1.76 (1H, m), 1.90-1.99 (1H, m), 2.00-2.05 (2H, m), 2.11-2.15 (2H, m), 5.72 (2H, s), 6.16-6.17 (1H, m), 7.15-7.17 (1H, m), 7.28-7.37 (3H, m), 7.56 (1H, s), 8.29 (1H, s). HRMS (ESI) m/z $[M+H]^+$ calcd for $C_{17}H_{19}N_4OS$: 327.1274, found: 327.1298.

Example 28. 1-(2-(Piperidin-3-yl)benzyl)-2-thioxo-1,2,3,5-tetrahydro-4H-pyrrolo[3,2-d]pyrimidin-4-one

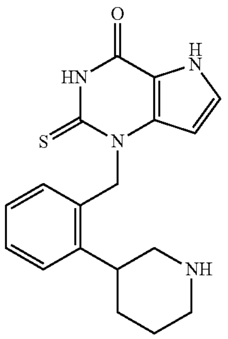 [SMILES: O=c1[nH]c(=S)n(Cc2ccccc2C2CCCNC2)c2cc[nH]c12]

TFA (2 mL) was added to a solution of tert-butyl 3-(2-((4-oxo-2-thioxo-2,3,4,5-tetrahydro-1H-pyrrolo[3,2-d]pyrimidin-1-yl)methyl)phenyl)piperidine-1-carboxylate Intermediate 34 (620 mg, 1.41 mmol) in DCM (10 mL) and the reaction was stirred at rt for 1 h. The solvent was removed in vacuo and the residue was dissolved in MeOH (10 mL) and loaded onto a 10 g SCX cartridge. The impurities were washed through with MeOH (100 mL) and discarded. The product was eluted with 1 M $NH_3$ in MeOH (100 mL) and evaporated in vacuo. The residue was stirred under reflux in IPA (10 mL) overnight then cooled to rt and the solid was filtered off to give an off-white solid. The solid was suspended in MeCN (5 mL) and stirred under reflux for 4 h. The suspension was cooled to rt and the solid filtered to give (223 mg, 46%) the title compound as an off white solid. $^1H$ NMR (400 MHz, DMSO) δ 1.50-1.77 (3H, m), 1.93 (1H, d), 2.49-2.60 (2H, m), 2.97 (2H, t), 3.08 (1H, d), 5.75 (2H, q), 5.98 (1H, d), 6.58 (1H, d), 7.04 (1H, td), 7.20 (1H, t), 7.31 (2H, t). HRMS (ESI) m/z $[M+H]^+$ $C_{18}H_{21}N_4OS$: 341.1430, found: 341.1432.

Example 29. rel-(R)-1-(2-(Morpholin-2-yl)benzyl)-2-thioxo-1,2,3,5-tetrahydro-4H-pyrrolo[3,2-d]pyrimidin-4-one (Isomer 1)

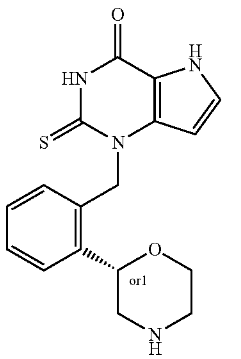

(Isomer 1)

The isomers of 1-(2-(morpholin-2-yl)benzyl)-2-thioxo-1,2,3,5-tetrahydro-4H-pyrrolo[3,2-d]pyrimidin-4-one Intermediate 35 were separated by preparative chiral chromatography on a on a Chiralpak AD-H column (5 μm, 250×20 mm ID) using heptane/EtOH/TEA (30/70/0.1) as mobile phase to give the first eluting compound Isomer 1: rel-(R)-1-(2-(morpholin-2-yl)benzyl)-2-thioxo-1,2,3,5-tetrahydro-4H-pyrrolo[3,2-d]pyrimidin-4-one Example 29 (12 mg). % ee=99.9. $^1H$ NMR (500 MHz, $CD_3OD$) δ 3.06-3.13 (3H, m), 3.95 (1H, dt), 4.14 (1H, d), 5.78 (1H, d), 5.92 (1H, d), 6.08 (1H, d), 6.75 (1H, d), 7.22 (1H, t), 7.31-7.38 (2H, m), 7.51 (1H, d). (2 protons overlaps with the solvent peaks). HRMS (ESI) m/z $[M+H]^+$ calcd for $C_{17}H_{19}N_4O_2S$: 341.1066, found: 341.1068.

Example 30. 1-(2-(Piperidin-4-yl)benzyl)-2-thioxo-1,2,3,5-tetrahydro-4H-pyrrolo[3,2-d]pyrimidin-4-one

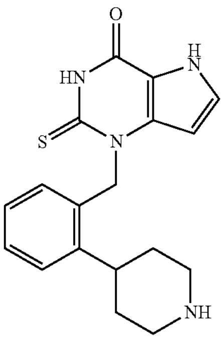 [SMILES: O=c1[nH]c(=S)n(Cc2ccccc2C2CCNCC2)c2cc[nH]c12]

TFA (1.6 mL) was added to a solution of tert-butyl 4-(2-((4-oxo-2-thioxo-2,3,4,5-tetrahydro-1H-pyrrolo[3,2-d]pyrimidin-1-yl)methyl)phenyl)piperidine-1-carboxylate Intermediate 36 (705 mg, 1.60 mmol) in DCM (17 mL) and stirred at rt for 2 h. The reaction mixture was concentrated in vacuo and co-evaporated with MeCN to give the crude product (760 mg) as a white solid. A solution of the crude product in water/MeCN (~30 mL, warmed to 50° C.) was filtered through a syringe filter to remove solid particles. The solution was concentrated on a rotavapor to remove some MeCN and when it started to get turbit the vacuum was removed and heating (50° C.) continued until everything was in solution again. The bottle was removed from the rotavapor and titrated with 1 M NaOH (aq) The product precipitated and was filtered off and washed a couple of times with cold water. The solid was slurried in MeCN and co-evaporated twice and dried in vacuo to give (487 mg, 89%) the title compound as a white solid. $^1H$ NMR (400 MHz, DMSO) δ 1.49-1.63 (2H, m), 1.72 (2H, d), 2.66 (2H, t), 2.95 (1H, t), 3.04 (2H, d), 5.75 (2H, s), 5.95 (1H, d), 6.62 (1H, d), 7.04 (1H, t), 7.21 (1H, t), 7.27-7.33 (2H, m). HRMS (ESI) m/z $[M+H]^+$ calcd for $C_{18}H_{21}N_4OS$: 341.1430, found: 341.1410

Example 31. rac-2-Thioxo-1-((2-((2R,4R)-4-(trifluoromethyl)piperidin-2-yl)pyridin-3-yl)methyl)-1,2,3,5-tetrahydro-4H-pyrrolo[3,2-d]pyrimidin-4-one

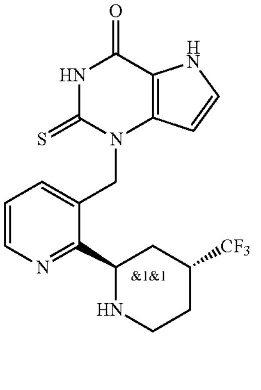 [SMILES: O=c1[nH]c(=S)n(Cc2cccnc2[C@H]2C[C@H](C(F)(F)F)CCN2)c2cc[nH]c12]

TFA (6 mL) was added to a stirred slurry of rac-tert-butyl (2R,4R)-2-(3-((4-oxo-2-thioxo-2,3,4,5-tetrahydro-1H-pyrrolo[3,2-d]pyrimidin-1-yl)methyl)pyridin-2-yl)-4-(trifluoromethyl)piperidine-1-carboxylate Intermediate 37 (1.58 g, 3.09 mmol) in DCM (20 mL), and the mixture was stirred at rt for 2 h. The mixture was concentrated. DCM and 8% aqueous $NaHCO_3$ were added and the phases separated. The organic layer was concentrated to yield the title compound (1.22 g, 96%) as an off white-solid; MS (ESI) m/z $[M+H]^+$ 410.

Example 31a. rel-2-Thioxo-1-((2-((2R,4R)-4-(trifluoromethyl)piperidin-2-yl)pyridin-3-yl)methyl)-1,2,3,5-tetrahydro-4H-pyrrolo[3,2-d]pyrimidin-4-one (Isomer 1) & Example 31b. rel-2-Thioxo-1-((2-((2R,4R)-4-(trifluoromethyl)piperidin-2-yl)pyridin-3-yl)methyl)-1,2,3,5-tetrahydro-4H-pyrrolo[3,2-d]pyrimidin-4-one (Isomer 2)

Example 31a (Isomer 1)

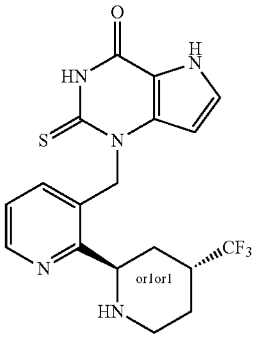

Example 31b (Isomer 2)

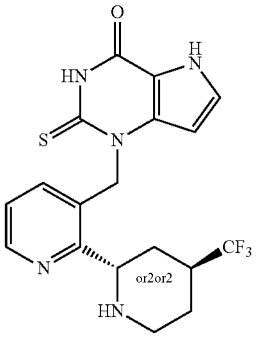

The enantiomers of rel-2-thioxo-1-((2-((2R,4R)-4-(trifluoromethyl)piperidin-2-yl)pyridin-3-yl)methyl)-1,2,3,5-tetrahydro-4H-pyrrolo[3,2-d]pyrimidin-4-one Example 31 (1.22 g, 2.98 mmol) were separated by chiral SFC on a YMC SZ (imob C2)-column (30×250 mm) using 20% MeOH/DEA (100/20 mM) in $CO_2$, at 130 bar as mobile phase to yield the first eluting compound Isomer 1 rel-2-thioxo-1-((2-((2R,4R)-4-(trifluoromethyl)piperidin-2-yl)pyridin-3-yl)methyl)-1,2,3,5-tetrahydro-4H-pyrrolo[3,2-d]pyrimidin-4-one Example 31a (0.535 g 44%) as an off-white solid; MS (ESI) m/z $[M+H]^+$ 410; $^1H$ NMR (500 MHz, DMSO-$d_6$) δ 1.46 (1H, q), 1.66-1.81 (2H, m), 2.28-2.44 (2H, m), 2.59 (1H, q), 2.85 (1H, d), 4.58 (1H, s), 5.79 (1H, d), 5.97-6.08 (2H, m), 7.07 (1H, d), 7.16 (1H, dd), 7.28 (1H, d), 8.40 (1H, dd); $[a]_D^{22}$: +11.5 (c 1.0, MeOH); and the second eluted compound Isomer 2 rel-2-thioxo-1-((2-((2R,4R)-4-(trifluoromethyl)piperidin-2-yl)pyridin-3-yl)methyl)-1,2,3,5-tetrahydro-4H-pyrrolo[3,2-d]pyrimidin-4-one Example 31b (0.440 g 36%) as an off-white solid; HRMS (ESI) m/z $[M+H]^+$; calcd for $C_{18}H_{19}F_3N_5OS$: 410.1262, found: 410.1266; $^1H$ NMR (500 MHz, DMSO-$d_6$) δ 1.46 (1H, q), 1.74 (2H, ddd), 2.29-2.44 (2H, m), 2.66 (1H, q), 2.85 (1H, d), 4.58 (1H, s), 5.79 (1H, d), 5.92-6.11 (2H, m), 7.07 (1H, d), 7.16 (1H, dd), 7.28 (1H, d), 8.40 (1H, dd); $[\alpha]_D^{22}$: −12.1 (c 1.0, MeOH).

Example 32. Assessment of MPO and TPO Activity (IC50)

The experiments were performed in phosphate-buffered saline (PBS), pH7.4. A 10 mM luminol (A4695, Sigma Aldrich, St Louis, MO, USA) stock was prepared in distilled water and further diluted in PBS to a final concentration of 100 μM. $H_2O_2$ was prepared as 1 mM stock in PBS, yielding a final concentration of 50 μM after addition into the assay. The compounds were serially diluted in DMSO in a separate plate as a 100× stock solution, and MPO (purified from HL60 cells) and TPO (produced in insect cells, RSR Ltd, Cardiff, UK), were diluted to yield a final concentration of approximately 14 and 150 ng/mL, generating 5600 and 9300 light counts per seconds (LCPS) upon incubation with luminol.

The experiment was run by pipetting 2 μL 100× stock solution of the compound and 200 μL diluted enzyme in PBS into wells in a 96-well Optiplate (6005290, Perkin Elmer/Thermo Fischer, Waltham, MS, USA), followed by addition of 10 μL $H_2O_2$ containing PBS. Chemiluminescence measurement (Perkin Elmer Wallac Microbeta Trilux 1450-029 (12-detector), Turkuu, Finland) was started directly and recorded after 2, 10 and 15 minutes. Chemiluminescence recorded after 15 minutes was used to calculate the $IC_{50}$ values.

The $IC_{50}$ values (MPO and TPO) for the Example compounds are set forth in Table 1 herein below.

TABLE 1

| Example Number | MPO IC50 (μM) | TPO IC50 (μM) |
|---|---|---|
| 1a | 0.0121 | 1.01 |
| 1b | 0.0021 | 0.85 |
| 2a | 0.0122 | 1.04 |
| 2b | 0.0036 | 0.55 |
| 3a | 0.0030 | 0.55 |
| 3b | 0.0275 | 0.70 |
| 4a | 0.0187 | 0.37 |
| 4b | 0.1267 | 0.81 |
| 5 | 0.1944 | 1.68 |
| 6a | 0.0196 | 0.42 |
| 6b | 0.0028 | 0.30 |
| 7 | 0.0071 | 0.61 |
| 8 | 0.0670 | 0.93 |
| 9 | 0.0101 | 1.27 |
| 10a | 0.0060 | 1.20 |
| 10b | 0.0015 | 0.43 |
| 11 | 0.0130 | 0.54 |
| 12a | 0.0270 | 0.67 |
| 12b | 0.0027 | 0.32 |
| 13a | 0.0160 | 1.05 |
| 13b | 0.0023 | 0.43 |
| 14 | 0.0072 | 0.54 |
| 15 | 0.0160 | 0.54 |
| 16a | 0.0314 | 1.61 |
| 16b | 0.0039 | 0.78 |
| 17a | 0.0165 | 0.76 |
| 17b | 0.0034 | 0.63 |

TABLE 1-continued

| Example Number | MPO IC50 (μM) | TPO IC50 (μM) |
|---|---|---|
| 18a | 0.0563 | 0.73 |
| 18b | 0.0027 | 0.41 |
| 19a | 0.0119 | 1.76 |
| 19b | 0.0013 | 0.57 |
| 20 | 0.0460 | 2.76 |
| 21 | 0.0057 | 0.54 |
| 22 | 0.0115 | 0.95 |
| 23 | 0.0100 | 0.38 |
| 24 | 0.0120 | 0.56 |
| 25 | 0.1030 | 0.57 |
| 26 | 0.0130 | 0.84 |
| 27 | 0.0050 | 0.67 |
| 28 | 0.0030 | 0.68 |
| 29 | 0.0150 | 0.54 |
| 30 | 0.0290 | 0.59 |
| 31a | 0.030 | 1.7 |
| 31b | 0.048 | 2.9 |

All references cited herein, including patents, patent applications, papers, text books, and the like, and the references cited therein, to the extent that they are not already, are hereby incorporated herein by reference in their entirety for all purposes.

1. Davies, M. J. & Hawkins, C. L. The Role of Myeloperoxidase in Biomolecule Modification, Chronic Inflammation, and Disease. *Antioxid Redox Signal* 32, 957-981 (2020).
2. Stamp, L. K., et al. Myeloperoxidase and oxidation of uric acid in gout: implications for the clinical consequences of hyperuricaemia. *Rheumatology* (*Oxford*) 53, 1958-1965 (2014).
3. Hampton, M. B., Kettle, A. J. & Winterbourn, C. C. Inside the neutrophil phagosome: oxidants, myeloperoxidase, and bacterial killing. *Blood* 92, 3007-3017 (1998).
4. Kolaczkowska, E. & Kubes, P. Neutrophil recruitment and function in health and inflammation. *Nat Rev Immunol* 13, 159-175 (2013).
5. Nauseef, W. M. Biosynthesis of human myeloperoxidase. *Arch Biochem Biophys* 642, 1-9 (2018).
6. Hawkins, C. L. & Davies, M. J. Role of myeloperoxidase and oxidant formation in the extracellular environment in inflammation-induced tissue damage. *Free Radic Biol Med* 172, 633-651 (2021).
7. Piedrafita, F. J., et al. An Alu element in the myeloperoxidase promoter contains a composite SP1-thyroid hormone-retinoic acid response element. *J Biol Chem* 271, 14412-14420 (1996).
8. Van Schooten, F. J., et al. Myeloperoxidase (MPO)—463G-→A reduces MPO activity and DNA adduct levels in bronchoalveolar lavages of smokers. *Cancer epidemiology, biomarkers & prevention: a publication of the American Association for Cancer Research, cosponsored by the American Society of Preventive Oncology* 13, 828-833 (2004).
9. Mäkelä, R., et al. Myeloperoxidase gene variation and coronary flow reserve in young healthy men. *Journal of biomedical science* 11, 59-64 (2004).
10. Rudolph, V., et al. A myeloperoxidase promoter polymorphism is independently associated with mortality in patients with impaired left ventricular function. *Free Radic Biol Med* 47, 1584-1590 (2009).
11. Tang, N., Wang, Y. & Mei, Q. Myeloperoxidase G-463A polymorphism and susceptibility to coronary artery disease: a meta-analysis. *Gene* 523, 152-157 (2013).
12. Asselbergs, F. W., Reynolds, W. F., Cohen-Tervaert, J. W., Jessurun, G. A. & Tio, R. A. Myeloperoxidase polymorphism related to cardiovascular events in coronary artery disease. *The American journal of medicine* 116, 429-430 (2004).
13. do Carmo, R. F., et al. Myeloperoxidase gene polymorphism predicts fibrosis severity in women with hepatitis C. *Human immunology* 75, 766-770 (2014).
14. Nahon, P., et al. A variant in myeloperoxidase promoter hastens the emergence of hepatocellular carcinoma in patients with HCV-related cirrhosis. *Journal of hepatology* 56, 426-432 (2012).
15. Nahon, P., et al. Myeloperoxidase and superoxide dismutase 2 polymorphisms comodulate the risk of hepatocellular carcinoma and death in alcoholic cirrhosis. *Hepatology* (*Baltimore, Md.*) 50, 1484-1493 (2009).
16. Ali, M., et al. Myeloperoxidase Inhibition Improves Ventricular Function and Remodeling After Experimental Myocardial Infarction. *JACC. Basic to translational science* 1, 633-643 (2016).
17. Rashid, I., et al. Myeloperoxidase is a potential molecular imaging and therapeutic target for the identification and stabilization of high-risk atherosclerotic plaque. *Eur Heart J* 39, 3301-3310 (2018).
18. Klinke, A., et al. Myeloperoxidase aggravates pulmonary arterial hypertension by activation of vascular Rho-kinase. *JCI insight* 3(2018).
19. Antonelou, M., et al. Therapeutic Myeloperoxidase Inhibition Attenuates Neutrophil Activation, ANCA-Mediated Endothelial Damage, and Crescentic GN. *Journal of the American Society of Nephrology: JASN* 31, 350-364 (2020).
20. Dickerhof, N., et al. Myeloperoxidase inhibition decreases morbidity and oxidative stress in mice with cystic fibrosis-like lung inflammation. *Free Radic Biol Med* 152, 91-99 (2020).
21. Koop, A. C., et al. Therapeutic Targeting of Myeloperoxidase Attenuates NASH in Mice. *Hepatology communications* 4, 1441-1458 (2020).
22. Piek, A., et al. Pharmacological myeloperoxidase (MPO) inhibition in an obese/hypertensive mouse model attenuates obesity and liver damage, but not cardiac remodeling. *Scientific Reports* 9, 18765 (2019).
23. Cheng, D., et al. Inhibition of MPO (Myeloperoxidase) Attenuates Endothelial Dysfunction in Mouse Models of Vascular Inflammation and Atherosclerosis. *Arteriosclerosis, thrombosis, and vascular biology* 39, 1448-1457 (2019).
24. Chai, W., et al. Inhibiting myeloperoxidase prevents onset and reverses established high-fat diet-induced microvascular insulin resistance. *American journal of physiology. Endocrinology and metabolism* 317, E1063-e1069 (2019).
25. Ramachandra, C. J. A., et al. Inhibiting cardiac myeloperoxidase alleviates the relaxation defect in hypertrophic cardiomyocytes. *Cardiovascular research* (2021).
26. Björnsdottir, H., et al. Neutrophil NET formation is regulated from the inside by myeloperoxidase-processed reactive oxygen species. *Free Radic Biol Med* 89, 1024-1035 (2015).
27. Lau, D., et al. Myeloperoxidase mediates neutrophil activation by association with CD11b/CD18 integrins. *Proc Natl Acad Sci USA* 102, 431-436 (2005).
28. Ra, H. J. & Parks, W. C. Control of matrix metalloproteinase catalytic activity. *Matrix biology: journal of the International Society for Matrix Biology* 26, 587-596 (2007).

29. Mollenhauer, M., et al. Myeloperoxidase Mediates Postischemic Arrhythmogenic Ventricular Remodeling. Circulation research 121, 56-70 (2017). 30. DeNichilo, M. O., et al. Peroxidase enzymes regulate collagen extracellular matrix biosynthesis. *Am J Pathol* 185, 1372-1384 (2015).

31. Eiserich, J. P., et al. Myeloperoxidase, a leukocyte-derived vascular NO oxidase. *Science* 296, 2391-2394 (2002).

32. Baldus, S., et al. Endothelial transcytosis of myeloperoxidase confers specificity to vascular ECM proteins as targets of tyrosine nitration. *The Journal of clinical investigation* 108, 1759-1770 (2001).

33. Ekerot, P., et al. Systems pharmacology modeling of drug-induced modulation of thyroid hormones in dogs and translation to human. *Pharmaceutical research* 30, 1513-1524 (2013).

The invention claimed is:

1. A Compound of formula (I)

(I)

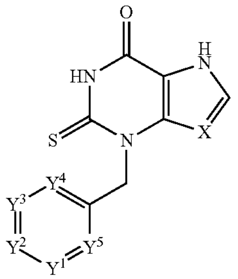

wherein

X=CH or N $Y^1$=$CZ^1$ or N, $Y^2$=$CZ^2$ or N, $Y^3$=$CZ^3$ or N, $Y^4$=$CZ^4$ or N, and $Y^5$=$CZ^5$ or N $Z^1$, $Z^2$, $Z^3$, $Z^4$, and $Z^5$, are, if present, independently, H, halo, $CF_3$, Q or T, provided that no more than one of $Y^1$, $Y^2$, $Y^3$, $Y^4$, or $Y^5$ is N, at least two of $Y^1$, $Y^2$, $Y^3$, $Y^4$, or $Y^5$ are CH, no more than one of $Z^1$, $Z^2$, $Z^3$, $Z^4$, and $Z^5$ is halo or $CF_3$, and one, and only one, of $Z^1$, $Z^2$, $Z^3$, $Z^4$, and $Z^5$ is Q or T, Q is

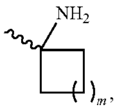

wherein m is 0, 1, 2, or 3,

T is

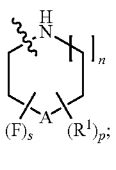

p is 0 or 1, s is 0, 1 or 2, n is 1 or 2,

A is $CH_2$, $CF_2$, CHF, $CHR^2$, $CFR^2$, $NR^3$, or O, wherein;

$R^1$ and $R^2$, if present, are independently $CH_2F$, $CHF_2$, or $CF_3$ $R^3$, if present, is independently H or $CH_3$, or any stereoisomer thereof or pharmaceutically acceptable salt thereof.

2. The compound of claim 1, having the structure:

(III)

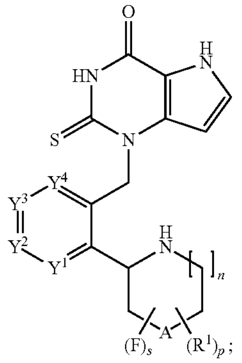

or any stereoisomer thereof or pharmaceutically acceptable salt thereof.

3. The compound or any stereoisomer thereof or pharmaceutically acceptable salt thereof of claim 1, wherein $Y^1$ is N and $Y^2$, $Y^3$, are $Y^4$ are CH.

4. The compound or any stereoisomer thereof or pharmaceutically acceptable salt thereof of claim 1 wherein n is 1.

5. The compound or any stereoisomer thereof or pharmaceutically acceptable salt thereof of claim 1 wherein A is $CH_2$, $CF_2$, CHF, $CHR^2$, or $CFR^2$.

6. The compound or any stereoisomer thereof or pharmaceutically acceptable salt thereof of claim 1, wherein A is $CHR^2$.

7. The compound or any stereoisomer thereof or pharmaceutically acceptable salt thereof of claim 6, wherein $R^2$ is $CHF_2$ or $CF_3$.

8. The compound or any stereoisomer thereof or pharmaceutically acceptable salt thereof of claim 1, wherein s is 0.

9. The compound or any stereoisomer thereof or pharmaceutically acceptable salt thereof of claim 1, wherein p is 0.

10. The compound or any stereoisomer thereof or pharmaceutically acceptable salt thereof of claim 1 wherein $Y^5$ is $CZ^5$, and $Z^5$ is T or Q.

11. The compound or any stereoisomer thereof or pharmaceutically acceptable salt thereof of claim 10 wherein $Z^5$ is T.

12. The compound or any stereoisomer thereof or pharmaceutically acceptable salt thereof of claim 11 wherein T is

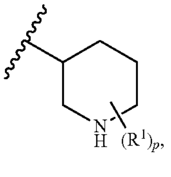

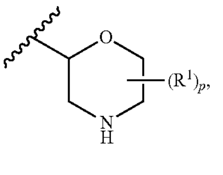

or

-continued

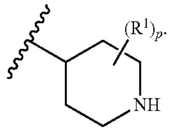

13. The compound or any stereoisomer thereof or pharmaceutically acceptable salt thereof of claim 10 wherein $Y^1$, $Y^2$, $Y^3$ and $Y^4$ are CH.

14. The compound or any stereoisomer thereof or pharmaceutically acceptable salt thereof of claim 10 wherein X is CH.

15. A compound of claim 1, selected from:

1-(2-(Piperidin-2-yl)benzyl)-2-thioxo-1,2,3,5-tetrahydro-4H-pyrrolo[3,2-d]pyrimidin-4-one, (R)-1-(2-(piperidin-2-yl)benzyl)-2-thioxo-1,2,3,5-tetrahydro-4H-pyrrolo[3,2-d]pyrimidin-4-one, (S)-1-(2-(piperidin-2-yl)benzyl)-2-thioxo-1,2,3,5-tetrahydro-4H-pyrrolo[3,2-d]pyrimidin-4-one, 1-(4-Chloro-2-(piperidin-2-yl)benzyl)-2-thioxo-1,2,3,5-tetrahydro-4H-pyrrolo[3,2-d]pyrimidin-4-one, (R)-1-(4-Chloro-2-(piperidin-2-yl)benzyl)-2-thioxo-1,2,3,5-tetrahydro-4H-pyrrolo[3,2-d]pyrimidin-4-one, (S)-1-(4-Chloro-2-(piperidin-2-yl)benzyl)-2-thioxo-1,2,3,5-tetrahydro-4H-pyrrolo[3,2-d]pyrimidin-4-one, 1-(4-Chloro-2-(pyrrolidin-2-yl)benzyl)-2-thioxo-1,2,3,5-tetrahydro-4H-pyrrolo[3,2-d]pyrimidin-4-one, (R)-1-(4-Chloro-2-(pyrrolidin-2-yl)benzyl)-2-thioxo-1,2,3,5-tetrahydro-4H-pyrrolo[3,2-d]pyrimidin-4-one, (S)-1-(4-Chloro-2-(pyrrolidin-2-yl)benzyl)-2-thioxo-1,2,3,5-tetrahydro-4H-pyrrolo[3,2-d]pyrimidin-4-one, 1-(4-Chloro-2-(morpholin-3-yl)benzyl)-2-thioxo-1,2,3,5-tetrahydro-4H-pyrrolo[3,2-d]pyrimidin-4-one, (R)-1-(4-Chloro-2-(morpholin-3-yl)benzyl)-2-thioxo-1,2,3,5-tetrahydro-4H-pyrrolo[3,2-d]pyrimidin-4-one, (S)-1-(4-chloro-2-(morpholin-3-yl)benzyl)-2-thioxo-1,2,3,5-tetrahydro-4H-pyrrolo[3,2-d]pyrimidin-4-one, 3-(4-Chloro-2-(morpholin-3-yl)benzyl)-2-thioxo-1,2,3,7-tetrahydro-6H-purin-6-one, 1-(2-(Azepan-2-yl)benzyl)-2-thioxo-1,2,3,5-tetrahydro-4H-pyrrolo[3,2-d]pyrimidin-4-one, (R)-1-(2-(Azepan-2-yl)benzyl)-2-thioxo-1,2,3,5-tetrahydro-4H-pyrrolo[3,2-d]pyrimidin-4-one, (S)-1-(2-(Azepan-2-yl)benzyl)-2-thioxo-1,2,3,5-tetrahydro-4H-pyrrolo[3,2-d]pyrimidin-4-one, (R)-3-(2-(Azepan-2-yl)-4-chlorobenzyl)-2-thioxo-1,2,3,7-tetrahydro-6H-purin-6-one, (S)-3-(2-(Azepan-2-yl)-4-chlorobenzyl)-2-thioxo-1,2,3,7-tetrahydro-6H-purin-6-one, (R)-1-(2-(Morpholin-3-yl)benzyl)-2-thioxo-1,2,3,5-tetrahydro-4H-pyrrolo[3,2-d]pyrimidin-4-one, (S)-1-(2-(Morpholin-3-yl)benzyl)-2-thioxo-1,2,3,5-tetrahydro-4H-pyrrolo[3,2-d]pyrimidin-4-one 1-(2-(4-Methylpiperazin-2-yl)benzyl)-2-thioxo-1,2,3,5-tetrahydro-4H-pyrrolo[3,2-d]pyrimidin-4-one, rac-2-Thioxo-1-(2-((2R,4S)-4-(trifluoromethyl)piperidin-2-yl)benzyl)-1,2,3,5-tetrahydro-4H-pyrrolo[3,2-d]pyrimidin-4-one, 2-Thioxo-1-(2-((2R,4S)-4-(trifluoromethyl)piperidin-2-yl)benzyl)-1,2,3,5-tetrahydro-4H-pyrrolo[3,2-d]pyrimidin-4-one, 2-Thioxo-1-(2-((2S,4R)-4-(trifluoromethyl)piperidin-2-yl)benzyl)-1,2,3,5-tetrahydro-4H-pyrrolo[3,2-d]pyrimidin-4-one, 2-Thioxo-1-(2-(5-(trifluoromethyl)piperidin-2-yl)benzyl)-1,2,3,5-tetrahydro-4H-pyrrolo[3,2-d]pyrimidin-4-one, 1-(2-(4,4-Difluoropiperidin-2-yl)benzyl)-2-thioxo-1,2,3,5-tetrahydro-4H-pyrrolo[3,2-d]pyrimidin-4-one, (R)-1-(2-(4,4-Difluoropiperidin-2-yl)benzyl)-2-thioxo-1,2,3,5-tetrahydro-4H-pyrrolo[3,2-d]pyrimidin-4-one, (S)-1-(2-(4,4-Difluoropiperidin-2-yl)benzyl)-2-thioxo-1,2,3,5-tetrahydro-4H-pyrrolo[3,2-d]pyrimidin-4-one, rac-2-Thioxo-3-(2-((2R,4S)-4-(trifluoromethyl)piperidin-2-yl)benzyl)-1,2,3,7-tetrahydro-6H-purin-6-one, 2-Thioxo-3-(2-((2R,4S)-4-(trifluoromethyl)piperidin-2-yl)benzyl)-1,2,3,7-tetrahydro-6H-purin-6-one, 2-Thioxo-3-(2-((2S,4R)-4-(trifluoromethyl)piperidin-2-yl)benzyl)-1,2,3,7-tetrahydro-6H-purin-6-one, 3-(2-(4,4-Difluoropiperidin-2-yl)benzyl)-2-thioxo-1,2,3,7-tetrahydro-6H-purin-6-one, 3-(2-(5-Fluoropiperidin-2-yl)benzyl)-2-thioxo-1,2,3,7-tetrahydro-6H-purin-6-one, 2-Thioxo-1-((2-(−4-(trifluoromethyl)piperidin-2-yl) pyridin-3-yl)methyl)-1,2,3,5-tetrahydro-4H-pyrrolo[3,2-d]pyrimidin-4-one, rac-2-Thioxo-1-((2-((2R,4S)-4-(trifluoromethyl)piperidin-2-yl) pyridin-3-yl)methyl)-1,2,3,5-tetrahydro-4H-pyrrolo[3,2-d]pyrimidin-4-one, 2-Thioxo-1-((2-((cis)-4-(trifluoromethyl)piperidin-2-yl) pyridin-3-yl)methyl)-1,2,3,5-tetrahydro-4H-pyrrolo[3,2-d]pyrimidin-4-one, 2-Thioxo-1-((2-((2R,4S)-4-(trifluoromethyl)piperidin-2-yl) pyridin-3-yl)methyl)-1,2,3,5-tetrahydro-4H-pyrrolo[3,2-d]pyrimidin-4-one, 2-Thioxo-1-((2-((2S,4R)-4-(trifluoromethyl)piperidin-2-yl) pyridin-3-yl)methyl)-1,2,3,5-tetrahydro-4H-pyrrolo[3,2-d]pyrimidin-4-one, rac-2-Thioxo-1-(2-((2R,4R)-4-(trifluoromethyl)piperidin-2-yl)benzyl)-1,2,3,5-tetrahydro-4H-pyrrolo[3,2-d]pyrimidin-4-one, 2-Thioxo-1-(2-((trans)-4-(trifluoromethyl)piperidin-2-yl) benzyl)-1,2,3,5-tetrahydro-4H-pyrrolo[3,2-d]pyrimidin-4-one, 2-Thioxo-1-(2-((2R,4R)-4-(trifluoromethyl)piperidin-2-yl)benzyl)-1,2,3,5-tetrahydro-4H-pyrrolo[3,2-d]pyrimidin-4-one, 2-Thioxo-1-(2-((2S,4S)-4-(trifluoromethyl)piperidin-2-yl)benzyl)-1,2,3,5-tetrahydro-4H-pyrrolo[3,2-d]pyrimidin-4-one, rac-2-thioxo-3-(2-((2R,4R)-4-(trifluoromethyl)piperidin-2-yl)benzyl)-1,2,3,7-tetrahydro-6H-purin-6-one, 2-thioxo-3-(2-((trans)-4-(trifluoromethyl)piperidin-2-yl) benzyl)-1,2,3,7-tetrahydro-6H-purin-6-one, 2-Thioxo-3-(2-((2R,4R)-4-(trifluoromethyl)piperidin-2-yl)benzyl)-1,2,3,7-tetrahydro-6H-purin-6-one, 2-Thioxo-3-(2-((2S,4S)-4-(trifluoromethyl)piperidin-2-yl)benzyl)-1,2,3,7-tetrahydro-6H-purin-6-one, rac-1-(2-((2R,4S)-4-(Difluoromethyl)piperidin-2-yl)benzyl)-2-thioxo-1,2,3,5-tetrahydro-4H-pyrrolo[3,2-d]pyrimidin-4-one, 1-(2-((2R,4S)-4-(Difluoromethyl)piperidin-2-yl)benzyl)-2-thioxo-1,2,3,5-tetrahydro-4H-pyrrolo[3,2-d]pyrimidin-4-one, 1-(2-((2S,4R)-4-(difluoromethyl)piperidin-2-yl)benzyl)-2-thioxo-1,2,3,5-tetrahydro-4H-pyrrolo[3,2-d]pyrimidin-4-one, 1-((2-(Piperidin-2-yl) pyridin-3-yl)methyl)-2-thioxo-1,2,3,5-tetrahydro-4H-pyrrolo[3,2-d]pyrimidin-4-one, rac-2-Thioxo-1-((3-((2R,4S)-4-(trifluoromethyl)piperidin-2-yl) pyridin-2-yl)methyl)-1,2,3,5-tetrahydro-4H-pyrrolo[3,2-d]pyrimidin-4-one, 2-Thioxo-1-((3-((cis)-4-(trifluoromethyl)piperidin-2-yl) pyridin-2-yl)methyl)-1,2,3,5-tetrahydro-4H-pyrrolo[3,2-d]pyrimidin-4-one, 2-Thioxo-1-((3-((2R,4S)-4-(trifluoromethyl)piperidin-2-yl) pyridin-2-yl)methyl)-1,2,3,5-tetrahydro-4H-pyrrolo[3,2-d]pyrimidin-4-one, 2-Thioxo-1-((3-((2S,4R)-4-(trifluoromethyl)piperidin-2-yl) pyridin-2-yl)methyl)-1,2,3,5-tetrahydro-4H-pyrrolo[3,2-d]pyrimidin-4-one, rac-2-Thioxo-1-((3-((2R,4S)-4-(trifluoromethyl)piperidin-2-yl) pyridin-4-yl)methyl)-1,2,3,5-tetrahydro-4H-pyrrolo[3,2-d]pyrimidin-4-one, 2-Thioxo-1-((3-((cis)-4-(trifluoromethyl)piperidin-2-yl) pyridin-4-yl)methyl)-1,2,3,5-tetrahydro-4H-pyrrolo[3,2-d]pyrimidin-4-one, 2-Thioxo-1-((3-((2R,4S)-4-(trifluoromethyl)piperidin-2-yl) pyridin-4-yl)methyl)-1,2,3,5-tetrahydro-4H-pyrrolo[3,2-d]pyrimidin-4-one, 2-Thioxo-1-((3-((2S,4R)-4-(trifluoromethyl)piperidin-2-yl) pyridin-4-yl)methyl)-1,2,3,5-tetrahydro-4H-pyrrolo[3,2-d]pyrimidin-4-one, 1-(4-(1-Aminocyclobutyl)benzyl)-2-thioxo-1,2,3,5-tetrahydro-4H-pyrrolo[3,2-d]pyrimidin-4-one, 1-(3-(1-Aminocyclobutyl)benzyl)-2-thioxo-1,2,3,5-tetrahydro-4H-pyrrolo[3,2-d]pyrimidin-4-one, 1-(2-(Piperidin-3-yl)benzyl)-2-thioxo-1,2,3,5-tetrahydro-4H-pyrrolo[3,2-d]pyrimidin-4-one, 1-(2-(morpholin-2-yl)benzyl)-2-thioxo-1,2,3,5-tetrahydro-4H-pyrrolo[3,2-d]pyrimidin-4-one, (R)-1-(2-(Morpholin-2-yl)benzyl)-2-thioxo-1,2,3,5-tetrahydro-4H-pyrrolo[3,2-d]pyrimidin-4-one, (S)-1-(2-(morpholin-2-yl)benzyl)-2-thioxo-1,2,3,5-tetrahydro-4H-pyrrolo[3,2-d]pyrimidin-4-one, 1-(2-(Piperidin-4-yl)benzyl)-2-thioxo-1,2,3,5-tetrahydro-4H-pyrrolo[3,2-d]pyrimidin-4-one, rac-2-Thioxo-1-((2-((2R,4R)-4-(trifluoromethyl)piperidin-2-yl) pyridin-3-yl)methyl)-1,2,3,5-tetrahydro-4H-pyrrolo[3,2-d]pyrimidin-4-one, 2-Thioxo-1-((2-((trans)-4-(trifluoromethyl)piperidin-2-yl) pyridin-3-yl)methyl)-1,2,3,5-tetrahydro-4H-pyrrolo[3,2-d]pyrimidin-4-one, 2-Thioxo-1-((2-((2R,4R)-4-(trifluoromethyl)piperidin-2-yl) pyridin-3-yl)methyl)-1,2,3,5-tetrahydro-4H-pyrrolo[3,2-d]pyrimidin-4-one, 2-Thioxo-1-((2-((2S,4S)-4-(trifluoromethyl)piperidin-2-yl) pyridin-3-yl)methyl)-1,2,3,5-tetrahydro-4H-pyrrolo[3,2-d]pyrimidin-4-one, and pharmaceutically acceptable salts thereof.

16. The compound of claim 1, having the structure:

(IIIa)

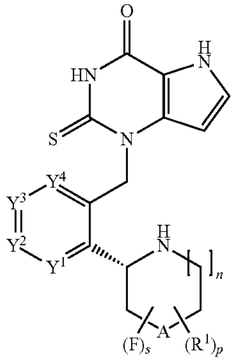

or (IIIb)

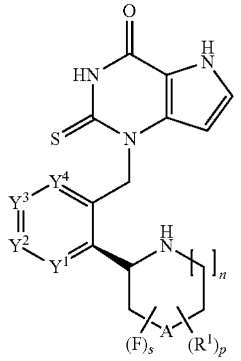

or any stereoisomer thereof or pharmaceutically acceptable salt thereof.

17. A pharmaceutical composition comprising a compound of formula (I), or a pharmaceutically acceptable salt thereof, as claimed in claim 1 in admixture with a pharmaceutically acceptable adjuvant, diluent or carrier.

* * * * *